US012441811B2

(12) United States Patent
Czyzyk

(10) Patent No.: US 12,441,811 B2
(45) Date of Patent: Oct. 14, 2025

(54) COMPOSITIONS AND METHODS FOR TREATING SERPIN B13 DISORDERS

(71) Applicant: REGENTS OF THE UNIVERSITY OF MINNESOTA, Minneapolis, MN (US)

(72) Inventor: Jan Czyzyk, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 922 days.

(21) Appl. No.: 17/633,012

(22) PCT Filed: Aug. 3, 2020

(86) PCT No.: PCT/US2020/044729
§ 371 (c)(1),
(2) Date: Feb. 4, 2022

(87) PCT Pub. No.: WO2021/026064
PCT Pub. Date: Feb. 11, 2021

(65) Prior Publication Data

US 2022/0267468 A1 Aug. 25, 2022

Related U.S. Application Data

(60) Provisional application No. 63/040,356, filed on Jun. 17, 2020, provisional application No. 62/883,443, filed on Aug. 6, 2019.

(51) Int. Cl.
*C07K 16/38* (2006.01)

(52) U.S. Cl.
CPC .......... *C07K 16/38* (2013.01); *C07K 2317/21* (2013.01); *C07K 2317/24* (2013.01); *C07K 2317/565* (2013.01); *C07K 2317/76* (2013.01)

(58) Field of Classification Search
CPC ..... C07K 16/38; C07K 231/24; C07K 231/21
See application file for complete search history.

(56) References Cited

U.S. PATENT DOCUMENTS

| | | | | |
|---|---|---|---|---|
| 2009/0270480 | A1 | 10/2009 | Amegadzie et al. | |
| 2015/0306193 | A1 * | 10/2015 | Czyzyk | C07K 14/8121 424/193.1 |
| 2016/0176953 | A1 | 6/2016 | Purcell Ngambo et al. | |
| 2017/0211055 | A1 | 7/2017 | Brogdon et al. | |

FOREIGN PATENT DOCUMENTS

| | | | |
|---|---|---|---|
| WO | 2010099923 | A1 | 9/2010 |
| WO | 2011026064 | A1 | 3/2011 |
| WO | 2011149943 | A1 | 12/2011 |
| WO | 2019075433 | A1 | 4/2019 |

OTHER PUBLICATIONS

Baldzizhar, R , et al., "Anti-serpin Antibody-mediated Regulation of Proteases in Autoimmune Diabetes", Journal of Biological Chemistry 288(3), 1612-1619 (2013).
Czyzyk, J , et al., "Enhanced Anti-Serpin Antibody Activity Inhibits Autoimmune Inflammation in Type 1 Diabetes", Journal of Immunology 188, 6319-6327 (2012).
Kryvalap, Y , et al., "Antibody Response to Serpin B13 Induces Adaptive Changes in Mouse Pancreatic Islets and Slows Down the Decline in the Residual Beta Cell Function in Children with Recent Onset of Type 1 Diabetes Mellitus", Journal of Biological Chemistry 291 (1), 266-278 (2016).
Kryvalap, Y , et al., "SerpinB13 antibodies promote B cell development and resistance to type 1 diabetes", Sci Transl Med 13, eabf1587, 12 pages (2021).
Lo, C, et al., "Cellular proliferation in mouse and human pancreatic islets is regulated by serpin B13 inhibition and downstream targeting of E-cadherin by cathepsin L", Diabetologia 62, 822-834 (2019).
Patent Cooperation Treaty , International Search Report and Written Opinion for PCT/US2020/044729, 10 pages, dated Feb. 22, 2021.

* cited by examiner

*Primary Examiner* — Janet L Epps-Smith
*Assistant Examiner* — Nada Ahmed Mahmou Elmansy
(74) *Attorney, Agent, or Firm* — Viksnins Harris Padys Malen LLP

(57) ABSTRACT

Provided herein are anti-OVA-serine proteinase inhibitor (serpin) B13 monoclonal antibodies and antigen-binding antibody fragments that selectively and specifically bind to an epitope of serpin B13, compositions containing these antibodies and antibody fragments, and methods of using these antibodies and antibody fragments. These antibodies and antigen-binding fragments thereof are useful for inhibiting serpin B13 and for treating serpin B13-related diseases, e.g., type I diabetes.

15 Claims, 85 Drawing Sheets

Specification includes a Sequence Listing.

```
5' gacggatcgggagatctcccgatcccctatggtgcactctcagtacaatctgctctgatgccgcatagtt 70
3' ctgcctagccctctagagggctaggggataccacgtgagagtcatgttagacgagactacggcgtatcaa

5' aagccagtatctgctccctgcttgtgtgttggaggtcgctgagtagtgcgcgagcaaaatttaagctaca 140
3' ttcggtcatagacgagggacgaacacacaacctccagcgactcatcacgcgctcgttttaaattcgatgt

5' acaaggcaaggcttgaccgacaattgcatgaagaatctgcttagggttaggcgttttgcgctgcttcgcg 210
3' tgttccgttccgaactggctgttaacgtacttcttagacgaatcccaatccgcaaaacgcgacgaagcgc

5' accattgcatacgttgtatccatatcataatatgtacatttatattggctcatgtccaacattaccgcca 280
3' tggtaacgtatgcaacataggtatagtattatacatgtaaatataaccgagtacaggttgtaatggcggt

5' tgttgacattgattattgactagttattaatagtaatcaattacggggtcattagttcatagcccatata 350
3' acaactgtaactaataactgatcaataattatcattagttaatgccccagtaatcaagtatcgggtatat
   CMV

5' tggagttccgcgttacataacttacggtaaatggcccgcctggctgaccgcccaacgacccccgcccatt 420
3' acctcaaggcgcaatgtattgaatgccatttaccgggcggaccgactggcgggttgctgggggcgggtaa
   CMV

5' gacgtcaataatgacgtatgttcccatagtaacgccaatagggactttccattgacgtcaatgggtggac 490
3' ctgcagttattactgcatacaagggtatcattgcggttatccctgaaaggtaactgcagttacccacctg
   CMV

5' tatttacggtaaactgcccacttggcagtacatcaagtgtatcatatgccaagtacgccccctattgacg 560
3' ataaatgccatttgacgggtgaaccgtcatgtagttcacatagtatacggttcatgcgggggataactgc
   CMV

5' tcaatgacggtaaatggcccgcctggcattatgcccagtacatgaccttatgggactttcctacttggca 630
3' agttactgccatttaccgggcggaccgtaatacgggtcatgtactggaatacctgaaaggatgaaccgt
   CMV

5' gtacatctacgtattagtcatcgctattaccatggtgatgcggttttggcagtacatcaatgggcgtgga 700
3' catgtagatgcataatcagtagcgataatggtaccactacgccaaaaccgtcatgtagttacccgcacct
   CMV

5' tagcggtttgactcacggggatttccaagtctccaccccattgacgtcaatgggagtttgttttggcacc 770
3' atcgccaaactgagtgcccctaaaggttcagaggtggggtaactgcagttaccctcaaacaaaaccgtgg
   CMV
```

FIG. 1A

5' aaaatcaacgggactttccaaaatgtcgtaacaactccgccccattgacgcaaatgggcggtaggcgtgt 840
3' ttttagttgccctgaaaggttttacagcattgttgaggcggggtaactgcgtttacccgccatccgcaca
CMV 5' acggtgggaggtctatataagcagagctcgtttagtgaaccgtcagatcgcctggagacgccatccacgc 910
3' tgccaccctccagatatattcgtctcgagcaaatcacttggcagtctagcggacctctgcggtaggtgcg
CMV 5' tgttttgacctccatagaagacaccgggaccgatccagcctccgcggccgggaacggtgcattggaacgc 980
3' acaaaactggaggtatcttctgtggccctggctaggtcggaggcgccggcccttgccacgtaaccttgcg
CMV 5' ggattccccgtgccaagagtgacgtaagtaccgcctatagactctataggcacacccctttggctcttat 1050
3' cctaaggggcacggttctcactgcattcatggcggatatctgagatatccgtgtggggaaaccgagaata
CMV 5' gcatgctatactgtttttggcttggggcctatacacccccgcttccttatgctataggtgatggtatagc 1120
3' cgtacgatatgacaaaaaccgaaccccggatatgtgggggcgaaggaatacgatatccactaccatatcg
CMV 5' ttagcctataggtgtgggttattgaccattattgaccactcccctattggtgacgatactttccattact 1190
3' aatcggatatccacacccaataactggtaataactggtgaggggataaccactgctatgaaaggtaatga
CMV 5' aatccataacatggctctttgccacaactatctctattggctatatgccaatactctgtccttcagagac 1260
3' ttaggtattgtaccgagaaacggtgttgatagagataaccgatatacggttatgagacaggaagtctctg
CMV 5' tgacacggactctgtatttttacaggatggggtcccatttattatttacaaattcacatatacaacaacg 1330
3' actgtgcctgagacataaaaatgtcctaccccagggtaaataataaatgtttaagtgtatatgttgttgc
CMV 5' ccgtcccccgtgcccgcagtttttattaaacatagcgtgggatctccacgcgaatctcgggtacgtgttc 1400
3' ggcagggggcacgggcgtcaaaaataatttgtatcgcaccctagaggtgcgcttagagcccatgcacaag
CMV 5' cggacatgggctcttctccggtagcggcggagcttccacatccgagccctggtcccatgcctccagcggc 1470
3' gcctgtacccgagaagaggccatcgccgcctcgaaggtgtaggctcgggaccagggtacggaggtcgccg
CMV

FIG. 1B

5' tcatggtcgctcggcagctccttgctcctaacagtggaggccagacttaggcacagcacaatgcccacca 1540
3' agtaccagcgagccgtcgaggaacgaggattgtcacctccggtctgaatccgtgtcgtgttacgggtggt
CMV 5' ccaccagtgtgccgcacaaggccgtggcggtagggtatgtgtctgaaaatgagcgtggagattgggctcg 1610
3' ggtggtcacacggcgtgttccggcaccgccatcccatacacagacttttactcgcacctctaacccgagc
CMV 5' cacggctgacgcagatggaagacttaaggcagcggcagaagaagatgcaggcagctgagttgttgtattc 1680
3' gtgccgactgcgtctaccttctgaattccgtcgccgtcttcttctacgtccgtcgactcaacaacataag
CMV 5' tgataagagtcagaggtaactcccgttgcggtgctgttaacggtggagggcagtgtagtctgagcagaac 1750
3' actattctcagtctccattgagggcaacgccacgacaattgccacctcccgtcacatcagactcgtcttg
CMV 5' tcgttgctgccgcgcgcgccaccagacataatagctgacagactaacagactgttcctttccatgggtct 1820
3' agcaacgacggcgcgcgcggtggtctgtattatcgactgtctgattgtctgacaaggaaaggtacccaga
CMV

*Hin dIII*
5' tttctgcagtcaccgtcctgacacgaagcttgccgccaccatgggctggtccctgattctgctgttcctg 1890
3' aaagacgtcagtggcaggactgtgcttcgaacggcggtggtacccgaccagggactaagacgacaaggac
CMV
H-chain 5' gtggctgtggctaccagggtgctgagtgagatccagctggtggagagcggaggaggactggtgcagccag 1960
3' caccgacaccgatggtcccacgactcactctaggtcgaccacctctcgcctcctcctgaccacgtcggtc
H-chain
B29_graft-VH 5' gaggatctgtgaggctgagctgcgcagcatccggatacaacttcaagacctatggcatgtcctgggtgcg 2030
3' ctcctagacactccgactcgacgcgtcgtaggcctatgttgaagttctggataccgtacaggacccacgc
H-chain
B29_graft-VH 5' ccaggcaccaggcaagggactggagtggatgggctggatcaatacctactctggcatgcctacatatgcc 2100
3' ggtccgtggtccgttccctgacctcacctacccgacctagttatggatgagaccgtacggatgtatacgg
H-chain
B29_graft-VH

FIG. 1C

5' gacgatttcaagggccggttcaccttttctctggacaccagcaagaacacagcctacctgcagatcaatt 2170
3' ctgctaaagttcccggccaagtggaaaagagacctgtggtcgttcttgtgtcggatggacgtctagttaa
H-chain
B29_graft-VH 5' ccctgcgggccgaggacacagccgtgtacttttgtgccagacccctgctgggcctggattattggggcca 2240
3' gggacgcccggctcctgtgtcggcacatgaaaacacggtctggggacgacccggacctaataaccccggt
H-chain
B29_graft-VH 5' gggcaccctggtgacagtgagctccgctagcaccaagggcccatcggtcttccccctggcaccctcctcc 2310
3' cccgtgggaccactgtcactcgaggcgatcgtggttcccgggtagccagaagggggaccgtgggaggagg
H-chain
B29_graft-VH 5' aagagcacctctgggggcacagcggccctgggctgcctggtcaaggactacttccccgaaccggtgacgg 2380
3' ttctcgtggagacccccgtgtcgccgggacccgacggaccagttcctgatgaaggggcttggccactgcc
H-chain 5' tgtcgtggaactcaggcgccctgaccagcggcgtgcacaccttcccggctgtcctacagtcctcaggact 2450
3' acagcaccttgagtccgcgggactggtcgccgcacgtgtggaagggccgacaggatgtcaggagtcctga
H-chain 5' ctactccctcagcagcgtggtgaccgtgccctccagcagcttgggcacccagacctacatctgcaacgtg 2520
3' gatgagggagtcgtcgcaccactggcacgggaggtcgtcgaacccgtgggtctggatgtagacgttgcac
H-chain 5' aatcacaagcccagcaacaccaaggtggacaagaaagttgagcccaaatcttgtgacaaaactcacacat 2590
3' ttagtgttcgggtcgttgtggttccacctgttctttcaactcgggtttagaacactgttttgagtgtgta
H-chain 5' gcccaccgtgcccagcacctgaactcctgggggggaccgtcagtcttcctcttccccccaaaacccaagga 2660
3' cgggtggcacgggtcgtggacttgaggacccccctggcagtcagaaggagaaggggggttttgggttcct
H-chain 5' caccctcatgatctcccggacccctgaggtcacatgcgtggtggtggacgtgagccacgaagaccctgag 2730
3' gtgggagtactagagggcctggggactccagtgtacgcaccaccacctgcactcggtgcttctgggactc
H-chain

FIG. 1D

5' gtcaagttcaactggtacgtggacggcgtggaggtgcataatgccaagacaaagccgcgggaggagcagt 2800
3' cagttcaagttgaccatgcacctgccgcacctccacgtattacggttctgtttcggcgccctcctcgtca
H-chain 5' acaacagcacgtaccgtgtggtcagcgtcctcaccgtcctgcaccaggactggctgaatggcaaggagta 2870
3' tgttgtcgtgcatggcacaccagtcgcaggagtggcaggacgtggtcctgaccgacttaccgttcctcat
H-chain 5' caagtgcaaggtctccaacaaagccctcccagcccccatcgagaaaaccatctccaaagccaaagggcag 2940
3' gttcacgttccagaggttgtttcgggagggtcgggggtagctcttttggtagaggtttcggtttcccgtc
H-chain 5' ccccgagaaccacaggtgtacaccctgcccccatcccgggaggagatgaccaagaaccaggtcagcctga 3010
3' ggggctcttggtgtccacatgtgggacgggggtagggccctcctctactggttcttggtccagtcggact
H-chain 5' cctgcctggtcaaaggcttctatcccagcgacatcgccgtggagtgggagagcaatgggcagccggagaa 3080
3' ggacggaccagtttccgaagatagggtcgctgtagcggcacctcaccctctcgttacccgtcggcctctt
H-chain 5' caactacaagaccacgcctcccgtgctggactccgacggctccttcttcctctacagcaagctcaccgtg 3150
3' gttgatgttctggtgcggagggcacgacctgaggctgccgaggaagaaggagatgtcgttcgagtggcac
H-chain 5' gacaagagcaggtggcagcaggggaacgtcttctcatgctccgtgatgcatgaggctctgcacaaccact 3220
3' ctgttctcgtccaccgtcgtccccttgcagaagagtacgaggcactacgtactccgagacgtgttggtga
H-chain

*Eco RI*
5' acacgcagaagagcctctccctgtctccgggtaaatgagaattctgcagatatccatcacactggcggcc 3290
3' tgtgcgtcttctcggagagggacagaggcccatttactcttaagacgtctataggtagtgtgaccgccgg
H-chain 5' gctcgagcatgcatctagagggccctattctatagtgtcacctaaatgctagagctcgctgatcagcctc 3360
3' cgagctcgtacgtagatctcccgggataagatatcacagtggatttacgatctcgagcgactagtcggag 5' gactgtgccttctagttgccagccatctgttgtttgcccctcccccgtgccttccttgaccctggaaggt 3430
3' ctgacacggaagatcaacggtcggtagacaacaaacggggagggggcacggaaggaactgggaccttcca

FIG. 1E

```
5' gccactcccactgtcctttcctaataaaatgaggaaattgcatcgcattgtctgagtaggtgtcattcta
                                                                          3500
3' cggtgagggtgacaggaaaggattattttactcctttaacgtagcgtaacagactcatccacagtaagat

5' ttctggggggtggggtggggcaggacagcaagggggaggattgggaagacaatagcaggcatgctgggga
                                                                          3570
3' aagaccccccaccccaccccgtcctgtcgttccccctcctaacccttctgttatcgtccgtacgacccct

5' tgcggtgggctctatggcttctgaggcggaaagaaccagctgcattaatgaatcggccaacgcgcgggga
                                                                          3640
3' acgccacccgagataccgaagactccgcctttcttggtcgacgtaattacttagccggttgcgcgcccct

5' gaggcggtttgcgtattgggcgctcttcgctcgcgatctggaggacaaattacacacacttgcgcctgag
                                                                          3710
3' ctccgccaaacgcataacccgcgagaagcgagcgctagacctcctgtttaatgtgtgtgaacgcggactc

5' cgccaagcacagggttgttggtcctcatattcacgaggtcgctgagagcacggtgggctaatgttgccat
                                                                          3780
3' gcggttcgtgtcccaacaaccaggagtataagtgctccagcgactctcgtgccacccgattacaacggta

5' gggtagcatatactacccaaatatctggatagcatatgctatcctaatctatatctgggtagcataggct
                                                                          3850
3' cccatcgtatatgatgggtttatagacctatcgtatacgataggattagatatagacccatcgtatccga

5' atcctaatctatatctgggtagcatatgctatcctaatctatatctgggtagtatatgctatcctaattt
                                                                          3920
3' taggattagatatagacccatcgtatacgataggattagatatagacccatcatatacgataggattaaa

5' atatctgggtagcataggctatcctaatctatatctgggtagcatatgctatcctaatctatatctgggt
                                                                          3990
3' tatagacccatcgtatccgataggattagatatagacccatcgtatacgataggattagatatagaccca

5' agtatatgctatcctaatctgtatccgggtagcatatgctatcctaatagagattagggtagtatatgct
                                                                          4060
3' tcatatacgataggattagacataggcccatcgtatacgataggattatctctaatcccatcatatacga

5' atcctaatttatatctgggtagcatatactacccaaatatctggatagcatatgctatcctaatctatat
                                                                          4130
3' taggattaaatatagacccatcgtatatgatgggtttatagacctatcgtatacgataggattagatata

5' ctgggtagcatatgctatcctaatctatatctgggtagcataggctatcctaatctatatctgggtagca
                                                                          4200
3' gacccatcgtatacgataggattagatatagacccatcgtatccgataggattagatatagacccatcgt

5' tatgctatcctaatctatatctgggtagtatatgctatcctaatttatatctgggtagcataggctatcc
                                                                          4270
3' atacgataggattagatatagacccatcatatacgataggattaaatatagacccatcgtatccgatagg

5' taatctatatctgggtagcatatgctatcctaatctatatctgggtagtatatgctatcctaatctgtat
                                                                          4340
3' attagatatagacccatcgtatacgataggattagatatagacccatcatatacgataggattagacata
```

FIG. 1F

5' ccgggtagcatatgctatcctcatgcatatacagtcagcatatgatacccagtagtagagtgggagtgct 4410
3' ggcccatcgtatacgataggagtacgtatatgtcagtcgtatactatgggtcatcatctcaccctcacga 5' atcctttgcatatgccgccacctcccaagggggcgtgaattttcgctgcttgtccttttcctgcagccgg 4480
3' taggaaacgtatacggcggtggagggttcccccgcacttaaaagcgacgaacaggaaaaggacgtcggcc 5' ccgcttcctcgctcactgactcgctgcgctcggtcgttcggctgcggcgagcggtatcagctcactcaaa 4550
3' ggcgaaggagcgagtgactgagcgacgcgagccagcaagccgacgccgctcgccatagtcgagtgagttt 5' ggcggtaatacggttatccacagaatcaggggataacgcaggaaagaacatgtgagcaaaaggccagcaa 4620
3' ccgccattatgccaataggtgtcttagtcccctattgcgtcctttcttgtacactcgttttccggtcgtt puc Ori 5' aaggccaggaaccgtaaaaaggccgcgttgctggcgtttttccataggctccgcccccctgacgagcatc 4690
3' ttccggtccttggcatttttccggcgcaacgaccgcaaaaaggtatccgaggcggggggactgctcgtag puc Ori 5' acaaaaatcgacgctcaagtcagaggtggcgaaacccgacaggactataaagataccaggcgtttccccc 4760
3' tgtttttagctgcgagttcagtctccaccgctttgggctgtcctgatatttctatggtccgcaaaggggg puc Ori 5' tggaagctccctcgtgcgctctcctgttccgaccctgccgcttaccggatacctgtccgcctttctccct 4830
3' accttcgagggagcacgcgagaggacaaggctgggacggcgaatggcctatggacaggcggaaagaggga puc Ori 5' tcgggaagcgtggcgctttctcaatgctcacgctgtaggtatctcagttcggtgtaggtcgttcgctcca 4900
3' agcccttcgcaccgcgaaagagttacgagtgcgacatccatagagtcaagccacatccagcaagcgaggt puc Ori 5' agctgggctgtgtgcacgaaccccccgttcagcccgaccgctgcgccttatccggtaactatcgtcttga 4970
3' tcgacccgacacacgtgcttggggggcaagtcgggctggcgacgcggaataggccattgatagcagaact puc Ori 5' gtccaacccggtaagacacgacttatcgccactggcagcagccactggtaacaggattagcagagcgagg 5040
3' caggttgggccattctgtgctgaatagcggtgaccgtcgtcggtgaccattgtcctaatcgtctcgctcc puc Ori 5' tatgtaggcggtgctacagagttcttgaagtggtggcctaactacggctacactagaaggacagtatttg 5110
3' atacatccgccacgatgtctcaagaacttcaccaccggattgatgccgatgtgatcttcctgtcataaac
caggttgggccattctgtgctgaatagcggtgaccgtcgtcggtgaccattgtcctaatcgtctcgctcc puc Ori

FIG. 1G

5' atgatcccccatgttgtgcaaaaaagcggttagctccttcggtcctccgatcgttgtcagaagtaagttg 5880
3' tactagggggtacaacacgttttttcgccaatcgaggaagccaggaggctagcaacagtcttcattcaac

AMP

5' gccgcagtgttatcactcatggttatggcagcactgcataattctcttactgtcatgccatccgtaagat 5950
3' cggcgtcacaatagtgagtaccaataccgtcgtgacgtattaagagaatgacagtacggtaggcattcta

AMP

5' gcttttctgtgactggtgagtattcaaccaagtcattctgagaatagtgtatgcggcgaccgagttgctc 6020
3' cgaaaagacactgaccactcataagttggttcagtaagactcttatcacatacgccgctggctcaacgag

AMP

5' ttgcccggcgtcaatacgggataataccgcgccacatagcagaactttaaaagtgctcatcattggaaaa 6090
3' aacgggccgcagttatgccctattatggcgcggtgtatcgtcttgaaattttcacgagtagtaacctttt

AMP

5' cgttcttcggggcgaaaactctcaaggatcttaccgctgttgagatccagttcgatgtaacccactcgtg 6160
3' gcaagaagccccgcttttgagagttcctagaatggcgacaactctaggtcaagctacattgggtgagcac

AMP

5' cacccaactgatcttcagcatcttttactttcaccagcgtttctgggtgagcaaaaacaggaaggcaaaa 6230
3' gtgggttgactagaagtcgtagaaaatgaaagtggtcgcaaagacccactcgtttttgtccttccgtttt

AMP

5' tgccgcaaaaaagggaataagggcgacacggaaatgttgaatactcatactcttcctttttcaatattat 6300
3' acggcgttttttcccttattcccgctgtgcctttacaacttatgagtatgagaaggaaaaagttataata AMP Bla promoter 5' tgaagcatttatcagggttattgtctcatgagcggatacatatttgaatgtatttagaaaaataaacaaa 6370
3' acttcgtaaatagtcccaataacagagtactcgcctatgtataaacttacataaatctttttatttgttt Bla promoter 5' taggggttccgcgcacatttccccgaaaagtgccacctgacgtc 6414
3' atccccaaggcgcgtgtaaaggggcttttcacggtggactgcag Bla p...oter

FIG. 1I

5' gacggatcgggagatctcccgatcccctatggtgcactctcagtacaatctgctctgatgccgcatagtt 70
3' ctgcctagccctctagagggctaggggataccacgtgagagtcatgttagacgagactacggcgtatcaa 5' aagccagtatctgctccctgcttgtgtgttggaggtcgctgagtagtgcgcgagcaaaatttaagctaca 140
3' ttcggtcatagacgagggacgaacacacaacctccagcgactcatcacgcgctcgttttaaattcgatgt 5' acaaggcaaggcttgaccgacaattgcatgaagaatctgcttagggttaggcgttttgcgctgcttcgcg 210
3' tgttccgttccgaactggctgttaacgtacttcttagacgaatcccaatccgcaaaacgcgacgaagcgc 5' accattgcatacgttgtatccatatcataatatgtacatttatattggctcatgtccaacattaccgcca 280
3' tggtaacgtatgcaacataggtatagtattatacatgtaaatataaccgagtacaggttgtaatggcggt 5' tgttgacattgattattgactagttattaatagtaatcaattacggggtcattagttcatagcccatata 350
3' acaactgtaactaataactgatcaataattatcattagttaatgccccagtaatcaagtatcgggtatat
CMV 5' tggagttccgcgttacataacttacggtaaatggcccgcctggctgaccgcccaacgacccccgcccatt 420
3' acctcaaggcgcaatgtattgaatgccatttaccgggcggaccgactggcgggttgctgggggcgggtaa
CMV 5' gacgtcaataatgacgtatgttcccatagtaacgccaatagggactttccattgacgtcaatgggtggac 490
3' ctgcagttattactgcatacaagggtatcattgcggttatccctgaaaggtaactgcagttacccacctg
CMV 5' tatttacggtaaactgcccacttggcagtacatcaagtgtatcatatgccaagtacgccccctattgacg 560
3' ataaatgccatttgacgggtgaaccgtcatgtagttcacatagtatacggttcatgcggggggataactgc
CMV 5' tcaatgacggtaaatggcccgcctggcattatgcccagtacatgaccttatgggactttcctacttggca 630
3' agttactgccatttaccgggcggaccgtaatacgggtcatgtactggaataccctgaaaggatgaaccgt
CMV 5' gtacatctacgtattagtcatcgctattaccatggtgatgcggttttggcagtacatcaatgggcgtgga 700
3' catgtagatgcataatcagtagcgataatggtaccactacgccaaaaccgtcatgtagttacccgcacct
CMV 5' tagcggtttgactcacggggatttccaagtctccaccccattgacgtcaatgggagtttgttttggcacc 770
3' atcgccaaactgagtgcccctaaaggttcagaggtggggtaactgcagttaccctcaaacaaaaccgtgg
CMV

FIG. 2A

5' aaaatcaacgggactttccaaaatgtcgtaacaactccgccccattgacgcaaatgggcggtaggcgtgt 840
3' ttttagttgccctgaaaggttttacagcattgttgaggcggggtaactgcgtttacccgccatccgcaca
CMV 5' acggtgggaggtctatataagcagagctcgtttagtgaaccgtcagatcgcctggagacgccatccacgc 910
3' tgccaccctccagatatattcgtctcgagcaaatcacttggcagtctagcggacctctgcggtaggtgcg
CMV 5' tgttttgacctccatagaagacaccgggaccgatccagcctccgcggccgggaacggtgcattggaacgc 980
3' acaaaactggaggtatcttctgtggccctggctaggtcggaggcgccggcccttgccacgtaaccttgcg
CMV 5' ggattccccgtgccaagagtgacgtaagtaccgcctatagactctataggcacacccctttggctcttat 1050
3' cctaaggggcacggttctcactgcattcatggcggatatctgagatatccgtgtggggaaaccgagaata
CMV 5' gcatgctatactgtttttggcttggggcctatacacccccgcttccttatgctataggtgatggtatagc 1120
3' cgtacgatatgacaaaaaccgaaccccggatatgtgggggcgaaggaatacgatatccactaccatatcg
CMV 5' ttagcctataggtgtgggttattgaccattattgaccactcccctattggtgacgatactttccattact 1190
3' aatcggatatccacacccaataactggtaataactggtgaggggataaccactgctatgaaaggtaatga
CMV 5' aatccataacatggctctttgccacaactatctctattggctatatgccaatactctgtccttcagagac 1260
3' ttaggtattgtaccgagaaacggtgttgatagagataaccgatatacggttatgagacaggaagtctctg
CMV 5' tgacacggactctgtatttttacaggatggggtcccatttattatttacaaattcacatatacaacaacg 1330
3' actgtgcctgagacataaaaatgtcctaccccagggtaaataataaatgtttaagtgtatatgttgttgc
CMV 5' ccgtcccccgtgcccgcagtttttattaaacatagcgtgggatctccacgcgaatctcgggtacgtgttc 1400
3' ggcagggggcacgggcgtcaaaaataatttgtatcgcaccctagaggtgcgcttagagcccatgcacaag
CMV 5' cggacatgggctcttctccggtagcggcggagcttccacatccgagccctggtcccatgcctccagcggc 1470
3' gcctgtacccgagaagaggccatcgccgcctcgaaggtgtaggctcgggaccagggtacggaggtcgccg
CMV

FIG. 2B

5' tcatggtcgctcggcagctccttgctcctaacagtggaggccagacttaggcacagcacaatgcccacca 1540
3' agtaccagcgagccgtcgaggaacgaggattgtcacctccggtctgaatccgtgtcgtgttacgggtggt
CMV 5' ccaccagtgtgccgcacaaggccgtggcggtagggtatgtgtctgaaaatgagcgtggagattgggctcg 1610
3' ggtggtcacacggcgtgttccggcaccgccatcccatacacagacttttactcgcacctctaacccgagc
CMV 5' cacggctgacgcagatggaagacttaaggcagcggcagaagaagatgcaggcagctgagttgttgtattc 1680
3' gtgccgactgcgtctaccttctgaattccgtcgccgtcttcttctacgtccgtcgactcaacaacataag
CMV 5' tgataagagtcagaggtaactcccgttgcggtgctgttaacggtggagggcagtgtagtctgagcagaac 1750
3' actattctcagtctccattgagggcaacgccacgacaattgccacctcccgtcacatcagactcgtcttg
CMV 5' tcgttgctgccgcgcgcgccaccagacataatagctgacagactaacagactgttcctttccatgggtct 1820
3' agcaacgacggcgcgcgcggtggtctgtattatcgactgtctgattgtctgacaaggaaaggtacccaga
CMV

*Hin dIII*
5' tttctgcagtcaccgtcctgacacgaagcttgccgccaccatggctggtccctgattctgctgttcctg 1890
3' aaagacgtcagtggcaggactgtgcttcgaacggcggtggtacccgaccagggactaagacgacaaggac
CMV
L-chain 5' gtggctgtggctaccagggtgctgagtgagatccagctggtggagagcggaggaggactggtgcagccag 1960
3' caccgacaccgatggtcccacgactcactctaggtcgaccacctctcgcctcctcctgaccacgtcggtc
L-chain
B29_graft-VL 5' tgggcgatagggtgaccatcacatgcaagtctagccagtctctgctgcacagcgacggcaagaccttcct 2030
3' acccgctatcccactggtagtgtacgttcagatcggtcagagacgacgtgtcgctgccgttctggaagga
L-chain
B29_graft-VL 5' gaactggtttcagcagaagcccggcaagtctcctaagctgctgatctacctggtgtccaagctggagtct 2100
3' cttgaccaaagtcgtcttcgggccgttcagaggattcgacgactagatggaccacaggttcgacctcaga
L-chain
B29_graft-VL

FIG. 2C

5' ggcgtgcccagcagattctctggcagcggctccggcacagactttaccctgacaatctcctctctgcagc 2170
3' ccgcacgggtcgtctaagagaccgtcgccgaggccgtgtctgaaatgggactgttagaggagagacgtcg
L-chain
B29_graft-VL 5' cagaggatttcgccacctactattgtctgcagcacacccacttcccctgacatttggccagggcaccaa 2240
3' gtctcctaaagcggtggatgataacagacgtcgtgtgggtgaaggggactgtaaaccggtcccgtggtt
L-chain
B29_graft-VL 5' ggtggagatcaagcgtacggtggctgcaccatctgtcttcatcttcccgccatctgatgagcagttgaaa 2310
3' ccacctctagttcgcatgccaccgacgtggtagacagaagtagaagggcggtagactactcgtcaacttt
L-chain
B29_graft-VL 5' tctggaactgcctctgttgtgtgcctgctgaataacttctatcccagagaggccaaagtacagtggaagg 2380
3' agaccttgacggagacaacacacggacgacttattgaagatagggtctctccggtttcatgtcaccttcc
L-chain 5' tggataacgccctccaatcgggtaactcccaggagagtgtcacagagcaggacagcaaggacagcaccta 2450
3' acctattgcgggaggttagcccattgagggtcctctcacagtgtctcgtcctgtcgttcctgtcgtggat
L-chain 5' cagcctcagcagcaccctgacgctgagcaaagcagactacgagaaacacaaagtctacgcctgcgaagtc 2520
3' gtcggagtcgtcgtgggactgcgactcgtttcgtctgatgctctttgtgtttcagatgcggacgcttcag
L-chain ECO RI
5' acccatcagggcctgagctcgcccgtcacaaagagcttcaacaggggagagtgttaggaattctgcagat 2590
3' tgggtagtcccggactcgagcgggcagtgtttctcgaagttgtcccctctcacaatccttaagacgtcta
L-chain 5' atccatcacactggcggccgctcgagcatgcatctagagggccctattctatagtgtcacctaaatgcta 2660
3' taggtagtgtgaccgccggcgagctcgtacgtagatctcccgggataagatatcacagtggatttacgat 5' gagctcgctgatcagcctcgactgtgccttctagttgccagccatctgttgtttgcccctcccccgtgcc 2730
3' ctcgagcgactagtcggagctgacacggaagatcaacggtcggtagacaacaaacggggagggggcacgg

FIG. 2D

5' ttccttgaccctggaaggtgccactcccactgtcctttcctaataaaatgaggaaattgcatcgcattgt 2800
3' aaggaactgggaccttccacggtgagggtgacaggaaaggattattttactcctttaacgtagcgtaaca 5' ctgagtaggtgtcattctattctggggggtggggtggggcaggacagcaagggggaggattgggaagaca 2870
3' gactcatccacagtaagataagaccccccaccccaccccgtcctgtcgttccccctcctaacccttctgt 5' atagcaggcatgctggggatgcggtgggctctatggcttctgaggcggaaagaaccagctgcattaatga 2940
3' tatcgtccgtacgacccctacgccacccgagataccgaagactccgcctttcttggtcgacgtaattact 5' atcggccaacgcgcggggagaggcggtttgcgtattgggcgctcttcgctagcgatctggaggacaaatt 3010
3' tagccggttgcgcgcccctctccgccaaacgcataacccgcgagaagcgatcgctagacctcctgtttaa 5' acacacacttgcgcctgagcgccaagcacagggttgttggtcctcatattcacgaggtcgctgagagcac 3080
3' tgtgtgtgaacgcggactcgcggttcgtgtcccaacaaccaggagtataagtgctccagcgactctcgtg 5' ggtgggctaatgttgccatgggtagcatatactacccaaatatctggatagcatatgctatcctaatcta 3150
3' ccacccgattacaacggtacccatcgtatatgatgggtttatagacctatcgtatacgataggattagat 5' tatctgggtagcataggctatcctaatctatatctgggtagcatatgctatcctaatctatatctgggta 3220
3' atagacccatcgtatccgataggattagatatagacccatcgtatacgataggattagatatagacccat 5' gtatatgctatcctaatttatatctgggtagcataggctatcctaatctatatctgggtagcatatgcta 3290
3' catatacgataggattaaatatagacccatcgtatccgataggattagatatagacccatcgtatacgat 5' gtatatgctatcctaatttatatctgggtagcataggctatcctaatctatatctgggtagcatatgcta 3360
3' catatacgataggattaaatatagacccatcgtatccgataggattagatatagacccatcgtatacgat 5' gattagggtagtatatgctatcctaatttatatctgggtagcatatactacccaaatatctggatagcat 3430
3' ctaatcccatcatatacgataggattaaatatagacccatcgtatatgatgggtttatagacctatcgta 5' atgctatcctaatctatatctgggtagcatatgctatcctaatctatatctgggtagcataggctatcct 3500
3' tacgataggattagatatagacccatcgtatacgataggattagatatagacccatcgtatccgatagga 5' aatctatatctgggtagcatatgctatcctaatctatatctgggtagtatatgctatcctaatttatatc 3570
3' ttagatatagacccatcgtatacgataggattagatatagacccatcatatacgataggattaaatatag 5' tgggtagcataggctatcctaatctatatctgggtagcatatgctatcctaatctatatctgggtagtat 3640
3' acccatcgtatccgataggattagatatagacccatcgtatacgataggattagatatagacccatcata

FIG. 2E

5' atgctatcctaatctgtatccgggtagcatatgctatcctcatgcatatacagtcagcatatgataccca 3710
3' tacgataggattagacataggcccatcgtatacgataggagtacgtatatgtcagtcgtatactatgggt 5' gtagtagagtgggagtgctatcctttgcatatgccgccacctcccaagggggcgtgaattttcgctgctt 3780
3' catcatctcaccctcacgataggaaacgtatacggcggtggagggttcccccgcacttaaaagcgacgaa 5' gtccttttcctgcagctagccgcttcctcgctcactgactcgctgcgctcggtcgttcggctgcggcgag 3850
3' caggaaaaggacgtcgatcggcgaaggagcgagtgactgagcgacgcgagccagcaagccgacgccgctc 5' cggtatcagctcactcaaaggcggtaatacggttatccacagaatcaggggataacgcaggaaagaacat 3920
3' gccatagtcgagtgagtttccgccattatgccaataggtgtcttagtcccctattgcgtcctttcttgta 5' gtgagcaaaaggccagcaaaaggccaggaaccgtaaaaaggccgcgttgctggcgtttttccataggctc 3990
3' cactcgttttccggtcgttttccggtccttggcatttttccggcgcaacgaccgcaaaaaggtatccgagqq puc Ori 5' cgcccccctgacgagcatcacaaaaatcgacgctcaagtcagaggtggcgaaacccgacaggactataaa 4060
3' gcggggggactgctcgtagtgtttttagctgcgagttcagtctccaccgctttgggctgtcctgatattt puc Ori 5' gataccaggcgtttccccctggaagctccctcgtgcgctctcctgttccgaccctgccgcttaccggata 4130
3' ctatggtccgcaaagggggaccttcgagggagcacgcgagaggacaaggctgggacggcgaatggcctat puc Ori 5' cctgtccgcctttctcccttcgggaagcgtggcgctttctcaatgctcacgctgtaggtatctcagttcg 4200
3' ggacaggcggaaagagggaagcccttcgcaccgcgaaagagttacgagtgcgacatccatagagtcaagc puc Ori 5' gtgtaggtcgttcgctccaagctgggctgtgtgcacgaaccccccgttcagcccgaccgctgcgccttat 4270
3' cacatccagcaagcgaggttcgacccgacacacgtgcttggggggcaagtcgggctggcgacgcggaata puc Ori 5' ccggtaactatcgtcttgagtccaacccggtaagacacgacttatcgccactggcagcagccactggtaa 4340
3' ggccattgatagcagaactcaggttgggccattctgtgctgaatagcggtgaccgtcgtcggtgaccatt puc Ori 5' caggattagcagagcgaggtatgtaggcggtgctacagagttcttgaagtggtggcctaactacggctac 4410
3' gtcctaatcgtctcgctccatacatccgccacgatgtctcaagaacttcaccaccggattgatgccgatg puc Ori

FIG. 2F

5' actagaaggacagtatttggtatctgcgctctgctgaagccagttaccttcggaaaaagagttggtagct 4480
3' tgatcttcctgtcataaaccatagacgcgagacgacttcggtcaatggaagcctttttctcaaccatcga
puc Ori 5' cttgatccggcaaacaaaccaccgctggtagcggtggtttttttgtttgcaagcagcagattacgcgcag 4550
3' gaactaggccgtttgtttggtggcgaccatcgccaccaaaaaaacaaacgttcgtcgtctaatgcgcgtc
puc Ori 5' aaaaaaaggatctcaagaagatcctttgatcttttctacggggtctgacgctcagtggaacgaaaactca 4620
3' tttttttcctagagttcttctaggaaactagaaaagatgccccagactgcgagtcaccttgcttttgagt
puc Ori 5' cgttaagggattttggtcatgagattatcaaaaaggatcttcacctagatccttttaaattaaaaatgaa 4690
3' gcaattccctaaaaccagtactctaatagtttttcctagaagtggatctaggaaaatttaatttttactt 5' gttttaaatcaatctaaagtatatatgagtaaacttggtctgacagttaccaatgcttaatcagtgaggc 4760
3' caaaatttagttagatttcatatatactcatttgaaccagactgtcaatggttacgaattagtcactccg
AMP 5' acctatctcagcgatctgtctatttcgttcatccatagttgcctgactccccgtcgtgtagataactacg 4830
3' tggatagagtcgctagacagataaagcaagtaggtatcaacggactgaggggcagcacatctattgatgc
AMP 5' atacgggagggcttaccatctggccccagtgctgcaatgataccgcgagacccacgctcaccggctccag 4900
3' tatgccctcccgaatggtagaccggggtcacgacgttactatggcgctctgggtgcgagtggccgaggtc
AMP 5' atttatcagcaataaaccagccagccggaagggccgagcgcagaagtggtcctgcaactttatccgcctc 4970
3' taaatagtcgttatttggtcggtcggccttcccggctcgcgtcttcaccaggacgttgaaataggcggag
AMP 5' catccagtctattaattgttgccgggaagctagagtaagtagttcgccagttaatagtttgcgcaacgtt 5040
3' gtaggtcagataattaacaacggcccttcgatctcattcatcaagcggtcaattatcaaacgcgttgcaa
AMP 5' gttgccattgctacaggcatcgtggtgtcacgctcgtcgtttggtatggcttcattcagctccggttccc 5110
3' caacggtaacgatgtccgtagcaccacagtgcgagcagcaaaccataccgaagtaagtcgaggccaaggg
AMP

FIG. 2G

```
5' gacggatcgggagatctcccgatcccctatggtgcactctcagtacaatctgctctgatgccgcatagtt
   70
3' ctgcctagccctctagagggctaggggataccacgtgagagtcatgttagacgagactacggcgtatcaa

5' aagccagtatctgctccctgcttgtgtgttggaggtcgctgagtagtgcgcgagcaaaatttaagctaca
   140
3' ttcggtcatagacgagggacgaacacacaacctccagcgactcatcacgcgctcgttttaaattcgatgt

5' acaaggcaaggcttgaccgacaattgcatgaagaatctgcttagggttaggcgttttgcgctgcttcgcg
   210
3' tgttccgttccgaactggctgttaacgtacttcttagacgaatcccaatccgcaaaacgcgacgaagcgc

5' accattgcatacgttgtatccatatcataatatgtacatttatattggctcatgtccaacattaccgcca
   280
3' tggtaacgtatgcaacataggtatagtattatacatgtaaatataaccgagtacaggttgtaatggcggt

5' tgttgacattgattattgactagttattaatagtaatcaattacggggtcattagttcatagcccatata
   350
3' acaactgtaactaataactgatcaataattatcattagttaatgccccagtaatcaagtatcgggtatat
   CMV

5' tggagttccgcgttacataacttacggtaaatggcccgcctggctgaccgcccaacgacccccgcccatt
   420
3' acctcaaggcgcaatgtattgaatgccatttaccgggcggaccgactggcgggttgctgggggcgggtaa
   CMV

5' gacgtcaataatgacgtatgttcccatagtaacgccaatagggactttccattgacgtcaatgggtggac
   490
3' ctgcagttattactgcatacaagggtatcattgcggttatccctgaaaggtaactgcagttacccacctg
   CMV

5' tatttacggtaaactgcccacttggcagtacatcaagtgtatcatatgccaagtacgccccctattgacg
   560
3' ataaatgccatttgacgggtgaaccgtcatgtagttcacatagtatacggttcatgcgggggataactgc
   CMV

5' tcaatgacggtaaatggcccgcctggcattatgcccagtacatgaccttatgggactttcctacttggca
   630
3' agttactgccatttaccgggcggaccgtaatacgggtcatgtactggaatacctgaaaggatgaaccgt
   CMV

5' gtacatctacgtattagtcatcgctattaccatggtgatgcggttttggcagtacatcaatgggcgtgga
   700
3' catgtagatgcataatcagtagcgataatggtaccactacgccaaaaccgtcatgtagttacccgcacct
   CMV

5' tagcggtttgactcacggggatttccaagtctccaccccattgacgtcaatgggagtttgttttggcacc
   770
3' atcgccaaactgagtgcccctaaaggttcagaggtggggtaactgcagttaccctcaaacaaaaccgtgg
   CMV
```

FIG. 3A

5' aaaatcaacgggactttccaaaatgtcgtaacaactccgccccattgacgcaaatgggcggtaggcgtgt 840
3' ttttagttgccctgaaaggttttacagcattgttgaggcggggtaactgcgtttacccgccatccgcaca
CMV 5' acggtgggaggtctatataagcagagctcgtttagtgaaccgtcagatcgcctggagacgccatccacgc 910
3' tgccaccctccagatatattcgtctcgagcaaatcacttggcagtctagcggacctctgcggtaggtgcg
CMV 5' tgttttgacctccatagaagacaccgggaccgatccagcctccgcggccgggaacggtgcattggaacgc 980
3' acaaaactggaggtatcttctgtggccctggctaggtcggaggcgccggcccttgccacgtaaccttgcg
CMV 5' ggattccccgtgccaagagtgacgtaagtaccgcctatagactctataggcacacccctttggctcttat 1050
3' cctaaggggcacggttctcactgcattcatggcggatatctgagatatccgtgtggggaaaccgagaata
CMV 5' gcatgctatactgtttttggcttggggcctatacacccccgcttccttatgctataggtgatggtatagc 1120
3' cgtacgatatgacaaaaaccgaaccccggatatgtgggggcgaaggaatacgatatccactaccatatcg
CMV 5' ttagcctataggtgtgggttattgaccattattgaccactcccctattggtgacgatactttccattact 1190
3' aatcggatatccacacccaataactggtaataactggtgaggggataaccactgctatgaaaggtaatga
CMV 5' aatccataacatggctctttgccacaactatctctattggctatatgccaatactctgtccttcagagac 1260
3' ttaggtattgtaccgagaaacggtgttgatagagataaccgatatacggttatgagacaggaagtctctg
CMV 5' tgacacggactctgtatttttacaggatggggtcccatttattatttacaaattcacatatacaacaacg 1330
3' actgtgcctgagacataaaaatgtcctaccccagggtaaataataaatgtttaagtgtatatgttgttgc
CMV 5' ccgtcccccgtgcccgcagtttttattaaacatagcgtgggatctccacgcgaatctcgggtacgtgttc 1400
3' ggcagggggcacgggcgtcaaaaataatttgtatcgcaccctagaggtgcgcttagagcccatgcacaag
CMV 5' cggacatgggctcttctccggtagcggcggagcttccacatccgagccctggtcccatgcctccagcggc 1470
3' gcctgtacccgagaagaggccatcgccgcctcgaaggtgtaggctcgggaccagggtacggaggtcgccg
CMV

FIG. 3B

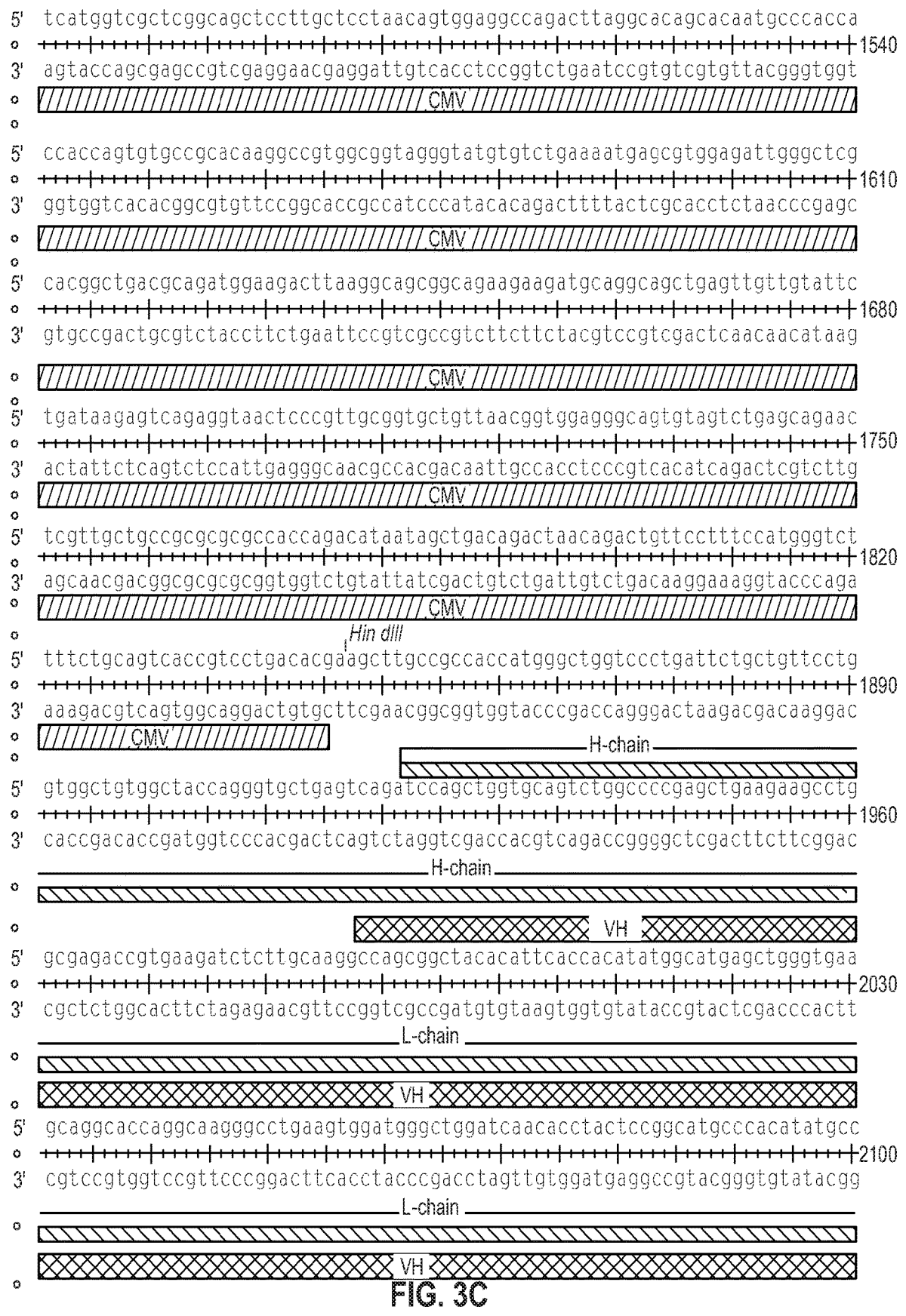

5' tcatggtcgctcggcagctccttgctcctaacagtggaggccagacttaggcacagcacaatgcccacca 1540
3' agtaccagcgagccgtcgaggaacgaggattgtcacctccggtctgaatccgtgtcgtgttacgggtggt
CMV 5' ccaccagtgtgccgcacaaggccgtggcggtagggtatgtgtctgaaaatgagcgtggagattgggctcg 1610
3' ggtggtcacacggcgtgttccggcaccgccatcccatacacagacttttactcgcacctctaacccgagc
CMV 5' cacggctgacgcagatggaagacttaaggcagcggcagaagaagatgcaggcagctgagttgttgtattc 1680
3' gtgccgactgcgtctaccttctgaattccgtcgccgtcttcttctacgtccgtcgactcaacaacataag
CMV 5' tgataagagtcagaggtaactcccgttgcggtgctgttaacggtggagggcagtgtagtctgagcagaac 1750
3' actattctcagtctccattgagggcaacgccacgacaattgccacctcccgtcacatcagactcgtcttg
CMV 5' tcgttgctgccgcgcgcgccaccagacataatagctgacagactaacagactgttcctttccatgggtct 1820
3' agcaacgacggcgcgcgcggtggtctgtattatcgactgtctgattgtctgacaaggaaaggtacccaga
CMV

*Hin dIII*
5' tttctgcagtcaccgtcctgacacgaagcttgccgccaccatgggctggtccctgattctgctgttcctg 1890
3' aaagacgtcagtggcaggactgtgcttcgaacggcggtggtacccgaccagggactaagacgacaaggac
CMV
H-chain 5' gtggctgtggctaccagggtgctgagtcagatccagctggtgcagtctggccccgagctgaagaagcctg 1960
3' caccgacaccgatggtcccacgactcagtctaggtcgaccacgtcagaccggggctcgacttcttcggac
H-chain
VH 5' gcgagaccgtgaagatctcttgcaaggccagcggctacacattcaccacatatggcatgagctgggtgaa 2030
3' cgctctggcacttctagagaacgttccggtcgccgatgtgtaagtggtgtataccgtactcgacccactt
L-chain
VH 5' gcaggcaccaggcaagggcctgaagtggatgggctggatcaacacctactccggcatgcccacatatgcc 2100
3' cgtccgtggtccgttcccggacttcacctacccgacctagttgtggatgaggccgtacgggtgtatacgg
L-chain
VH

FIG. 3C

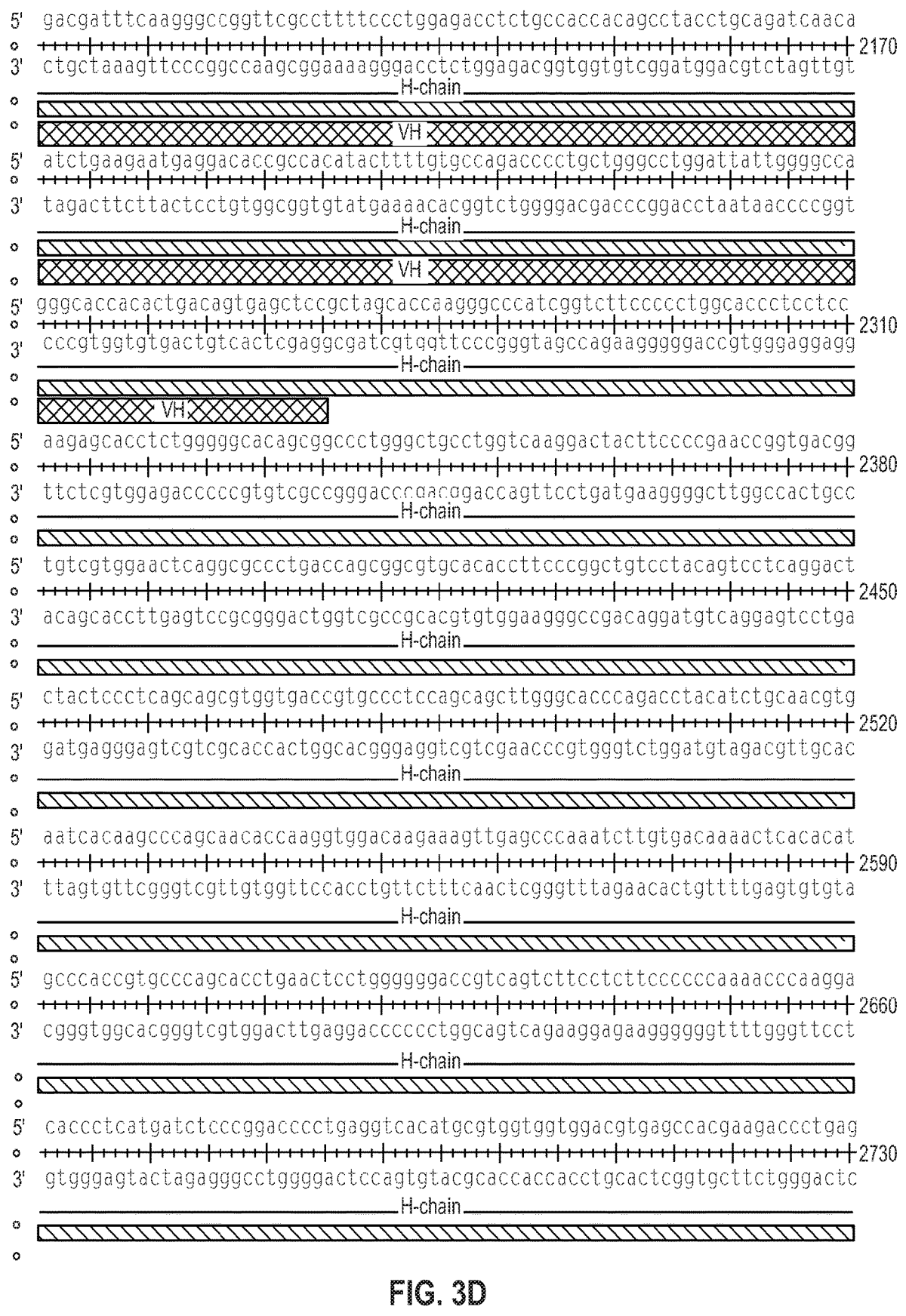

5' gacgatttcaagggccggttcgccttttccctggagacctctgccaccacagcctacctgcagatcaaca 2170
3' ctgctaaagttcccggccaagcggaaaagggacctctggagacggtggtgtcggatggacgtctagttgt
H-chain
VH 5' atctgaagaatgaggacaccgccacatacttttgtgccagacccctgctgggcctggattattggggcca
3' tagacttcttactcctgtggcggtgtatgaaaacacggtctggggacgacccggacctaataaccccggt
H-chain
VH 5' gggcaccacactgacagtgagctccgctagcaccaagggcccatcggtcttccccctggcaccctcctcc 2310
3' cccgtggtgtgactgtcactcgaggcgatcgtggttcccgggtagccagaagggggaccgtgggaggagg
H-chain
VH 5' aagagcacctctgggggcacagcggccctgggctgcctggtcaaggactacttccccgaaccggtgacgg 2380
3' ttctcgtggagacccccgtgtcgccgggacccgacggaccagttcctgatgaaggggcttggccactgcc
H-chain 5' tgtcgtggaactcaggcgccctgaccagcggcgtgcacaccttcccggctgtcctacagtcctcaggact 2450
3' acagcaccttgagtccgcgggactggtcgccgcacgtgtggaagggccgacaggatgtcaggagtcctga
H-chain 5' ctactccctcagcagcgtggtgaccgtgccctccagcagcttgggcacccagacctacatctgcaacgtg 2520
3' gatgagggagtcgtcgcaccactggcacgggaggtcgtcgaacccgtgggtctggatgtagacgttgcac
H-chain 5' aatcacaagcccagcaacaccaaggtggacaagaaagttgagcccaaatcttgtgacaaaactcacacat 2590
3' ttagtgttcgggtcgttgtggttccacctgttctttcaactcgggtttagaacactgttttgagtgtgta
H-chain 5' gcccaccgtgcccagcacctgaactcctggggggaccgtcagtcttcctcttccccccaaaacccaagga 2660
3' cgggtggcacgggtcgtggacttgaggacccccctggcagtcagaaggagaaggggggttttgggttcct
H-chain 5' caccctcatgatctcccggacccctgaggtcacatgcgtggtggtggacgtgagccacgaagaccctgag 2730
3' gtgggagtactagagggcctggggactccagtgtacgcaccaccacctgcactcggtgcttctgggactc
H-chain

FIG. 3D

```
5' gtcaagttcaactggtacgtggacggcgtggaggtgcataatgccaagacaaagccgcgggaggagcagt
                                                                         2800
3' cagttcaagttgaccatgcacctgccgcacctccacgtattacggttctgtttcggcgccctcctcgtca
                              H-chain

5' acaacagcacgtaccgtgtggtcagcgtcctcaccgtcctgcaccaggactggctgaatggcaaggagta
                                                                         2870
3' tgttgtcgtgcatggcacaccagtcgcaggagtggcaggacgtggtcctgaccgacttaccgttcctcat
                              H-chain

5' caagtgcaaggtctccaacaaagccctcccagcccccatcgagaaaaccatctccaaagccaaagggcag
                                                                         2940
3' gttcacgttccagaggttgtttcgggagggtcgggggtagctcttttggtagaggtttcggtttcccgtc
                              H-chain

5' tgcggcgaccgagttgctcttgcccggcgtcaatacgggataataccgcgccacatagcagaactttaaa
                                                                         3010
3' acgccgctggctcaacgagaacgggccgcagttatgccctattatggcgcggtgtatcgtcttgaaattt
                              H-chain

5' ccccgagaaccacaggtgtacaccctgcccccatcccgggaggagatgaccaagaaccaggtcagcctga
                                                                         3080
3' ggggctcttggtgtccacatgtgggacgggggtagggccctcctctactggttcttggtccagtcggact
                              H-chain

5' cctgcctggtcaaaggcttctatcccagcgacatcgccgtggagtgggagagcaatgggcagccggagaa
                                                                         3150
3' gttgatgttctggtgcggagggcacgacctgaggctgccgaggaagaaggagatgtcgttcgagtggcac
                              H-chain

5' gacaagagcaggtggcagcaggggaacgtcttctcatgctccgtgatgcatgaggctctgcacaaccact
                                                                         3220
3' ctgttctcgtccaccgtcgtccccttgcagaagagtacgaggcactacgtactccgagacgtgttggtga
                              H-chain
                                                 Eco RI
5' acacgcagaagagcctctccctgtctccgggtaaatgagaattctgcagatatccatcacactggcggcc
                                                                         3290
3' tgtgcgtcttctcggagagggacagaggcccatttactcttaagacgtctataggtagtgtgaccgccgg
                 H-chain

5' gctcgagcatgcatctagagggccctattctatagtgtcacctaaatgctagagctcgctgatcagcctc
                                                                         3360
3' cgagctcgtacgtagatctcccgggataagatatcacagtggatttacgatctcgagcgactagtcggag

5' gactgtgccttctagttgccagccatctgttgtttgcccctcccccgtgccttccttgaccctggaaggt
                                                                         3430
3' ctgacacggaagatcaacggtcggtagacaacaaacggggagggggcacggaaggaactgggaccttcca
```

FIG. 3E

```
5' gccactcccactgtcctttcctaataaaatgaggaaattgcatcgcattgtctgaggtaggtgtcattcta
                                                                      3500
3' cggtgagggtgacaggaaaggattattttactcctttaacgtagcgtaacagactcatccacagtaagat

5' ttctggggggtggggtggggcaggacagcaagggggaggattgggaagacaatagcaggcatgctgggga
                                                                      3570
3' aagaccccccaccccaccccgtcctgtcgttccccctcctaacccttctgttatcgtccgtacgacccct

5' tgcggtgggctctatggcttctgaggcggaaagaaccagctgcattaatgaatcggccaacgcgcgggga
                                                                      3640
3' acgccacccgagataccgaagactccgcctttcttggtcgacgtaattacttagccggttgcgcgcccct

5' gaggcggtttgcgtattgggcgctcttcgctcgcgatctggaggacaaattacacacacttgcgcctgag
                                                                      3710
3' ctccgccaaacgcataacccgcgagaagcgagcgctagacctcctgtttaatgtgtgtgaacgcggactc

5' cgccaagcacagggttgttggtcctcatattcacgaggtcgctgagagcacggtgggctaatgttgccat
                                                                      3780
3' gcggttcgtgtcccaacaaccaggagtataagtgctccagcgactctcgtgccacccgattacaacggta

5' gggtagcatatactacccaaatatctggatagcatatgctatcctaatctatatctgggtagcataggct
                                                                      3850
3' cccatcgtatatgatgggtttatagacctatcgtatacgataggattagatatagacccatcgtatccga

5' atcctaatctatatctgggtagcatatgctatcctaatctatatctgggtagtatatgctatcctaattt
                                                                      3920
3' taggattagatatagacccatcgtatacgataggattagatatagacccatcatatacgataggattaaa

5' atatctgggtagcataggctatcctaatctatatctgggtagcatatgctatcctaatctatatctgggt
                                                                      3990
3' tatagacccatcgtatccgataggattagatatagacccatcgtatacgataggattagatatagaccca

5' agtatatgctatcctaatctgtatccgggtagcatatgctatcctaatagagattagggtagtatatgct
                                                                      4060
3' tcatatacgataggattagacataggcccatcgtatacgataggattatctctaatcccatcatatacga

5' atcctaatttatatctgggtagcatatactacccaaatatctggatagcatatgctatcctaatctatat
                                                                      4130
3' taggattaaatatagacccatcgtatatgatgggtttatagacctatcgtatacgataggattagatata

5' ctgggtagcatatgctatcctaatctatatctgggtagcataggctatcctaatctatatctgggtagca
                                                                      4200
3' gacccatcgtatacgataggattagatatagacccatcgtatccgataggattagatatagacccatcgt

5' tatgctatcctaatctatatctgggtagtatatgctatcctaatttatatctgggtagcataggctatcc
                                                                      4270
3' atacgataggattagatatagacccatcatatacgataggattaaatatagacccatcgtatccgatagg

5' taatctatatctgggtagcatatgctatcctaatctatatctgggtagtatatgctatcctaatctgtat
                                                                      4340
3' attagatatagacccatcgtatacgataggattagatatagacccatcatatacgataggattagacata
```

FIG. 3F

```
5' ccgggtagcatatgctatcctcatgcatatacagtcagcatatgatacccagtagtagagtgggagtgct
                                                                          4410
3' ggcccatcgtatacgataggagtacgtatatgtcagtcgtatactatgggtcatcatctcaccctcacga

5' atcctttgcatatgccgccacctcccaagggggcgtgaattttcgctgcttgtccttttcctgcagccgg
                                                                          4480
3' taggaaacgtatacggcggtggagggttcccccgcacttaaaagcgacgaacaggaaaaggacgtcggcc

5' ccgcttcctcgctcactgactcgctgcgctcggtcgttcggctgcggcgagcggtatcagctcactcaaa
                                                                          4550
3' ggcgaaggagcgagtgactgagcgacgcgagccagcaagccgacgccgctcgccatagtcgagtgagttt

5' ggcggtaatacggttatccacagaatcaggggataacgcaggaaagaacatgtgagcaaaaggccagcaa
                                                                          4620
3' ccgccattatgccaataggtgtcttagtcccctattgcgtcctttcttgtacactcgttttccggtcgtt
                                                          <== puc Ori

5' aaggccaggaaccgtaaaaaggccgcgttgctggcgtttttccataggctccgcccccctgacgagcatc
                                                                          4690
3' ttccggtccttggcatttttccggcgcaacgaccgcaaaaaggtatccgaggcggggggactgctcgtag
                              puc Ori

5' acaaaaatcgacgctcaagtcagaggtggcgaaacccgacaggactataaagataccaggcgtttccccc
                                                                          4760
3' tgtttttagctgcgagttcagtctccaccgctttgggctgtcctgatatttctatggtccgcaaaggggg
                              puc Ori

5' tggaagctccctcgtgcgctctcctgttccgaccctgccgcttaccggatacctgtccgcctttctccct
                                                                          4830
3' accttcgagggagcacgcgagaggacaaggctgggacggcgaatggcctatggacaggcggaaagaggga
                              puc Ori

5' tcgggaagcgtggcgctttctcaatgctcacgctgtaggtatctcagttcggtgtaggtcgttcgctcca
                                                                          4900
3' agcccttcgcaccgcgaaagagttacgagtgcgacatccatagagtcaagccacatccagcaagcgaggt
                              puc Ori

5' agctgggctgtgtgcacgaaccccccgttcagcccgaccgctgcgccttatccggtaactatcgtcttga
                                                                          4970
3' tcgacccgacacacgtgcttggggggcaagtcgggctggcgacgcggaataggccattgatagcagaact
                              puc Ori

5' gtccaacccggtaagacacgacttatcgccactggcagcagccactggtaacaggattagcagagcgagg
                                                                          5040
3' caggttgggccattctgtgctgaatagcggtgaccgtcgtcggtgaccattgtcctaatcgtctcgctcc
                              puc Ori

5' tatgtaggcggtgctacagagttcttgaagtggtggcctaactacggctacactagaaggacagtatttg
                                                                          5110
3' atacatccgccacgatgtctcaagaacttcaccaccggattgatgccgatgtgatcttcctgtcataaac
                              puc Ori
```

FIG. 3G

5' atgatcccccatgttgtgcaaaaaagcggttagctccttcggtcctccgatcgttgtcagaagtaagttg 5880
3' tactagggggtacaacacgttttttcgccaatcgaggaagccaggaggctagcaacagtcttcattcaac 5' gccgcagtgttatcactcatggttatggcagcactgcataattctcttactgtcatgccatccgtaagat 5950
3' cggcgtcacaatagtgagtaccaataccgtcgtgacgtattaagagaatgacagtacggtaggcattcta 5' gcttttctgtgactggtgagtattcaaccaagtcattctgagaatagtgtatgcggcgaccgagttgctc 6020
3' cgaaaagacactgaccactcataagttggttcagtaagactcttatcacatacgccgctggctcaacgag 5' ttgcccggcgtcaatacgggataataccgcgccacatagcagaactttaaaagtgctcatcattggaaaa 6090
3' aacgggccgcagttatgccctattatggcgcggtgtatcgtcttgaaattttcacgagtagtaacctttt 5' cgttcttcggggcgaaaactctcaaggatcttaccgctgttgagatccagttcgatgtaacccactcgtg 6160
3' gcaagaagccccgcttttgagagttcctagaatggcgacaactctaggtcaagctacattgggtgagcac 5' cacccaactgatcttcagcatcttttactttcaccagcgtttctgggtgagcaaaaacaggaaggcaaaa 6230
3' gtgggttgactagaagtcgtagaaaatgaaagtggtcgcaaagacccactcgtttttgtccttccgtttt
AMP 5' tgccgcaaaaaagggaataagggcgacacggaaatgttgaatactcatactcttcctttttcaatattat 6300
3' acggcgtttttcccttattcccgctgtgcctttacaacttatgagtatgagaaggaaaaagttataata
AMP
Bla promoter 5' tgaagcatttatcagggttattgtctcatgagcggatacatatttgaatgtatttagaaaaataaacaaa 6370
3' acttcgtaaatagtcccaataacagagtactcgcctatgtataaacttacataaatctttttatttgttt
Bla promoter 5' taggggttccgcgcacatttccccgaaaagtgccacctgacgtc 6414
3' atccccaaggcgcgtgtaaaggggcttttcacggtggactgcag
Bla p...oter

FIG. 3I

```
5' gacggatcgggagatctcccgatcccctatggtgcactctcagtacaatctgctctgatgccgcatagtt
                                                                         70
3' ctgcctagccctctagagggctaggggataccacgtgagagtcatgttagacgagactacggcgtatcaa

5' aagccagtatctgctccctgcttgtgtgttggaggtcgctgagtagtgcgcgagcaaaatttaagctaca
                                                                         140
3' ttcggtcatagacgagggacgaacacacaacctccagcgactcatcacgcgctcgttttaaattcgatgt

5' acaaggcaaggcttgaccgacaattgcatgaagaatctgcttagggttaggcgttttgcgctgcttcgcg
                                                                         210
3' tgttccgttccgaactggctgttaacgtacttcttagacgaatcccaatccgcaaaacgcgacgaagcgc

5' accattgcatacgttgtatccatatcataatatgtacatttatattggctcatgtccaacattaccgcca
                                                                         280
3' tggtaacgtatgcaacataggtatagtattatacatgtaaatataaccgagtacaggttgtaatggcggt

5' tgttgacattgattattgactagttattaatagtaatcaattacggggtcattagttcatagcccatata
                                                                         350
3' acaactgtaactaataactgatcaataattatcattagttaatgccccagtaatcaagtatcgggtatat
   CMV

5' tggagttccgcgttacataacttacggtaaatggcccgcctggctgaccgcccaacgacccccgcccatt
                                                                         420
3' acctcaaggcgcaatgtattgaatgccatttaccgggcggaccgactggcgggttgctgggggcgggtaa
   CMV

5' gacgtcaataatgacgtatgttcccatagtaacgccaatagggactttccattgacgtcaatgggtggac
                                                                         490
3' ctgcagttattactgcatacaagggtatcattgcggttatccctgaaaggtaactgcagttacccacctg
   CMV

5' tatttacggtaaactgcccacttggcagtacatcaagtgtatcatatgccaagtacgccccctattgacg
                                                                         560
3' ataaatgccatttgacgggtgaaccgtcatgtagttcacatagtatacggttcatgcgggggataactgc
   CMV

5' tcaatgacggtaaatggcccgcctggcattatgcccagtacatgaccttatgggactttcctacttggca
                                                                         630
3' agttactgccatttaccgggcggaccgtaatacgggtcatgtactggaatacccctgaaaggatgaaccgt
   CMV

5' gtacatctacgtattagtcatcgctattaccatggtgatgcggttttggcagtacatcaatgggcgtgga
                                                                         700
3' catgtagatgcataatcagtagcgataatggtaccactacgccaaaaccgtcatgtagttacccgcacct
   CMV

5' tagcggtttgactcacggggatttccaagtctccaccccattgacgtcaatgggagtttgttttggcacc
                                                                         770
3' atcgccaaactgagtgcccctaaaggttcagaggtggggtaactgcagttaccctcaaacaaaaccgtgg
   CMV
```

FIG. 4A

5' aaaatcaacgggactttccaaaatgtcgtaacaactccgccccattgacgcaaatgggcggtaggcgtgt 840
3' ttttagttgccctgaaaggttttacagcattgttgaggcggggtaactgcgtttacccgccatccgcaca
CMV 5' acggtgggaggtctatataagcagagctcgtttagtgaaccgtcagatcgcctggagacgccatccacgc 910
3' tgccaccctccagatatattcgtctcgagcaaatcacttggcagtctagcggacctctgcggtaggtgcg
CMV 5' tgttttgacctccatagaagacaccgggaccgatccagcctccgcggccgggaacggtgcattggaacgc 980
3' acaaaactggaggtatcttctgtggccctggctaggtcggaggcgccggcccttgccacgtaaccttgcg
CMV 5' ggattccccgtgccaagagtgacgtaagtaccgcctatagactctataggcacacccctttggctcttat 1050
3' cctaaggggcacggttctcactgcattcatggcggatatctgagatatccgtgtggggaaaccgagaata
CMV 5' gcatgctatactgtttttggcttggggcctatacacccccgcttccttatgctataggtgatggtatagc 1120
3' cgtacgatatgacaaaaaccgaaccccggatatgtgggggcgaaggaatacgatatccactaccatatcg
CMV 5' ttagcctataggtgtgggttattgaccattattgaccactcccctattggtgacgatactttccattact 1190
3' aatcggatatccacacccaataactggtaataactggtgaggggataaccactgctatgaaaggtaatga
CMV 5' aatccataacatggctctttgccacaactatctctattggctatatgccaatactctgtccttcagagac 1260
3' ttaggtattgtaccgagaaacggtgttgatagagataaccgatatacggttatgagacaggaagtctctg
CMV 5' tgacacggactctgtatttttacaggatggggtcccatttattatttacaaattcacatatacaacaacg 1330
3' actgtgcctgagacataaaaatgtcctaccccagggtaaataataaatgtttaagtgtatatgttgttgc
CMV 5' ccgtcccccgtgcccgcagtttttattaaacatagcgtgggatctccacgcgaatctcgggtacgtgttc 1400
3' ggcagggggcacgggcgtcaaaaataatttgtatcgcaccctagaggtgcgcttagagcccatgcacaag
CMV 5' cggacatgggctcttctccggtagcggcggagcttccacatccgagccctggtcccatgcctccagcggc 1470
3' gcctgtacccgagaagaggccatcgccgcctcgaaggtgtaggctcgggaccagggtacggaggtcgccg
CMV

FIG. 4B

5' tcatggtcgctcggcagctccttgctcctaacagtggaggccagacttaggcacagcacaatgcccacca 1540
3' agtaccagcgagccgtcgaggaacgaggattgtcacctccggtctgaatccgtgtcgtgttacgggtggt
CMV 5' ccaccagtgtgccgcacaaggccgtggcggtagggtatgtgtctgaaaatgagcgtggagattgggctcg 1610
3' ggtggtcacacggcgtgttccggcaccgccatcccatacacagacttttactcgcacctctaacccgagc
CMV 5' cacggctgacgcagatggaagacttaaggcagcggcagaagaagatgcaggcagctgagttgttgtattc 1680
3' gtgccgactgcgtctaccttctgaattccgtcgccgtcttcttctacgtccgtcgactcaacaacataag
CMV 5' tgataagagtcagaggtaactcccgttgcggtgctgttaacggtggagggcagtgtagtctgagcagaac 1750
3' actattctcagtctccattgagggcaacgccacgacaattgccacctcccgtcacatcagactcgtcttg
CMV 5' tcgttgctgccgcgcgcgccaccagacataatagctgacagactaacagactgttcctttccatgggtct 1820
3' agcaacgacggcgcgcgcggtggtctgtattatcgactgtctgattgtctgacaaggaaaggtacccaga
CMV

*Hin dIII*
5' tttctgcagtcaccgtcctgacacgaagcttgccgccaccatggctggtcctgtatcatcctgttcctg 1890
3' aaagacgtcagtggcaggactgtgcttcgaacggcggtggtacccgaccaggacatagtaggacaaggac
CMV
L-chain 5' gtggctgtggctaccagggtgctgagtcagatccagctggtgcagtctggccccgagctgaagaagcctg 1960
3' caccgacaccgatggtcccacgactcagtctaggtcgaccacgtcagaccggggctcgacttcttcggac
L-chain
VL 5' tcggccagcccgcctccatctcttgcaagagctcccagagcctgctgcactccgatggcaagaccttcct 2030
3' agccggtcgggcggaggtagagaacgttctcgagggtctcggacgacgtgaggctaccgttctggaagga
L-chain
VL 5' gaactggtttctgcagaggccaggacagtcccctaagctgctgatctacctggtgtctaagctggagagc 2100
3' cttgaccaaagacgtctccggtcctgtcaggggattcgacgactagatggaccacagattcgacctctcg
L-chain
VL

FIG. 4C

```
5' ggaatccctgaccggttcagcggatccggatctggaaccgacttcaccctgaagatctctagagtggagg
                                                                          2170
3' ccttagggactggccaagtcgcctaggcctagaccttggctgaagtgggacttctagagatctcacctcc
                                  L-chain
                                    VL

5' tggaggacctgggcgtgtactattgtctgcagcacacccacttcccctgacatttggcgccggcaccaa
                                                                          2240
3' acctcctggacccgcacatgataacagacgtcgtgggtgaaggggactgtaaaccgcggccgtggtt
                                  L-chain
                                    VL

5' gctggagatcaagcgtacggtggctgcaccatctgtcttcatcttcccgccatctgatgagcagttgaaa
                                                                          2310
3' cgacctctagttcgcatgccaccgacgtggtagacagaagtagaagggcggtagactactcgtcaacttt
                                  L-chain
      VL

5' tctggaactgcctctgttgtgtgcctgctgaataacttctatcccagagaggccaaagtacagtggaagg
                                                                          2380
3' agaccttgacggagacaacacacggacgacttattgaagatagggtctctccggtttcatgtcaccttcc
                                  L-chain

5' tggataacgccctccaatcgggtaactcccaggagagtgtcacagagcaggacagcaaggacagcaccta
                                                                          2450
3' acctattgcgggaggttagcccattgagggtcctctcacagtgtctcgtcctgtcgttcctgtcgtggat
                                  L-chain

5' cagcctcagcagcaccctgacgctgagcaaagcagactacgagaaacacaaagtctacgcctgcgaagtc
                                                                          2520
3' gtcggagtcgtcgtgggactgcgactcgtttcgtctgatgctctttgtgtttcagatgcggacgcttcag
                                  L-chain

                                                            | ECO RI
5' acccatcagggcctgagctcgcccgtcacaaagagcttcaacaggggagagtgttaggaattctgcagat
                                                                          2590
3' tgggtagtcccggactcgagcgggcagtgtttctcgaagttgtcccctctcacaatccttaagacgtcta
                    L-chain

5' atccatcacactggcggccgctcgagcatgcatctagagggccctattctatagtgtcacctaaatgcta
                                                                          2660
3' taggtagtgtgaccgccggcgagctcgtacgtagatctcccgggataagatatcacagtggatttacgat

5' gagctcgctgatcagcctcgactgtgccttctagttgccagccatctgttgtttgcccctcccccgtgcc
                                                                          2730
3' ctcgagcgactagtcggagctgacacggaagatcaacggtcggtagacaacaaacggggagggggcacgg
```

FIG. 4D

```
5' ttccttgaccctggaaggtgccactcccactgtcctttcctaataaaatgaggaaattgcatcgcattgt
                                                                          2800
3' aaggaactgggaccttccacggtgagggtgacaggaaaggattattttactcctttaacgtagcgtaaca

5' ctgagtaggtgtcattctattctggggggtggggtggggcaggacagcaagggggaggattgggaagaca
                                                                          2870
3' gactcatccacagtaagataagaccccccaccccaccccgtcctgtcgttccccctcctaacccttctgt

5' atagcaggcatgctggggatgcggtgggctctatggcttctgaggcggaaagaaccagctgcattaatga
                                                                          2940
3' tatcgtccgtacgacccctacgccacccgagataccgaagactccgcctttcttggtcgacgtaattact

5' atcggccaacgcgcggggagaggcggtttgcgtattgggcgctcttcgctagcgatctggaggacaaatt
                                                                          3010
3' tagccggttgcgcgcccctctccgccaaacgcataacccgcgagaagcgatcgctagacctcctgtttaa

5' acacacacttgcgcctgagcgccaagcacagggttgttggtcctcatattcacgaggtcgctgagagcac
                                                                          3080
3' tgtgtgtgaacgcggactcgcggttcgtgtcccaacaaccaggagtataagtgctccagcgactctcgtg

5' ggtgggctaatgttgccatgggtagcatatactacccaaatatctggatagcatatgctatcctaatcta
                                                                          3150
3' ccacccgattacaacggtacccatcgtatatgatgggtttatagacctatcgtatacgataggattagat

5' tatctgggtagcataggctatcctaatctatatctgggtagcatatgctatcctaatctatatctgggta
                                                                          3220
3' atagacccatcgtatccgataggattagatatagacccatcgtatacgataggattagatatagacccat

5' gtatatgctatcctaatttatatctgggtagcataggctatcctaatctatatctgggtagcatatgcta
                                                                          3290
3' catatacgataggattaaatatagacccatcgtatccgataggattagatatagacccatcgtatacgat

5' tcctaatctatatctgggtagtatatgctatcctaatctgtatccgggtagcatatgctatcctaataga
                                                                          3360
3' aggattagatatagacccatcatatacgataggattagacataggcccatcgtatacgataggattatct

5' gattagggtagtatatgctatcctaatttatatctgggtagcatatactacccaaatatctggatagcat
                                                                          3430
3' ctaatcccatcatatacgataggattaaatatagacccatcgtatatgatgggtttatagacctatcgta

5' atgctatcctaatctatatctgggtagcatatgctatcctaatctatatctgggtagcataggctatcct
                                                                          3500
3' tacgataggattagatatagacccatcgtatacgataggattagatatagacccatcgtatccgatagga

5' aatctatatctgggtagcatatgctatcctaatctatatctgggtagtatatgctatcctaatttatatc
                                                                          3570
3' ttagatatagacccatcgtatacgataggattagatatagacccatcatatacgataggattaaatatag

5' tgggtagcataggctatcctaatctatatctgggtagcatatgctatcctaatctatatctgggtagtat
                                                                          3640
3' acccatcgtatccgataggattagatatagacccatcgtatacgataggattagatatagacccatcata
```

FIG. 4E

5' atgctatcctaatctgtatccgggtagcatatgctatcctcatgcatatacagtcagcatatgataccca 3710
3' tacgataggattagacataggcccatcgtatacgataggagtacgtatatgtcagtcgtatactatgggt 5' gtagtagagtgggagtgctatcctttgcatatgccgccacctcccaaggggggcgtgaattttcgctgctt 3780
3' catcatctcaccctcacgataggaaacgtatacggcggtggagggttccccccgcacttaaaagcgacgaa 5' gtccttttcctgcagctagccgcttcctcgctcactgactcgctgcgctcggtcgttcggctgcggcgag 3850
3' caggaaaaggacgtcgatcggcgaaggagcgagtgactgagcgacgcgagccagcaagccgacgccgctc 5' cggtatcagctcactcaaaggcggtaatacggttatccacagaatcaggggataacgcaggaaagaacat 3920
3' gccatagtcgagtgagtttccgccattatgccaataggtgtcttagtcccctattgcgtcctttcttgta 5' gtgagcaaaaggccagcaaaaggccaggaaccgtaaaaaggccgcgttgctggcgtttttccataggctc 3990
3' cactcgttttccggtcgttttccggtccttggcatttttccggcgcaacgaccgcaaaaaggtatccgag
puc Ori 5' cgcccccctgacgagcatcacaaaaatcgacgctcaagtcagaggtggcgaaacccgacaggactataaa 4060
3' gcggggggactgctcgtagtgtttttagctgcgagttcagtctccaccgctttgggctgtcctgatattt
puc Ori 5' gataccaggcgtttccccctggaagctccctcgtgcgctctcctgttccgaccctgccgcttaccggata 4130
3' ctatggtccgcaaagggggaccttcgagggagcacgcgagaggacaaggctgggacggcgaatggcctat
puc Ori 5' cctgtccgcctttctcccttcgggaagcgtggcgctttctcaatgctcacgctgtaggtatctcagttcg 4200
3' ggacaggcggaaagagggaagcccttcgcaccgcgaaagagttacgagtgcgacatccatagagtcaagc
puc Ori 5' gtgtaggtcgttcgctccaagctgggctgtgtgcacgaaccccccgttcagcccgaccgctgcgccttat 4270
3' cacatccagcaagcgaggttcgacccgacacacgtgcttggggggcaagtcgggctggcgacgcggaata
puc Ori 5' ccggtaactatcgtcttgagtccaacccggtaagacacgacttatcgccactggcagcagccactggtaa 4340
3' ggccattgatagcagaactcaggttgggccattctgtgctgaatagcggtgaccgtcgtcggtgaccatt
puc Ori 5' caggattagcagagcgaggtatgtaggcggtgctacagagttcttgaagtggtggcctaactacggctac 4410
3' gtcctaatcgtctcgctccatacatccgccacgatgtctcaagaacttcaccaccggattgatgccgatg
puc Ori

FIG. 4F

5' actagaaggacagtatttggtatctgcgctctgctgaagccagttaccttcggaaaaagagttggtagct 4480
3' tgatcttcctgtcataaaccatagacgcgagacgacttcggtcaatggaagcctttttctcaaccatcga
puc Ori 5' cttgatccggcaaacaaaccaccgctggtagcggtggtttttttgtttgcaagcagcagattacgcgcag 4550
3' gaactaggccgtttgtttggtggcgaccatcgccaccaaaaaaacaaacgttcgtcgtctaatgcgcgtc
puc Ori 5' aaaaaaaggatctcaagaagatcctttgatcttttctacggggtctgacgctcagtggaacgaaaactca 4620
3' tttttttcctagagttcttctaggaaactagaaaagatgccccagactgcgagtcaccttgcttttgagt
puc Ori 5' cgttaagggattttggtcatgagattatcaaaaaggatcttcacctagatccttttaaattaaaaatgaa 4690
3' gcaattccctaaaaccagtactctaatagtttttcctagaagtggatctaggaaaatttaatttttactt 5' gttttaaatcaatctaaagtatatatgagtaaacttggtctgacagttaccaatgcttaatcagtgaggc 4760
3' caaaatttagttagatttcatatatactcatttgaaccagactgtcaatggttacgaattagtcactccg
AMP 5' acctatctcagcgatctgtctatttcgttcatccatagttgcctgactccccgtcgtgtagataactacg 4830
3' tggatagagtcgctagacagataaagcaagtaggtatcaacggactgaggggcagcacatctattgatgc
AMP 5' atacgggagggcttaccatctggccccagtgctgcaatgataccgcgagacccacgctcaccggctccag 4900
3' tatgccctcccgaatggtagaccggggtcacgacgttactatggcgctctgggtgcgagtggccgaggtc
AMP 5' atttatcagcaataaaccagccagccggaagggccgagcgcagaagtggtcctgcaactttatccgcctc 4970
3' taaatagtcgttatttggtcggtcggccttcccggctcgcgtcttcaccaggacgttgaaataggcggag
AMP 5' catccagtctattaattgttgccgggaagctagagtaagtagttcgccagttaatagtttgcgcaacgtt 5040
3' gtaggtcagataattaacaacggcccttcgatctcattcatcaagcggtcaattatcaaacgcgttgcaa
AMP 5' gttgccattgctacaggcatcgtggtgtcacgctcgtcgtttggtatggcttcattcagctccggttccc 5110
3' caacggtaacgatgtccgtagcaccacagtgcgagcagcaaaccataccgaagtaagtcgaggccaaggg
AMP

FIG. 4G

5' aacgatcaaggcgagttacatgatcccccatgttgtgcaaaaaagcggttagctccttcggtcctccgat 5180
3' ttgctagttccgctcaatgtactagggggtacaacacgttttttcgccaatcgaggaagccaggaggcta
AMP 5' cgttgtcagaagtaagttggccgcagtgttatcactcatggttatggcagcactgcataattctcttact 5250
3' gcaacagtcttcattcaaccggcgtcacaatagtgagtaccaataccgtcgtgacgtattaagagaatga
AMP 5' gtcatgccatccgtaagatgcttttctgtgactggtgagtattcaaccaagtcattctgagaatagtgta 5320
3' cagtacggtaggcattctacgaaaagacactgaccactcataagttggttcagtaagactcttatcacat
AMP 5' tgcggcgaccgagttgctcttgcccggcgtcaatacgggataataccgcgccacatagcagaactttaaa 5390
3' acgccgctggctcaacgagaacgggccgcagttatgccctattatggcgcggtgtatcgtcttgaaattt
AMP 5' agtgctcatcattggaaaacgttcttcggggcgaaaactctcaaggatcttaccgctgttgagatccagt 5460
3' tcacgagtagtaaccttttgcaagaagccccgcttttgagagttcctagaatggcgacaactctaggtca
AMP 5' tcgatgtaacccactcgtgcacccaactgatcttcagcatcttttactttcaccagcgtttctgggtgag 5530
3' agctacattgggtgagcacgtgggttgactagaagtcgtagaaaatgaaagtggtcgcaaagacccactc
AMP 5' caaaaacaggaaggcaaaatgccgcaaaaaagggaataagggcgacacggaaatgttgaatactcatact 5600
3' gtttttgtccttccgttttacggcgttttttcccttattcccgctgtgcctttacaacttatgagtatga
AMP
B...

5' cttcctttttcaatattattgaagcatttatcagggttattgtctcatgagcggatacatatttgaatgt 5670
3' gaaggaaaaagttataataacttcgtaaatagtcccaataacagagtactcgcctatgtataaacttaca
Bla promoter 5' atttagaaaaataaacaaataggggttccgcgcacatttccccgaaaagtgccacctgacgtc 5733
3' taaatctttttatttgtttatccccaaggcgcgtgtaaaggggcttttcacggtggactgcag
Bla promoter

FIG. 4H

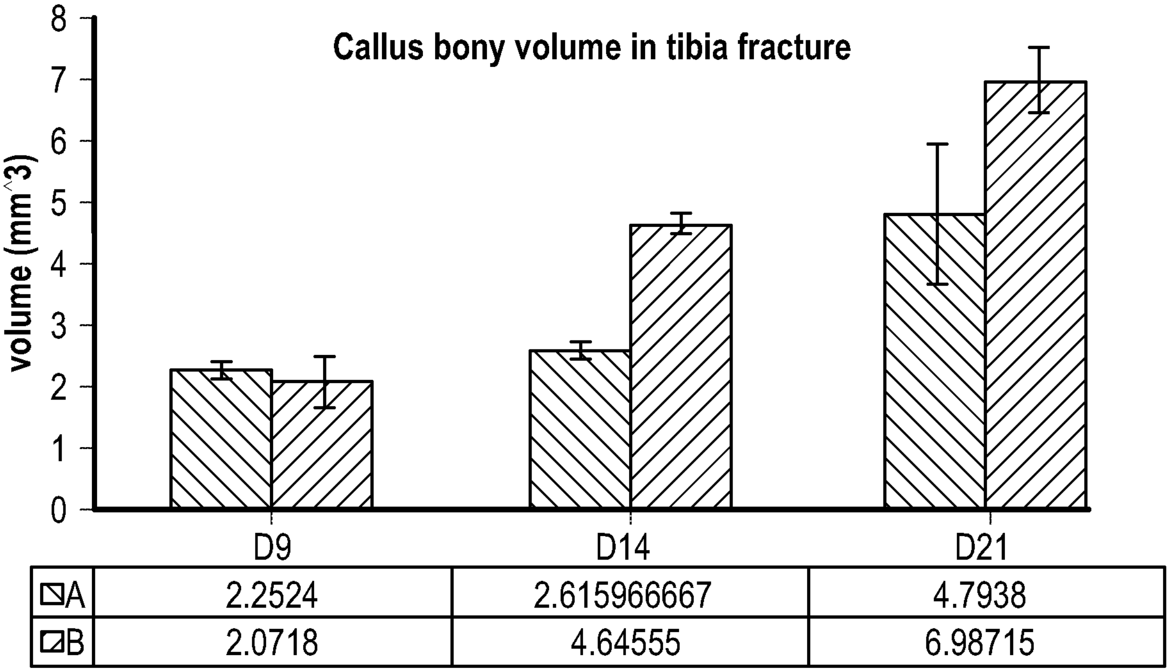
| | D9 | D14 | D21 |
|---|---|---|---|
| A | 2.2524 | 2.615966667 | 4.7938 |
| B | 2.0718 | 4.64555 | 6.98715 |
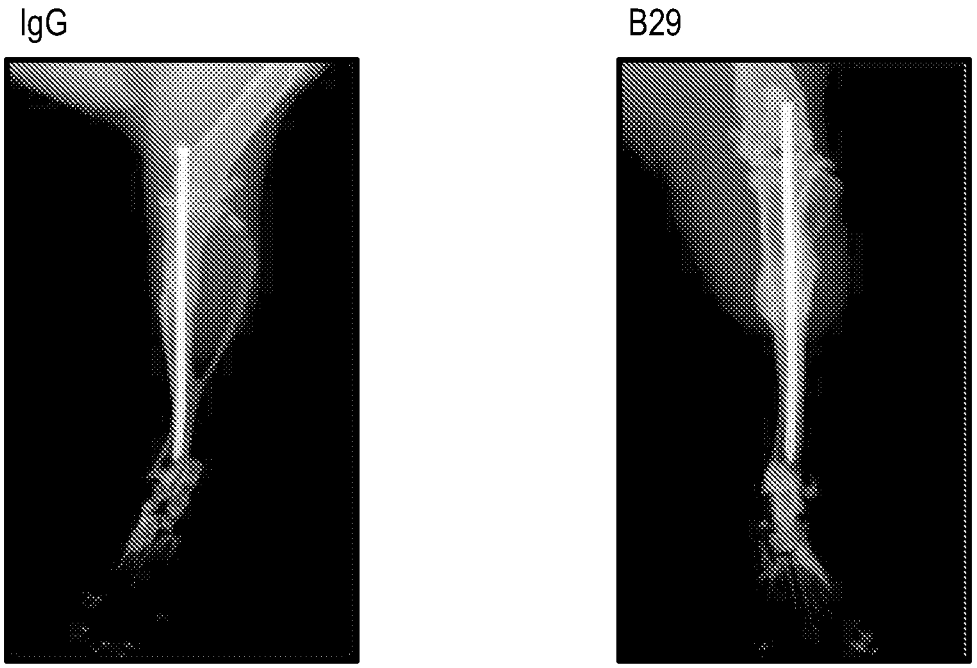
FIG. 6A

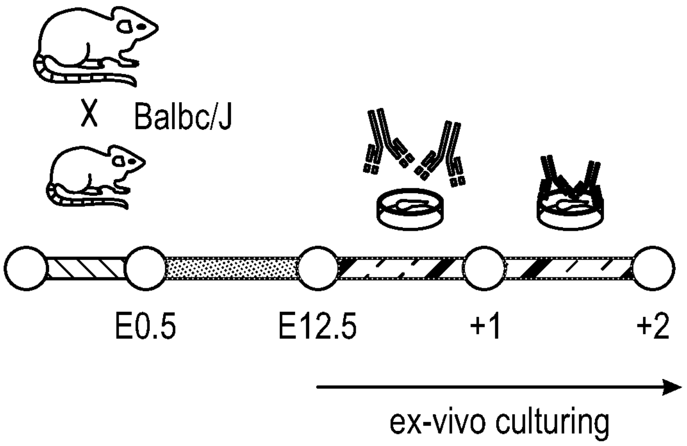
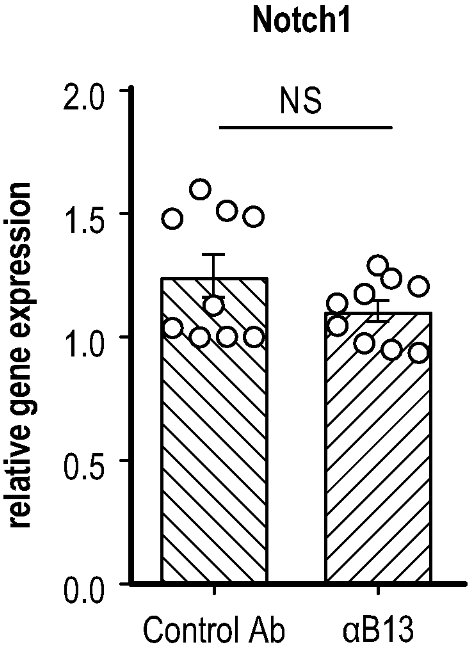
FIG. 22A

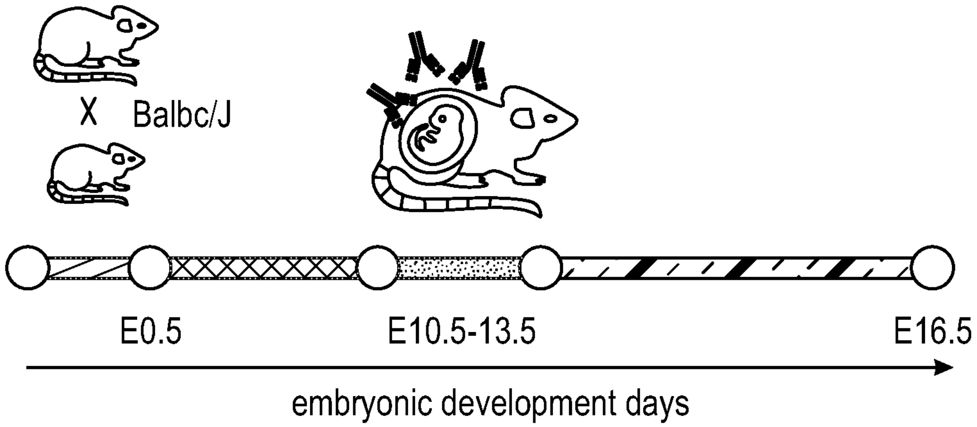
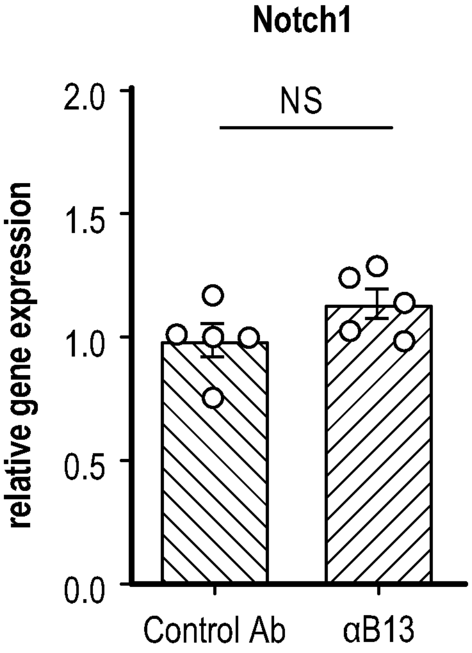
FIG. 22B

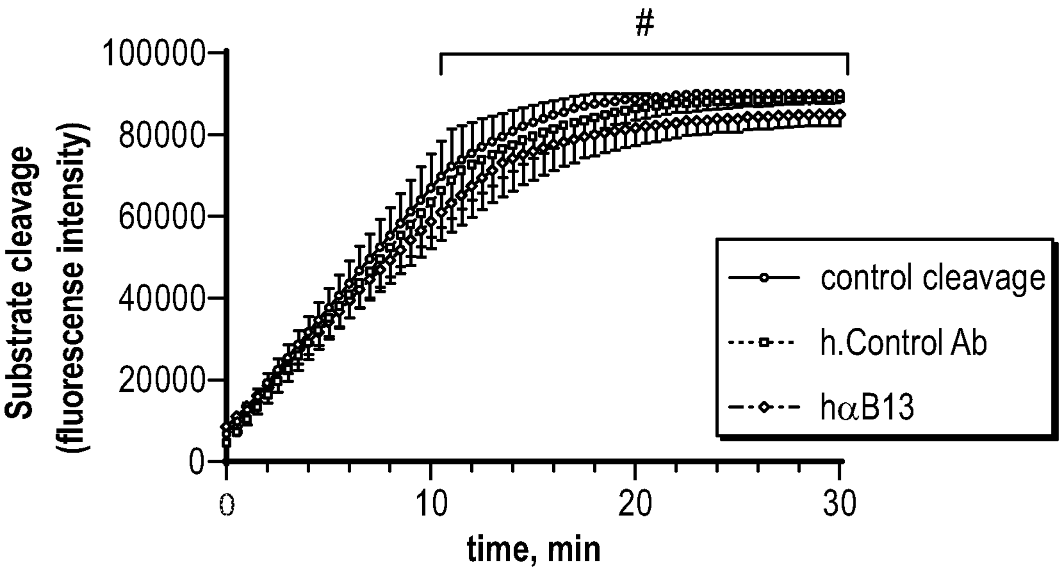
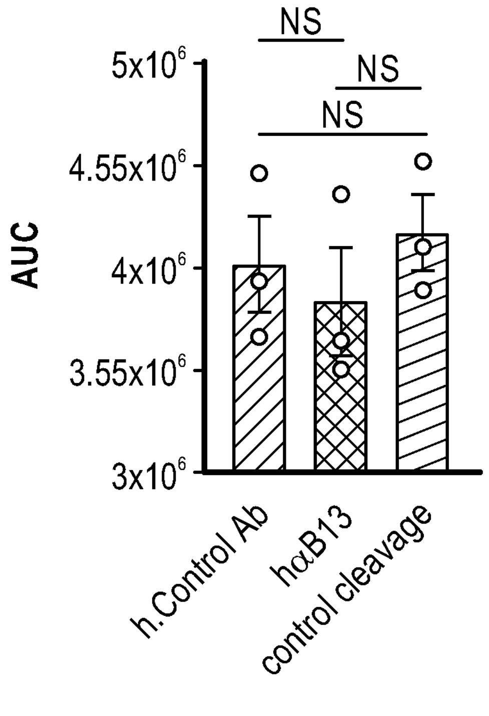
FIG. 26B

CDR Analysis (clone 1)

```
                      ----CDR1--->   <--CDR2-->   <---CDR3----
Heavy chain  (IgG3)   GFTFSSYG....___ISYDGSNK..___ARDLGAVIAVAGTSTPYNWFDP
Light chain  (K)      QSLLHSNGHNY.___LAS.......___MQALQTPYT
```

Heavy chain: CDR1=SEQ ID NO:60, CDR2=SEQ ID NO:61, CDR3=SEQ ID NO:62
Light chain: CDR1=SEQ ID NO:63, CDR2=SEQ ID NO:64, CDR3=SEQ ID NO:65

FIG. 27A

CDR Analysis (clone 2)

```
                      ----CDR1--->   <--CDR2-->   <---CDR3----
Heavy chain  (IgG3)   GFTFDDYG....___INWNGGST..___ARESSMTTVTTYLLREVGVGLDFDY
Light chain  (K)      QTVSGSY.....___GAS.......___QDYGSSRT
```

Heavy chain: CDR1=SEQ ID NO:70, CDR2=SEQ ID NO:71, CDR3=SEQ ID NO:72
Light chain: CDR1=SEQ ID NO:73, CDR2=SEQ ID NO:74, CDR3=SEQ ID NO:75

FIG. 27B

CDR Analysis (clone 3)

```
                               ----CDR1--->   <--CDR2-->   <---CDR3----
Heavy chain  (IgG4)            GGSFSGYY....___INHSGST...___ARRYCSGGSCYLVGTGSELDY
Llght chain  (KV pseudogene)   QSISSW......___KAS.......___LQYSTHST
```

Heavy chain: CDR1=SEQ ID NO:80, CDR2=SEQ ID NO:81, CDR3=SEQ ID NO:82

Light chain: CDR1=SEQ ID NO:83, CDR2=SEQ ID NO:84, CDR3=SEQ ID NO:85

FIG. 27C

SEQUENCE LISTING

```
<160> NUMBER OF SEQ ID NOS: 96

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Tyr Asn Phe Lys Thr Tyr
1               5


<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Tyr Thr Phe Thr Thr Tyr
1               5


<210> SEQ ID NO 3
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3

gggtatacct tcacaaccta t                                          21


<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Asn Thr Tyr Ser Gly Met
1               5


<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5

aacacctact ctggaatg                                              18


<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Pro Leu Leu Gly Leu Asp Tyr
1               5


<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7

cctctcctgg gacttgacta t                                          21


<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Lys Ser Ser Gln Ser Leu Leu His Ser Asp Gly Lys
1               5                   10
```

<210> SEQ ID NO 9
<211> LENGTH: 36
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 9
aagtcaagtc agagcctctt acatagtgat ggaaag 36

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 10

Leu Val Ser Lys Leu Glu Ser
1 5

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 11
ctggtgtcta aactggaatc t 21

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 12

Leu Gln His Thr His Phe Pro Leu Thr
1 5

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 13
ttgcaacata cacattttcc gctcacg 27

<210> SEQ ID NO 14
<211> LENGTH: 116
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 14

Gln Ile Gln Leu Val Gln Ser Gly Pro Glu Leu Lys Lys Pro Gly Glu

```
1               5                   10                  15

Thr Val Lys Ile Ser Cys Lys Ala Ser Gly Tyr Thr Phe Thr Thr Tyr
            20                  25                  30

Gly Met Ser Trp Val Lys Gln Ala Pro Gly Lys Gly Leu Lys Trp Met
        35                  40                  45

Gly Trp Ile Asn Thr Tyr Ser Gly Met Pro Thr Tyr Ala Asp Asp Phe
    50                  55                  60

Lys Gly Arg Phe Ala Phe Ser Leu Glu Thr Ser Ala Thr Thr Ala Tyr
65                  70                  75                  80

Leu Gln Ile Asn Asn Leu Lys Asn Glu Asp Thr Ala Thr Tyr Phe Cys
                85                  90                  95

Ala Arg Pro Leu Leu Gly Leu Asp Tyr Trp Gly Gln Gly Thr Thr Leu
            100                 105                 110

Thr Val Ser Ser
        115


<210> SEQ ID NO 15
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15

cagatccagt tggtacagtc tggacctgag ctgaagaagc ctggagagac agtcaagatc      60

tcctgcaagg cctccgggta taccttcaca acctatggaa tgagctgggt gaaacaggct     120

ccaggaaagg gtttaaagtg gatgggctgg ataaacacct actctggaat gccaacatat     180

gctgatgact tcaagggacg gtttgccttc tctttggaaa cctctgccac cactgcctat     240

ttgcagatca acaacctcaa aaatgaggac acggctacat atttctgtgc aagacctctc     300

ctgggacttg actattgggg ccaaggcacc actctcacag tctcctca                  348


<210> SEQ ID NO 16
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Asp Ile Val Met Thr Gln Thr Pro Leu Ser Leu Ser Val Thr Ile Gly
1               5                   10                  15

Gln Pro Ala Ser Ile Ser Cys Lys Ser Ser Gln Ser Leu Leu His Ser
            20                  25                  30

Asp Gly Lys Thr Phe Leu Asn Trp Phe Leu Gln Arg Pro Gly Gln Ser
        35                  40                  45

Pro Lys Leu Leu Ile Tyr Leu Val Ser Lys Leu Glu Ser Gly Ile Pro
    50                  55                  60

Asp Arg Phe Ser Gly Ser Gly Ser Gly Thr Asp Phe Thr Leu Lys Ile
65                  70                  75                  80

Ser Arg Val Glu Val Glu Asp Leu Gly Val Tyr Tyr Cys Leu Gln His
                85                  90                  95

Thr His Phe Pro Leu Thr Phe Gly Ala Gly Thr Lys Leu Glu Ile Lys
            100                 105                 110
```

<210> SEQ ID NO 17
<211> LENGTH: 336
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 17
gatattgtga tgacccagac tccactgtct ttgtcggtta ccattggaca accagcctcc 60
atctcttgca agtcaagtca gagcctctta catagtgatg gaaagacatt tttgaattgg 120
tttttacaga ggccaggcca gtctccaaag ctcctaatct atctggtgtc taaactggaa 180
tctggcatcc ctgacaggtt cagtggcagt ggatcaggga cagatttcac actgaaaatc 240
agcagagtgg aggttgagga tttgggagtt tattactgct tgcaacatac acattttccg 300
ctcacgttcg gtgctgggac caaactggaa ataaaa 336

<210> SEQ ID NO 18
<211> LENGTH: 446
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 18

Glu Ile Gln Leu Val Glu Ser Gly Gly Gly Leu Val Gln Pro Gly Gly
1 5 10 15

Ser Val Arg Leu Ser Cys Ala Ala Ser Gly Tyr Asn Phe Lys Thr Tyr
20 25 30

Gly Met Ser Trp Val Arg Gln Ala Pro Gly Lys Gly Leu Glu Trp Met
35 40 45

Gly Trp Ile Asn Thr Tyr Ser Gly Met Pro Thr Tyr Ala Asp Asp Phe
50 55 60

Lys Gly Arg Phe Thr Phe Ser Leu Asp Thr Ser Lys Asn Thr Ala Tyr
65 70 75 80

Leu Gln Ile Asn Ser Leu Arg Ala Glu Asp Thr Ala Val Tyr Phe Cys
85 90 95

Ala Arg Pro Leu Leu Gly Leu Asp Tyr Trp Gly Gln Gly Thr Leu Val
100 105 110

Thr Val Ser Ser Ala Ser Thr Lys Gly Pro Ser Val Phe Pro Leu Ala
115 120 125

Pro Ser Ser Lys Ser Thr Ser Gly Gly Thr Ala Ala Leu Gly Cys Leu
130 135 140

Val Lys Asp Tyr Phe Pro Glu Pro Val Thr Val Ser Trp Asn Ser Gly
145 150 155 160

Ala Leu Thr Ser Gly Val His Thr Phe Pro Ala Val Leu Gln Ser Ser
165 170 175

Gly Leu Tyr Ser Leu Ser Ser Val Val Thr Val Pro Ser Ser Ser Leu
180 185 190

Gly Thr Gln Thr Tyr Ile Cys Asn Val Asn His Lys Pro Ser Asn Thr
195 200 205

Lys Val Asp Lys Lys Val Glu Pro Lys Ser Cys Asp Lys Thr His Thr
210 215 220

Cys Pro Pro Cys Pro Ala Pro Glu Leu Leu Gly Gly Pro Ser Val Phe
225 230 235 240

Leu Phe Pro Pro Lys Pro Lys Asp Thr Leu Met Ile Ser Arg Thr Pro

```
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445
```

<210> SEQ ID NO 19
<211> LENGTH: 1407
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19

```
gccgccacca tgggctggtc cctgattctg ctgttcctgg tggctgtggc taccagggtg     60

ctgagtgaga tccagctggt ggagagcgga ggaggactgg tgcagccagg aggatctgtg    120

aggctgagct gcgcagcatc cggatacaac ttcaagacct atggcatgtc ctgggtgcgc    180

caggcaccag gcaagggact ggagtggatg ggctggatca atacctactc tggcatgcct    240

acatatgccg acgatttcaa gggccggttc accttttctc tggacaccag caagaacaca    300

gcctacctgc agatcaattc cctgcgggcc gaggacacag ccgtgtactt ttgtgccaga    360

cccctgctgg gcctggatta ttggggccag ggcaccctgg tgacagtgag ctccgctagc    420

accaagggcc catcggtctt ccccctggca ccctcctcca agagcacctc tgggggcaca    480

gcggccctgg gctgcctggt caaggactac ttccccgaac cggtgacggt gtcgtggaac    540

tcaggcgccc tgaccagcgg cgtgcacacc ttcccggctg tcctacagtc ctcaggactc    600

tactccctca gcagcgtggt gaccgtgccc tccagcagct tgggcaccca gacctacatc    660

tgcaacgtga atcacaagcc cagcaacacc aaggtggaca agaaagttga gcccaaatct    720

tgtgacaaaa ctcacacatg cccaccgtgc ccagcacctg aactcctggg gggaccgtca    780

gtcttcctct tccccccaaa acccaaggac accctcatga tctcccggac ccctgaggtc    840

acatgcgtgg tggtggacgt gagccacgaa gaccctgagg tcaagttcaa ctggtacgtg    900
```

```
gacggcgtgg aggtgcataa tgccaagaca aagccgcggg aggagcagta caacagcacg    960

taccgtgtgg tcagcgtcct caccgtcctg caccaggact ggctgaatgg caaggagtac   1020

aagtgcaagg tctccaacaa agccctccca gcccccatcg agaaaaccat ctccaaagcc   1080

aaagggcagc cccgagaacc acaggtgtac accctgcccc catcccggga ggagatgacc   1140

aagaaccagg tcagcctgac ctgcctggtc aaaggcttct atcccagcga catcgccgtg   1200

gagtgggaga gcaatgggca gccggagaac aactacaaga ccacgcctcc cgtgctggac   1260

tccgacggct ccttcttcct ctacagcaag ctcaccgtgg acaagagcag gtggcagcag   1320

gggaacgtct tctcatgctc cgtgatgcat gaggctctgc acaaccacta cacgcagaag   1380

agcctctccc tgtctccggg taaatga                                       1407
```

```
<210> SEQ ID NO 20
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu His Ser
            20                  25                  30

Asp Gly Lys Thr Phe Leu Asn Trp Phe Gln Gln Lys Pro Gly Lys Ser
        35                  40                  45

Pro Lys Leu Leu Ile Tyr Leu Val Ser Lys Leu Glu Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Leu Gln His
                85                  90                  95

Thr His Phe Pro Leu Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

```
<210> SEQ ID NO 21
<211> LENGTH: 726
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 21

```
gccgccacca tgggctggtc ctgtatcatc ctgttcctgg tggctacagc cacaggagtg     60

catagtgaca tccagatgac acagtcccct agctccctga gcgcctccgt gggcgatagg    120

gtgaccatca catgcaagtc tagccagtct ctgctgcaca gcgacggcaa gaccttcctg    180

aactggtttc agcagaagcc cggcaagtct cctaagctgc tgatctacct ggtgtccaag    240

ctggagtctg gcgtgcccag cagattctct ggcagcggct ccggcacaga ctttaccctg    300

acaatctcct ctctgcagcc agaggatttc gccacctact attgtctgca gcacacccac    360

ttccccctga catttggcca gggcaccaag gtggagatca agcgtacggt ggctgcacca    420

tctgtcttca tcttcccgcc atctgatgag cagttgaaat ctggaactgc ctctgttgtg    480

tgcctgctga ataacttcta tcccagagag gccaaagtac agtggaaggt ggataacgcc    540

ctccaatcgg gtaactccca ggagagtgtc acagagcagg acagcaagga cagcacctac    600

agcctcagca gcaccctgac gctgagcaaa gcagactacg agaaacacaa agtctacgcc    660

tgcgaagtca cccatcaggg cctgagctcg cccgtcacaa agagcttcaa caggggagag    720

tgttag                                                               726
```

<210> SEQ ID NO 22
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Thr Tyr
            20                  25                  30

Gly Met Ser Trp Val Lys Gln Ala Pro Gly Lys Gly Leu Lys Trp Met
        35                  40                  45

Gly Trp Ile Asn Thr Tyr Ser Gly Met Pro Thr Tyr Ala Asp Asp Phe
    50                  55                  60

Lys Gly Arg Phe Ala Phe Ser Leu Glu Thr Ser Ala Thr Thr Ala Tyr
65                  70                  75                  80

Leu Gln Ile Asn Asn Leu Lys Asn Glu Asp Thr Ala Thr Tyr Phe Cys
                85                  90                  95

Ala Arg Pro Leu Leu Gly Leu Asp Tyr Trp Gly Gln Gly Thr Thr Leu
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205
```

```
Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445
```

<210> SEQ ID NO 23
<211> LENGTH: 1407
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 23

```
gccgccacca tgggctggtc cctgattctg ctgttcctgg tggctgtggc taccagggtg     60

ctgagtcaga tccagctggt gcagtctggc cccgagctga agaagcctgg cgagaccgtg    120

aagatctctt gcaaggccag cggctacaca ttcaccacat atggcatgag ctgggtgaag    180

caggcaccag gcaagggcct gaagtggatg ggctggatca acacctactc cggcatgccc    240

acatatgccg acgatttcaa gggccggttc gccttttccc tggagacctc tgccaccaca    300

gcctacctgc agatcaacaa tctgaagaat gaggacaccg ccacatactt ttgtgccaga    360

cccctgctgg gcctggatta ttggggccag ggcaccacac tgacagtgag ctccgctagc    420

accaagggcc catcggtctt ccccctggca ccctcctcca agagcacctc tgggggcaca    480

gcggccctgg gctgcctggt caaggactac ttccccgaac cggtgacggt gtcgtggaac    540

tcaggcgccc tgaccagcgg cgtgcacacc ttcccggctg tcctacagtc ctcaggactc    600

tactccctca gcagcgtggt gaccgtgccc tccagcagct tgggcaccca gacctacatc    660

tgcaacgtga atcacaagcc cagcaacacc aaggtggaca agaaagttga gcccaaatct    720
```

```
tgtgacaaaa ctcacacatg cccaccgtgc ccagcacctg aactcctggg gggaccgtca    780

gtcttcctct tccccccaaa acccaaggac accctcatga tctcccggac ccctgaggtc    840

acatgcgtgg tggtggacgt gagccacgaa gaccctgagg tcaagttcaa ctggtacgtg    900

gacggcgtgg aggtgcataa tgccaagaca aagccgcggg aggagcagta caacagcacg    960

taccgtgtgg tcagcgtcct caccgtcctg caccaggact ggctgaatgg caaggagtac   1020

aagtgcaagg tctccaacaa agccctccca gcccccatcg agaaaaccat ctccaaagcc   1080

aaagggcagc cccgagaacc acaggtgtac accctgcccc catcccggga ggagatgacc   1140

aagaaccagg tcagcctgac ctgcctggtc aaaggcttct atcccagcga catcgccgtg   1200

gagtgggaga gcaatgggca gccggagaac aactacaaga ccacgcctcc cgtgctggac   1260

tccgacggct ccttcttcct ctacagcaag ctcaccgtgg acaagagcag gtggcagcag   1320

gggaacgtct tctcatgctc cgtgatgcat gaggctctgc acaaccacta cacgcagaag   1380

agcctctccc tgtctccggg taaatga                                      1407
```

```
<210> SEQ ID NO 24
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Asp Ile Val Met Thr Gln Thr Pro Leu Ser Leu Ser Val Thr Ile Gly
1               5                   10                  15

Gln Pro Ala Ser Ile Ser Cys Lys Ser Ser Gln Ser Leu Leu His Ser
            20                  25                  30

Asp Gly Lys Thr Phe Leu Asn Trp Phe Leu Gln Arg Pro Gly Gln Ser
        35                  40                  45

Pro Lys Leu Leu Ile Tyr Leu Val Ser Lys Leu Glu Ser Gly Ile Pro
    50                  55                  60

Asp Arg Phe Ser Gly Ser Gly Ser Gly Thr Asp Phe Thr Leu Lys Ile
65                  70                  75                  80

Ser Arg Val Glu Val Glu Asp Leu Gly Val Tyr Tyr Cys Leu Gln His
                85                  90                  95

Thr His Phe Pro Leu Thr Phe Gly Ala Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

```
<210> SEQ ID NO 25
<211> LENGTH: 726
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25

gccgccacca tgggctggtc ctgtatcatc ctgttcctgg tggctacagc cacaggagtg     60

catagtgaca tcgtgatgac ccagacacca ctgtctctga gcgtgacaat cggccagccc    120

gcctccatct cttgcaagag ctcccagagc ctgctgcact ccgatggcaa gaccttcctg    180

aactggtttc tgcagaggcc aggacagtcc cctaagctgc tgatctacct ggtgtctaag    240

ctggagagcg gaatccctga ccggttcagc ggatccggat ctggaaccga cttcaccctg    300

aagatctcta gagtggaggt ggaggacctg ggcgtgtact attgtctgca gcacacccac    360

ttccccctga catttggcgc cggcaccaag ctggagatca agcgtacggt ggctgcacca    420

tctgtcttca tcttcccgcc atctgatgag cagttgaaat ctggaactgc ctctgttgtg    480

tgcctgctga ataacttcta tcccagagag gccaaagtac agtggaaggt ggataacgcc    540

ctccaatcgg gtaactccca ggagagtgtc acagagcagg acagcaagga cagcacctac    600

agcctcagca gcaccctgac gctgagcaaa gcagactacg agaaacacaa agtctacgcc    660

tgcgaagtca cccatcaggg cctgagctcg cccgtcacaa agagcttcaa caggggagag    720

tgttag                                                               726


<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Thr Tyr Gly Met Ser
1               5


<210> SEQ ID NO 27
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Trp Ile Asn Thr Tyr Ser Gly Met Pro Thr Tyr Ala Asp Asp Phe Lys
1               5                   10                  15

Gly


<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Pro Leu Leu Gly Leu Asp Tyr
1               5
```

<210> SEQ ID NO 29
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 29

Lys Ser Ser Gln Ser Leu Leu His Ser Asp Gly Lys Thr Phe Leu Asn
1 5 10 15

<210> SEQ ID NO 30
<211> LENGTH: 1380
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 30
caggtgcagc tgcaggagtc cgggggaggc gtggtccagc ctgggaggtc cctgagactc 60
tcctgtgcag cctctggatt caccttcagt agctatggca tgcactgggt ccgccaggct 120
ccaggcaagg ggctggagtg ggtggcagtt atatcatatg atggaagtaa taaatactat 180
gcagactccg tgaagggccg attcaccatc tccagagaca attccaagaa cacgctgtat 240
ctgcaaatga acagcctgag agccgaggac acggctgtgt attactgtgc gagagatctc 300
ggcgccgtta tagcagtggc tggtacttcc accccgtaca actggttcga cccctggggc 360
cagggaaccc tggtcaccgt ctcaagcgcc tccaccaagg gcccatcggt cttccccctg 420
gcaccctcct ccaagagcac ctctgggggc acagcggccc tgggctgcct ggtcaaggac 480
tacttccccg aaccggtgac ggtgtcgtgg aactcaggcg ccctgaccag cggcgtccac 540
accttcccgg ctgtcctaca gtcctcagga ctctactccc tcagcagcgt agtgaccgtg 600
ccctccagca gcttgggcac ccagacctac atctgcaacg tgaatcacaa gcccagcaac 660
accaaggtgg acaagaaagt tgagcccaaa tcttgtgaca aaactcacac atgcccaccg 720
tgcccagcac ctgaactcct ggggggaccg tcagtcttcc tcttcccccc aaaacccaag 780
gacaccctca tgatctcccg gacccctgag gtcacatgcg tggtggtgga cgtgagccac 840
gaagaccctg aggtcaagtt caactggtac gtggacggcg tggaggtgca taatgccaag 900
acaaagccgc gggaggagca gtacaacagc acgtaccgtg tggtcagcgt cctcaccgtc 960
ctgcaccagg actggctgaa tggcaaggag tacaagtgca aggtctccaa caaagccctc 1020
ccagccccca tcgagaaaac catctccaaa gccaaagggc agccccgaga accacaggtg 1080
tacaccctgc ccccatcccg ggatgagctg accaagaacc aggtcagcct gacctgcctg 1140
gtcaaaggct tctatcccag cgacatcgcc gtggagtggg agagcaatgg gcagccggag 1200
aacaactaca agaccacgcc tcccgtgctg gactccgacg gctccttctt cctctacagc 1260
aagctcaccg tggacaagag caggtggcag caggggaacg tcttctcatg ctccgtgatg 1320
catgaggctc tgcacaacca ctacacgcag aagagcctct ccctgtctcc gggtaaatga 1380

<210> SEQ ID NO 31
<211> LENGTH: 459
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 31

```
Gln Val Gln Leu Gln Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Gly Ala Val Ile Ala Val Ala Gly Thr Ser Thr Pro
            100                 105                 110

Tyr Asn Trp Phe Asp Pro Trp Gly Gln Gly Thr Leu Val Thr Val Ser
        115                 120                 125

Ser Ala Ser Thr Lys Gly Pro Ser Val Phe Pro Leu Ala Pro Ser Ser
    130                 135                 140

Lys Ser Thr Ser Gly Gly Thr Ala Ala Leu Gly Cys Leu Val Lys Asp
145                 150                 155                 160

Tyr Phe Pro Glu Pro Val Thr Val Ser Trp Asn Ser Gly Ala Leu Thr
                165                 170                 175

Ser Gly Val His Thr Phe Pro Ala Val Leu Gln Ser Ser Gly Leu Tyr
            180                 185                 190

Ser Leu Ser Ser Val Val Thr Val Pro Ser Ser Ser Leu Gly Thr Gln
        195                 200                 205

Thr Tyr Ile Cys Asn Val Asn His Lys Pro Ser Asn Thr Lys Val Asp
    210                 215                 220

Lys Lys Val Glu Pro Lys Ser Cys Asp Lys Thr His Thr Cys Pro Pro
225                 230                 235                 240

Cys Pro Ala Pro Glu Leu Leu Gly Gly Pro Ser Val Phe Leu Phe Pro
                245                 250                 255

Pro Lys Pro Lys Asp Thr Leu Met Ile Ser Arg Thr Pro Glu Val Thr
            260                 265                 270

Cys Val Val Val Asp Val Ser His Glu Asp Pro Glu Val Lys Phe Asn
        275                 280                 285

Trp Tyr Val Asp Gly Val Glu Val His Asn Ala Lys Thr Lys Pro Arg
    290                 295                 300

Glu Glu Gln Tyr Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Ala Leu Pro Ala Pro Ile Glu Lys Thr Ile Ser Lys Ala Lys
            340                 345                 350

Gly Gln Pro Arg Glu Pro Gln Val Tyr Thr Leu Pro Pro Ser Arg Asp
        355                 360                 365

Glu Leu Thr Lys Asn Gln Val Ser Leu Thr Cys Leu Val Lys Gly Phe
    370                 375                 380

Tyr Pro Ser Asp Ile Ala Val Glu Trp Glu Ser Asn Gly Gln Pro Glu
385                 390                 395                 400
```

```
Asn Asn Tyr Lys Thr Thr Pro Pro Val Leu Asp Ser Asp Gly Ser Phe
                405                 410                 415

Phe Leu Tyr Ser Lys Leu Thr Val Asp Lys Ser Arg Trp Gln Gln Gly
            420                 425                 430

Asn Val Phe Ser Cys Ser Val Met His Glu Ala Leu His Asn His Tyr
        435                 440                 445

Thr Gln Lys Ser Leu Ser Leu Ser Pro Gly Lys
    450                 455


<210> SEQ ID NO 32
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32

atggagacag acacactcct gctatgggta ctgctgctct gggttccagg ttccactggc     60

gccggatca                                                             69


<210> SEQ ID NO 33
<211> LENGTH: 1449
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33

atggagacag acacactcct gctatgggta ctgctgctct gggttccagg ttccactggc     60

gccggatcac aggtgcagct gcaggagtcc gggggaggcg tggtccagcc tgggaggtcc    120

ctgagactct cctgtgcagc ctctggattc accttcagta gctatggcat gcactgggtc    180

cgccaggctc caggcaaggg gctggagtgg gtggcagtta tatcatatga tggaagtaat    240

aaatactatg cagactccgt gaagggccga ttcaccatct ccagagacaa ttccaagaac    300

acgctgtatc tgcaaatgaa cagcctgaga gccgaggaca cggctgtgta ttactgtgcg    360

agagatctcg gcgccgttat agcagtggct ggtacttcca ccccgtacaa ctggttcgac    420

ccctggggcc agggaaccct ggtcaccgtc tcaagcgcct ccaccaaggg cccatcggtc    480

ttccccctgg caccctcctc caagagcacc tctgggggca cagcggccct gggctgcctg    540

gtcaaggact acttccccga accggtgacg gtgtcgtgga actcaggcgc cctgaccagc    600

ggcgtccaca ccttcccggc tgtcctacag tcctcaggac tctactccct cagcagcgta    660

gtgaccgtgc cctccagcag cttgggcacc cagacctaca tctgcaacgt gaatcacaag    720

cccagcaaca ccaaggtgga caagaaagtt gagcccaaat cttgtgacaa aactcacaca    780

tgcccaccgt gcccagcacc tgaactcctg gggggaccgt cagtcttcct cttcccccca    840

aaacccaagg acaccctcat gatctcccgg acccctgagg tcacatgcgt ggtggtggac    900

gtgagccacg aagaccctga ggtcaagttc aactggtacg tggacggcgt ggaggtgcat    960

aatgccaaga caaagccgcg ggaggagcag tacaacagca cgtaccgtgt ggtcagcgtc   1020

ctcaccgtcc tgcaccagga ctggctgaat ggcaaggagt acaagtgcaa ggtctccaac   1080

aaagccctcc cagcccccat cgagaaaacc atctccaaag ccaaagggca gccccgagaa   1140

ccacaggtgt acaccctgcc cccatcccgg gatgagctga ccaagaacca ggtcagcctg   1200

acctgcctgg tcaaaggctt ctatcccagc gacatcgccg tggagtggga gagcaatggg   1260
```

```
cagccggaga acaactacaa gaccacgcct cccgtgctgg actccgacgg ctccttcttc   1320

ctctacagca agctcaccgt ggacaagagc aggtggcagc aggggaacgt cttctcatgc   1380

tccgtgatgc atgaggctct gcacaaccac tacacgcaga agagcctctc cctgtctccg   1440

ggtaaatga                                                            1449


<210> SEQ ID NO 34
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Met Glu Thr Asp Thr Leu Leu Leu Trp Val Leu Leu Leu Trp Val Pro
1               5                   10                  15

Gly Ser Thr Gly Ala Gly Ser
            20


<210> SEQ ID NO 35
<211> LENGTH: 482
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Met Glu Thr Asp Thr Leu Leu Leu Trp Val Leu Leu Leu Trp Val Pro
1               5                   10                  15

Gly Ser Thr Gly Ala Gly Ser Gln Val Gln Leu Gln Glu Ser Gly Gly
            20                  25                  30

Gly Val Val Gln Pro Gly Arg Ser Leu Arg Leu Ser Cys Ala Ala Ser
        35                  40                  45

Gly Phe Thr Phe Ser Ser Tyr Gly Met His Trp Val Arg Gln Ala Pro
    50                  55                  60

Gly Lys Gly Leu Glu Trp Val Ala Val Ile Ser Tyr Asp Gly Ser Asn
65                  70                  75                  80

Lys Tyr Tyr Ala Asp Ser Val Lys Gly Arg Phe Thr Ile Ser Arg Asp
                85                  90                  95

Asn Ser Lys Asn Thr Leu Tyr Leu Gln Met Asn Ser Leu Arg Ala Glu
            100                 105                 110

Asp Thr Ala Val Tyr Tyr Cys Ala Arg Asp Leu Gly Ala Val Ile Ala
        115                 120                 125

Val Ala Gly Thr Ser Thr Pro Tyr Asn Trp Phe Asp Pro Trp Gly Gln
    130                 135                 140

Gly Thr Leu Val Thr Val Ser Ser Ala Ser Thr Lys Gly Pro Ser Val
145                 150                 155                 160

Phe Pro Leu Ala Pro Ser Ser Lys Ser Thr Ser Gly Gly Thr Ala Ala
                165                 170                 175

Leu Gly Cys Leu Val Lys Asp Tyr Phe Pro Glu Pro Val Thr Val Ser
            180                 185                 190

Trp Asn Ser Gly Ala Leu Thr Ser Gly Val His Thr Phe Pro Ala Val
        195                 200                 205

Leu Gln Ser Ser Gly Leu Tyr Ser Leu Ser Ser Val Val Thr Val Pro
    210                 215                 220
```

```
Ser Ser Ser Leu Gly Thr Gln Thr Tyr Ile Cys Asn Val Asn His Lys
225                 230                 235                 240

Pro Ser Asn Thr Lys Val Asp Lys Lys Val Glu Pro Lys Ser Cys Asp
                245                 250                 255

Lys Thr His Thr Cys Pro Pro Cys Pro Ala Pro Glu Leu Leu Gly Gly
            260                 265                 270

Pro Ser Val Phe Leu Phe Pro Pro Lys Pro Lys Asp Thr Leu Met Ile
        275                 280                 285

Ser Arg Thr Pro Glu Val Thr Cys Val Val Val Asp Val Ser His Glu
    290                 295                 300

Asp Pro Glu Val Lys Phe Asn Trp Tyr Val Asp Gly Val Glu Val His
305                 310                 315                 320

Asn Ala Lys Thr Lys Pro Arg Glu Glu Gln Tyr Asn Ser Thr Tyr Arg
                325                 330                 335

Val Val Ser Val Leu Thr Val Leu His Gln Asp Trp Leu Asn Gly Lys
            340                 345                 350

Glu Tyr Lys Cys Lys Val Ser Asn Lys Ala Leu Pro Ala Pro Ile Glu
        355                 360                 365

Lys Thr Ile Ser Lys Ala Lys Gly Gln Pro Arg Glu Pro Gln Val Tyr
    370                 375                 380

Thr Leu Pro Pro Ser Arg Asp Glu Leu Thr Lys Asn Gln Val Ser Leu
385                 390                 395                 400

Thr Cys Leu Val Lys Gly Phe Tyr Pro Ser Asp Ile Ala Val Glu Trp
                405                 410                 415

Glu Ser Asn Gly Gln Pro Glu Asn Asn Tyr Lys Thr Thr Pro Pro Val
            420                 425                 430

Leu Asp Ser Asp Gly Ser Phe Phe Leu Tyr Ser Lys Leu Thr Val Asp
        435                 440                 445

Lys Ser Arg Trp Gln Gln Gly Asn Val Phe Ser Cys Ser Val Met His
    450                 455                 460

Glu Ala Leu His Asn His Tyr Thr Gln Lys Ser Leu Ser Leu Ser Pro
465                 470                 475                 480

Gly Lys


<210> SEQ ID NO 36
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36

gatgttgtga tgactcagtc tccactctcc ctgcccgtca cccctggaga gccggcctcc     60

atctcctgca ggtctcgtca gagcctcctg catagcaatg gacacaacta tttgggttgg    120

tacctgcaga agccagggca gtctccacag ctcctgatct atctggcttc tattcgggcc    180

tccgggatcc ctgacaggtt cagtggcagt ggatcaggca cagattttac actgaaaatc    240

agcagagtgg aggctgagga tgttggcgtt tattactgca tgcaagctct acaaacaccc    300

tacacttttg gccaggggac caagctggag atcaagcgaa ctgtggctgc accatctgtc    360

ttcatcttcc cgccatctga tgagcagttg aaatctggaa ctgcctctgt tgtgtgcctg    420

ctgaataact tctatcccag agaggccaaa gtacagtgga aggtggataa cgccctccaa    480

tcgggtaact cccaggagag tgtcacagag caggacagca aggacagcac ctacagcctc    540
```

agcagcaccc tgacgctgag caaagcagac tacgagaaac acaaagtcta cgcctgcgaa 600
gtcacccatc agggcctgag ctcgcccgtc acaaagagct tcaacagggg agagtgttag 660

<210> SEQ ID NO 37
<211> LENGTH: 219
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 37

Asp Val Val Met Thr Gln Ser Pro Leu Ser Leu Pro Val Thr Pro Gly
1 5 10 15

Glu Pro Ala Ser Ile Ser Cys Arg Ser Arg Gln Ser Leu Leu His Ser
20 25 30

Asn Gly His Asn Tyr Leu Gly Trp Tyr Leu Gln Lys Pro Gly Gln Ser
35 40 45

Pro Gln Leu Leu Ile Tyr Leu Ala Ser Ile Arg Ala Ser Gly Ile Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met Gln Ala
85 90 95

Leu Gln Thr Pro Tyr Thr Phe Gly Gln Gly Thr Lys Leu Glu Ile Lys
100 105 110

Arg Thr Val Ala Ala Pro Ser Val Phe Ile Phe Pro Pro Ser Asp Glu
115 120 125

Gln Leu Lys Ser Gly Thr Ala Ser Val Val Cys Leu Leu Asn Asn Phe
130 135 140

Tyr Pro Arg Glu Ala Lys Val Gln Trp Lys Val Asp Asn Ala Leu Gln
145 150 155 160

Ser Gly Asn Ser Gln Glu Ser Val Thr Glu Gln Asp Ser Lys Asp Ser
165 170 175

Thr Tyr Ser Leu Ser Ser Thr Leu Thr Leu Ser Lys Ala Asp Tyr Glu
180 185 190

Lys His Lys Val Tyr Ala Cys Glu Val Thr His Gln Gly Leu Ser Ser
195 200 205

Pro Val Thr Lys Ser Phe Asn Arg Gly Glu Cys
210 215

<210> SEQ ID NO 38
<211> LENGTH: 729
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 38
atggagacag acacactcct gctatgggta ctgctgctct gggttccagg ttccactggc 60
gccggatcag atgttgtgat gactcagtct ccactctccc tgcccgtcac ccctggagag 120
ccggcctcca tctcctgcag gtctcgtcag agcctcctgc atagcaatgg acacaactat 180
ttgggttggt acctgcagaa gccagggcag tctccacagc tcctgatcta tctggcttct 240
attcgggcct ccgggatccc tgacaggttc agtggcagtg gatcaggcac agattttaca 300
ctgaaaatca gcagagtgga ggctgaggat gttggcgttt attactgcat gcaagctcta 360

```
caaacaccct acacttttgg ccaggggacc aagctggaga tcaagcgaac tgtggctgca    420

ccatctgtct tcatcttccc gccatctgat gagcagttga aatctggaac tgcctctgtt    480

gtgtgcctgc tgaataactt ctatcccaga gaggccaaag tacagtggaa ggtggataac    540

gccctccaat cgggtaactc ccaggagagt gtcacagagc aggacagcaa ggacagcacc    600

tacagcctca gcagcaccct gacgctgagc aaagcagact acgagaaaca caaagtctac    660

gcctgcgaag tcacccatca gggcctgagc tcgcccgtca caaagagctt caacagggga    720

gagtgttag                                                            729
```

```
<210> SEQ ID NO 39
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Met Glu Thr Asp Thr Leu Leu Leu Trp Val Leu Leu Leu Trp Val Pro
1               5                   10                  15

Gly Ser Thr Gly Ala Gly Ser Asp Val Val Met Thr Gln Ser Pro Leu
            20                  25                  30

Ser Leu Pro Val Thr Pro Gly Glu Pro Ala Ser Ile Ser Cys Arg Ser
        35                  40                  45

Arg Gln Ser Leu Leu His Ser Asn Gly His Asn Tyr Leu Gly Trp Tyr
    50                  55                  60

Leu Gln Lys Pro Gly Gln Ser Pro Gln Leu Leu Ile Tyr Leu Ala Ser
65                  70                  75                  80

Ile Arg Ala Ser Gly Ile Pro Asp Arg Phe Ser Gly Ser Gly Ser Gly
                85                  90                  95

Thr Asp Phe Thr Leu Lys Ile Ser Arg Val Glu Ala Glu Asp Val Gly
            100                 105                 110

Val Tyr Tyr Cys Met Gln Ala Leu Gln Thr Pro Tyr Thr Phe Gly Gln
        115                 120                 125

Gly Thr Lys Leu Glu Ile Lys Arg Thr Val Ala Ala Pro Ser Val Phe
    130                 135                 140

Ile Phe Pro Pro Ser Asp Glu Gln Leu Lys Ser Gly Thr Ala Ser Val
145                 150                 155                 160

Val Cys Leu Leu Asn Asn Phe Tyr Pro Arg Glu Ala Lys Val Gln Trp
                165                 170                 175

Lys Val Asp Asn Ala Leu Gln Ser Gly Asn Ser Gln Glu Ser Val Thr
            180                 185                 190

Glu Gln Asp Ser Lys Asp Ser Thr Tyr Ser Leu Ser Ser Thr Leu Thr
        195                 200                 205

Leu Ser Lys Ala Asp Tyr Glu Lys His Lys Val Tyr Ala Cys Glu Val
    210                 215                 220

Thr His Gln Gly Leu Ser Ser Pro Val Thr Lys Ser Phe Asn Arg Gly
225                 230                 235                 240

Glu Cys
```

```
<210> SEQ ID NO 40
<211> LENGTH: 1389
<212> TYPE: DNA
<213> ORGANISM: Artificial Sequence
<220> FEATURE:
```

<223> OTHER INFORMATION: Description of Artificial Sequence: Synthetic
polynucleotide

<400> SEQUENCE: 40
cagatgcagc tggtgcagtc ggggggaggt gtggtacggc ctggggggtc cctgagactc 60
tcctgtgcag cctctggatt cacctttgat gattatggca tgagctgggt ccgccaagct 120
ccagggaagg ggctggagtg ggtctctggt attaattgga atggtggtag cacaggttat 180
gcagactctg tgaagggccg attcaccatc tccagagaca acgccaagaa ctccctgtat 240
ctgcaaatga acagtctgag agccgaggac acggccttgt attactgtgc gagagaaagc 300
tcgatgacta cagtaactac gtatctccta cgggaagtag gggtagggtt ggactttgac 360
tactggggcc agggcaccct ggtcaccgtc tcaagcgcct ccaccaaggg cccatcggtc 420
ttccccctgg caccctcctc caagagcacc tctgggggca cagcggccct gggctgcctg 480
gtcaaggact acttccccga accggtgacg gtgtcgtgga actcaggcgc cctgaccagc 540
ggcgtccaca ccttcccggc tgtcctacag tcctcaggac tctactccct cagcagcgta 600
gtgaccgtgc cctccagcag cttgggcacc cagacctaca tctgcaacgt gaatcacaag 660
cccagcaaca ccaaggtgga caagaaagtt gagcccaaat cttgtgacaa aactcacaca 720
tgcccaccgt gcccagcacc tgaactcctg gggggaccgt cagtcttcct cttcccccca 780
aaacccaagg acaccctcat gatctcccgg acccctgagg tcacatgcgt ggtggtggac 840
gtgagccacg aagaccctga ggtcaagttc aactggtacg tggacggcgt ggaggtgcat 900
aatgccaaga caaagccgcg ggaggagcag tacaacagca cgtaccgtgt ggtcagcgtc 960
ctcaccgtcc tgcaccagga ctggctgaat ggcaaggagt acaagtgcaa ggtctccaac 1020
aaagccctcc cagcccccat cgagaaaacc atctccaaag ccaaagggca gccccgagaa 1080
ccacaggtgt acaccctgcc cccatcccgg gatgagctga ccaagaacca ggtcagcctg 1140
acctgcctgg tcaaaggctt ctatcccagc gacatcgccg tggagtggga gagcaatggg 1200
cagccggaga acaactacaa gaccacgcct cccgtgctgg actccgacgg ctccttcttc 1260
ctctacagca agctcaccgt ggacaagagc aggtggcagc aggggaacgt cttctcatgc 1320
tccgtgatgc atgaggctct gcacaaccac tacacgcaga agagcctctc cctgtctccg 1380
ggtaaatga 1389

<210> SEQ ID NO 41
<211> LENGTH: 462
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 41

Gln Met Gln Leu Val Gln Ser Gly Gly Gly Val Val Arg Pro Gly Gly
1 5 10 15

Ser Leu Arg Leu Ser Cys Ala Ala Ser Gly Phe Thr Phe Asp Asp Tyr
20 25 30

Gly Met Ser Trp Val Arg Gln Ala Pro Gly Lys Gly Leu Glu Trp Val
35 40 45

Ser Gly Ile Asn Trp Asn Gly Gly Ser Thr Gly Tyr Ala Asp Ser Val
50 55 60

Lys Gly Arg Phe Thr Ile Ser Arg Asp Asn Ala Lys Asn Ser Leu Tyr
65 70 75 80

```
Leu Gln Met Asn Ser Leu Arg Ala Glu Asp Thr Ala Leu Tyr Tyr Cys
                85                  90                  95

Ala Arg Glu Ser Ser Met Thr Thr Val Thr Thr Tyr Leu Leu Arg Glu
            100                 105                 110

Val Gly Val Gly Leu Asp Phe Asp Tyr Trp Gly Gln Gly Thr Leu Val
        115                 120                 125

Thr Val Ser Ser Ala Ser Thr Lys Gly Pro Ser Val Phe Pro Leu Ala
    130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Lys Val Glu Pro Lys Ser Cys Asp Lys Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Arg Asp Glu Leu Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
    450                 455                 460
```

<210> SEQ ID NO 42
<211> LENGTH: 1458
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 42

```
atggagacag acacactcct gctatgggta ctgctgctct gggttccagg ttccactggc     60
gccggatcac agatgcagct ggtgcagtcg gggggaggtg tggtacggcc tggggggtcc    120
ctgagactct cctgtgcagc ctctggattc acctttgatg attatggcat gagctgggtc    180
cgccaagctc cagggaaggg gctggagtgg gtctctggta ttaattggaa tggtggtagc    240
acaggttatg cagactctgt gaagggccga ttcaccatct ccagagacaa cgccaagaac    300
tccctgtatc tgcaaatgaa cagtctgaga gccgaggaca cggccttgta ttactgtgcg    360
agagaaagct cgatgactac agtaactacg tatctcctac gggaagtagg ggtagggttg    420
gactttgact actggggcca gggcaccctg gtcaccgtct caagcgcctc caccaagggc    480
ccatcggtct tccccctggc accctcctcc aagagcacct ctgggggcac agcggccctg    540
ggctgcctgg tcaaggacta cttccccgaa ccggtgacgg tgtcgtggaa ctcaggcgcc    600
ctgaccagcg gcgtccacac cttcccggct gtcctacagt cctcaggact ctactccctc    660
agcagcgtag tgaccgtgcc ctccagcagc ttgggcaccc agacctacat ctgcaacgtg    720
aatcacaagc ccagcaacac caaggtggac aagaaagttg agcccaaatc ttgtgacaaa    780
actcacacat gcccaccgtg cccagcacct gaactcctgg ggggaccgtc agtcttcctc    840
ttccccccaa aacccaagga caccctcatg atctcccgga cccctgaggt cacatgcgtg    900
gtggtggacg tgagccacga agaccctgag gtcaagttca actggtacgt ggacggcgtg    960
gaggtgcata atgccaagac aaagccgcgg gaggagcagt acaacagcac gtaccgtgtg   1020
gtcagcgtcc tcaccgtcct gcaccaggac tggctgaatg gcaaggagta caagtgcaag   1080
gtctccaaca aagccctccc agcccccatc gagaaaacca tctccaaagc caaagggcag   1140
ccccgagaac cacaggtgta caccctgccc ccatcccggg atgagctgac caagaaccag   1200
gtcagcctga cctgcctggt caaaggcttc tatcccagcg acatcgccgt ggagtgggag   1260
agcaatgggc agccggagaa caactacaag accacgcctc ccgtgctgga ctccgacggc   1320
tccttcttcc tctacagcaa gctcaccgtg gacaagagca ggtggcagca ggggaacgtc   1380
ttctcatgct ccgtgatgca tgaggctctg cacaaccact acacgcagaa gagcctctcc   1440
ctgtctccgg gtaaatga                                                 1458
```

<210> SEQ ID NO 43
<211> LENGTH: 485
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 43

```
Met Glu Thr Asp Thr Leu Leu Leu Trp Val Leu Leu Leu Trp Val Pro
1               5                   10                  15

Gly Ser Thr Gly Ala Gly Ser Gln Met Gln Leu Val Gln Ser Gly Gly
            20                  25                  30

Gly Val Val Arg Pro Gly Gly Ser Leu Arg Leu Ser Cys Ala Ala Ser
        35                  40                  45

Gly Phe Thr Phe Asp Asp Tyr Gly Met Ser Trp Val Arg Gln Ala Pro
    50                  55                  60

Gly Lys Gly Leu Glu Trp Val Ser Gly Ile Asn Trp Asn Gly Gly Ser
65                  70                  75                  80
```

```
Thr Gly Tyr Ala Asp Ser Val Lys Gly Arg Phe Thr Ile Ser Arg Asp
                85                  90                  95

Asn Ala Lys Asn Ser Leu Tyr Leu Gln Met Asn Ser Leu Arg Ala Glu
            100                 105                 110

Asp Thr Ala Leu Tyr Tyr Cys Ala Arg Glu Ser Ser Met Thr Thr Val
        115                 120                 125

Thr Thr Tyr Leu Leu Arg Glu Val Gly Val Gly Leu Asp Phe Asp Tyr
    130                 135                 140

Trp Gly Gln Gly Thr Leu Val Thr Val Ser Ser Ala Ser Thr Lys Gly
145                 150                 155                 160

Pro Ser Val Phe Pro Leu Ala Pro Ser Ser Lys Ser Thr Ser Gly Gly
                165                 170                 175

Thr Ala Ala Leu Gly Cys Leu Val Lys Asp Tyr Phe Pro Glu Pro Val
            180                 185                 190

Thr Val Ser Trp Asn Ser Gly Ala Leu Thr Ser Gly Val His Thr Phe
        195                 200                 205

Pro Ala Val Leu Gln Ser Ser Gly Leu Tyr Ser Leu Ser Ser Val Val
    210                 215                 220

Thr Val Pro Ser Ser Ser Leu Gly Thr Gln Thr Tyr Ile Cys Asn Val
225                 230                 235                 240

Asn His Lys Pro Ser Asn Thr Lys Val Asp Lys Lys Val Glu Pro Lys
                245                 250                 255

Ser Cys Asp Lys Thr His Thr Cys Pro Pro Cys Pro Ala Pro Glu Leu
            260                 265                 270

Leu Gly Gly Pro Ser Val Phe Leu Phe Pro Pro Lys Pro Lys Asp Thr
        275                 280                 285

Leu Met Ile Ser Arg Thr Pro Glu Val Thr Cys Val Val Val Asp Val
    290                 295                 300

Ser His Glu Asp Pro Glu Val Lys Phe Asn Trp Tyr Val Asp Gly Val
305                 310                 315                 320

Glu Val His Asn Ala Lys Thr Lys Pro Arg Glu Glu Gln Tyr Asn Ser
                325                 330                 335

Thr Tyr Arg Val Val Ser Val Leu Thr Val Leu His Gln Asp Trp Leu
            340                 345                 350

Asn Gly Lys Glu Tyr Lys Cys Lys Val Ser Asn Lys Ala Leu Pro Ala
        355                 360                 365

Pro Ile Glu Lys Thr Ile Ser Lys Ala Lys Gly Gln Pro Arg Glu Pro
    370                 375                 380

Gln Val Tyr Thr Leu Pro Pro Ser Arg Asp Glu Leu Thr Lys Asn Gln
385                 390                 395                 400

Val Ser Leu Thr Cys Leu Val Lys Gly Phe Tyr Pro Ser Asp Ile Ala
                405                 410                 415

Val Glu Trp Glu Ser Asn Gly Gln Pro Glu Asn Asn Tyr Lys Thr Thr
            420                 425                 430

Pro Pro Val Leu Asp Ser Asp Gly Ser Phe Phe Leu Tyr Ser Lys Leu
        435                 440                 445

Thr Val Asp Lys Ser Arg Trp Gln Gln Gly Asn Val Phe Ser Cys Ser
    450                 455                 460

Val Met His Glu Ala Leu His Asn His Tyr Thr Gln Lys Ser Leu Ser
465                 470                 475                 480

Leu Ser Pro Gly Lys
                485
```

<210> SEQ ID NO 44
<211> LENGTH: 645
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44
gaaacgacac tcacgcagtc tccaggcacc ctgtccttgt ctccagggga aagagccacc     60
ctctcctgca gggccagtca gactgttagc ggcagctact tagcctggta ccagcagaaa    120
cctggccagc ctcccaggct cctcatctat ggtgcatcca gcagggccac tggcatccca    180
gacaggttca gtggcagtgg gtccgggaca gacttcactc tcaccatcag cagactggag    240
cctgaagatt ttgcagtgta ttactgtcag gactatggta gctcacggac gttcggccaa    300
gggaccaagg tggaactcaa acgaactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa ctctacgcct gcgaagtcac ccatcagggc    600
ctgagctcgc ccgtcacaaa gagcttcaac aggggagagt gttag                    645

<210> SEQ ID NO 45
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Glu Thr Thr Leu Thr Gln Ser Pro Gly Thr Leu Ser Leu Ser Pro Gly
1               5                   10                  15

Glu Arg Ala Thr Leu Ser Cys Arg Ala Ser Gln Thr Val Ser Gly Ser
            20                  25                  30

Tyr Leu Ala Trp Tyr Gln Gln Lys Pro Gly Gln Pro Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Asp Tyr Gly Ser Ser Arg
                85                  90                  95

Thr Phe Gly Gln Gly Thr Lys Val Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Leu Tyr
            180                 185                 190

```
Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 46
<211> LENGTH: 714
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 46

```
atggagacag acacactcct gctatgggta ctgctgctct gggttccagg ttccactggc      60

gccggatcag aaacgacact cacgcagtct ccaggcaccc tgtccttgtc tccaggggaa     120

agagccaccc tctcctgcag ggccagtcag actgttagcg gcagctactt agcctggtac     180

cagcagaaac ctggccagcc tcccaggctc ctcatctatg gtgcatccag cagggccact     240

ggcatcccag acaggttcag tggcagtggg tccgggacag acttcactct caccatcagc     300

agactggagc ctgaagattt tgcagtgtat tactgtcagg actatggtag ctcacggacg     360

ttcggccaag ggaccaaggt ggaactcaaa cgaactgtgg ctgcaccatc tgtcttcatc     420

ttcccgccat ctgatgagca gttgaaatct ggaactgcct ctgttgtgtg cctgctgaat     480

aacttctatc ccagagaggc caaagtacag tggaaggtgg ataacgccct ccaatcgggt     540

aactcccagg agagtgtcac agagcaggac agcaaggaca gcacctacag cctcagcagc     600

accctgacgc tgagcaaagc agactacgag aaacacaaac tctacgcctg cgaagtcacc     660

catcagggcc tgagctcgcc cgtcacaaag agcttcaaca ggggagagtg ttag           714
```

<210> SEQ ID NO 47
<211> LENGTH: 237
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 47

```
Met Glu Thr Asp Thr Leu Leu Leu Trp Val Leu Leu Leu Trp Val Pro
1               5                   10                  15

Gly Ser Thr Gly Ala Gly Ser Glu Thr Thr Leu Thr Gln Ser Pro Gly
            20                  25                  30

Thr Leu Ser Leu Ser Pro Gly Glu Arg Ala Thr Leu Ser Cys Arg Ala
        35                  40                  45

Ser Gln Thr Val Ser Gly Ser Tyr Leu Ala Trp Tyr Gln Gln Lys Pro
    50                  55                  60

Gly Gln Pro Pro Arg Leu Leu Ile Tyr Gly Ala Ser Ser Arg Ala Thr
65                  70                  75                  80

Gly Ile Pro Asp Arg Phe Ser Gly Ser Gly Ser Gly Thr Asp Phe Thr
                85                  90                  95

Leu Thr Ile Ser Arg Leu Glu Pro Glu Asp Phe Ala Val Tyr Tyr Cys
            100                 105                 110

Gln Asp Tyr Gly Ser Ser Arg Thr Phe Gly Gln Gly Thr Lys Val Glu
        115                 120                 125

Leu Lys Arg Thr Val Ala Ala Pro Ser Val Phe Ile Phe Pro Pro Ser
    130                 135                 140
```

```
Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Leu Tyr Ala Cys Glu Val Thr His Gln Gly Leu
    210                 215                 220

Ser Ser Pro Val Thr Lys Ser Phe Asn Arg Gly Glu Cys
225                 230                 235
```

<210> SEQ ID NO 48
<211> LENGTH: 1374
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 48

```
caggtgcagc tacagcagtg gggcgcagga ctgttgaagc cttcggagac cctgtccctc     60

acctgcgctg tctatggtgg gtccttcagt ggttactact ggagctggat ccgccagccc    120

ccagggaagg ggctggagtg gattggggaa atcaatcata gtggaagcac caactacaac    180

ccgtccctca agagtcgagt caccatatca gtagacacgt ccaagaacca gttctccctg    240

aagctgagct ctgtgaccgc cgcggacacg gctgtgtatt actgtgcgag acgatattgt    300

agtggtggta gctgctactt agttggaacg ggtctgaat tggactactg gggccaggga    360

accctggtca ccgtctcaag cgcctccacc aagggcccat cggtcttccc cctggcaccc    420

tcctccaaga gcacctctgg gggcacagcg gccctgggct gcctggtcaa ggactacttc    480

cccgaaccgg tgacggtgtc gtggaactca ggcgccctga ccagcggcgt ccacaccttc    540

ccggctgtcc tacagtcctc aggactctac tccctcagca gcgtagtgac cgtgccctcc    600

agcagcttgg gcacccagac ctacatctgc aacgtgaatc acaagcccag caacaccaag    660

gtggacaaga aagttgagcc caaatcttgt gacaaaactc acacatgccc accgtgccca    720

gcacctgaac tcctgggggg accgtcagtc ttcctcttcc ccccaaaacc caaggacacc    780

ctcatgatct cccggacccc tgaggtcaca tgcgtggtgg tggacgtgag ccacgaagac    840

cctgaggtca agttcaactg gtacgtggac ggcgtggagg tgcataatgc caagacaaag    900

ccgcgggagg agcagtacaa cagcacgtac cgtgtggtca gcgtcctcac cgtcctgcac    960

caggactggc tgaatggcaa ggagtacaag tgcaaggtct ccaacaaagc cctcccagcc   1020

cccatcgaga aaaccatctc caaagccaaa gggcagcccc gagaaccaca ggtgtacacc   1080

ctgcccccat cccgggatga gctgaccaag aaccaggtca gcctgacctg cctggtcaaa   1140

ggcttctatc ccagcgacat cgccgtggag tgggagagca atgggcagcc ggagaacaac   1200

tacaagacca cgcctcccgt gctggactcc gacggctcct tcttcctcta cagcaagctc   1260

accgtggaca agagcaggtg gcagcagggg aacgtcttct catgctccgt gatgcatgag   1320

gctctgcaca accactacac gcagaagagc ctctccctgt ctccgggtaa atga         1374
```

<210> SEQ ID NO 49
<211> LENGTH: 457

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 49

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Arg Tyr Cys Ser Gly Gly Ser Cys Tyr Leu Val Gly Thr Gly Ser
            100                 105                 110

Glu Leu Asp Tyr Trp Gly Gln Gly Thr Leu Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
    210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Asp Glu Leu
        355                 360                 365

Thr Lys Asn Gln Val Ser Leu Thr Cys Leu Val Lys Gly Phe Tyr Pro
    370                 375                 380
```

```
Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly Lys
    450                 455


<210> SEQ ID NO 50
<211> LENGTH: 1443
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50

atggagacag acacactcct gctatgggta ctgctgctct gggttccagg ttccactggc     60

gccggatcac aggtgcagct acagcagtgg ggcgcaggac tgttgaagcc ttcggagacc    120

ctgtccctca cctgcgctgt ctatggtggg tccttcagtg gttactactg gagctggatc    180

cgccagcccc cagggaaggg gctggagtgg attggggaaa tcaatcatag tggaagcacc    240

aactacaacc cgtccctcaa gagtcgagtc accatatcag tagacacgtc caagaaccag    300

ttctccctga agctgagctc tgtgaccgcc gcggacacgg ctgtgtatta ctgtgcgaga    360

cgatattgta gtggtggtag ctgctactta gttggaacgg ggtctgaatt ggactactgg    420

ggccagggaa ccctggtcac cgtctcaagc gcctccacca agggcccatc ggtcttcccc    480

ctggcaccct cctccaagag cacctctggg ggcacagcgg ccctgggctg cctggtcaag    540

gactacttcc ccgaaccggt gacggtgtcg tggaactcag gcgccctgac cagcggcgtc    600

cacaccttcc cggctgtcct acagtcctca ggactctact ccctcagcag cgtagtgacc    660

gtgccctcca gcagcttggg cacccagacc tacatctgca acgtgaatca caagcccagc    720

aacaccaagg tggacaagaa agttgagccc aaatcttgtg acaaaactca cacatgccca    780

ccgtgcccag cacctgaact cctgggggga ccgtcagtct tcctcttccc cccaaaaccc    840

aaggacaccc tcatgatctc ccggacccct gaggtcacat gcgtggtggt ggacgtgagc    900

cacgaagacc ctgaggtcaa gttcaactgg tacgtggacg gcgtggaggt gcataatgcc    960

aagacaaagc cgcgggagga gcagtacaac agcacgtacc gtgtggtcag cgtcctcacc   1020

gtcctgcacc aggactggct gaatggcaag gagtacaagt gcaaggtctc caacaaagcc   1080

ctcccagccc ccatcgagaa aaccatctcc aaagccaaag ggcagccccg agaaccacag   1140

gtgtacaccc tgcccccatc ccgggatgag ctgaccaaga accaggtcag cctgacctgc   1200

ctggtcaaag gcttctatcc cagcgacatc gccgtggagt gggagagcaa tgggcagccg   1260

gagaacaact acaagaccac gcctcccgtg ctggactccg acggctcctt cttcctctac   1320

agcaagctca ccgtggacaa gagcaggtgg cagcagggga acgtcttctc atgctccgtg   1380

atgcatgagg ctctgcacaa ccactacacg cagaagagcc tctccctgtc tccgggtaaa   1440

tga                                                                 1443


<210> SEQ ID NO 51
```

<211> LENGTH: 480
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

```
Met Glu Thr Asp Thr Leu Leu Leu Trp Val Leu Leu Leu Trp Val Pro
1               5                   10                  15

Gly Ser Thr Gly Ala Gly Ser Gln Val Gln Leu Gln Gln Trp Gly Ala
            20                  25                  30

Gly Leu Leu Lys Pro Ser Glu Thr Leu Ser Leu Thr Cys Ala Val Tyr
        35                  40                  45

Gly Gly Ser Phe Ser Gly Tyr Tyr Trp Ser Trp Ile Arg Gln Pro Pro
    50                  55                  60

Gly Lys Gly Leu Glu Trp Ile Gly Glu Ile Asn His Ser Gly Ser Thr
65                  70                  75                  80

Asn Tyr Asn Pro Ser Leu Lys Ser Arg Val Thr Ile Ser Val Asp Thr
                85                  90                  95

Ser Lys Asn Gln Phe Ser Leu Lys Leu Ser Ser Val Thr Ala Ala Asp
            100                 105                 110

Thr Ala Val Tyr Tyr Cys Ala Arg Arg Tyr Cys Ser Gly Gly Ser Cys
        115                 120                 125

Tyr Leu Val Gly Thr Gly Ser Glu Leu Asp Tyr Trp Gly Gln Gly Thr
    130                 135                 140

Leu Val Thr Val Ser Ser Ala Ser Thr Lys Gly Pro Ser Val Phe Pro
145                 150                 155                 160

Leu Ala Pro Ser Ser Lys Ser Thr Ser Gly Gly Thr Ala Ala Leu Gly
                165                 170                 175

Cys Leu Val Lys Asp Tyr Phe Pro Glu Pro Val Thr Val Ser Trp Asn
            180                 185                 190

Ser Gly Ala Leu Thr Ser Gly Val His Thr Phe Pro Ala Val Leu Gln
        195                 200                 205

Ser Ser Gly Leu Tyr Ser Leu Ser Ser Val Val Thr Val Pro Ser Ser
    210                 215                 220

Ser Leu Gly Thr Gln Thr Tyr Ile Cys Asn Val Asn His Lys Pro Ser
225                 230                 235                 240

Asn Thr Lys Val Asp Lys Lys Val Glu Pro Lys Ser Cys Asp Lys Thr
                245                 250                 255

His Thr Cys Pro Pro Cys Pro Ala Pro Glu Leu Leu Gly Gly Pro Ser
            260                 265                 270

Val Phe Leu Phe Pro Pro Lys Pro Lys Asp Thr Leu Met Ile Ser Arg
        275                 280                 285

Thr Pro Glu Val Thr Cys Val Val Val Asp Val Ser His Glu Asp Pro
    290                 295                 300

Glu Val Lys Phe Asn Trp Tyr Val Asp Gly Val Glu Val His Asn Ala
305                 310                 315                 320

Lys Thr Lys Pro Arg Glu Glu Gln Tyr Asn Ser Thr Tyr Arg Val Val
                325                 330                 335

Ser Val Leu Thr Val Leu His Gln Asp Trp Leu Asn Gly Lys Glu Tyr
            340                 345                 350

Lys Cys Lys Val Ser Asn Lys Ala Leu Pro Ala Pro Ile Glu Lys Thr
        355                 360                 365

Ile Ser Lys Ala Lys Gly Gln Pro Arg Glu Pro Gln Val Tyr Thr Leu
```

```
    370                 375                 380

Pro Pro Ser Arg Asp Glu Leu Thr Lys Asn Gln Val Ser Leu Thr Cys
385                 390                 395                 400

Leu Val Lys Gly Phe Tyr Pro Ser Asp Ile Ala Val Glu Trp Glu Ser
                405                 410                 415

Asn Gly Gln Pro Glu Asn Asn Tyr Lys Thr Thr Pro Pro Val Leu Asp
            420                 425                 430

Ser Asp Gly Ser Phe Phe Leu Tyr Ser Lys Leu Thr Val Asp Lys Ser
        435                 440                 445

Arg Trp Gln Gln Gly Asn Val Phe Ser Cys Ser Val Met His Glu Ala
    450                 455                 460

Leu His Asn His Tyr Thr Gln Lys Ser Leu Ser Leu Ser Pro Gly Lys
465                 470                 475                 480


<210> SEQ ID NO 52
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52

gacatccaga tgacccagtc tccttccacc ctgtctgcat ctgtaggaga cagagtcacc     60

ataacttgcc gggccagtca gagcattagt agctggttgg cctggtatca gcagaaacca    120

gggaaagccc ctaaactcct aatctataag gcgtctagtt tagaaattgg ggtcccatca    180

aggttcagcg gcagtggata tgggacagaa ttcactctca ccatcagcag cctgcagcct    240

gatgatttcg caacttatta ttgcctacag tatagtactc attcgacgtt cggccaaggg    300

accagggtgg aaatcaaacg aactgtggct gcaccatctg tcttcatctt cccgccatct    360

gatgagcagt tgaaatctgg aactgcctct gttgtgtgcc tgctgaataa cttctatccc    420

agagaggcca aagtacagtg gaaggtggat aacgccctcc aatcgggtaa ctcccaggag    480

agtgtcacag agcaggacag caaggacagc acctacagcc tcagcagcac cctgacgctg    540

agcaaagcag actacgagaa acacaaactc tacgcctgcg aagtcaccca tcagggcctg    600

agctcgcccg tcacaaagag cttcaacagg ggagagtgtt ag                       642


<210> SEQ ID NO 53
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ile Gly Val Pro Ser Arg Phe Ser Gly
    50                  55                  60

Ser Gly Tyr Gly Thr Glu Phe Thr Leu Thr Ile Ser Ser Leu Gln Pro
65                  70                  75                  80
```

```
Asp Asp Phe Ala Thr Tyr Tyr Cys Leu Gln Tyr Ser Thr His Ser Thr
                85                  90                  95

Phe Gly Gln Gly Thr Arg Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Leu Tyr Ala
            180                 185                 190

Cys Glu Val Thr His Gln Gly Leu Ser Ser Pro Val Thr Lys Ser Phe
        195                 200                 205

Asn Arg Gly Glu Cys
    210


<210> SEQ ID NO 54
<211> LENGTH: 711
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54

atggagacag acacactcct gctatgggta ctgctgctct gggttccagg ttccactggc     60

gccggatcag acatccagat gacccagtct ccttccaccc tgtctgcatc tgtaggagac    120

agagtcacca taacttgccg ggccagtcag agcattagta gctggttggc ctggtatcag    180

cagaaaccag ggaaagcccc taaactccta atctataagg cgtctagttt agaaattggg    240

gtcccatcaa ggttcagcgg cagtggatat gggacagaat tcactctcac catcagcagc    300

ctgcagcctg atgatttcgc aacttattat tgcctacagt atagtactca ttcgacgttc    360

ggccaaggga ccagggtgga aatcaaacga actgtggctg caccatctgt cttcatcttc    420

ccgccatctg atgagcagtt gaaatctgga actgcctctg ttgtgtgcct gctgaataac    480

ttctatccca gagaggccaa agtacagtgg aaggtggata acgccctcca atcgggtaac    540

tcccaggaga gtgtcacaga gcaggacagc aaggacagca cctacagcct cagcagcacc    600

ctgacgctga gcaaagcaga ctacgagaaa cacaaactct acgcctgcga agtcacccat    660

cagggcctga gctcgcccgt cacaaagagc ttcaacaggg gagagtgtta g             711


<210> SEQ ID NO 55
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Met Glu Thr Asp Thr Leu Leu Leu Trp Val Leu Leu Leu Trp Val Pro
1               5                   10                  15

Gly Ser Thr Gly Ala Gly Ser Asp Ile Gln Met Thr Gln Ser Pro Ser
            20                  25                  30
```

```
Thr Leu Ser Ala Ser Val Gly Asp Arg Val Thr Ile Thr Cys Arg Ala
        35                  40                  45

Ser Gln Ser Ile Ser Ser Trp Leu Ala Trp Tyr Gln Gln Lys Pro Gly
    50                  55                  60

Lys Ala Pro Lys Leu Leu Ile Tyr Lys Ala Ser Ser Leu Glu Ile Gly
65                  70                  75                  80

Val Pro Ser Arg Phe Ser Gly Ser Gly Tyr Gly Thr Glu Phe Thr Leu
                85                  90                  95

Thr Ile Ser Ser Leu Gln Pro Asp Asp Phe Ala Thr Tyr Tyr Cys Leu
            100                 105                 110

Gln Tyr Ser Thr His Ser Thr Phe Gly Gln Gly Thr Arg Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Leu Tyr Ala Cys Glu Val Thr His Gln Gly Leu Ser
    210                 215                 220

Ser Pro Val Thr Lys Ser Phe Asn Arg Gly Glu Cys
225                 230                 235
```

<210> SEQ ID NO 56
<211> LENGTH: 383
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 56

```
caggtgcagc tgcaggagtc cgggggaggc gtggtccagc ctgggaggtc cctgagactc     60

tcctgtgcag cctctggatt caccttcagt agctatggca tgcactgggt ccgccaggct    120

ccaggcaagg ggctggagtg ggtggcagtt atatcatatg atggaagtaa taaatactat    180

gcagactccg tgaagggccg attcaccatc tccagagaca attccaagaa cacgctgtat    240

ctgcaaatga acagcctgag agccgaggac acggctgtgt attactgtgc gagagatctc    300

ggcgccgtta tagcagtggc tggtacttcc accccgtaca actggttcga cccctggggc    360

cagggaaccc tggtcaccgt ctc                                            383
```

<210> SEQ ID NO 57
<211> LENGTH: 128
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 57

```
Gln Val Gln Leu Gln Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
```

```
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Gly Ala Val Ile Ala Val Ala Gly Thr Ser Thr Pro
            100                 105                 110

Tyr Asn Trp Phe Asp Pro Trp Gly Gln Gly Thr Leu Val Thr Val Ser
        115                 120                 125


<210> SEQ ID NO 58
<211> LENGTH: 335
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58

gatgttgtga tgactcagtc tccactctcc ctgcccgtca cccctggaga gccggcctcc      60

atctcctgca ggtctcgtca gagcctcctg catagcaatg gacacaacta tttgggttgg     120

tacctgcaga agccagggca gtctccacag ctcctgatct atctggcttc tattcgggcc     180

tccgggatcc ctgacaggtt cagtggcagt ggatcaggca cagattttac actgaaaatc     240

agcagagtgg aggctgagga tgttggcgtt tattactgca tgcaagctct acaaacaccc     300

tacacttttg gccaggggac caagctggag atcaa                                335


<210> SEQ ID NO 59
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Asp Val Val Met Thr Gln Ser Pro Leu Ser Leu Pro Val Thr Pro Gly
1               5                   10                  15

Glu Pro Ala Ser Ile Ser Cys Arg Ser Arg Gln Ser Leu Leu His Ser
            20                  25                  30

Asn Gly His Asn Tyr Leu Gly Trp Tyr Leu Gln Lys Pro Gly Gln Ser
        35                  40                  45

Pro Gln Leu Leu Ile Tyr Leu Ala Ser Ile Arg Ala Ser Gly Ile Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Tyr Thr Phe Gly Gln Gly Thr Lys Leu Glu Ile Lys
            100                 105                 110


<210> SEQ ID NO 60
<211> LENGTH: 8
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 60

Gly Phe Thr Phe Ser Ser Tyr Gly
1               5

<210> SEQ ID NO 61
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Ile Ser Tyr Asp Gly Ser Asn Lys
1               5

<210> SEQ ID NO 62
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Ala Arg Asp Leu Gly Ala Val Ile Ala Val Ala Gly Thr Ser Thr Pro
1               5                   10                  15

Tyr Asn Trp Phe Asp Pro
            20

<210> SEQ ID NO 63
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gln Ser Leu Leu His Ser Asn Gly His Asn Tyr
1               5                   10

<210> SEQ ID NO 64
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Leu Ala Ser
1

<210> SEQ ID NO 65
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Met Gln Ala Leu Gln Thr Pro Tyr Thr
1 5

<210> SEQ ID NO 66
<211> LENGTH: 392
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 66
cagatgcagc tggtgcagtc gggggaggt gtggtacggc ctgggggtc cctgagactc 60 tcctgtgcag cctctggatt cacctttgat gattatggca tgagctgggt ccgccaagct 120
ccagggaagg ggctggagtg ggtctctggt attaattgga atggtggtag cacaggttat 180
gcagactctg tgaagggccg attcaccatc tccagagaca acgccaagaa ctccctgtat 240
ctgcaaatga acagtctgag agccgaggac acggccttgt attactgtgc gagagaaagc 300
tcgatgacta cagtaactac gtatctccta cgggaagtag gggtagggtt ggactttgac 360
tactggggcc agggcaccct ggtcaccgtc tc 392

<210> SEQ ID NO 67
<211> LENGTH: 131
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 67

Gln Met Gln Leu Val Gln Ser Gly Gly Gly Val Val Arg Pro Gly Gly
1 5 10 15

Ser Leu Arg Leu Ser Cys Ala Ala Ser Gly Phe Thr Phe Asp Asp Tyr
20 25 30

Gly Met Ser Trp Val Arg Gln Ala Pro Gly Lys Gly Leu Glu Trp Val
35 40 45

Ser Gly Ile Asn Trp Asn Gly Gly Ser Thr Gly Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Leu Tyr Tyr Cys
85 90 95

Ala Arg Glu Ser Ser Met Thr Thr Val Thr Thr Tyr Leu Leu Arg Glu
100 105 110

Val Gly Val Gly Leu Asp Phe Asp Tyr Trp Gly Gln Gly Thr Leu Val
115 120 125

Thr Val Ser
130

<210> SEQ ID NO 68
<211> LENGTH: 322
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 68
gaaacgacac tcacgcagtc tccaggcacc ctgtccttgt ctccagggga aagagccacc 60

```
ctctcctgca gggccagtca gactgttagc ggcagctact tagcctggta ccagcagaaa    120

cctggccagc ctcccaggct cctcatctat ggtgcatcca gcagggccac tggcatccca    180

gacaggttca gtggcagtgg gtccgggaca gacttcactc tcaccatcag cagactggag    240

cctgaagatt ttgcagtgta ttactgtcag gactatggta gctcacggac gttcggccaa    300

gggaccaagg tggaactcaa ac                                             322


<210> SEQ ID NO 69
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Glu Thr Thr Leu Thr Gln Ser Pro Gly Thr Leu Ser Leu Ser Pro Gly
1               5                   10                  15

Glu Arg Ala Thr Leu Ser Cys Arg Ala Ser Gln Thr Val Ser Gly Ser
            20                  25                  30

Tyr Leu Ala Trp Tyr Gln Gln Lys Pro Gly Gln Pro Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Asp Tyr Gly Ser Ser Arg
                85                  90                  95

Thr Phe Gly Gln Gly Thr Lys Val Glu Leu Lys
            100                 105


<210> SEQ ID NO 70
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gly Phe Thr Phe Asp Asp Tyr Gly
1               5


<210> SEQ ID NO 71
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Ile Asn Trp Asn Gly Gly Ser Thr
1               5


<210> SEQ ID NO 72
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 72

Ala Arg Glu Ser Ser Met Thr Thr Val Thr Thr Tyr Leu Leu Arg Glu
1 5 10 15

Val Gly Val Gly Leu Asp Phe Asp Tyr
20 25

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 73

Gln Thr Val Ser Gly Ser Tyr
1 5

<210> SEQ ID NO 74
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 74

Gly Ala Ser
1

<210> SEQ ID NO 75
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 75

Gln Asp Tyr Gly Ser Ser Arg Thr
1 5

<210> SEQ ID NO 76
<211> LENGTH: 377
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 76
caggtgcagc tacagcagtg gggcgcagga ctgttgaagc cttcggagac cctgtccctc 60
acctgcgctg tctatggtgg gtccttcagt ggttactact ggagctggat ccgccagccc 120
ccagggaagg ggctggagtg gattggggaa atcaatcata gtggaagcac caactacaac 180
ccgtccctca agagtcgagt caccatatca gtagacacgt ccaagaacca gttctccctg 240
aagctgagct ctgtgaccgc cgcggacacg gctgtgtatt actgtgcgag acgatattgt 300
agtggtggta gctgctactt agttggaacg gggtctgaat tggactactg gggccaggga 360
accctggtca ccgtctc 377

<210> SEQ ID NO 77
<211> LENGTH: 126

<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 77

Gln Val Gln Leu Gln Gln Trp Gly Ala Gly Leu Leu Lys Pro Ser Glu
1 5 10 15

Thr Leu Ser Leu Thr Cys Ala Val Tyr Gly Gly Ser Phe Ser Gly Tyr
20 25 30

Tyr Trp Ser Trp Ile Arg Gln Pro Pro Gly Lys Gly Leu Glu Trp Ile
35 40 45

Gly Glu Ile Asn His Ser Gly Ser Thr Asn Tyr Asn Pro Ser Leu Lys
50 55 60

Ser Arg Val Thr Ile Ser Val Asp Thr Ser Lys Asn Gln Phe Ser Leu
65 70 75 80

Lys Leu Ser Ser Val Thr Ala Ala Asp Thr Ala Val Tyr Tyr Cys Ala
85 90 95

Arg Arg Tyr Cys Ser Gly Gly Ser Cys Tyr Leu Val Gly Thr Gly Ser
100 105 110

Glu Leu Asp Tyr Trp Gly Gln Gly Thr Leu Val Thr Val Ser
115 120 125

<210> SEQ ID NO 78
<211> LENGTH: 319
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 78
gacatccaga tgacccagtc tccttccacc ctgtctgcat ctgtaggaga cagagtcacc 60
ataacttgcc gggccagtca gagcattagt agctggttgg cctggtatca gcagaaacca 120
gggaaagccc ctaaactcct aatctataag gcgtctagtt tagaaattgg ggtcccatca 180
aggttcagcg gcagtggata tgggacagaa ttcactctca ccatcagcag cctgcagcct 240
gatgatttcg caacttatta ttgcctacag tatagtactc attcgacgtt cggccaaggg 300
accagggtgg aaatcaaac 319

<210> SEQ ID NO 79
<211> LENGTH: 106
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 79

Asp Ile Gln Met Thr Gln Ser Pro Ser Thr Leu Ser Ala Ser Val Gly
1 5 10 15

Asp Arg Val Thr Ile Thr Cys Arg Ala Ser Gln Ser Ile Ser Ser Trp
20 25 30

Leu Ala Trp Tyr Gln Gln Lys Pro Gly Lys Ala Pro Lys Leu Leu Ile
35 40 45

Tyr Lys Ala Ser Ser Leu Glu Ile Gly Val Pro Ser Arg Phe Ser Gly
50 55 60

Ser Gly Tyr Gly Thr Glu Phe Thr Leu Thr Ile Ser Ser Leu Gln Pro 65 70 75 80

Asp Asp Phe Ala Thr Tyr Tyr Cys Leu Gln Tyr Ser Thr His Ser Thr
85 90 95

Phe Gly Gln Gly Thr Arg Val Glu Ile Lys
100 105

<210> SEQ ID NO 80
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 80

Gly Gly Ser Phe Ser Gly Tyr Tyr
1 5

<210> SEQ ID NO 81
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 81

Ile Asn His Ser Gly Ser Thr
1 5

<210> SEQ ID NO 82
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 82

Ala Arg Arg Tyr Cys Ser Gly Gly Ser Cys Tyr Leu Val Gly Thr Gly
1 5 10 15

Ser Glu Leu Asp Tyr
20

<210> SEQ ID NO 83
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 83

Gln Ser Ile Ser Ser Trp
1 5

<210> SEQ ID NO 84
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 84

Lys Ala Ser

1

<210> SEQ ID NO 85
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 85

Leu Gln Tyr Ser Thr His Ser Thr
1 5

<210> SEQ ID NO 86
<211> LENGTH: 20
<212> TYPE: PRT
<213> ORGANISM: Mus sp.

<400> SEQUENCE: 86

Ser Glu Glu Glu Glu Ile Glu Lys Arg Glu Glu Ile His His Gln Leu
1 5 10 15

Gln Met Leu Leu
20

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 87
ctacagggga caccacccac 20

<210> SEQ ID NO 88
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 88
tacagtactg acccgtccac tc 22

<210> SEQ ID NO 89
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 89
ctctggctcc tagcaccatg aaga 24

<210> SEQ ID NO 90
<211> LENGTH: 26
<212> TYPE: DNA
<213> ORGANISM: Artificial Sequence
<220> FEATURE:
<223> OTHER INFORMATION: Description of Artificial Sequence: Synthetic
primer

<400> SEQUENCE: 90
gtaaaacgca gctcagtaac agtccg 26

<210> SEQ ID NO 91
<211> LENGTH: 6414
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 91
gacggatcgg gagatctccc gatcccctat ggtgcactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg accattgcat acgttgtatc catatcataa 240
tatgtacatt tatattggct catgtccaac attaccgcca tgttgacatt gattattgac 300
tagttattaa tagtaatcaa ttacggggtc attagttcat agcccatata tggagttccg 360
cgttacataa cttacggtaa atggcccgcc tggctgaccg cccaacgacc cccgcccatt 420
gacgtcaata atgacgtatg ttcccatagt aacgccaata gggactttcc attgacgtca 480
atgggtggac tatttacggt aaactgccca cttggcagta catcaagtgt atcatatgcc 540
aagtacgccc cctattgacg tcaatgacgg taaatggccc gcctggcatt atgcccagta 600
catgacctta tgggactttc ctacttggca gtacatctac gtattagtca tcgctattac 660
catggtgatg cggttttggc agtacatcaa tgggcgtgga tagcggtttg actcacgggg 720
atttccaagt ctccacccca ttgacgtcaa tgggagtttg ttttggcacc aaaatcaacg 780
ggactttcca aaatgtcgta acaactccgc cccattgacg caaatgggcg gtaggcgtgt 840
acggtgggag gtctatataa gcagagctcg tttagtgaac cgtcagatcg cctggagacg 900
ccatccacgc tgttttgacc tccatagaag acaccgggac cgatccagcc tccgcggccg 960
ggaacggtgc attggaacgc ggattccccg tgccaagagt gacgtaagta ccgcctatag 1020
actctatagg cacacccctt tggctcttat gcatgctata ctgtttttgg cttggggcct 1080
atacaccccc gcttccttat gctataggtg atggtatagc ttagcctata ggtgtgggtt 1140
attgaccatt attgaccact cccctattgg tgacgatact ttccattact aatccataac 1200
atggctcttt gccacaacta tctctattgg ctatatgcca atactctgtc cttcagagac 1260
tgacacggac tctgtatttt tacaggatgg ggtcccattt attatttaca aattcacata 1320
tacaacaacg ccgtcccccg tgcccgcagt ttttattaaa catagcgtgg gatctccacg 1380
cgaatctcgg gtacgtgttc cggacatggg ctcttctccg gtagcggcgg agcttccaca 1440
tccgagccct ggtcccatgc ctccagcggc tcatggtcgc tcggcagctc cttgctccta 1500
acagtggagg ccagacttag gcacagcaca atgcccacca ccaccagtgt gccgcacaag 1560
gccgtggcgg tagggtatgt gtctgaaaat gagcgtggag attgggctcg cacggctgac 1620
gcagatggaa gacttaaggc agcggcagaa gaagatgcag gcagctgagt tgttgtattc 1680
tgataagagt cagaggtaac tcccgttgcg gtgctgttaa cggtggaggg cagtgtagtc 1740
tgagcagaac tcgttgctgc cgcgcgcgcc accagacata atagctgaca gactaacaga 1800
ctgttccttt ccatgggtct tttctgcagt caccgtcctg acacgaagct tgccgccacc 1860
atgggctggt ccctgattct gctgttcctg gtggctgtgg ctaccagggt gctgagtgag 1920
atccagctgg tggagagcgg aggaggactg gtgcagccag gaggatctgt gaggctgagc 1980

```
tgcgcagcat ccggatacaa cttcaagacc tatggcatgt cctgggtgcg ccaggcacca   2040
ggcaagggac tggagtggat gggctggatc aatacctact ctggcatgcc tacatatgcc   2100
gacgatttca agggccggtt caccttttct ctggacacca gcaagaacac agcctacctg   2160
cagatcaatt ccctgcgggc cgaggacaca gccgtgtact tttgtgccag accccctgctg   2220
ggcctggatt attggggcca gggcaccctg gtgacagtga gctccgctag caccaagggc   2280
ccatcggtct tccccctggc accctcctcc aagagcacct ctgggggcac agcggccctg   2340
ggctgcctgg tcaaggacta cttccccgaa ccggtgacgg tgtcgtggaa ctcaggcgcc   2400
ctgaccagcg gcgtgcacac cttcccggct gtcctacagt cctcaggact ctactccctc   2460
agcagcgtgg tgaccgtgcc ctccagcagc ttgggcaccc agacctacat ctgcaacgtg   2520
aatcacaagc ccagcaacac caaggtggac aagaaagttg agcccaaatc ttgtgacaaa   2580
actcacacat gcccaccgtg cccagcacct gaactcctgg ggggaccgtc agtcttcctc   2640
ttccccccaa aacccaagga caccctcatg atctcccgga cccctgaggt cacatgcgtg   2700
gtggtggacg tgagccacga agaccctgag gtcaagttca actggtacgt ggacggcgtg   2760
gaggtgcata atgccaagac aaagccgcgg gaggagcagt acaacagcac gtaccgtgtg   2820
gtcagcgtcc tcaccgtcct gcaccaggac tggctgaatg gcaaggagta caagtgcaag   2880
gtctccaaca aagccctccc agcccccatc gagaaaacca tctccaaagc caaagggcag   2940
ccccgagaac cacaggtgta caccctgccc ccatcccggg aggagatgac caagaaccag   3000
gtcagcctga cctgcctggt caaaggcttc tatcccagcg acatcgccgt ggagtgggag   3060
agcaatgggc agccggagaa caactacaag accacgcctc ccgtgctgga ctccgacggc   3120
tccttcttcc tctacagcaa gctcaccgtg gacaagagca ggtggcagca ggggaacgtc   3180
ttctcatgct ccgtgatgca tgaggctctg cacaaccact acacgcagaa gagcctctcc   3240
ctgtctccgg gtaaatgaga attctgcaga tatccatcac actggcggcc gctcgagcat   3300
gcatctagag ggccctattc tatagtgtca cctaaatgct agagctcgct gatcagcctc   3360
gactgtgcct tctagttgcc agccatctgt tgtttgcccc tcccccgtgc cttccttgac   3420
cctggaaggt gccactccca ctgtcctttc ctaataaaat gaggaaattg catcgcattg   3480
tctgagtagg tgtcattcta ttctgggggg tggggtgggg caggacagca agggggagga   3540
ttgggaagac aatagcaggc atgctgggga tgcggtgggc tctatggctt ctgaggcgga   3600
aagaaccagc tgcattaatg aatcggccaa cgcgcgggga gaggcggttt gcgtattggg   3660
cgctcttcgc tcgcgatctg gaggacaaat tacacacact tgcgcctgag cgccaagcac   3720
agggttgttg gtcctcatat tcacgaggtc gctgagagca cggtgggcta atgttgccat   3780
gggtagcata tactacccaa atatctggat agcatatgct atcctaatct atatctgggt   3840
agcataggct atcctaatct atatctgggt agcatatgct atcctaatct atatctgggt   3900
agtatatgct atcctaattt atatctgggt agcataggct atcctaatct atatctgggt   3960
agcatatgct atcctaatct atatctgggt agtatatgct atcctaatct gtatccgggt   4020
agcatatgct atcctaatag agattagggt agtatatgct atcctaattt atatctgggt   4080
agcatatact acccaaatat ctggatagca tatgctatcc taatctatat ctgggtagca   4140
tatgctatcc taatctatat ctgggtagca taggctatcc taatctatat ctgggtagca   4200
tatgctatcc taatctatat ctgggtagta tatgctatcc taatttatat ctgggtagca   4260
taggctatcc taatctatat ctgggtagca tatgctatcc taatctatat ctgggtagta   4320
```

```
tatgctatcc taatctgtat ccgggtagca tatgctatcc tcatgcatat acagtcagca   4380
tatgataccc agtagtagag tgggagtgct atcctttgca tatgccgcca cctcccaagg   4440
gggcgtgaat tttcgctgct tgtccttttc ctgcagccgg ccgcttcctc gctcactgac   4500
tcgctgcgct cggtcgttcg gctgcggcga gcggtatcag ctcactcaaa ggcggtaata   4560
cggttatcca cagaatcagg ggataacgca ggaaagaaca tgtgagcaaa aggccagcaa   4620
aaggccagga accgtaaaaa ggccgcgttg ctggcgtttt tccataggct ccgcccccct   4680
gacgagcatc acaaaaatcg acgctcaagt cagaggtggc gaaacccgac aggactataa   4740
agataccagg cgtttccccc tggaagctcc ctcgtgcgct ctcctgttcc gaccctgccg   4800
cttaccggat acctgtccgc ctttctccct tcgggaagcg tggcgctttc tcaatgctca   4860
cgctgtaggt atctcagttc ggtgtaggtc gttcgctcca agctgggctg tgtgcacgaa   4920
ccccccgttc agcccgaccg ctgcgcctta tccggtaact atcgtcttga gtccaacccg   4980
gtaagacacg acttatcgcc actggcagca gccactggta acaggattag cagagcgagg   5040
tatgtaggcg gtgctacaga gttcttgaag tggtggccta actacggcta cactagaagg   5100
acagtatttg gtatctgcgc tctgctgaag ccagttacct tcggaaaaag agttggtagc   5160
tcttgatccg gcaaacaaac caccgctggt agcggtggtt tttttgtttg caagcagcag   5220
attacgcgca gaaaaaaagg atctcaagaa gatcctttga tcttttctac ggggtctgac   5280
gctcagtgga acgaaaactc acgttaaggg attttggtca tgagattatc aaaaaggatc   5340
ttcacctaga tccttttaaa ttaaaaatga agttttaaat caatctaaag tatatatgag   5400
taaacttggt ctgacagtta ccaatgctta atcagtgagg cacctatctc agcgatctgt   5460
ctatttcgtt catccatagt tgcctgactc cccgtcgtgt agataactac gatacgggag   5520
ggcttaccat ctggccccag tgctgcaatg ataccgcgag acccacgctc accggctcca   5580
gatttatcag caataaacca gccagccgga agggccgagc gcagaagtgg tcctgcaact   5640
ttatccgcct ccatccagtc tattaattgt tgccgggaag ctagagtaag tagttcgcca   5700
gttaatagtt tgcgcaacgt tgttgccatt gctacaggca tcgtggtgtc acgctcgtcg   5760
tttggtatgg cttcattcag ctccggttcc caacgatcaa ggcgagttac atgatccccc   5820
atgttgtgca aaaaagcggt tagctccttc ggtcctccga tcgttgtcag aagtaagttg   5880
gccgcagtgt tatcactcat ggttatggca gcactgcata attctcttac tgtcatgcca   5940
tccgtaagat gcttttctgt gactggtgag tattcaacca agtcattctg agaatagtgt   6000
atgcggcgac cgagttgctc ttgcccggcg tcaatacggg ataataccgc gccacatagc   6060
agaactttaa aagtgctcat cattggaaaa cgttcttcgg ggcgaaaact ctcaaggatc   6120
ttaccgctgt tgagatccag ttcgatgtaa cccactcgtg cacccaactg atcttcagca   6180
tcttttactt tcaccagcgt ttctgggtga gcaaaaacag gaaggcaaaa tgccgcaaaa   6240
aagggaataa gggcgacacg gaaatgttga atactcatac tcttcctttt tcaatattat   6300
tgaagcattt atcagggtta ttgtctcatg agcggataca tatttgaatg tatttagaaa   6360
aataaacaaa taggggttcc gcgcacattt ccccgaaaag tgccacctga cgtc         6414
```

<210> SEQ ID NO 92
<211> LENGTH: 5733
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 92

```
gacggatcgg gagatctccc gatcccctat ggtgcactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg accattgcat acgttgtatc catatcataa    240
tatgtacatt tatattggct catgtccaac attaccgcca tgttgacatt gattattgac    300
tagttattaa tagtaatcaa ttacggggtc attagttcat agcccatata tggagttccg    360
cgttacataa cttacggtaa atggcccgcc tggctgaccg cccaacgacc cccgcccatt    420
gacgtcaata atgacgtatg ttcccatagt aacgccaata gggactttcc attgacgtca    480
atgggtggac tatttacggt aaactgccca cttggcagta catcaagtgt atcatatgcc    540
aagtacgccc cctattgacg tcaatgacgg taaatggccc gcctggcatt atgcccagta    600
catgacctta tgggactttc ctacttggca gtacatctac gtattagtca tcgctattac    660
catggtgatg cggttttggc agtacatcaa tgggcgtgga tagcggtttg actcacgggg    720
atttccaagt ctccacccca ttgacgtcaa tgggagtttg ttttggcacc aaaatcaacg    780
ggactttcca aaatgtcgta acaactccgc cccattgacg caaatgggcg gtaggcgtgt    840
acggtgggag gtctatataa gcagagctcg tttagtgaac cgtcagatcg cctggagacg    900
ccatccacgc tgttttgacc tccatagaag acaccgggac cgatccagcc tccgcggccg    960
ggaacggtgc attggaacgc ggattccccg tgccaagagt gacgtaagta ccgcctatag   1020
actctatagg cacacccctt tggctcttat gcatgctata ctgtttttgg cttggggcct   1080
atacaccccc gcttccttat gctataggtg atggtatagc ttagcctata ggtgtgggtt   1140
attgaccatt attgaccact cccctattgg tgacgatact ttccattact aatccataac   1200
atggctcttt gccacaacta tctctattgg ctatatgcca atactctgtc cttcagagac   1260
tgacacggac tctgtatttt tacaggatgg ggtcccattt attatttaca aattcacata   1320
tacaacaacg ccgtcccccg tgcccgcagt ttttattaaa catagcgtgg gatctccacg   1380
cgaatctcgg gtacgtgttc cggacatggg ctcttctccg gtagcggcgg agcttccaca   1440
tccgagccct ggtcccatgc ctccagcggc tcatggtcgc tcggcagctc cttgctccta   1500
acagtggagg ccagacttag gcacagcaca atgcccacca ccaccagtgt gccgcacaag   1560
gccgtggcgg tagggtatgt gtctgaaaat gagcgtggag attgggctcg cacggctgac   1620
gcagatggaa gacttaaggc agcggcagaa gaagatgcag gcagctgagt tgttgtattc   1680
tgataagagt cagaggtaac tcccgttgcg gtgctgttaa cggtggaggg cagtgtagtc   1740
tgagcagaac tcgttgctgc cgcgcgcgcc accagacata atagctgaca gactaacaga   1800
ctgttccttt ccatgggtct ttctgcagt caccgtcctg acacgaagct tgccgccacc   1860
atgggctggt cctgtatcat cctgttcctg gtggctacag ccacaggagt gcatagtgac   1920
atccagatga cacagtcccc tagctccctg agcgcctccg tgggcgatag ggtgaccatc   1980
acatgcaagt ctagccagtc tctgctgcac agcgacggca agaccttcct gaactggttt   2040
cagcagaagc ccggcaagtc tcctaagctg ctgatctacc tggtgtccaa gctggagtct   2100
ggcgtgccca gcagattctc tggcagcggc tccggcacag actttaccct gacaatctcc   2160
tctctgcagc cagaggattt cgccacctac tattgtctgc agcacaccca cttccccctg   2220
acatttggcc agggcaccaa ggtggagatc aagcgtacgg tggctgcacc atctgtcttc   2280
atcttcccgc catctgatga gcagttgaaa tctggaactg cctctgttgt gtgcctgctg   2340
```

aataacttct atcccagaga ggccaaagta cagtggaagg tggataacgc cctccaatcg 2400
ggtaactccc aggagagtgt cacagagcag gacagcaagg acagcaccta cagcctcagc 2460
agcaccctga cgctgagcaa agcagactac gagaaacaca aagtctacgc ctgcgaagtc 2520
acccatcagg gcctgagctc gcccgtcaca aagagcttca acaggggaga gtgttaggaa 2580
ttctgcagat atccatcaca ctggcggccg ctcgagcatg catctagagg gccctattct 2640
atagtgtcac ctaaatgcta gagctcgctg atcagcctcg actgtgcctt ctagttgcca 2700
gccatctgtt gtttgcccct cccccgtgcc ttccttgacc ctggaaggtg ccactcccac 2760
tgtcctttcc taataaaatg aggaaattgc atcgcattgt ctgagtaggt gtcattctat 2820
tctggggggt ggggtggggc aggacagcaa gggggaggat tgggaagaca atagcaggca 2880
tgctggggat gcggtgggct ctatggcttc tgaggcggaa agaaccagct gcattaatga 2940
atcggccaac gcgcggggag aggcggtttg cgtattgggc gctcttcgct agcgatctgg 3000
aggacaaatt acacacactt gcgcctgagc gccaagcaca gggttgttgg tcctcatatt 3060
cacgaggtcg ctgagagcac ggtgggctaa tgttgccatg ggtagcatat actacccaaa 3120
tatctggata gcatatgcta tcctaatcta tatctgggta gcataggcta tcctaatcta 3180
tatctgggta gcatatgcta tcctaatcta tatctgggta gtatatgcta tcctaattta 3240
tatctgggta gcataggcta tcctaatcta tatctgggta gcatatgcta tcctaatcta 3300
tatctgggta gtatatgcta tcctaatctg tatccgggta gcatatgcta tcctaataga 3360
gattagggta gtatatgcta tcctaattta tatctgggta gcatatacta cccaaatatc 3420
tggatagcat atgctatcct aatctatatc tgggtagcat atgctatcct aatctatatc 3480
tgggtagcat aggctatcct aatctatatc tgggtagcat atgctatcct aatctatatc 3540
tgggtagtat atgctatcct aatttatatc tgggtagcat aggctatcct aatctatatc 3600
tgggtagcat atgctatcct aatctatatc tgggtagtat atgctatcct aatctgtatc 3660
cgggtagcat atgctatcct catgcatata cagtcagcat atgataccca gtagtagagt 3720
gggagtgcta tcctttgcat atgccgccac ctcccaaggg ggcgtgaatt ttcgctgctt 3780
gtccttttcc tgcagctagc cgcttcctcg ctcactgact cgctgcgctc ggtcgttcgg 3840
ctgcggcgag cggtatcagc tcactcaaag gcggtaatac ggttatccac agaatcaggg 3900
gataacgcag gaaagaacat gtgagcaaaa ggccagcaaa aggccaggaa ccgtaaaaag 3960
gccgcgttgc tggcgttttt ccataggctc cgcccccctg acgagcatca caaaaatcga 4020
cgctcaagtc agaggtggcg aaacccgaca ggactataaa gataccaggc gtttccccct 4080
ggaagctccc tcgtgcgctc tcctgttccg accctgccgc ttaccggata cctgtccgcc 4140
tttctccctt cgggaagcgt ggcgctttct caatgctcac gctgtaggta tctcagttcg 4200
gtgtaggtcg ttcgctccaa gctgggctgt gtgcacgaac cccccgttca gcccgaccgc 4260
tgcgccttat ccggtaacta tcgtcttgag tccaacccgg taagacacga cttatcgcca 4320
ctggcagcag ccactggtaa caggattagc agagcgaggt atgtaggcgg tgctacagag 4380
ttcttgaagt ggtggcctaa ctacggctac actagaagga cagtatttgg tatctgcgct 4440
ctgctgaagc cagttacctt cggaaaaaga gttggtagct cttgatccgg caaacaaacc 4500
accgctggta gcggtggttt ttttgtttgc aagcagcaga ttacgcgcag aaaaaaagga 4560
tctcaagaag atcctttgat cttttctacg gggtctgacg ctcagtggaa cgaaaactca 4620
cgttaaggga ttttggtcat gagattatca aaaaggatct tcacctagat ccttttaaat 4680

-continued taaaaatgaa gttttaaatc aatctaaagt atatatgagt aaacttggtc tgacagttac 4740
caatgcttaa tcagtgaggc acctatctca gcgatctgtc tatttcgttc atccatagtt 4800
gcctgactcc ccgtcgtgta gataactacg atacgggagg gcttaccatc tggccccagt 4860
gctgcaatga taccgcgaga cccacgctca ccggctccag atttatcagc aataaaccag 4920
ccagccggaa gggccgagcg cagaagtggt cctgcaactt tatccgcctc catccagtct 4980
attaattgtt gccgggaagc tagagtaagt agttcgccag ttaatagttt gcgcaacgtt 5040
gttgccattg ctacaggcat cgtggtgtca cgctcgtcgt ttggtatggc ttcattcagc 5100
tccggttccc aacgatcaag gcgagttaca tgatccccca tgttgtgcaa aaaagcggtt 5160
agctccttcg gtcctccgat cgttgtcaga agtaagttgg ccgcagtgtt atcactcatg 5220
gttatggcag cactgcataa ttctcttact gtcatgccat ccgtaagatg cttttctgtg 5280
actggtgagt attcaaccaa gtcattctga gaatagtgta tgcggcgacc gagttgctct 5340
tgcccggcgt caatacggga taataccgcg ccacatagca gaactttaaa agtgctcatc 5400
attggaaaac gttcttcggg gcgaaaactc tcaaggatct taccgctgtt gagatccagt 5460
tcgatgtaac ccactcgtgc acccaactga tcttcagcat cttttacttt caccagcgtt 5520
tctgggtgag caaaaacagg aaggcaaaat gccgcaaaaa agggaataag ggcgacacgg 5580
aaatgttgaa tactcatact cttccttttt caatattatt gaagcattta tcagggttat 5640
tgtctcatga gcggatacat atttgaatgt atttagaaaa ataaacaaat aggggttccg 5700
cgcacatttc cccgaaaagt gccacctgac gtc 5733

<210> SEQ ID NO 93
<211> LENGTH: 6414
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 93
gacggatcgg gagatctccc gatcccctat ggtgcactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg accattgcat acgttgtatc catatcataa 240
tatgtacatt tatattggct catgtccaac attaccgcca tgttgacatt gattattgac 300
tagttattaa tagtaatcaa ttacggggtc attagttcat agcccatata tggagttccg 360
cgttacataa cttacggtaa atggcccgcc tggctgaccg cccaacgacc cccgcccatt 420
gacgtcaata atgacgtatg ttcccatagt aacgccaata gggactttcc attgacgtca 480
atgggtggac tatttacggt aaactgccca cttggcagta catcaagtgt atcatatgcc 540
aagtacgccc cctattgacg tcaatgacgg taaatggccc gcctggcatt atgcccagta 600
catgacctta tgggactttc ctacttggca gtacatctac gtattagtca tcgctattac 660
catggtgatg cggttttggc agtacatcaa tgggcgtgga tagcggtttg actcacgggg 720
atttccaagt ctccacccca ttgacgtcaa tgggagtttg ttttggcacc aaaatcaacg 780
ggactttcca aaatgtcgta acaactccgc cccattgacg caaatgggcg gtaggcgtgt 840
acggtgggag gtctatataa gcagagctcg tttagtgaac cgtcagatcg cctggagacg 900
ccatccacgc tgttttgacc tccatagaag acaccgggac cgatccagcc tccgcggccg 960

```
ggaacggtgc attggaacgc ggattccccg tgccaagagt gacgtaagta ccgcctatag   1020
actctatagg cacacccctt tggctcttat gcatgctata ctgtttttgg cttggggcct   1080
atacaccccc gcttccttat gctataggtg atggtatagc ttagcctata ggtgtgggtt   1140
attgaccatt attgaccact cccctattgg tgacgatact ttccattact aatccataac   1200
atggctcttt gccacaacta tctctattgg ctatatgcca atactctgtc cttcagagac   1260
tgacacggac tctgtatttt tacaggatgg ggtcccattt attatttaca aattcacata   1320
tacaacaacg ccgtcccccg tgcccgcagt ttttattaaa catagcgtgg gatctccacg   1380
cgaatctcgg gtacgtgttc cggacatggg ctcttctccg gtagcggcgg agcttccaca   1440
tccgagccct ggtcccatgc ctccagcggc tcatggtcgc tcggcagctc cttgctccta   1500
acagtggagg ccagacttag gcacagcaca atgcccacca ccaccagtgt gccgcacaag   1560
gccgtggcgg tagggtatgt gtctgaaaat gagcgtggag attgggctcg cacggctgac   1620
gcagatggaa gacttaaggc agcggcagaa gaagatgcag gcagctgagt tgttgtattc   1680
tgataagagt cagaggtaac tcccgttgcg gtgctgttaa cggtggaggg cagtgtagtc   1740
tgagcagaac tcgttgctgc cgcgcgcgcc accagacata atagctgaca gactaacaga   1800
ctgttccttt ccatgggtct tttctgcagt caccgtcctg acacgaagct tgccgccacc   1860
atgggctggt ccctgattct gctgttcctg gtggctgtgg ctaccagggt gctgagtcag   1920
atccagctgg tgcagtctgg ccccgagctg aagaagcctg gcgagaccgt gaagatctct   1980
tgcaaggcca gcggctacac attcaccaca tatggcatga gctgggtgaa gcaggcacca   2040
ggcaagggcc tgaagtggat gggctggatc aacacctact ccggcatgcc cacatatgcc   2100
gacgatttca agggccggtt cgccttttcc ctggagacct ctgccaccac agcctacctg   2160
cagatcaaca atctgaagaa tgaggacacc gccacatact tttgtgccag accccctgctg   2220
ggcctggatt attggggcca gggcaccaca ctgacagtga gctccgctag caccaagggc   2280
ccatcggtct tccccctggc accctcctcc aagagcacct ctgggggcac agcggccctg   2340
ggctgcctgg tcaaggacta cttccccgaa ccggtgacgg tgtcgtggaa ctcaggcgcc   2400
ctgaccagcg gcgtgcacac cttcccggct gtcctacagt cctcaggact ctactccctc   2460
agcagcgtgg tgaccgtgcc ctccagcagc ttgggcaccc agacctacat ctgcaacgtg   2520
aatcacaagc ccagcaacac caaggtggac aagaaagttg agcccaaatc ttgtgacaaa   2580
actcacacat gcccaccgtg cccagcacct gaactcctgg ggggaccgtc agtcttcctc   2640
ttccccccaa aacccaagga caccctcatg atctcccgga cccctgaggt cacatgcgtg   2700
gtggtggacg tgagccacga agaccctgag gtcaagttca actggtacgt ggacggcgtg   2760
gaggtgcata atgccaagac aaagccgcgg gaggagcagt acaacagcac gtaccgtgtg   2820
gtcagcgtcc tcaccgtcct gcaccaggac tggctgaatg gcaaggagta caagtgcaag   2880
gtctccaaca aagccctccc agcccccatc gagaaaacca tctccaaagc caaagggcag   2940
ccccgagaac cacaggtgta caccctgccc ccatcccggg aggagatgac caagaaccag   3000
gtcagcctga cctgcctggt caaaggcttc tatcccagcg acatcgccgt ggagtgggag   3060
agcaatgggc agccggagaa caactacaag accacgcctc ccgtgctgga ctccgacggc   3120
tccttcttcc tctacagcaa gctcaccgtg gacaagagca ggtggcagca ggggaacgtc   3180
ttctcatgct ccgtgatgca tgaggctctg cacaaccact acacgcagaa gagcctctcc   3240
ctgtctccgg gtaaatgaga attctgcaga tatccatcac actggcggcc gctcgagcat   3300
gcatctagag ggccctattc tatagtgtca cctaaatgct agagctcgct gatcagcctc   3360
```

```
gactgtgcct tctagttgcc agccatctgt tgtttgcccc tcccccgtgc cttccttgac   3420
cctggaaggt gccactccca ctgtcctttc ctaataaaat gaggaaattg catcgcattg   3480
tctgagtagg tgtcattcta ttctgggggg tggggtgggg caggacagca agggggagga   3540
ttgggaagac aatagcaggc atgctgggga tgcggtgggc tctatggctt ctgaggcgga   3600
aagaaccagc tgcattaatg aatcggccaa cgcgcgggga gaggcggttt gcgtattggg   3660
cgctcttcgc tcgcgatctg gaggacaaat tacacacact tgcgcctgag cgccaagcac   3720
agggttgttg gtcctcatat tcacgaggtc gctgagagca cggtgggcta atgttgccat   3780
gggtagcata tactacccaa atatctggat agcatatgct atcctaatct atatctgggt   3840
agcataggct atcctaatct atatctgggt agcatatgct atcctaatct atatctgggt   3900
agtatatgct atcctaattt atatctgggt agcataggct atcctaatct atatctgggt   3960
agcatatgct atcctaatct atatctgggt agtatatgct atcctaatct gtatccgggt   4020
agcatatgct atcctaatag agattagggt agtatatgct atcctaattt atatctgggt   4080
agcatatact acccaaatat ctggatagca tatgctatcc taatctatat ctgggtagca   4140
tatgctatcc taatctatat ctgggtagca taggctatcc taatctatat ctgggtagca   4200
tatgctatcc taatctatat ctgggtagta tatgctatcc taatttatat ctgggtagca   4260
taggctatcc taatctatat ctgggtagca tatgctatcc taatctatat ctgggtagta   4320
tatgctatcc taatctgtat ccgggtagca tatgctatcc tcatgcatat acagtcagca   4380
tatgataccc agtagtagag tgggagtgct atcctttgca tatgccgcca cctcccaagg   4440
gggcgtgaat tttcgctgct tgtccttttc ctgcagccgg ccgcttcctc gctcactgac   4500
tcgctgcgct cggtcgttcg gctgcggcga gcggtatcag ctcactcaaa ggcggtaata   4560
cggttatcca cagaatcagg ggataacgca ggaaagaaca tgtgagcaaa aggccagcaa   4620
aaggccagga accgtaaaaa ggccgcgttg ctggcgtttt tccataggct ccgcccccct   4680
gacgagcatc acaaaaatcg acgctcaagt cagaggtggc gaaacccgac aggactataa   4740
agataccagg cgtttccccc tggaagctcc ctcgtgcgct ctcctgttcc gaccctgccg   4800
cttaccggat acctgtccgc ctttctccct tcgggaagcg tggcgctttc tcaatgctca   4860
cgctgtaggt atctcagttc ggtgtaggtc gttcgctcca agctgggctg tgtgcacgaa   4920
ccccccgttc agcccgaccg ctgcgcctta tccggtaact atcgtcttga gtccaacccg   4980
gtaagacacg acttatcgcc actggcagca gccactggta acaggattag cagagcgagg   5040
tatgtaggcg gtgctacaga gttcttgaag tggtggccta actacggcta cactagaagg   5100
acagtatttg gtatctgcgc tctgctgaag ccagttacct tcggaaaaag agttggtagc   5160
tcttgatccg gcaaacaaac caccgctggt agcggtggtt tttttgtttg caagcagcag   5220
attacgcgca gaaaaaaagg atctcaagaa gatcctttga tcttttctac ggggtctgac   5280
gctcagtgga acgaaaactc acgttaaggg attttggtca tgagattatc aaaaaggatc   5340
ttcacctaga tccttttaaa ttaaaaatga agttttaaat caatctaaag tatatatgag   5400
taaacttggt ctgacagtta ccaatgctta atcagtgagg cacctatctc agcgatctgt   5460
ctatttcgtt catccatagt tgcctgactc cccgtcgtgt agataactac gatacgggag   5520
ggcttaccat ctggccccag tgctgcaatg ataccgcgag acccacgctc accggctcca   5580
gatttatcag caataaacca gccagccgga agggccgagc gcagaagtgg tcctgcaact   5640
ttatccgcct ccatccagtc tattaattgt tgccgggaag ctagagtaag tagttcgcca   5700
```

gttaatagtt tgcgcaacgt tgttgccatt gctacaggca tcgtggtgtc acgctcgtcg 5760
tttggtatgg cttcattcag ctccggttcc caacgatcaa ggcgagttac atgatccccc 5820
atgttgtgca aaaaagcggt tagctccttc ggtcctccga tcgttgtcag aagtaagttg 5880
gccgcagtgt tatcactcat ggttatggca gcactgcata attctcttac tgtcatgcca 5940
tccgtaagat gcttttctgt gactggtgag tattcaacca agtcattctg agaatagtgt 6000
atgcggcgac cgagttgctc ttgcccggcg tcaatacggg ataataccgc gccacatagc 6060
agaactttaa aagtgctcat cattggaaaa cgttcttcgg ggcgaaaact ctcaaggatc 6120
ttaccgctgt tgagatccag ttcgatgtaa cccactcgtg cacccaactg atcttcagca 6180
tcttttactt tcaccagcgt ttctgggtga gcaaaaacag gaaggcaaaa tgccgcaaaa 6240
aagggaataa gggcgacacg gaaatgttga atactcatac tcttcctttt tcaatattat 6300
tgaagcattt atcagggtta ttgtctcatg agcggataca tatttgaatg tatttagaaa 6360
aataaacaaa taggggttcc gcgcacattt ccccgaaaag tgccacctga cgtc 6414

<210> SEQ ID NO 94
<211> LENGTH: 5733
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 94
gacggatcgg gagatctccc gatcccctat ggtgcactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg accattgcat acgttgtatc catatcataa 240
tatgtacatt tatattggct catgtccaac attaccgcca tgttgacatt gattattgac 300
tagttattaa tagtaatcaa ttacggggtc attagttcat agcccatata tggagttccg 360
cgttacataa cttacggtaa atggcccgcc tggctgaccg cccaacgacc cccgcccatt 420
gacgtcaata atgacgtatg ttcccatagt aacgccaata gggactttcc attgacgtca 480
atgggtggac tatttacggt aaactgccca cttggcagta catcaagtgt atcatatgcc 540
aagtacgccc cctattgacg tcaatgacgg taaatggccc gcctggcatt atgcccagta 600
catgacctta tgggactttc ctacttggca gtacatctac gtattagtca tcgctattac 660
catggtgatg cggttttggc agtacatcaa tgggcgtgga tagcggtttg actcacgggg 720
atttccaagt ctccacccca ttgacgtcaa tgggagtttg ttttggcacc aaaatcaacg 780
ggactttcca aaatgtcgta acaactccgc cccattgacg caaatgggcg gtaggcgtgt 840
acggtgggag gtctatataa gcagagctcg tttagtgaac cgtcagatcg cctggagacg 900
ccatccacgc tgttttgacc tccatagaag acaccgggac cgatccagcc tccgcggccg 960
ggaacggtgc attggaacgc ggattccccg tgccaagagt gacgtaagta ccgcctatag 1020
actctatagg cacacccctt tggctcttat gcatgctata ctgtttttgg cttggggcct 1080
atacaccccc gcttccttat gctataggtg atggtatagc ttagcctata ggtgtgggtt 1140
attgaccatt attgaccact cccctattgg tgacgatact ttccattact aatccataac 1200
atggctcttt gccacaacta tctctattgg ctatatgcca atactctgtc cttcagagac 1260
tgacacggac tctgtatttt tacaggatgg ggtcccattt attatttaca aattcacata 1320

```
tacaacaacg ccgtcccccg tgcccgcagt ttttattaaa catagcgtgg gatctccacg   1380
cgaatctcgg gtacgtgttc cggacatggg ctcttctccg gtagcggcgg agcttccaca   1440
tccgagccct ggtcccatgc ctccagcggc tcatggtcgc tcggcagctc cttgctccta   1500
acagtggagg ccagacttag gcacagcaca atgcccacca ccaccagtgt gccgcacaag   1560
gccgtggcgg tagggtatgt gtctgaaaat gagcgtggag attgggctcg cacggctgac   1620
gcagatggaa gacttaaggc agcggcagaa gaagatgcag gcagctgagt tgttgtattc   1680
tgataagagt cagaggtaac tcccgttgcg gtgctgttaa cggtggaggg cagtgtagtc   1740
tgagcagaac tcgttgctgc cgcgcgcgcc accagacata atagctgaca gactaacaga   1800
ctgttccttt ccatgggtct tttctgcagt caccgtcctg acacgaagct tgccgccacc   1860
atgggctggt cctgtatcat cctgttcctg gtggctacag ccacaggagt gcatagtgac   1920
atcgtgatga cccagacacc actgtctctg agcgtgacaa tcggccagcc cgcctccatc   1980
tcttgcaaga gctcccagag cctgctgcac tccgatggca agaccttcct gaactggttt   2040
ctgcagaggc caggacagtc ccctaagctg ctgatctacc tggtgtctaa gctggagagc   2100
ggaatccctg accggttcag cggatccgga tctggaaccg acttcaccct gaagatctct   2160
agagtggagg tggaggacct gggcgtgtac tattgtctgc agcacaccca cttcccccctg   2220
acatttggcg ccggcaccaa gctggagatc aagcgtacgg tggctgcacc atctgtcttc   2280
atcttcccgc catctgatga gcagttgaaa tctggaactg cctctgttgt gtgcctgctg   2340
aataacttct atcccagaga ggccaaagta cagtggaagg tggataacgc cctccaatcg   2400
ggtaactccc aggagagtgt cacagagcag gacagcaagg acagcaccta cagcctcagc   2460
agcaccctga cgctgagcaa agcagactac gagaaacaca aagtctacgc ctgcgaagtc   2520
acccatcagg gcctgagctc gcccgtcaca aagagcttca acaggggaga gtgttaggaa   2580
ttctgcagat atccatcaca ctggcggccg ctcgagcatg catctagagg gccctattct   2640
atagtgtcac ctaaatgcta gagctcgctg atcagcctcg actgtgcctt ctagttgcca   2700
gccatctgtt gtttgcccct cccccgtgcc ttccttgacc ctggaaggtg ccactcccac   2760
tgtcctttcc taataaaatg aggaaattgc atcgcattgt ctgagtaggt gtcattctat   2820
tctggggggt ggggtggggc aggacagcaa gggggaggat tgggaagaca atagcaggca   2880
tgctggggat gcggtgggct ctatggcttc tgaggcggaa agaaccagct gcattaatga   2940
atcggccaac gcgcggggag aggcggtttg cgtattgggc gctcttcgct agcgatctgg   3000
aggacaaatt acacacactt gcgcctgagc gccaagcaca gggttgttgg tcctcatatt   3060
cacgaggtcg ctgagagcac ggtgggctaa tgttgccatg ggtagcatat actacccaaa   3120
tatctggata gcatatgcta tcctaatcta tatctgggta gcataggcta tcctaatcta   3180
tatctgggta gcatatgcta tcctaatcta tatctgggta gtatatgcta tcctaattta   3240
tatctgggta gcataggcta tcctaatcta tatctgggta gcatatgcta tcctaatcta   3300
tatctgggta gtatatgcta tcctaatctg tatccgggta gcatatgcta tcctaataga   3360
gattagggta gtatatgcta tcctaattta tatctgggta gcatatacta cccaaatatc   3420
tggatagcat atgctatcct aatctatatc tgggtagcat atgctatcct aatctatatc   3480
tgggtagcat aggctatcct aatctatatc tgggtagcat atgctatcct aatctatatc   3540
tgggtagtat atgctatcct aatttatatc tgggtagcat aggctatcct aatctatatc   3600
tgggtagcat atgctatcct aatctatatc tgggtagtat atgctatcct aatctgtatc   3660
cgggtagcat atgctatcct catgcatata cagtcagcat atgataccca gtagtagagt   3720
```

```
gggagtgcta tcctttgcat atgccgccac ctcccaaggg ggcgtgaatt ttcgctgctt   3780

gtccttttcc tgcagctagc cgcttcctcg ctcactgact cgctgcgctc ggtcgttcgg   3840

ctgcggcgag cggtatcagc tcactcaaag gcggtaatac ggttatccac agaatcaggg   3900

gataacgcag gaaagaacat gtgagcaaaa ggccagcaaa aggccaggaa ccgtaaaaag   3960

gccgcgttgc tggcgttttt ccataggctc cgcccccctg acgagcatca caaaaatcga   4020

cgctcaagtc agaggtggcg aaacccgaca ggactataaa gataccaggc gtttccccct   4080

ggaagctccc tcgtgcgctc tcctgttccg accctgccgc ttaccggata cctgtccgcc   4140

tttctccctt cgggaagcgt ggcgctttct caatgctcac gctgtaggta tctcagttcg   4200

gtgtaggtcg ttcgctccaa gctgggctgt gtgcacgaac cccccgttca gcccgaccgc   4260

tgcgccttat ccggtaacta tcgtcttgag tccaacccgg taagacacga cttatcgcca   4320

ctggcagcag ccactggtaa caggattagc agagcgaggt atgtaggcgg tgctacagag   4380

ttcttgaagt ggtggcctaa ctacggctac actagaagga cagtatttgg tatctgcgct   4440

ctgctgaagc cagttacctt cggaaaaaga gttggtagct cttgatccgg caaacaaacc   4500

accgctggta gcggtggttt ttttgtttgc aagcagcaga ttacgcgcag aaaaaaagga   4560

tctcaagaag atcctttgat cttttctacg gggtctgacg ctcagtggaa cgaaaactca   4620

cgttaaggga ttttggtcat gagattatca aaaaggatct tcacctagat ccttttaaat   4680

taaaaatgaa gttttaaatc aatctaaagt atatatgagt aaacttggtc tgacagttac   4740

caatgcttaa tcagtgaggc acctatctca gcgatctgtc tatttcgttc atccatagtt   4800

gcctgactcc ccgtcgtgta gataactacg atacgggagg gcttaccatc tggccccagt   4860

gctgcaatga taccgcgaga cccacgctca ccggctccag atttatcagc aataaaccag   4920

ccagccggaa gggccgagcg cagaagtggt cctgcaactt tatccgcctc catccagtct   4980

attaattgtt gccgggaagc tagagtaagt agttcgccag ttaatagttt gcgcaacgtt   5040

gttgccattg ctacaggcat cgtggtgtca cgctcgtcgt ttggtatggc ttcattcagc   5100

tccggttccc aacgatcaag gcgagttaca tgatccccca tgttgtgcaa aaaagcggtt   5160

agctccttcg gtcctccgat cgttgtcaga agtaagttgg ccgcagtgtt atcactcatg   5220

gttatggcag cactgcataa ttctcttact gtcatgccat ccgtaagatg cttttctgtg   5280

actggtgagt attcaaccaa gtcattctga gaatagtgta tgcggcgacc gagttgctct   5340

tgcccggcgt caatacggga taataccgcg ccacatagca gaactttaaa agtgctcatc   5400

attggaaaac gttcttcggg gcgaaaactc tcaaggatct taccgctgtt gagatccagt   5460

tcgatgtaac ccactcgtgc acccaactga tcttcagcat cttttacttt caccagcgtt   5520

tctgggtgag caaaaacagg aaggcaaaat gccgcaaaaa agggaataag ggcgacacgg   5580

aaatgttgaa tactcatact cttccttttt caatattatt gaagcattta tcagggttat   5640

tgtctcatga gcggatacat atttgaatgt atttagaaaa ataaacaaat aggggttccg   5700

cgcacatttc cccgaaaagt gccacctgac gtc                                5733
```

<210> SEQ ID NO 95
<211> LENGTH: 116
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 95

-continued

```
Glu Ile Gln Leu Val Glu Ser Gly Gly Gly Leu Val Gln Pro Gly Gly
1               5                   10                  15

Ser Val Arg Leu Ser Cys Ala Ala Ser Gly Tyr Asn Phe Lys Thr Tyr
            20                  25                  30

Gly Met Ser Trp Val Arg Gln Ala Pro Gly Lys Gly Leu Glu Trp Met
        35                  40                  45

Gly Trp Ile Asn Thr Tyr Ser Gly Met Pro Thr Tyr Ala Asp Asp Phe
    50                  55                  60

Lys Gly Arg Phe Thr Phe Ser Leu Asp Thr Ser Lys Asn Thr Ala Tyr
65                  70                  75                  80

Leu Gln Ile Asn Ser Leu Arg Ala Glu Asp Thr Ala Val Tyr Phe Cys
                85                  90                  95

Ala Arg Pro Leu Leu Gly Leu Asp Tyr Trp Gly Gln Gly Thr Leu Val
            100                 105                 110

Thr Val Ser Ser
        115


<210> SEQ ID NO 96
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu His Ser
            20                  25                  30

Asp Gly Lys Thr Phe Leu Asn Trp Phe Gln Gln Lys Pro Gly Lys Ser
        35                  40                  45

Pro Lys Leu Leu Ile Tyr Leu Val Ser Lys Leu Glu Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Leu Gln His
                85                  90                  95

Thr His Phe Pro Leu Thr Phe Gly Gln Gly Thr Lys Val Glu Ile Lys
            100                 105                 110
```

COMPOSITIONS AND METHODS FOR TREATING SERPIN B13 DISORDERS

CROSS-REFERENCE TO RELATED APPLICATION

This application claims priority to U.S. Provisional Application No. 62/883,443 that was filed on Aug. 6, 2019, and U.S. Provisional Application No. 63/040,356 that was filed on Jun. 17, 2020. The entire content of the applications referenced above are hereby incorporated by reference herein.

SEQUENCE LISTING

The instant application contains a Sequence Listing which has been submitted electronically in ASCII format and is hereby incorporated by reference in its entirety. Said ASCII copy, created on Jun. 21, 2022, is named 09531_469US1_SL.txt and is 133,696 bytes in size.

BACKGROUND

Intracellular (clade B) OVA-serpin protease inhibitors play an important role in tissue homeostasis by protecting cells from death in response to hypo-osmotic stress, heat shock, and other stimuli. High levels of anti-serpinB13 Abs were accompanied by low levels of anti-insulin autoantibodies, reduced numbers of islet-associated T cells, and delayed onset of diabetes. In mice, exposure to anti-serpinB13 mAb alone also decreased islet inflammation, and coadministration of this reagent and a suboptimal dose of anti-CD3 mAb accelerated recovery from diabetes. Czyzyk et al., Enhanced Anti-Serpin Antibody Activity Inhibits Autoimmune Inflammation in Type 1 Diabetes, *Journal of Immunology,* 2012, 188: 6319-6327. It has also been observed that injecting anti-serpin B13 monoclonal Ab enhanced beta cell proliferation and Reg gene expression, induced the generation of ~80 pancreatic islets per animal, and ultimately led to increase in the beta cell mass. These findings are relevant to human T1D because the analysis of subjects recently diagnosed with T1D revealed an association between baseline anti-serpin activity and slower residual beta cell function decline in the first year after the onset of diabetes. Kryvalap et al., Antibody Response to Serpin B13 Induces Adaptive Changes in Mouse Pancreatic Islets and Slows Down the Decline in the Residual Beta Cell Function in Children with Recent Onset of Type 1 Diabetes Mellitus, *JBC,* 291(1): 266-278 (Jan. 1, 2016). It has been observed that cellular proliferation in mouse and human pancreatic islets is regulated by serpin B13 inhibition and downstream targeting of E-cadherin by cathepsin L. Lo et al., *Diabetologia* (2019) 62:822-834.

Thus, there is a continuing need for compositions and methods for the treatment of OVA-serine proteinase inhibitor (serpin) B13-related disorders in humans.

SUMMARY

The present disclosure is based, at least in part, on the development of new monoclonal antibodies that selectively and specifically bind to OVA-serine proteinase inhibitor (serpin) B13. These antibodies and antigen-binding fragments thereof are useful for inhibiting serpin B13 and for treating serpin B13-related diseases, e.g., type I diabetes. Provided herein are these antibodies and antigen-binding fragments thereof, compositions and kits containing these antibodies and antibody fragments, and various methods of using these antibodies and antigen-binding fragments.

The new antibodies or antigen-binding fragments thereof have anti-serpin B13 effects. In some embodiments, the new antibodies or antigen-binding fragments thereof are chimeric antibodies. In some embodiments, the new antibodies or antigen-binding fragments thereof are humanized. The antigen-binding fragments can be Fab fragments, $F(ab')_2$ fragments, scFv fragments, or diabodies.

In another general aspect, the disclosure includes compositions that include at least one isolated monoclonal antibody or antigen-binding fragment disclosed herein.

In yet another aspect, the disclosure includes methods of inhibiting serpin B13 and methods of treating serpin B13-related disorders in a subject, e.g., a human, as well as uses of the compositions described herein to treat such serpin B13-related disorders. The methods of inhibiting serpin B13 in a subject include administering to the subject an effective amount of one or more of the compositions disclosed herein. The methods of treating a serpin B13-related disorder in a subject include first identifying a subject that has an serpin B13-related disorder; and then administering to the subject an effective amount of a monoclonal antibody described herein, e.g., one that binds to serpin B13. The monoclonal antibodies disclosed herein can be administered by various routes, e.g., intravenously, intradermally, subcutaneously, or orally.

In some embodiments, the new monoclonal antibodies disclosed herein are used to treat diabetes, such as type I diabetes, type 2 diabetes and diabetes in patients with chronic pancreatitis who undergo total pancreatectomy with autologous islet transplantation and still remain insulin dependent. In some embodiments, the new monoclonal antibodies disclosed herein are used to treat a serpin B13-related disorder, wherein the disorder is inflammatory or central nervous system disease. In some embodiments, the new monoclonal antibodies disclosed herein are used to treat bone fracture, skin wound/ulcer healing including diabetic foot, hair loss, multiple sclerosis, or lupus.

In some embodiments, the isolated monoclonal antibodies or antigen-binding fragments thereof (1) bind to serpin B13, and (2) comprise a heavy chain CDR1, a heavy chain CDR2, and a heavy chain CDR3. The heavy chain CDR1 can comprise the amino acid sequence of SEQ ID NO:1, 2, 26, 60, 70 or 80 or the amino acid sequence of SEQ ID NO:1, 2, 26, 60, 70 or 80 with a substitution at one, two, or three amino acid positions. The heavy chain CDR2 can comprise the amino acid sequence of SEQ ID NO:4, 27, 61, 71 or 81 or the amino acid sequence of SEQ ID NO:4, 27 61, 71 or 81 with a substitution at one, two, or three amino acid positions. The heavy chain CDR3 can comprise the amino acid sequence of SEQ ID NO:6, 28, 62, 72 or 82 or the amino acid sequence of SEQ ID NO:6, 28, 62, 72 or 82 with a substitution at one, two, or three amino acid positions. In some embodiments, the isolated monoclonal antibodies or antigen-binding fragments can further include one or more of the following light chain CDRs: (1) a light chain CDR1 comprises the amino acid sequence of SEQ ID NO:8, 29, 63, 73 or 83 or the amino acid sequence of SEQ ID NO:8, 29, 63, 73 or 83 with a substitution at one, two, or three amino acid positions; (2) a light chain CDR2 comprises the amino acid sequence of SEQ ID NO:10, 64, 74 or 84, or the amino acid sequence of SEQ ID NO:10, 64, 74 or 84 with a substitution at one, two, or three amino acid positions; and (3) a light chain CDR3 comprises the amino acid sequence of SEQ ID NO:12, 65, 75 or 85 or the amino acid sequence of SEQ ID NO:12, 65, 75 or 85 with a substitution at one, two, or three amino acid positions.

In some embodiments, the heavy chain CDR1 comprises the amino acid sequence of SEQ ID NO:1.

In some embodiments, the heavy chain CDR1 comprises the amino acid sequence of SEQ ID NO:2.

In some embodiments, the heavy chain CDR1 comprises the amino acid sequence of SEQ ID NO:26.

In some embodiments, the heavy chain CDR1 comprises the amino acid sequence of SEQ ID NO:60.

In some embodiments, the heavy chain CDR1 comprises the amino acid sequence of SEQ ID NO:70.

In some embodiments, the heavy chain CDR1 comprises the amino acid sequence of SEQ ID NO:80.

In certain embodiments, the heavy chain CDR2 comprises the amino acid sequence of SEQ ID NO:4.

In certain embodiments, the heavy chain CDR2 comprises the amino acid sequence of SEQ ID NO:27.

In some embodiments, the heavy chain CDR2 comprises the amino acid sequence of SEQ ID NO:61.

In some embodiments, the heavy chain CDR2 comprises the amino acid sequence of SEQ ID NO:71.

In some embodiments, the heavy chain CDR2 comprises the amino acid sequence of SEQ ID NO:81.

In certain embodiments, the heavy chain CDR3 comprises the amino acid sequence of SEQ ID NO:6.

In certain embodiments, the heavy chain CDR3 comprises the amino acid sequence of SEQ ID NO:28.

In certain embodiments, the heavy chain CDR3 comprises the amino acid sequence of SEQ ID NO:62.

In certain embodiments, the heavy chain CDR3 comprises the amino acid sequence of SEQ ID NO:72.

In certain embodiments, the heavy chain CDR3 comprises the amino acid sequence of SEQ ID NO:82.

In certain embodiments, the light chain CDR1 comprises the amino acid sequence of SEQ ID NO:8.

In certain embodiments, the light chain CDR1 comprises the amino acid sequence of SEQ ID NO:29.

In certain embodiments, the light chain CDR1 comprises the amino acid sequence of SEQ ID NO:63.

In certain embodiments, the light chain CDR1 comprises the amino acid sequence of SEQ ID NO:73.

In certain embodiments, the light chain CDR1 comprises the amino acid sequence of SEQ ID NO:83.

In certain embodiments, the light chain CDR2 comprises the amino acid sequence of SEQ ID NO:64.

In certain embodiments, the light chain CDR2 comprises the amino acid sequence of SEQ ID NO:74.

In certain embodiments, the light chain CDR2 comprises the amino acid sequence of SEQ ID NO:84.

In certain embodiments, the light chain CDR3 comprises the amino acid sequence of SEQ ID NO:65.

In certain embodiments, the light chain CDR3 comprises the amino acid sequence of SEQ ID NO:75.

In certain embodiments, the light chain CDR1 comprises the amino acid sequence of SEQ ID NO:85.

In some embodiments, the one, two, or three amino acid substitutions are conservative amino acid substitutions. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Conservative amino acid substitutions typically include substitutions within the same family.

In some embodiments, the isolated monoclonal antibodies or antigen-binding fragments thereof are a humanized antibody. In certain embodiments, the heavy chain comprises the amino acid sequence of SEQ ID NO:18. In certain embodiments, the light chain comprises the amino acid sequence of SEQ ID NO:20.

In some embodiments, the isolated monoclonal antibodies or antigen-binding fragments thereof are a human recombinant antibody. In certain embodiments, the heavy chain comprises the amino acid sequence of SEQ ID NO: 31, SEQ ID NO:41 or SEQ ID NO:49. In certain embodiments, the light chain comprises the amino acid sequence of SEQ ID NO:37, SEQ ID NO: 45 or SEQ ID NO:53.

In certain embodiments, the heavy chain variable region comprises the amino acid sequence of SEQ ID NO: 57, SEQ ID NO:67 or SEQ ID NO:77. In certain embodiments, the light chain variable region comprises the amino acid sequence of SEQ ID NO:59, SEQ ID NO: 69 or SEQ ID NO:79.

In some embodiments, the antigen-binding fragments can be a Fab fragment, an $F(ab')_2$ fragment, a scFv fragment, or a $sc(Fv)_2$ diabody.

In some embodiments, the monoclonal antibodies and antigen-binding fragments disclosed herein bind to serpin B13 with an affinity of about 1 nM to about 8 nM. In certain embodiments, the monoclonal antibodies and antigen-binding fragments disclosed herein bind to serpin B13 with an affinity of about 1 nM to about 2 nM (e.g., 1.21 nM).

In some embodiments, the isolated monoclonal antibodies or antigen-binding fragments also bind to serpin B13. As used herein, the term "monoclonal antibody" refers to a population of antibody molecules that contain only one species of an antigen binding site capable of immunereacting with a particular epitope of a polypeptide or protein. A monoclonal antibody thus typically displays a single binding affinity for the protein to which it specifically binds.

As used herein, the term "chimeric antibody" refers to an antibody that has been engineered to comprise at least one human constant region. For example, one or all (e.g., one, two, or three) of the variable regions of the light chain(s) and/or one or all (e.g., one, two, or three) of the variable regions the heavy chain(s) of a mouse antibody (e.g., a mouse monoclonal antibody) can each be joined to a human constant region, such as, without limitation an IgG1 human constant region. In certain embodiments, the isolated monoclonal antibody or antigen-binding fragment is a chimeric antibody wherein the heavy chain comprises the amino acid sequence of SEQ ID NO:22. In certain embodiments, the isolated monoclonal antibody or antigen-binding fragment is a chimeric antibody wherein the light chain comprises the amino acid sequence of SEQ ID NO:24.

"Fragment" or "antibody fragment" as the terms are used herein refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full-length antibody polypeptide, although the term is not limited to such cleaved fragments.

"Humanized antibody," as the term is used herein, refers to an antibody that has been engineered to comprise one or more human framework regions in the variable region together with non-human (e.g., mouse, rat, or hamster) complementarity-determining regions (CDRs) of the heavy and/or light chain. In some embodiments, a humanized antibody comprises sequences that are entirely human except for the CDR regions. Humanized antibodies are typically less immunogenic to humans, relative to non-humanized antibodies, and thus offer therapeutic benefits in certain situations.

As used herein, the term "percent sequence identity" refers to the degree to which any given query sequence is the same as a subject sequence. Percentage of "sequence identity" is determined by comparing two optimally aligned sequences over a comparison window, where the fragment of the amino acid sequence in the comparison window may comprise additions or deletions (e.g., gaps or overhangs) as compared to the reference sequence (which does not comprise additions or deletions) for optimal alignment of the two sequences. The percentage is calculated by determining the number of positions at which the identical amino acid residue occurs in both sequences to yield the number of matched positions, dividing the number of matched positions by the total number of positions in the window of comparison, and multiplying the result by 100 to yield the percentage of sequence identity. The output is the percent identity of the subject sequence with respect to the query sequence. It is noted that a query nucleotide or amino acid sequence that aligns with a subject sequence can result in many different lengths, with each length having its own percent identity.

The term "therapeutic treatment" or "treatment" means the administration of one or more pharmaceutical agents to a subject or the performance of a medical procedure on the body of a subject (e.g., surgery, such as organ transplant or heart surgery). The term therapeutic treatment also includes an adjustment (e.g., increase or decrease) in the dose or frequency of one or more pharmaceutical agents that a subject can be taking, the administration of one or more new pharmaceutical agents to the subject, or the removal of one or more pharmaceutical agents from the subject's treatment plan.

As used herein, a "subject" is an animal, e.g., a mammal, e.g., a human, monkey, dog, cat, horse, cow, pig, goat, rabbit, or mouse.

An "effective amount" is an amount sufficient to effect beneficial or desired results. For example, a therapeutically effective amount is one that achieves the desired therapeutic effect. An effective amount can be administered in one or more administrations, applications or dosages. A therapeutically effective amount of a pharmaceutical composition (i.e., an effective dosage) depends on the pharmaceutical composition selected. The compositions can be administered from one or more times per day to one or more times per week, including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the pharmaceutical compositions described herein can include a single treatment or a series of treatments.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

FIGS. 1A-1I together provide the nucleic acid sequences of B29_graft heavy chain.

FIGS. 2A-2H together provide the nucleic acid sequences of B29_graft light chain.

FIGS. 3A-3I together provide the nucleic acid sequences of B29_chimeric heavy chain.

FIGS. 4A-4H together provide the nucleic acid sequences of B29_chimeric light chain.

FIGS. 6A-6C. Impact of mouse monoclonal antibody to serpin B13 (clone B29) on tissue regeneration in different organs. (FIG. 6A) Bone healing. B6 Mice (n=4/group) were subjected to tibia fracture on day zero and intraperitoneally injected 4 times with 50 μg of B29 (or IgG control) over one-week period. Mice were X-rayed on day 9, 14 and 21 to determine the size (volume) of bone callus. A representative image from each group is shown from analysis day 21 (right) as well as the average for all animals/group from the analysis on days 9, 14 and 21 (left). (FIG. 6B) Skin ulcer healing. B6 mice (n=3/group) were injected at the base of tail with 100 μL of CFA and 7 days later injected four times with B29 or IgG control (100 μg per injection). Mice were weekly followed for two months and their tails were photographed by the end of the study. One representative image from each group is shown. (FIG. 6C) Mortality rates in the experimental autoimmune encephalomyelitis (EAE). B6 mice (n=14/group) were immunized with 100 μg of pMOG antigen in Complete Freund's adjuvant (CFA) on day 0, and then again on day 7 with the same antigen in incomplete adjuvant. Immunized mice were intraperitoneally injected 4 times with 100 μg of B29 (or IgG) on days 7, 8, 11 and 13. Mice were observed daily for 31 days for limb paralysis and mortality.

Unpaired, two-sided Student t test. αB13, anti-serpinB13 mouse mAb. MFC, mean fluorescent channel.

Figure 1H:
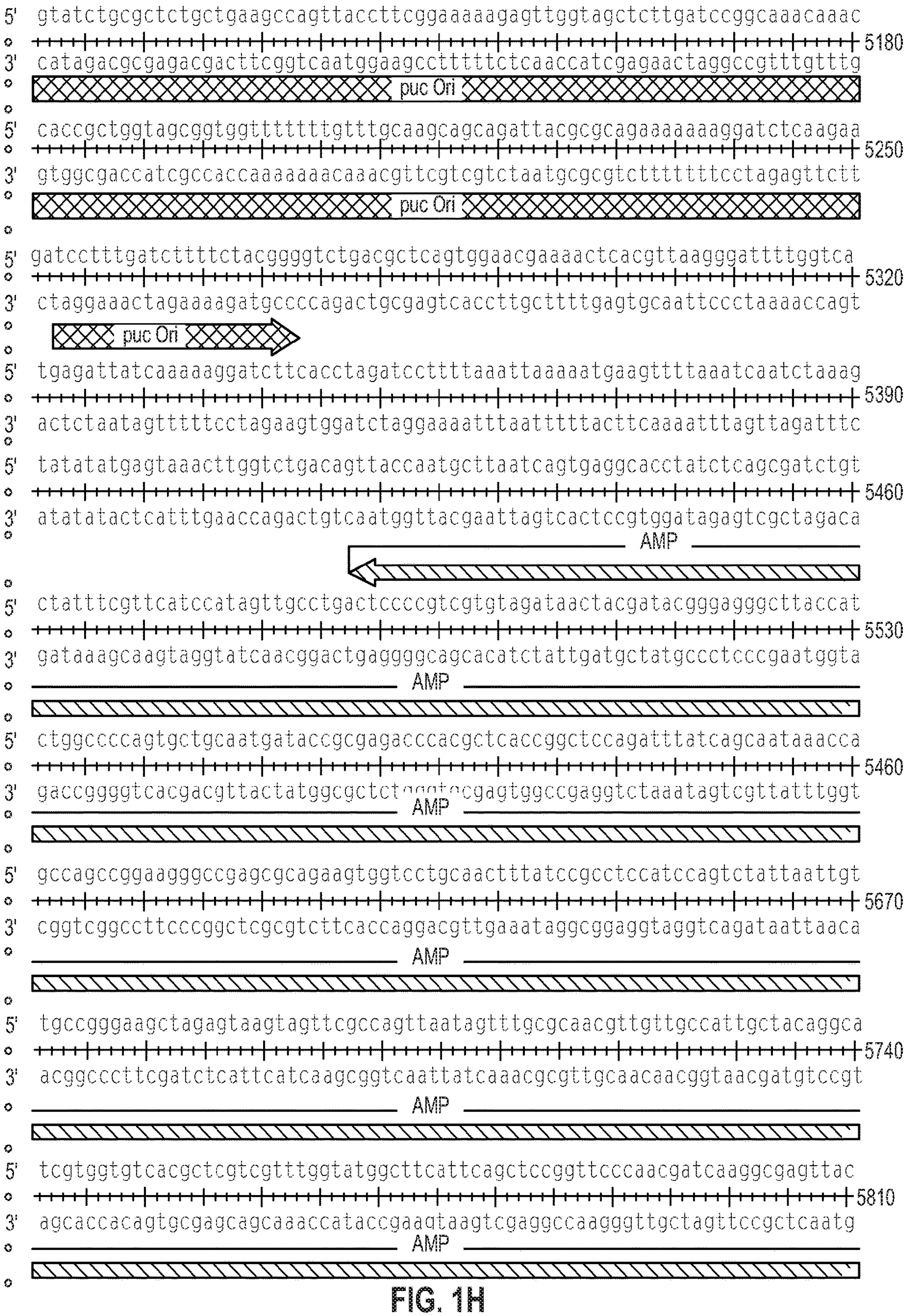
Figure 2H:
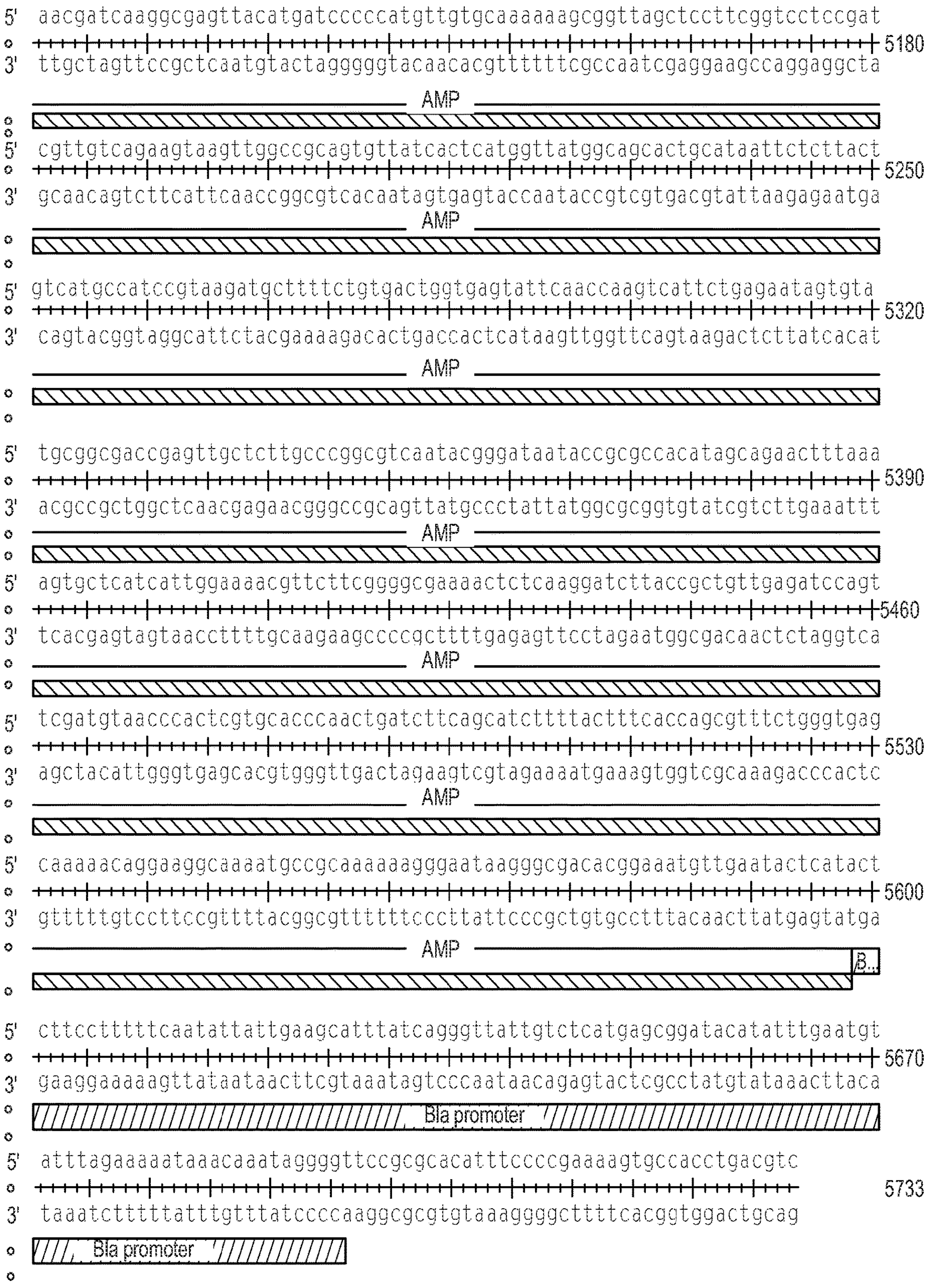

FIGS. 22A-22B. Analysis of Notch1 gene expression. (A) Embryonic E12.5 mouse pancreatic explants or (B) pregnant at E10.5 Balb/c mouse females were treated with anti-serpinB13 mAb (or control Ab), exactly as described in the schematics and legend to FIG. 1. The tissues were harvested and examined in biological duplicates or triplicates by quantitative PCR for expression of Notch1 gene. In (B lower), the analysis was performed on sorted viable ($EPCAM^+CD45^-CD31^-7AAD^-$) epithelial cells. The bars represent the average of three (A lower) and two (B lower) independent experiments. Unpaired Student's t test was used for the analysis. NS, not significant. αB13, anti-serpinB13 mouse mAb.

Figure 3H:
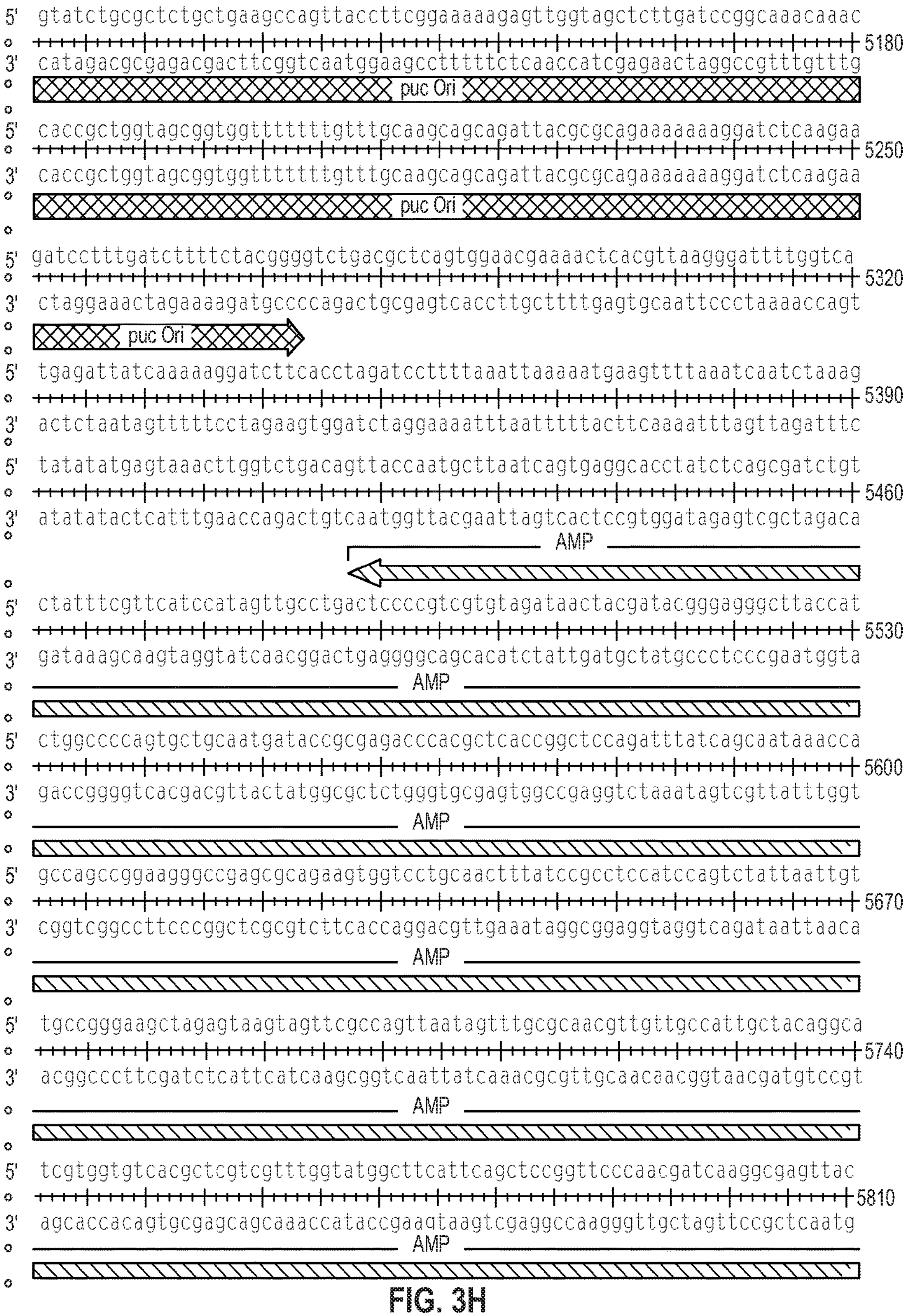
Figure 23A:
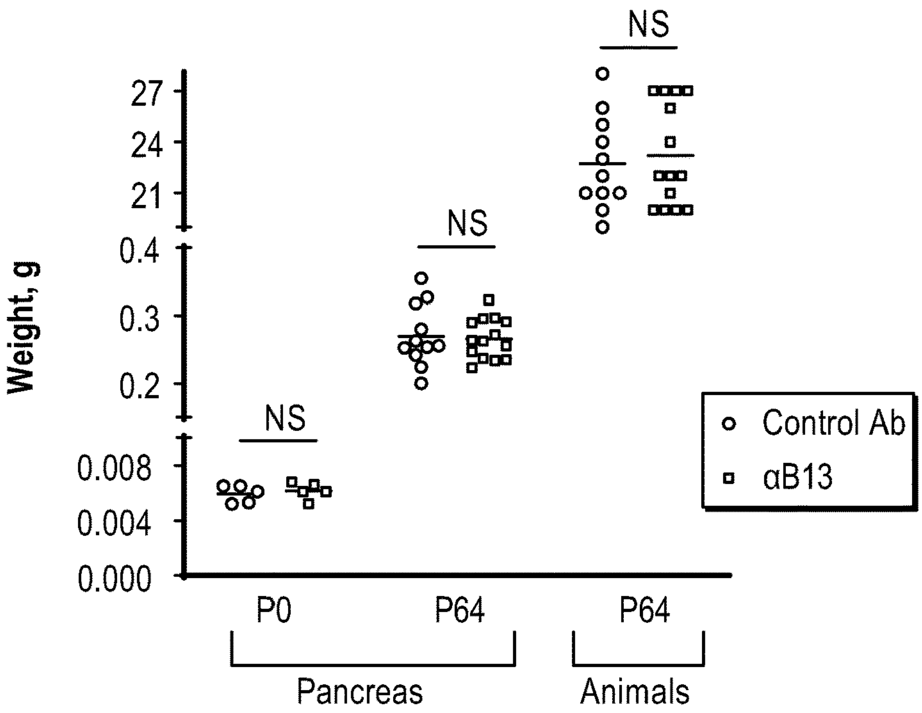
Figure 23B:
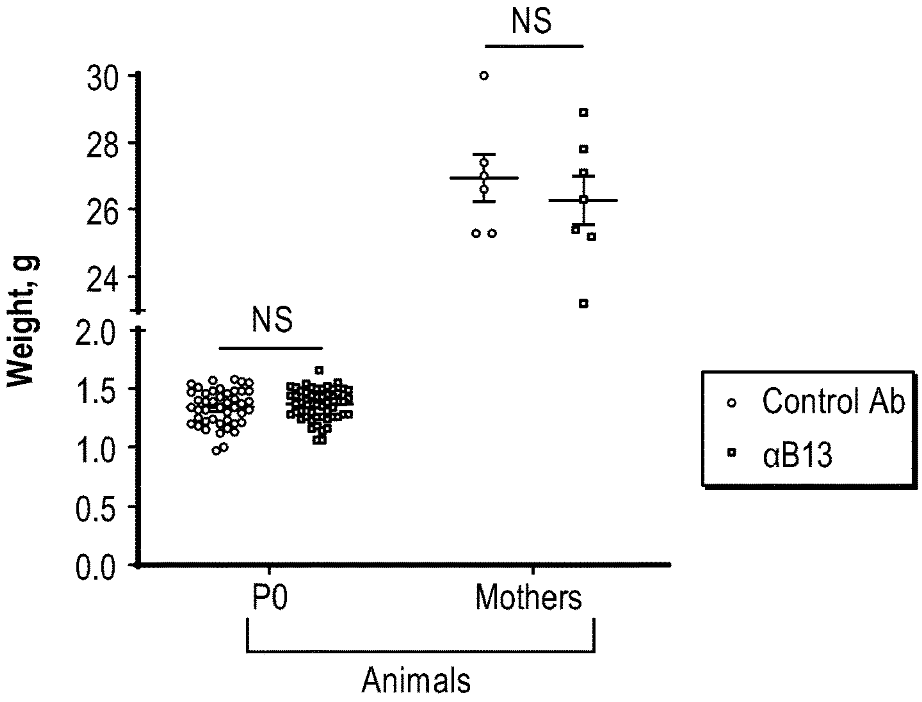

FIGS. 23A-23B. The pancreas and body weight in mice with exposure to anti-serpinB13 mAb during pregnancy and embryonic life. (A) The animals were injected with anti-serpinB13 mAb (or control Ab) during mid pregnancy, exactly as depicted in FIG. 3A, and followed for the weight of their body at 64 days of age (P64), and the pancreas at the same time (n=11 (control Ab), n=14 (αB13), two independent experiments), and at birth (PO) (n=5 per group, two independent experiments). (B) The pregnant mothers were injected with anti-serpinB13 mAb (or control Ab) during mid pregnancy, exactly as depicted in FIG. 3A, and followed for their body weight on a delivery day (n=6 (control Ab), n=7 (αB13), two independent experiments, as well as the body weight of their newborn pups (PO) (n=45 (control Ab), n=55 (αB13), two independent experiments). Data are presented as the mean±SEM Unpaired Student t test was used for the analysis. NS, not significant. αB13, anti-serpinB13 mAb.

Figure 24A:
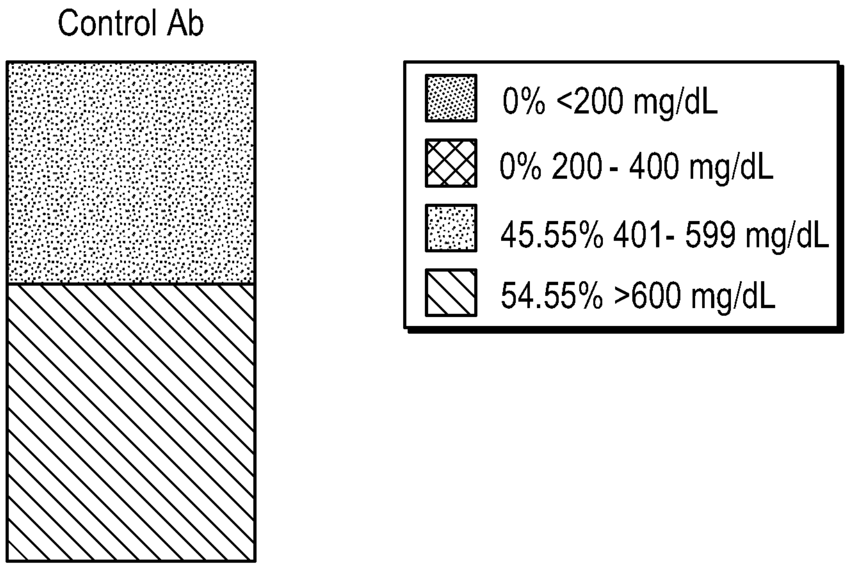
Figure 24B:
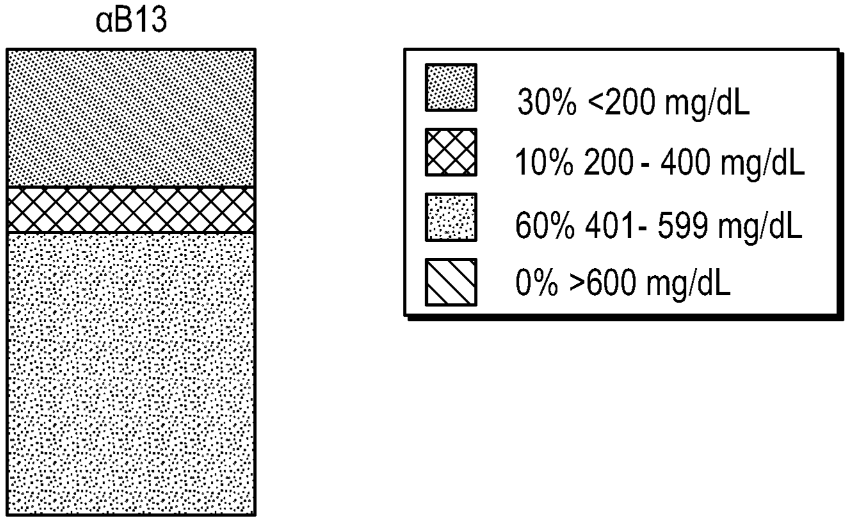

FIGS. 24A-24B. The severity of diabetes in adult mice following exposure to anti-serpinB13 mAb during embryonic life. Eight-week old Balb/c mice that received control Ab (A) or anti-serpinB13 mAb (B) during gestation were induced into a diabetic state with streptozotocin (STZ) during adulthood, and followed for diabetes according to the protocol depicted in FIG. 3G. The data are shown for mice at 4 weeks after STZ injection and displayed as the percentages of mice with distinct ranges of random blood glucose levels, as indicated. n=11 (control Ab); n=10 (αB13). αB13, anti-serpinB13 mouse mAb.

Figure 25:
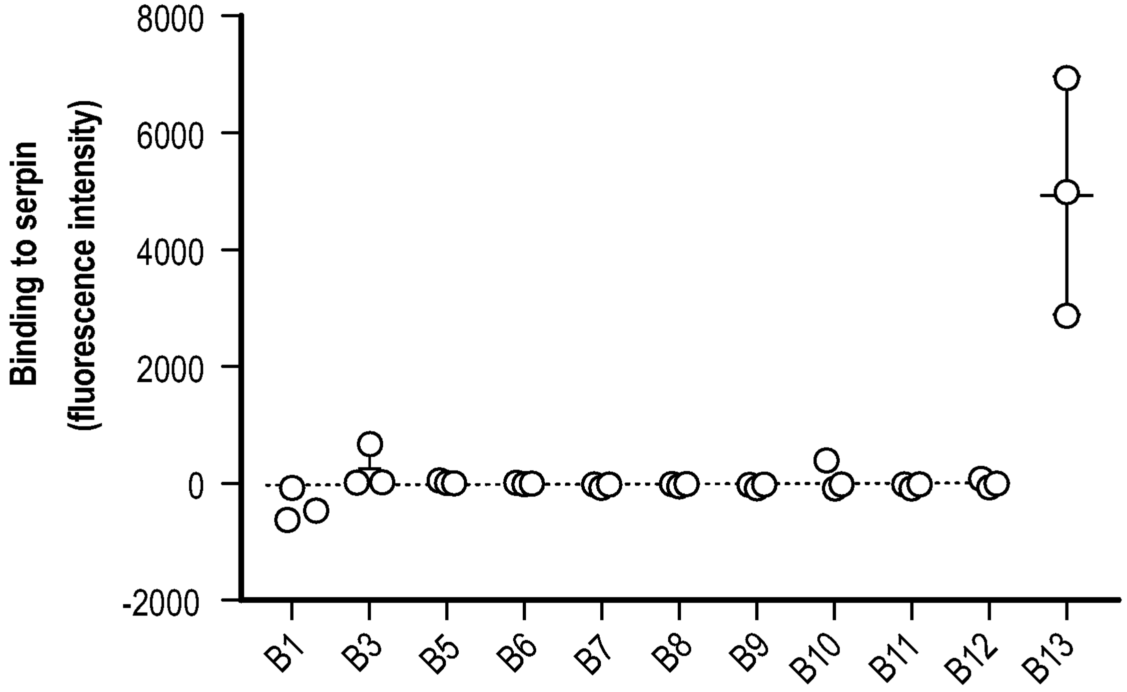

FIG. 25. The specificity of anti-serpin activity. Three recombinant human anti-serpinB13 antibodies were examined in the Luminex-based assay for binding to other clade B serpins, in order as indicated. The final concentration of each antibody was 1.0 μg/mL. The data are expressed as immunofluorescence intensity measured for binding to individual human serpin antigens after subtracting the background. The latter was determined as the average antibody binding to Luminex beads coated with Gfp and Scgn control antigens. Similar data were obtained for antigen binding of Fab fragments of these antibodies (data not shown).

Figure 26A:
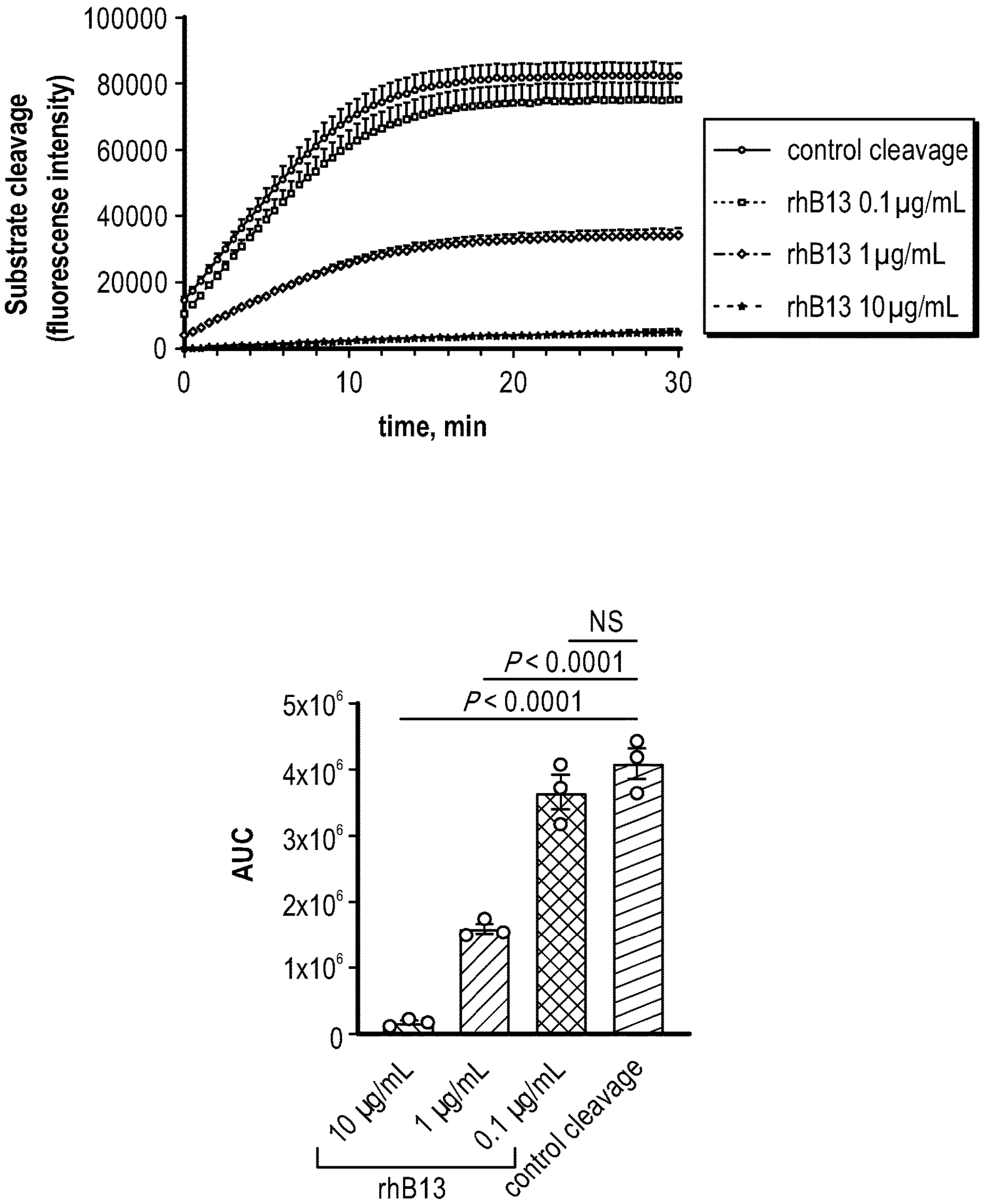

FIGS. 26A-26B. The dose-dependent control of Cathepsin L activity by recombinant human serpinB13 and antibody influence on substrate cleavage. (A) Inhibition of a substrate cleavage by CatL with different doses of recombinant human serpinB13 over time. The average of three independent experiments (left) and quantification of their areas under the curves (AUC) (right) is shown. (B) The substrate cleavage by CatL in a presence of either human mAb to serpinB13 (hαB13) or control human Ab (h.Control Ab) over time. The average of three independent experiments (left) and quantification of their areas under the curves (AUC) (right) is shown. Data are presented as the mean±SEM. One-way Anova with Sidak test (A right and B right). NS, not significant; hαB13, recombinant human anti-serpinB13 antibody; rhB13, recombinant human serpinB13; h.Control Ab, recombinant human Isotype control antibody; #, fluorescent signal readings limit; AUC, area under the curve.

FIGS. 27A-27C. Recombinant fully human antibody sequences were developed. The CDR Analysis for clone 1 is provided in FIG. 27A. The CDR Analysis for clone 2 is provided in FIG. 27B. The CDR Analysis for clone 3 is provided in FIG. 27C.

DETAILED DESCRIPTION

Proteases are ubiquitously expressed in the body and they play a critical role such as cell differentiation, proliferation, apoptosis and other processes. Protease activity is tightly controlled by a number of inhibitors, some of which are known as Serpins. One particular serpin molecule is Serpin B13. Serpin B13 is primarily expressed in the epithelial cells, and its main feature is to block Cathepsin L protease. The present disclosure is based, at least in part, on the development of new monoclonal antibodies that selectively and specifically bind to serpin B13. These antibodies and antigen-binding fragments thereof are useful for inhibiting serpin B13 and for treating serpin B13-related diseases, e.g., type I diabetes. Provided herein are these antibodies and antigen-binding fragments thereof, compositions and kits containing these antibodies and antibody fragments, and various methods of using these antibodies and antigen-binding fragments.

The term monoclonal antibody refers to a population of antibody molecules that contain only one species of an antigen binding site capable of immune-reacting with a particular epitope of a polypeptide or protein. A monoclonal antibody thus typically displays a single binding affinity for the protein to which it specifically binds.

In general, a given antibody can include one of five different types of heavy chains: alpha, delta, epsilon, gamma, and mu, which have different amino acid sequences in the constant region. These different types of heavy chains give rise to five classes of antibodies: IgA (including IgA1 and IgA2), IgD, IgE, IgG (IgG1, IgG2, IgG3, and IgG4) and IgM, respectively. An antibody also comprises one of two types of light chains: kappa or lambda, which differ in the amino acid sequence of the light chain constant domains. IgG, IgD, and IgE antibodies generally contain two identical heavy chains and two identical light chains, and contain two antigen combining domains, each composed of a heavy chain variable region ($V_H$) and a light chain variable region ($V_L$).

Antigen-binding fragments include any antibody fragments containing the active binding region of the antibody, such as a Fab fragment, a $F(ab')_2$ fragment, or a single-chain Fv (scFv) fragment. Such fragments can be produced from the antibody using techniques well established in the art. For example, the $F(ab')_2$ fragments can be produced by pepsin digestion of the antibody molecule, and the Fab fragments can be generated by reducing the disulfide bridges of the $F(ab')_2$ fragments.

ScFv antibodies are single-chain polypeptides produced by linking $V_L$ and a $V_H$ via a linker or such (see, e.g., Bird et al., Science, 242(4877):423-426 (1988)). The heavy chain variable region and light chain variable region of an scFv may be derived from any antibody described herein. The peptide linker for linking the variable regions is not particularly limited. For example, an arbitrary single-chain peptide containing about three to 25 residues can be used as the linker. A "diabody" is a noncovalent dimer of single-chain Fv (scFv) fragment that consists of the heavy chain variable ($V_H$) and light chain variable ($V_L$) regions connected by a small peptide linker. Another form of diabody is where two scFv fragments are covalently linked to each other. In general, the linker is short enough such that the $V_L$ and a $V_H$ cannot bind to each other in the dimer. In certain embodiments, the number of amino acid residues constituting the linker is, for example, about five residues. Thus, the $V_L$ and a $V_H$ encoded on the same polypeptide cannot form a single-chain variable region fragment and will form a dimer with another single-chain variable region fragment. As a result, the diabody has two antigen binding sites.

Antibodies and Antibody Fragments

Provided herein are novel monoclonal antibodies and antigen-binding fragments that bind to serpin B13. As known in the art, an antibody's specificity towards a given antigen is mediated by the heavy and light chain variable regions. In particular, the specificity of an antibody towards a given antigen is primarily determined by short sequences within the heavy and light chain variable regions called complementarity determining regions (CDRs). Provided herein are the nucleotide and amino acid sequences of the heavy and light chain variable regions and the heavy and light chain CDRs of the anti-serpin B13 antibodies and antibody fragments.

The nucleic acid sequence of B29_graft heavy chain is provided in FIGS. 1A-1I. The nucleic acid sequence of B29_graft light chain is provided in FIGS. 2A-2H. The nucleic acid sequence of B29_chimeric heavy chain is provided in FIGS. 3A-3I. The nucleic acid sequence of B29_chimeric light chain is provided in FIGS. 4A-4H. In some embodiments, the isolated monoclonal antibodies or antigen-binding fragments thereof (1) bind to serpin B13, and (2) comprise a heavy chain CDR1, a heavy chain CDR2, and a heavy chain CDR3. The heavy chain CDR1 can comprise the amino acid sequence of SEQ ID NO:1, 2 or 26, or the amino acid sequence of SEQ ID NO:1, 2 or 26, with a substitution at one, two, or three amino acid positions. The heavy chain CDR2 can comprise the amino acid sequence of SEQ ID NO:4 or 27, or the amino acid sequence of SEQ ID NO:4 or 27 with a substitution at one, two, or three amino acid positions. The heavy chain CDR3 can comprise the amino acid sequence of SEQ ID NO:6 or 28, or the amino acid sequence of SEQ ID NO:6 or 28 with a substitution at one, two, or three amino acid positions. In some embodiments, the isolated monoclonal antibodies or antigen-binding fragments can further include one or more of the following light chain CDRs: (1) a light chain CDR1 comprises the amino acid sequence of SEQ ID NO: 8 or 29, or the amino acid sequence of SEQ ID NO:8 or 29 with a substitution at one, two, or three amino acid positions; (2) a light chain CDR2 comprises the amino acid sequence of SEQ ID NO:10, or the amino acid sequence of SEQ ID NO:10 with a substitution at one, two, or three amino acid positions; and (3) a light chain CDR3 comprises the amino acid sequence of SEQ ID NO:12, or the amino acid sequence of SEQ ID NO:12 with a substitution at one, two, or three amino acid positions. In some embodiments, no amino acid substitutions are present in any of the above-described heavy chain CDR1, CDR2 or CDR3. In some embodiments, the one, two or three amino acid substitutions are made in positions other than those positions where a conserved amino acid residue is observed in the heavy chain CDR1, CDR2 or CDR3. In some embodiments, no amino acid substitutions are present in any of the above-described light chain CDR1, CDR2 or CDR3. In some embodiments, the one, two or three amino acid substitutions are made in positions other than those positions where a conserved amino acid residue is observed in the light chain CDR1, CDR2 or CDR3. In certain embodiments, the amino acid sequence of the protein is modified, for example by substitution, to create a polypeptide having substantially the same or improved qualities as compared to the original polypeptide. The substitution may be a conserved substitution. A "conserved substitution" is a substitution of an amino acid with another amino acid having a similar side chain. A conserved substitution would be a substitution with an amino acid that makes the smallest change possible in the charge of the amino acid or size of the side chain of the amino acid (alternatively, in the size, charge or kind of chemical group within the side chain) such that the overall peptide retains its spatial conformation but has altered biological activity. For example, common conserved changes might be Asp to Glu, Asn or Gln; His to Lys, Arg or Phe; Asn to Gln, Asp or Glu and Ser to Cys, Thr or Gly. Alanine is commonly used to substitute for other amino acids. The 20 essential amino acids can be grouped as follows: alanine, valine, leucine, isoleucine, proline, phenylalanine, tryptophan and methionine having nonpolar side chains; glycine, serine, threonine, cystine, tyrosine, asparagine and glutamine having uncharged polar side chains; aspartate and glutamate having acidic side chains; and lysine, arginine, and histidine having basic side chains. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Conservative amino acid substitutions typically include substitutions within the same family. In some embodiments, the monoclonal antibodies and antigen-binding fragments disclosed herein comprise the heavy chain CDR1-3 described above and one or more of the light chain CDRs described herein.

One can use the hydropathic index of amino acids in conferring interactive biological function on a polypeptide, wherein it is found that certain amino acids may be substituted for other amino acids having similar hydropathic indices and still retain a similar biological activity. Alternatively, substitution of like amino acids may be made based on hydrophilicity, particularly where the biological function desired in the polypeptide to be generated in intended for use in immunological embodiments. The greatest local average hydrophilicity of a protein, as governed by the hydrophilicity of its adjacent amino acids, correlates with its immunogenicity. Accordingly, it is noted that substitutions can be made based on the hydrophilicity assigned to each amino acid. In using either the hydrophilicity index or hydropathic index, which assigns values to each amino acid, it is preferred to conduct substitutions of amino acids where these values are 2, with 1 being particularly preferred, and those with in 0.5 being the most preferred substitutions.

In certain embodiments, the one, two, or three amino acid substitutions are conservative amino acid substitutions.

Chimeric and Humanized Antibodies

Recombinant forms of antibodies, such as chimeric and humanized antibodies, were prepared to minimize the response by a human patient to the antibody. When antibodies produced in non-human subjects or derived from the expression of non-human antibody genes are used therapeutically in humans, they are recognized to varying degrees as foreign, and an immune response may be generated in the patient. One approach to minimize or eliminate this immune reaction is to produce chimeric antibody derivatives, i.e., antibody molecules that combine a non-human animal variable region and a human constant region. Such antibodies retain the epitope binding specificity of the original monoclonal antibody, but may be less immunogenic when administered to humans, and therefore more likely to be tolerated by the patient. For example, one or all (e.g., one, two, or three) of the variable regions of the light chain(s) and/or one or all (e.g., one, two, or three) of the variable regions the heavy chain(s) of a mouse antibody (e.g., a mouse monoclonal antibody) can each be joined to a human constant region, such as, without limitation an IgG1 human constant region.

A chimeric antibody is further "humanized" by replacing portions of the variable region not involved in antigen binding with equivalent portions from human variable regions.

In the present invention, humanized antibodies were engineered to comprise one or more human framework regions in the variable region together with non-human (mouse) complementarity-determining regions (CDRs) of the heavy and/or light chain. In some embodiments, a humanized antibody comprises sequences that are entirely human except for the CDR regions. Humanized antibodies are typically less immunogenic to humans, relative to non-humanized antibodies, and thus offer therapeutic benefits in certain situations.

As used herein, "framework region" (FR) refers to amino acid sequences within the variable region of both heavy and light chain polypeptides that are not CDR sequences and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen. In some embodiments, humanized versions of the monoclonal antibodies described herein can be made by replacing one or more (e.g., one, two, three, four, five, or six) framework regions of the antibodies described herein, with one or more (e.g., one, two, three, four, five, or six) human framework regions.

In certain embodiments, the monoclonal antibodies and antigen-binding fragments disclosed herein comprises the light chain CDR1, CDR2 or CDR3 described above and one or more of the heavy chain CDRs described herein.

In certain embodiments, the monoclonal antibodies and antigen-binding fragments disclosed herein (1) bind to serpin B13, and (2) comprise a heavy chain variable region that is at least 65%, e.g., 65%, 70%, 75%, 80%, 85%, 90%, 95%, 100%, identical to SEQ ID NO:18, and a light chain variable region that is at least 65%, e.g., 65%, 70%, 75%, 80%, 85%, 90%, 95%, 100%, identical to SEQ ID NO:20.

In certain embodiments, the monoclonal antibodies and antigen-binding fragments disclosed herein (1) bind to serpin B13, and (2) comprise a heavy chain variable region that is at least 65%, e.g., 65%, 70%, 75%, 80%, 85%, 90%, 95%, 100%, identical to SEQ ID NO:22, and a light chain variable region that is at least 65%, e.g., 65%, 70%, 75%, 80%, 85%, 90%, 95%, 100%, identical to SEQ ID NO:24.

In some embodiments, the monoclonal antibodies and antigen-binding fragments disclosed herein bind to serpinB13 with an affinity of about 1 nM to about 8 nM. In certain embodiments, the monoclonal antibodies and antigen-binding fragments disclosed herein bind to serpin B13 with an affinity of about 1 nM to about 2 nM (e.g., 1.21 nM).

Methods of Using the Monoclonal Antibodies and Antibody Fragments

The antibodies and antigen-binding fragments described herein are used to inhibit or reduce serpin B13 and treat serpin B13-related disorders, e.g., type 1 diabetes, Methods of treating a serpin B13-related disorders in a subject can include (a) identifying a subject having an serpin B13-related disorders; and (b) administering to the subject an effective amount of one or more different ones of the monoclonal antibodies disclosed herein. In some embodiments, the subject is a human.

The serpin B13-related disorder can be, for example, diabetes, such as type I diabetes, type 2 diabetes, and diabetes in patients with chronic pancreatitis who undergo total pancreatectomy with autologous islet transplantation and still remain insulin dependent. In some embodiments, the new monoclonal antibodies disclosed herein are used to treat a serpin B13-related disorder, wherein the disorder is inflammatory or central nervous system disease. In some embodiments, the new monoclonal antibodies disclosed herein are used to treat bone fracture, skin wound/ulcer healing including diabetic foot, hair loss, multiple sclerosis, or lupus.

Formulations and Methods of Administration

The compositions of the invention may be formulated as pharmaceutical compositions (e.g., comprising fusion proteins or expression vectors) and administered to a mammalian host, such as a human patient, in a variety of forms adapted to the chosen route of administration, i.e., orally, intranasally, intradermally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard- or soft-shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts may be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient that are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with several of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions that can be used to deliver the compounds of the present invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of the present invention can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of the present invention in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 μM, preferably, about 1 to 50 μM, most preferably, about 2 to about 30 μM. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations, such as multiple inhalations from an insufflator or by application of a plurality of drops into the eye.

The new monoclonal antibodies disclosed herein, or antigen-binding fragments thereof, can be administered in an effective amount, at dosages and for periods of time necessary to achieve the desired result. An "effective amount" is an amount sufficient to effect beneficial or desired results. For example, a therapeutically effective amount is one that achieves the desired therapeutic effect. An effective amount can be administered in one or more administrations, applications or dosages. A therapeutically effective amount of a pharmaceutical composition (i.e., an effective dosage) depends on the pharmaceutical composition selected. The compositions can be administered from one or more times per day to one or more times per week, including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the pharmaceutical compositions described herein can include a single treatment or a series of treatments.

Dosage regimens can be adjusted to provide the optimum therapeutic response. For example, several divided doses can be administered daily, or the dose can be proportionally reduced as indicated by the exigencies of the therapeutic situation. Those skilled in the art will be aware of dosages and dosing regimens suitable for administration of the new monoclonal antibodies disclosed herein or antigen-binding fragments thereof to a subject. See e.g., Physicians' Desk Reference, 63rd edition, Thomson Reuters, Nov. 30, 2008. For example, Dosage, toxicity and therapeutic efficacy of the therapeutic compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In some embodiments, the monoclonal antibodies described herein are administered intravenously at about 0.1-20 mg/kg, e.g., about 0.5-15 mg/kg, about 1-12 mg/kg, about 2-10 mg/kg.

Kits

Also provided herein are kits that include at least one (e.g., two, three, four, five, or more) compositions containing at least one (e.g., one, two, three, four, five, or more different ones) of the isolated new monoclonal antibodies or antigen-binding fragments thereof described herein. In some embodiments, the kits described herein contain one or more humanized or human version of the monoclonal antibodies or antigen-binding fragments thereof.

Kits generally include the following major elements: packaging, reagents comprising binding compositions as described above, optionally a control, and instructions. Packaging can be a box-like structure for holding a vial (or number of vials) containing said binding compositions, a vial (or number of vials) containing a control, and instructions for use in a method described herein. Individuals skilled in the art can readily modify the packaging to suit individual needs.

In some embodiments, a kit provided herein can include at least one (e.g., one, two, three, four, five, or more) composition containing at least one (e.g., one, two, three, four, five, or more) of the isolated new monoclonal antibodies or antigen-binding fragments thereof described herein.

Compositions and kits as provided herein can be used in accordance with any of the methods (e.g., treatment methods) described above. For example, compositions and kits containing at least one (e.g., one, two, three, four, five, or more) of the isolated new monoclonal antibodies or antigen-binding fragments thereof described herein can be used to treat serpin B13-related disorder, e.g., type I diabetes. Those skilled in the art will be aware of other suitable uses for compositions and kits provided herein and will be able to employ the compositions and kits for such uses.

The invention will now be illustrated by the following non-limiting Examples.

Example 1

Inhibition of SerpinB13 Stimulates Beta-Cell Development Via Notch Signaling Pathway Methods for repopulating the pancreas with new insulin-producing cells have strong potential for therapy in diabetes. Recently, it was found that inhibition of serpinB13, which is a protease inhibitor of cathepsin L (catL), with mAb in mouse embryos lead to a robust increase in the number of pancreatic Ngn3$^{+}$ progenitor cells, significant expansion of islet mass, and improved resistance to severe diabetes in adulthood.

To unveil the molecular mechanism of the augmented Ngn3$^{+}$ cell response following inhibition of serpinB13 during gestation, the Notch communication system (a critical signaling pathway for pancreatic development) was studied. It was found that serpinB13 is expressed and secreted by epithelial cells in murine embryonic pancreases. Moreover, in vivo and in vitro inhibition of serpinB13 during embryogenesis caused protease-dependent cleavage of the extracellular domain of Notch1 receptor in the pancreas ($p<0.0001$). This partial loss of the extracellular Notch was followed by decreased translocation to the nucleus of active Notch intracellular domain (aNICD), a fragment of Notch that is critical for restraining endocrine cell development. Finally, embryonic pancreases of mice with genetic deficiency of catL had significantly fewer Ngn3$^{+}$ cells compared with wild type controls.

Together, the data point to a novel function of serpinB13 in maintaining Notch receptor-mediated repression of pancreatic endocrine progenitors. Consequently, the perturbation of this effect of serpinB13 enables protease activity to partially dismantle Notch signaling, thereby allowing for more efficient development of Ngn3$^{+}$ progenitors cells and a subsequent increase in islet mass.

Example 2

Cell lysates in TriZol solution were provided and cDNA was obtained from the total RNA followed by PCR amplification of the variable regions (both heavy and light chains) of the antibody. The resulted PCR fragments were then cloned into a standard vector separately and sequenced. Based on the gel analysis of PCR products, the type of hybridoma B29 light chain is kappa. The sequence information is the following:

B29 Heavy Chain

Amino acid sequence (CDR region in bold)

FR1-CDR1-FR2-CDR2-FR3-CDR3-FR4

QIQLVQSGPELKKPGETVKISCKASGYTFTTYGMSWVKQAPGKGLKWMGWINTYSGMPTYADDF

KGRFAFSLETSATTAYLQINNLKNEDTATYFCARPLLGLDYWGQGTTLTVSS

Nucleotide sequence (CDR region in bold)

FR1-CDR1-FR2-CDR2-FR3-CDR3-FR4

CAGATCCAGTTGGTACAGTCTGGACCTGAGCTGAAGAAGCCTGGAGAGACAGTCAAGATCTCCT

GCAAGGCCTCCGGGTATACCTTCACAACCTATGGAATGAGCTGGGTGAAACAGGCTCCAGGAAA

GGGTTTAAAGTGGATGGGCTGGATAAACACCTACTCTGGAATGCCAACATATGCTGATGACTTC

AAGGGACGGTTTGCCTTCTCTTTGGAAACCTCTGCCACCACTGCCTATTTGCAGATCAACAACC

TCAAAAATGAGGACACGGCTACATATTTCTGTGCAAGACCTCTCCTGGGACTTGACTATTGGGG

CCAAGGCACCACTCTCACAGTCTCCTCA

B29 Light Chain

Amino acid sequence (CDR region in bold)

FR1-CDR1-FR2-CDR2-FR3-CDR3-FR4

DIVMTQTPLSLSVTIGQPASISCKSSQSLLHSDGKTFLNWFLQRPGQSPKLLIYLVSKLESGIP

DRFSGSGSGTDFTLKISRVEVEDLGVYYCLQHTHFPLTFGAGTKLEIK

Nucleotide sequence (CDR region in bold)

FR1-CDR1-FR2-CDR2-FR3-CDR3-FR4

GATATTGTGATGACCCAGACTCCACTGTCTTTGTCGGTTACCATTGGACAACCAGCCTCCATCT

CTTGCAAGTCAAGTCAGAGCCTCTTACATAGTGATGGAAAGACATTTTTGAATTGGTTTTTACA

GAGGCCAGGCCAGTCTCCAAAGCTCCTAATCTATCTGGTGTCTAAACTGGAATCTGGCATCCCT

-continued

GACAGGTTCAGTGGCAGTGGATCAGGGACAGATTTCACACTGAAAATCAGCAGAGTGGAGGTTG

AGGATTTGGGAGTTTATTACTGCTTGCAACATACACATTTTCCGCTCACGTTCGGTGCTGGGAC

CAAACTGGAAATAAAA

After the B29 antibody sequence was obtained, comprehensive bioinformatics analysis of it was performed. It was determined that the heavy chain of B29 (B29_H) belongs to mouse IGHV9 subgroup and its nearest germline gene sequence is mouse IGHV9-3*01. The light chain (B29_L) belongs to mouse IGKV1 subgroup and its nearest germline gene sequence is mouse IGKV1-133*01. Then the risk evaluation of post-translation modification (PTM) sites in B29 CDR regions was performed. The B29_L CDRs had an asp isomerization risk site, aspartic acid0glicine (DG), while B29_H CDRs had three oxidation risk sites, two methionine (M) and on tryptophan and the overall developability risk of B29 antibody is low.

Figure 5A:
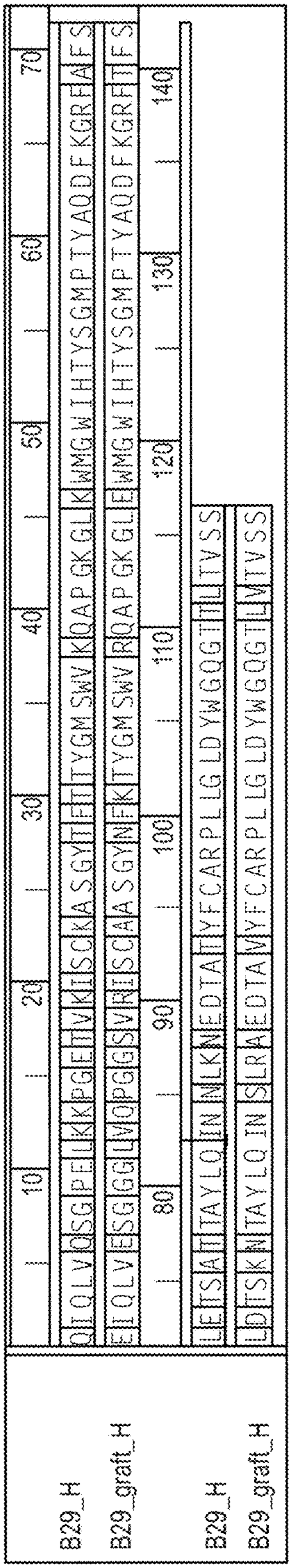
FIGS. 5A and 5B. The recipient of B29_H is human germline IGHV3_66*01. The sequence after CDR-grafted is named B29_graft_H. The sequence alignment of the germline gene before and after grafting is shown in FIG. 5A. Red color indicates the CDR region. The darker color indicates the more identical sequences. The recipient of B29_L is human germline IGKV1_39*01. The antibody sequence after CDR-grafted is named B29_graft_L. The sequence alignment of the germline gene before and after grafting is shown in FIG. 5B. Pink color indicates the CDR region. The darker color indicates the more identical sequences.
Figure 5B:
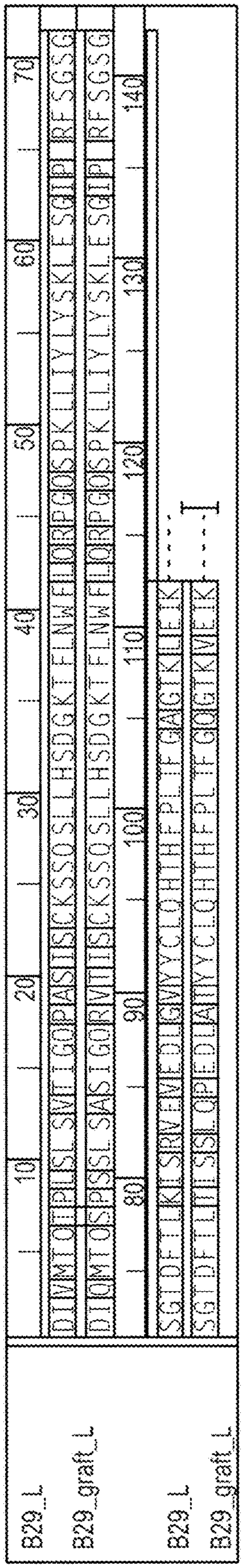

Based on the bioinformatics analysis result, human germline IGKV1_39*01 was chosen to perform the humanization of B29 light chain (B29_L) and human germline IGKV3_66*01 was used to humanize B29 heavy chain (B29_H). The sequence after CDR-grafting was named B29_graft_H. The sequence alignment of the germline gene before and after granting is shown in FIG. 5A. The antibody sequence after CDR-grafted is named B29_graft_L. The sequence alignment of the germline gene before and after grafting is shown in FIG. 5B. After CDR-grafting, the humanized heavy chain (named B29_graft_H) and light chain (named B29_graft_L) were obtained. The amino acid sequence of B29_graft is provided below:

B29_graft heavy chain
*EIQLVESGGGLVQPGGSVRLSCAASGYNFKTYGMSWVRQAPGKGLEWMGWI*

*NTYSGMPTYADDFKGRFTFSLDTSKNTAYLQINSLRAEDTAVYFCARPLLG*

*LDYWGQGTLVTVSS*ASTKGPSVFPLAPSSKSTSGGTAALGCLVKDYFPEPV

TVSWNSGALTSGVHTFPAVLQSSGLYSLSSVVTVPSSSLGTQTYICNVNHK

PSNTKVDKKVEPKSCDKTHTCPPCPAPELLGGPSVFLFPPKPKDTLMISRT

-continued

PEVTCVVVDVSHEDPEVKFNWYVDGVEVHNAKTKPREEQYNSTYRVVSVLT

VLHQDWLNGKEYKCKVSNKALPAPIEKTISKAKGQPREPQVYTLPPSREEM

TKNQVSLTCLVKGFYPSDIAVEWESNGQPENNYKTTPPVLDSDGSFFLYSK

LTVDKSRWQQGNVFSCSVMHEALHNHYTQKSLSLSPGK

B29_graft light chain
*DIQMTQSPSSLSASVGDRVTITCKSSQSLLHSDGKTFLNWFQQKPGKSPKL*

*LIYLVSKLESGVPSRFSGSGSGTDFTLTISSLQPEDFATYYCLQHTHFPLT*

*FGQGTKVEIK*RTVAAPSVFIFPPSDEQLKSGTASVVCLLNNFYPREAKVQW

KVDNALQSGNSQESVTEQDSKDSTYSLSSTLTLSKADYEKHKVYACEVTHQ

GLSSPVTKSFNRGEC

When the B29_graft antibody was evaluated, it was observed that both heavy chain and light chain had higher degree of humanization after CDR grafting. In detail, the B29graft_L shares 94% identities with the human germline gene (CDR region excluded) and the B29_graft_H shares 86.6% identities with the human germline gene (CDR region excluded). And about the aggregation tendency prediction, the CDR regions of B29 has high aggregation tendency, and after humanization, the aggregation tendency is reduced.

The humanized antibody and mouse/human chimeric IgG were expressed in HEK293 cells. The expression yield of the humanized antibody was 100 mg/L, while that of the chimeric IgG was 10 mg/L. SDS-PAGE QC result showed that both the humanized and the chimeric antibody were in good quality.

ELISA and SPR assays were performed to verify the affinity of the humanized and chimeric antibody. Both of the two antibodies showed obvious binding affinity for the target antigen. Thermostability (Tm and Tagg values) of the antigen, humanized antibody and chimeric antibody was measured using UNcle system. The result showed that both Tm and Tagg values were enhanced after humanization.

Amino acid sequences of the humanized and chimeric antibodies
B29_graft heavy chain
*EIQLVESGGGLVQPGGSVRLSCAASGYNFKTYGMSWVRQAPGKGLEWMGWINTYSGMPTYADDF*

*KGRFTFSLDTSKNTAYLQINSLRAEDTAVYFCARPLLGLDYWGQGTLVTVSS*ASTKGPSVFPLA

PSSKSTSGGTAALGCLVKDYFPEPVTVSWNSGALTSGVHTFPAVLQSSGLYSLSSVVTVPSSSL

GTQTYICNVNHKPSNTKVDKKVEPKSCDKTHTCPPCPAPELLGGPSVFLFPPKPKDTLMISRTP

EVTCVVVDVSHEDPEVKFNWYVDGVEVHNAKTKPREEQYNSTYRVVSVLTVLHQDWLNGKEYKC

KVSNKALPAPIEKTISKAKGQPREPQVYTLPPSREEMTKNQVSLTCLVKGFYPSDIAVEWESNG

QPENNYKTTPPVLDSDGSFFLYSKLTVDKSRWQQGNVFSCSVMHEALHNHYTQKSLSLSPGK

B29_graft light chain
*DIQMTQSPSSLSASVGDRVTITCKSSQSLLHSDGKTFLNWFQQKPGKSPKLLIYLVSKLESGVP*

*SRFSGSGSGTDFTLTISSLQPEDFATYYCLQHTHFPLTFGQGTKVEIK*RTVAAPSVFIFPPSDE

-continued

QLKSGTASVVCLLNNFYPREAKVQWKVDNALQSGNSQESVTEQDSKDSTYSLSSTLTLSKADYE

KHKVYACEVTHQGLSSPVTKSENRGEC

Chimeric _heavy chain
*QIQLVQSGPELKKPGETVKISCKASGYTFTTYGMSWVKQAPGKGLKWMGWINTYSGMPTYADDF*

*KGRFAFSLETSATTAYLQINNLKNEDTATYFCARPLLGLDYWGQGTTLTVSS*ASTKGPSVFPLA

PSSKSTSGGTAALGCLVKDYFPEPVTVSWNSGALTSGVHTFPAVLQSSGLYSLSSVVTVPSSSL

GTQTYICNVNHKPSNTKVDKKVEPKSCDKTHTCPPCPAPELLGGPSVFLFPPKPKDTLMISRTP

EVTCVVVDVSHEDPEVKFNWYVDGVEVHNAKTKPREEQYNSTYRVVSVLTVLHQDWLNGKEYKC

KVSNKALPAPIEKTISKAKGQPREPQVYTLPPSREEMTKNQVSLTCLVKGFYPSDIAVEWESNG

QPENNYKTTPPVLDSDGSFFLYSKLTVDKSRWQQGNVFSCSVMHEALHNHYTQKSLSLSPGK

Chimeric_ light chain
*DIVMTQTPLSLSVTIGQPASISCKSSQSLLHSDGKTFLNWFLQRPGQSPKLLIYLVSKLESGIP*

*DRFSGSGSGTDFTLKISRVEVEDLGVYYCLQHTHFPLTFGAGTKLEIK*RTVAAPSVFIFPPSDE

QLKSGTASVVCLLNNFYPREAKVQWKVDNALQSGNSQESVTEQDSKDSTYSLSSTLTLSKADYE

KHKVYACEVTHQGLSSPVTKSENRGEC

Nucleic acid sequences of the humanized and chimeric antibodies
B29_graft heavy chain
GCCGCCACCATGGGCTGGTCCCTGATTCTGCTGTTCCTGGTGGCTGTGGCTACCAGGGTGCTGA

GT*GAGATCCAGCTGGTGGAGAGCGGAGGAGGACTGGTGCAGCCAGGAGGATCTGTGAGGCTGAG*

*CTGCGCAGCATCCGGATACAACTTCAAGACCTATGGCATGTCCTGGGTGCGCCAGGCACCAGGC*

*AAGGGACTGGAGTGGATGGGCTGGATCAATACCTACTCTGGCATGCCTACATATGCCGACGATT*

*TCAAGGGCCGGTTCACCTTTTCTCTGGACACCAGCAAGAACACAGCCTACCTGCAGATCAATTC*

*CCTGCGGGCCGAGGACACAGCCGTGTACTTTTGTGCCAGACCCCTGCTGGGCCTGGATTATTGG*

*GGCCAGGGCACCCTGGTGACAGTGAGCTCC*GCTAGCACCAAGGGCCCATCGGTCTTCCCCCTGG

CACCCTCCTCCAAGAGCACCTCTGGGGGCACAGCGGCCCTGGGCTGCCTGGTCAAGGACTACTT

CCCCGAACCGGTGACGGTGTCGTGGAACTCAGGCGCCCTGACCAGCGGCGTGCACACCTTCCCG

GCTGTCCTACAGTCCTCAGGACTCTACTCCCTCAGCAGCGTGGTGACCGTGCCCTCCAGCAGCT

TGGGCACCCAGACCTACATCTGCAACGTGAATCACAAGCCCAGCAACACCAAGGTGGACAAGAA

AGTTGAGCCCAAATCTTGTGACAAAACTCACACATGCCCACCGTGCCCAGCACCTGAACTCCTG

GGGGGACCGTCAGTCTTCCTCTTCCCCCCAAAACCCAAGGACACCCTCATGATCTCCCGGACCC

CTGAGGTCACATGCGTGGTGGTGGACGTGAGCCACGAAGACCCTGAGGTCAAGTTCAACTGGTA

CGTGGACGGCGTGGAGGTGCATAATGCCAAGACAAAGCCGCGGGAGGAGCAGTACAACAGCACG

TACCGTGTGGTCAGCGTCCTCACCGTCCTGCACCAGGACTGGCTGAATGGCAAGGAGTACAAGT

GCAAGGTCTCCAACAAAGCCCTCCCAGCCCCCATCGAGAAAACCATCTCCAAAGCCAAAGGGCA

GCCCCGAGAACCACAGGTGTACACCCTGCCCCCATCCCGGGAGGAGATGACCAAGAACCAGGTC

AGCCTGACCTGCCTGGTCAAAGGCTTCTATCCCAGCGACATCGCCGTGGAGTGGGAGAGCAATG

GGCAGCCGGAGAACAACTACAAGACCACGCCTCCCGTGCTGGACTCCGACGGCTCCTTCTTCCT

CTACAGCAAGCTCACCGTGGACAAGAGCAGGTGGCAGCAGGGGAACGTCTTCTCATGCTCCGTG

ATGCATGAGGCTCTGCACAACCACTACACGCAGAAGAGCCTCTCCCTGTCTCCGGGTAAATGA

B29_graft light chain
GCCGCCACCATGGGCTGGTCCTGTATCATCCTGTTCCTGGTGGCTACAGCCACAGGAGTGCATA

GT*GACATCCAGATGACACAGTCCCCTAGCTCCCTGAGCGCCTCCGTGGGCGATAGGGTGACCAT*

*CACATGCAAGTCTAGCCAGTCTCTGCTGCACAGCGACGGCAAGACCTTCCTGAACTGGTTTCAG*

-continued

*CAGAAGCCCGGCAAGTCTCCTAAGCTGCTGATCTACCTGGTGTCCAAGCTGGAGTCTGGCGTGC*

*CCAGCAGATTCTCTGGCAGCGGCTCCGGCACAGACTTTACCCTGACAATCTCCTCTCTGCAGCC*

*AGAGGATTTCGCCACCTACTATTGTCTGCAGCACACCCACTTCCCCCTGACATTTGGCCAGGGC*

*ACCAAGGTGGAGATCAAG*CGTACGGTGGCTGCACCATCTGTCTTCATCTTCCCGCCATCTGATG

AGCAGTTGAAATCTGGAACTGCCTCTGTTGTGTGCCTGCTGAATAACTTCTATCCCAGAGAGGC

CAAAGTACAGTGGAAGGTGGATAACGCCCTCCAATCGGGTAACTCCCAGGAGAGTGTCACAGAG

CAGGACAGCAAGGACAGCACCTACAGCCTCAGCAGCACCCTGACGCTGAGCAAAGCAGACTACG

AGAAACACAAAGTCTACGCCTGCGAAGTCACCCATCAGGGCCTGAGCTCGCCCGTCACAAAGAG

CTTCAACAGGGGAGAGTGTTAG

Chimeric_heavy chain
GCCGCCACCATGGGCTGGTCCCTGATTCTGCTGTTCCTGGTGGCTGTGGCTACCAGGGTGCTGA

GT*CAGATCCAGCTGGTGCAGTCTGGCCCCGAGCTGAAGAAGCCTGGCGAGACCGTGAAGATCTC*

*TTGCAAGGCCAGCGGCTACACATTCACCACATATGGCATGAGCTGGGTGAAGCAGGCACCAGGC*

*AAGGGCCTGAAGTGGATGGGCTGGATCAACACCTACTCCGGCATGCCCACATATGCCGACGATT*

*TCAAGGGCCGGTTCGCCTTTTCCCTGGAGACCTCTGCCACCACAGCCTACCTGCAGATCAACAA*

*TCTGAAGAATGAGGACACCGCCACATACTTTTGTGCCAGACCCCTGCTGGGCCTGGATTATTGG*

*GGCCAGGGCACCACACTGACAGTGAGCTC*CGCTAGCACCAAGGGCCCATCGGTCTTCCCCCTGG

CACCCTCCTCCAAGAGCACCTCTGGGGGCACAGCGGCCCTGGGCTGCCTGGTCAAGGACTACTT

CCCCGAACCGGTGACGGTGTCGTGGAACTCAGGCGCCCTGACCAGCGGCGTGCACACCTTCCCG

GCTGTCCTACAGTCCTCAGGACTCTACTCCCTCAGCAGCGTGGTGACCGTGCCCTCCAGCAGCT

TGGGCACCCAGACCTACATCTGCAACGTGAATCACAAGCCCAGCAACACCAAGGTGGACAAGAA

AGTTGAGCCCAAATCTTGTGACAAAACTCACACATGCCCACCGTGCCCAGCACCTGAACTCCTG

GGGGGACCGTCAGTCTTCCTCTTCCCCCCAAAACCCAAGGACACCCTCATGATCTCCCGGACCC

CTGAGGTCACATGCGTGGTGGTGGACGTGAGCCACGAAGACCCTGAGGTCAAGTTCAACTGGTA

CGTGGACGGCGTGGAGGTGCATAATGCCAAGACAAAGCCGCGGGAGGAGCAGTACAACAGCACG

TACCGTGTGGTCAGCGTCCTCACCGTCCTGCACCAGGACTGGCTGAATGGCAAGGAGTACAAGT

GCAAGGTCTCCAACAAAGCCCTCCCAGCCCCCATCGAGAAAACCATCTCCAAAGCCAAAGGGCA

GCCCCGAGAACCACAGGTGTACACCCTGCCCCCATCCCGGGAGGAGATGACCAAGAACCAGGTC

AGCCTGACCTGCCTGGTCAAAGGCTTCTATCCCAGCGACATCGCCGTGGAGTGGGAGAGCAATG

GGCAGCCGGAGAACAACTACAAGACCACGCCTCCCGTGCTGGACTCCGACGGCTCCTTCTTCCT

CTACAGCAAGCTCACCGTGGACAAGAGCAGGTGGCAGCAGGGGAACGTCTTCTCATGCTCCGTG

ATGCATGAGGCTCTGCACAACCACTACACGCAGAAGAGCCTCTCCCTGTCTCCGGGTAAATGA

Chimeric_light chain
GCCGCCACCATGGGCTGGTCCTGTATCATCCTGTTCCTGGTGGCTACAGCCACAGGAGTGCATA

GT*GACATCGTGATGACCCAGACACCACTGTCTCTGAGCGTGACAATCGGCCAGCCCGCCTCCAT*

*CTCTTGCAAGAGCTCCCAGAGCCTGCTGCACTCCGATGGCAAGACCTTCCTGAACTGGTTTCTG*

*CAGAGGCCAGGACAGTCCCCTAAGCTGCTGATCTACCTGGTGTCTAAGCTGGAGAGCGGAATCC*

*CTGACCGGTTCAGCGGATCCGGATCTGGAACCGACTTCACCCTGAAGATCTCTAGAGTGGAGGT*

*GGAGGACCTGGGCGTGTACTATTGTCTGCAGCACACCCACTTCCCCCTGACATTTGGCGCCGGC*

*ACCAAGCTGGAGATCAAG*CGTACGGTGGCTGCACCATCTGTCTTCATCTTCCCGCCATCTGATG

AGCAGTTGAAATCTGGAACTGCCTCTGTTGTGTGCCTGCTGAATAACTTCTATCCCAGAGAGGC

-continued

CAAAGTACAGTGGAAGGTGGATAACGCCCTCCAATCGGGTAACTCCCAGGAGAGTGTCACAGAG

CAGGACAGCAAGGACAGCACCTACAGCCTCAGCAGCACCCTGACGCTGAGCAAAGCAGACTACG

AGAAACACAAAGTCTACGCCTGCGAAGTCACCCATCAGGGCCTGAGCTCGCCCGTCACAAAGAG

CTTCAACAGGGGAGAGTGTTAG

TABLE 1

Table of Sequences

| SEQ ID NO | Description | Sequence |
|---|---|---|
| 1 | B29_graft Heavy chain CDR1 - amino acid (B29) | **GYNFKTY** |
| 2 | B29_chimeric Heavy chain CDR1 - amino acid (B29) | **GYTFTTY** |
| 3 | Heavy chain CDR1 - nucleic acid (B29) | **GGGTATACCTTCACAACCTAT** |
| 4 | Heavy chain CDR2 - amino acid (B29) | **NTYSGM** |
| 5 | Heavy chain CDR2 - nucleic acid (B29) | **AACACCTACTCTGGAATG** |
| 6 | Heavy chain CDR3 - amino acid (B29) | **PLLGLDY** |
| 7 | Heavy chain CDR3 - nucleic acid (B29) | **CCTCTCCTGGGACTTGACTAT** |
| 8 | Light chain CDR1 - amino acid (B29) | **KSSQSLLHSDGK** |
| 9 | Light chain CDR1 - nucleic acid (B29) | **AAGTCAAGTCAGAGCCTCTTACATAGTGATGGAAAG** |
| 10 | Light chain CDR2 - amino acid (B29) | **LVSKLES** |
| 11 | Light chain CDR2 - nucleic acid (B29) | **CTGGTGTCTAAACTGGAATCT** |
| 12 | Light chain CDR3 - amino acid (B29) | **LQHTHFPLT** |

TABLE 1-continued

Table of Sequences

| SEQ ID NO | Description | Sequence |
|---|---|---|
| 13 | Light chain CDR3 - nucleic acid (B29) | **TTGCAACATACACATTTTCCGCTCACG** |
| 14 | B29 Heavy Chain - amino acid | QIQLVQSGPELKKPGETVKISCKAS**GYTFTTY**GMSWVKQAPGKGLKWMG<br>WI**NTYSGM**PTYADDFKGRFAFSLETSATTAYLQINNLKNEDTATYFCAR<br>**PLLGLDY**WGQGTTLTVSS |
| 15 | B29 Heavy Chain - nucleic acid | CAGATCCAGTTGGTACAGTCTGGACCTGAGCTGAAGAAGCCTGGAGAGA<br>CAGTCAAGATCTCCTGCAAGGCCTCC**GGGTATACCTTCACAACCTAT**GG<br>AATGAGCTGGGTGAAACAGGCTCCAGGAAAGGGTTTAAAGTGGATGGGC<br>TGGATA**AACACCTACTCTGGAATG**CCAACATATGCTGATGACTTCAAGG<br>GACGGTTTGCCTTCTCTTTGGAAACCTCTGCCACCACTGCCTATTTGCA<br>GATCAACAACCTCAAAAATGAGGACACGGCTACATATTTCTGTGCAAGA<br>**CCTCTCCTGGGACTTGACTAT**TGGGGCCAAGGCACCACTCTCACAGTCT<br>CCTCA |
| 16 | B29 Light Chain - amino acid | DIVMTQTPLSLSVTIGQPASISC**KSSQSLLHSDGK**TFLNWFLQRPGQSP<br>KLLIY**LVSKLES**GIPDRFSGSGSGTDFTLKISRVEVEDLGVYYC**LQHTH**<br>**FPLT**FGAGTKLEIK |
| 17 | B29 Light Chain - nucleic acid | GATATTGTGATGACCCAGACTCCACTGTCTTTGTCGGTTACCATTGGAC<br>AACCAGCCTCCATCTCTTGC**AAGTCAAGTCAGAGCCTCTTACATAGTGA**<br>**TGGAAAG**ACATTTTTGAATTGGTTTTTACAGAGGCCAGGCCAGTCTCCA<br>AAGCTCCTAATCTAT**CTGGTGTCTAAACTGGAATCT**GGCATCCCTGACA<br>GGTTCAGTGGCAGTGGATCAGGGACAGATTTCACACTGAAAATCAGCAG<br>AGTGGAGGTTGAGGATTTGGGAGTTTATTACTGC**TTGCAACATACACAT**<br>**TTTCCGCTCACG**TTCGGTGCTGGGACCAAACTGGAAATAAAA |
| 18 | B29_graft heavy chain Amino acid | *EIQLVESGGGLVQPGGSVRLSCAASGYNFKTYGMSWVRQAPGKGLEWMG*<br>*WINTYSGMPTYADDFKGRFTFSLDTSKNTAYLQINSLRAEDTAVYFCAR*<br>*PLLGLDYWGQGTLVTVSS*ASTKGPSVFPLAPSSKSTSGGTAALGCLVKD<br>YFPEPVTVSWNSGALTSGVHTFPAVLQSSGLYSLSSVVTVPSSSLGTQT<br>YICNVNHKPSNTKVDKKVEPKSCDKTHTCPPCPAPELLGGPSVFLFPPK<br>PKDTLMISRTPEVTCVVVDVSHEDPEVKFNWYVDGVEVHNAKTKPREEQ<br>YNSTYRVVSVLTVLHQDWLNGKEYKCKVSNKALPAPIEKTISKAKGQPR<br>EPQVYTLPPSREEMTKNQVSLTCLVKGFYPSDIAVEWESNGQPENNYKT<br>TPPVLDSDGSFFLYSKLTVDKSRWQQGNVFSCSVMHEALHNHYTQKSLS<br>LSPGK |
| 19 | B29_graft heavy chain nucleic acid | GCCGCCACCATGGGCTGGTCCCTGATTCTGCTGTTCCTGGTGGCTGTGG<br>CTACCAGGGTGCTGAGT*GAGATCCAGCTGGTGGAGAGCGGAGGAGGACT*<br>*GGTGCAGCCAGGAGGATCTGTGAGGCTGAGCTGCGCAGCATCC* ***GGATAC***<br>***AACTTCAAGACCTAT*** *GGCATGTCCTGGGTGCGCCAGGCACCAGGCAAGG*<br>*GACTGGAGTGGATGGGCTGGATC* ***AATACCTACTCTGGCATG*** *CCTACATA*<br>*TGCCGACGATTTCAAGGGCCGGTTCACCTTTTCTCTGGACACCAGCAAG*<br>*AACACAGCCTACCTGCAGATCAATTCCCTGCGGGCCGAGGACACAGCCG*<br>*TGTACTTTTGTGCCAGA* ***CCCCTGCTGGGCCTGGATTAT*** *TGGGGCCAGGG*<br>*CACCCTGGTGACAGTGAGCTCC*GCTAGCACCAAGGGCCCATCGGTCTTC<br>CCCCTGGCACCCTCCTCCAAGAGCACCTCTGGGGGCACAGCGGCCCTGG<br>GCTGCCTGGTCAAGGACTACTTCCCCGAACCGGTGACGGTGTCGTGGAA<br>CTCAGGCGCCCTGACCAGCGGCGTGCACACCTTCCCGGCTGTCCTACAG<br>TCCTCAGGACTCTACTCCCTCAGCAGCGTGGTGACCGTGCCCTCCAGCA<br>GCTTGGGCACCCAGACCTACATCTGCAACGTGAATCACAAGCCCAGCAA<br>CACCAAGGTGGACAAGAAAGTTGAGCCCAAATCTTGTGACAAAACTCAC<br>ACATGCCCACCGTGCCCAGCACCTGAACTCCTGGGGGGACCGTCAGTCT<br>TCCTCTTCCCCCCAAAACCCAAGGACACCCTCATGATCTCCCGGACCCC<br>TGAGGTCACATGCGTGGTGGTGGACGTGAGCCACGAAGACCCTGAGGTC<br>AAGTTCAACTGGTACGTGGACGGCGTGGAGGTGCATAATGCCAAGACAA<br>AGCCGCGGGAGGAGCAGTACAACAGCACGTACCGTGTGGTCAGCGTCCT<br>CACCGTCCTGCACCAGGACTGGCTGAATGGCAAGGAGTACAAGTGCAAG<br>GTCTCCAACAAAGCCCTCCCAGCCCCCATCGAGAAAACCATCTCCAAAG<br>CCAAAGGGCAGCCCCGAGAACCACAGGTGTACACCCTGCCCCCATCCCG<br>GGAGGAGATGACCAAGAACCAGGTCAGCCTGACCTGCCTGGTCAAAGGC<br>TTCTATCCCAGCGACATCGCCGTGGAGTGGGAGAGCAATGGGCAGCCGG<br>AGAACAACTACAAGACCACGCCTCCCGTGCTGGACTCCGACGGCTCCTT |

TABLE 1-continued

| SEQ ID NO | Description | Sequence |
|---|---|---|
| | | Table of Sequences |
| | | CTTCCTCTACAGCAAGCTCACCGTGGACAAGAGCAGGTGGCAGCAGGGG<br>AACGTCTTCTCATGCTCCGTGATGCATGAGGCTCTGCACAACCACTACA<br>CGCAGAAGAGCCTCTCCCTGTCTCCGGGTAAATGA<br>**Bold regions correspond to CDRs**<br>**First bold region corresponds to CDR1**<br>**Second bold region corresponds to CDR2**<br>**Third bold region corresponds to CDR3** |
| 20 | B29_graft light chain | *DIQMTQSPSSLSASVGDRVTITCKSSQSLLHSDGKTFLNWFQQKPGKSP*<br>*KLLIYLVSKLESGVPSRFSGSGSGTDFTLTISSLQPEDFATYYCLQHTH*<br>*FPLTFGQGTKVEIK*RTVAAPSVFIFPPSDEQLKSGTASVVCLLNNFYPR<br>EAKVQWKVDNALQSGNSQESVTEQDSKDSTYSLSSTLTLSKADYEKHKV<br>YACEVTHQGLSSPVTKSFNRGEC |
| 21 | B29_graft light chain | GCCGCCACCATGGGCTGGTCCTGTATCATCCTGTTCCTGGTGGCTACAG<br>CCACAGGAGTGCATAGT*GACATCCAGATGACACAGTCCCCTAGCTCCCT*<br>*GAGCGCCTCCGTGGGCGATAGGGTGACCATCACATGC***AAGTCTAGCCAG**<br>**TCTCTGCTGCACAGCGACGGCAAG***ACCTTCCTGAACTGGTTTCAGCAGA*<br>*AGCCCGGCAAGTCTCCTAAGCTGCTGATCTAC***CTGGTGTCCAAGCTGGA**<br>**CTCT***GGCGTGCCCAGCAGATTCTCTGGCAGCGGCTCCGGCACAGACTTT*<br>*ACCCTGACAATCTCCTCTCTGCAGCCAGAGGATTTCGCCACCTACTATT*<br>*GT***CTGCAGCACACCCACTTCCCCCTGACA***TTTGGCCAGGGCACCAAGGT*<br>*GGAGATCAAG*CGTACGGTGGCTGCACCATCTGTCTTCATCTTCCCGCCA<br>TCTGATGAGCAGTTGAAATCTGGAACTGCCTCTGTTGTGTGCCTGCTGA<br>ATAACTTCTATCCCAGAGAGGCCAAAGTACAGTGGAAGGTGGATAACGC<br>CCTCCAATCGGGTAACTCCCAGGAGAGTGTCACAGAGCAGGACAGCAAG<br>GACAGCACCTACAGCCTCAGCAGCACCCTGACGCTGAGCAAAGCAGACT<br>ACGAGAAACACAAAGTCTACGCCTGCGAAGTCACCCATCAGGGCCTGAG<br>CTCGCCCGTCACAAAGAGCTTCAACAGGGGAGAGTGTTAG<br>**Bold regions correspond to CDRs**<br>**First bold region corresponds to CDR1**<br>**Second bold region corresponds to CDR2**<br>**Third bold region corresponds to CDR3** |
| 22 | Chimeric_heavy chain | *QIQLVQSGPELKKPGETVKISCKASGYTFTTYGMSWVKQAPGKGLKWMG*<br>*WINTYSGMPTYADDFKGRFAFSLETSATTAYLQINNIKNEDTATYFCAR*<br>*PLLGLDYWGQGTTLTVSS*ASTKGPSVFPLAPSSKSTSGGTAALGCLVKD<br>YFPEPVTVSWNSGALTSGVHTFPAVLQSSGLYSLSSVVTVPSSSLGTQT<br>YICNVNHKPSNTKVDKKVEPKSCDKTHTCPPCPAPELLGGPSVFLFPPK<br>PKDTLMISRTPEVTCVVVDVSHEDPEVKFNWYVDGVEVHNAKTKPREEQ<br>YNSTYRVVSVLTVLHQDWLNGKEYKCKVSNKALPAPIEKTISKAKGQPR<br>EPQVYTLPPSREEMTKNQVSLTCLVKGFYPSDIAVEWESNGQPENNYKT<br>TPPVLDSDGSFFLYSKLTVDKSRWQQGNVFSCSVMHEALHNHYTQKSLS<br>LSPGK |
| 23 | Chimeric_heavy chain | GCCGCCACCATGGGCTGGTCCCTGATTCTGCTGTTCCTGGTGGCTGTGG<br>CTACCAGGGTGCTGAGT*CAGATCCAGCTGGTGCAGTCTGGCCCCGAGCT*<br>*GAAGAAGCCTGGCGAGACCGTGAAGATCTCTTGCAAGGCCAGC***GGCTAC**<br>**ACATTCACCACATAT***GGCATGAGCTGGGTGAAGCAGGCACCAGGCAAGG*<br>*GCCTGAAGTGGATGGGCTGGATC***AACACCTACTCCGGCATG***CCCACATA*<br>*TGCCGACGATTTCAAGGGCCGGTTCGCCTTTTCCCTGGAGACCTCTGCC*<br>*ACCACAGCCTACCTGCAGATCAACAATCTGAAGAATGAGGACACCGCCA*<br>*CATACTTTTGTGCCAGA***CCCCTGCTGGGCCTGGATTAT***TGGGGCCAGGG*<br>*CACCACACTGACAGTGAGCTCC*GCTAGCACCAAGGGCCCATCGGTCTTC<br>CCCCTGGCACCCTCCTCCAAGAGCACCTCTGGGGGCACAGCGGCCCTGG<br>GCTGCCTGGTCAAGGACTACTTCCCCGAACCGGTGACGGTGTCGTGGAA<br>CTCAGGCGCCCTGACCAGCGGCGTGCACACCTTCCCGGCTGTCCTACAG<br>TCCTCAGGACTCTACTCCCTCAGCAGCGTGGTGACCGTGCCCTCCAGCA<br>GCTTGGGCACCCAGACCTACATCTGCAACGTGAATCACAAGCCCAGCAA<br>CACCAAGGTGGACAAGAAAGTTGAGCCCAAATCTTGTGACAAAACTCAC<br>ACATGCCCACCGTGCCCAGCACCTGAACTCCTGGGGGGACCGTCAGTCT<br>TCCTCTTCCCCCCAAAACCCAAGGACACCCTCATGATCTCCCGGACCCC<br>TGAGGTCACATGCGTGGTGGTGGACGTGAGCCACGAAGACCCTGAGGTC<br>AAGTTCAACTGGTACGTGGACGGCGTGGAGGTGCATAATGCCAAGACAA<br>AGCCGCGGGAGGAGCAGTACAACAGCACGTACCGTGTGGTCAGCGTCCT<br>CACCGTCCTGCACCAGGACTGGCTGAATGGCAAGGAGTACAAGTGCAAG<br>GTCTCCAACAAAGCCCTCCCAGCCCCCATCGAGAAAACCATCTCCAAAG<br>CCAAAGGGCAGCCCCGAGAACCACAGGTGTACACCCTGCCCCCATCCCG<br>GGAGGAGATGACCAAGAACCAGGTCAGCCTGACCTGCCTGGTCAAAGGC<br>TTCTATCCCAGCGACATCGCCGTGGAGTGGGAGAGCAATGGGCAGCCGG<br>AGAACAACTACAAGACCACGCCTCCCGTGCTGGACTCCGACGGCTCCTT<br>CTTCCTCTACAGCAAGCTCACCGTGGACAAGAGCAGGTGGCAGCAGGGG<br>AACGTCTTCTCATGCTCCGTGATGCATGAGGCTCTGCACAACCACTACA<br>CGCAGAAGAGCCTCTCCCTGTCTCCGGGTAAATGA |

TABLE 1-continued

Table of Sequences

| SEQ ID NO | Description | Sequence |
| --- | --- | --- |
| | | **Bold regions correspond to CDRs:**<br>**First bold region corresponds to CDR1**<br>**Second bold region corresponds to CDR2**<br>**Third bold region corresponds to CDR3** |
| 24 | Chimeric_light chain | *DIVMTQTPLSLSVTIGQPASISCKSSQSLLHSDGKTFLNWFLQRPGQSP*<br>*KLLIYLVSKLESGIPDRFSGSGSGTDFTLKISRVEVEDLGVYYCLQHTH*<br>*FPLTFGAGTKLEIK*RTVAAPSVFIFPPSDEQLKSGTASVVCLLNNFYPR<br>EAKVQWKVDNALQSGNSQESVTEQDSKDSTYSLSSTLTLSKADYEKHKV<br>YACEVTHQGLSSPVTKSFNRGEC |
| 25 | Chimeric_light chain | GCCGCCACCATGGGCTGGTCCTGTATCATCCTGTTCCTGGTGGCTACAG<br>CCACAGGAGTGCATAGT*GACATCGTGATGACCCAGACACCACTGTCTCT*<br>*GAGCGTGACAATCGGCCAGCCCGCCTCCATCTCTTGC* ***AAGAGCTCCCAG***<br>***AGCCTGCTGCACTCCGATGGCAAG*** *ACCTTCCTGAACTGGTTTCTGCAGA*<br>*GGCCAGGACAGTCCCCTAAGCTGCTGATCTAC* ***CTGGTGTCTAAGCTGGA***<br>***GAGC*** *GGAATCCCTGACCGGTTCAGCGGATCCGGATCTGGAACCGACTTC*<br>*ACCCTGAAGATCTCTAGAGTGGAGGTGGAGGACCTGGGCGTGTACTATT*<br>*GT* ***CTGCAGCACACCCACTTCCCCCTGACA*** *TTTGGCGCCGGCACCAAGCT*<br>*GGAGATCAAG*CGTACGGTGGCTGCACCATCTGTCTTCATCTTCCCGCCA<br>TCTGATGAGCAGTTGAAATCTGGAACTGCCTCTGTTGTGTGCCTGCTGA<br>ATAACTTCTATCCCAGAGAGGCCAAAGTACAGTGGAAGGTGGATAACGC<br>CCTCCAATCGGGTAACTCCCAGGAGAGTGTCACAGAGCAGGACAGCAAG<br>GACAGCACCTACAGCCTCAGCAGCACCCTGACGCTGAGCAAAGCAGACT<br>ACGAGAAACACAAAGTCTACGCCTGCGAAGTCACCCATCAGGGCCTGAG<br>CTCGCCCGTCACAAAGAGCTTCAACAGGGGAGAGTGTTAG<br>**Bold regions correspond to CDRs:**<br>**First bold region corresponds to CDR1**<br>**Second bold region corresponds to CDR2**<br>**Third bold region corresponds to CDR3** |
| 26 | B29_graft Heavy chain CDR1 - amino acid (B29) | **TYGMS** |
| 27 | B29 graft Heavy chain CDR2 - amino acid (B29) | **WINTYSGMPTYADDFKG** |
| 28 | B29 graft Heavy chain CDR3 - amino acid (B29) | **PLLGLDY** |
| 29 | Light chain CDR1 - amino acid (B29) | **KSSQSLLHSDGKTFLN** |

Example 3

Regulation of the equilibrium between proteases and their inhibitors is fundamental to the survival of multicellular organisms. The immunological response to serpinB13, which is a protease inhibitor of cathepsin L (catL), plays an important role in slowing down, and preventing the development, of insulin-dependent diabetes. This hypothesis is rooted in translational and experimental animal studies. Specifically, previous analysis of baseline autoantibody (AA) activity to serpinB13 in first-degree relatives of type 1 diabetes (T1D) probands during their enrollment in the DPT-1 prevention trial revealed a significantly lower incidence of diabetes in individuals with detectable anti-serpin activity compared with subjects negative for anti-serpin activity. Moreover, studies in animals demonstrated that injecting a monoclonal antibody (mAb) to serpinB13 led to a robust increase in the number of pancreatic Ngn3+ progenitor cells, a significant expansion of islet mass, and improved resistance to severe diabetes in adulthood.

SerpinB13 AA is examined in a cohort of DPT-1 subjects with an emphasis on samples that were collected during the follow-up period rather than at baseline. Intermediate-to-high risk individuals are studied and the patterns of serological binding activity to serpinB13 over time is assessed along with their association with progression to clinical diabetes.

Regulation of the Notch pathway, a highly conserved signaling pathway that restricts generation of $Ngn3^{+}$ endocrine progenitors is examined. Using pancreatic embryonic explants, it is examined whether human serpinB13 AA and humanized mAb to serpinB13 induce Ngn3$^{+}$ cells via catL-mediated cleavage of Notch receptors and subsequent disruption of Notch signaling.

Example 4

Figure 6B:
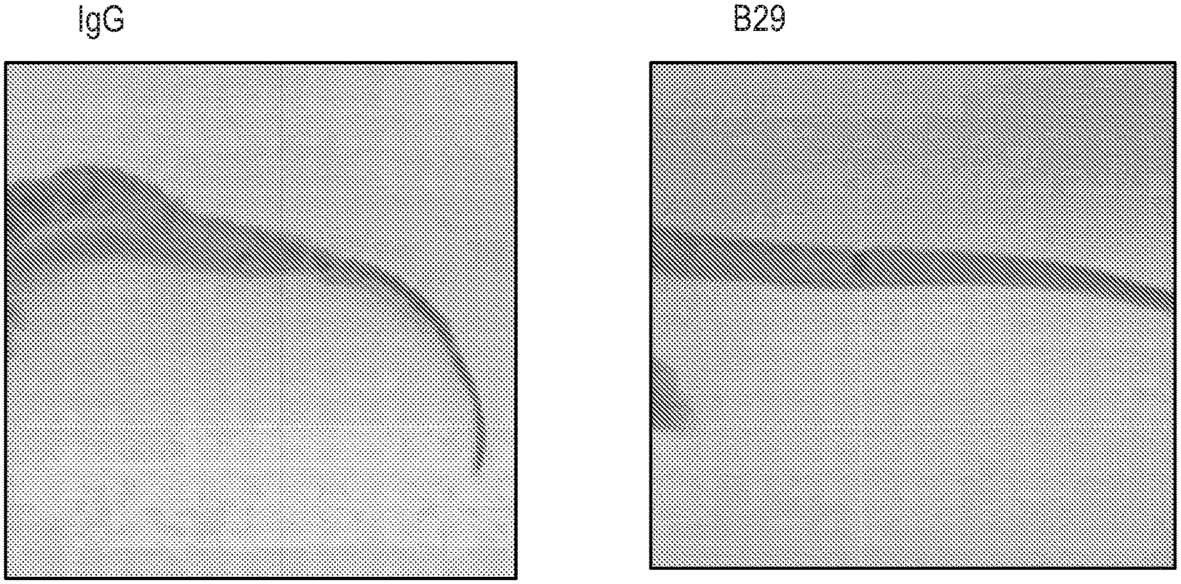
Figure 6C:
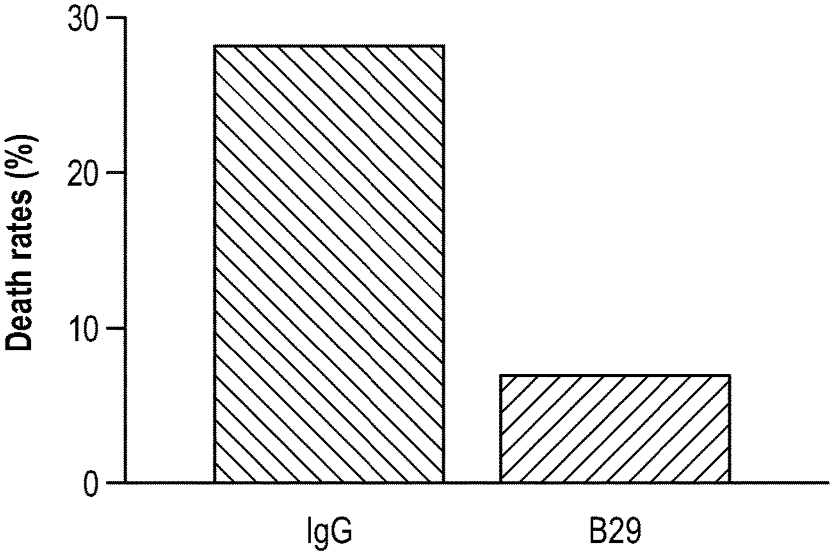

The impact of mouse monoclonal antibody to serpin B13 (clone B29) on tissue regeneration in different organs was studied. FIGS. 6A-6C.

Example 5

The inventors identified a novel autoantibody (AA) to serpin B13, a protease inhibitor of cathepsin L (catL). Quite unexpectedly, when using human samples from several consortia it was found that, unlike other AAs in T1D, serpinB13 AA was associated with improved outcomes. In particular, recent examination of healthy individuals at risk for type 1 diabetes (T1D), and who had been enrolled in the Diabetes Prevention Trial for Type 1 Diabetes (DPT-1), revealed significant benefits for those who were positive for anti-serpinB13 activity at baseline. These subjects demonstrated a lower rate of progression to the clinical onset of T1D, and their overall incidence of diabetes by the end of a seven-year follow-up was also lower compared with individuals who were negative at baseline for serpinB13 AA. In addition to these translational studies, a novel mouse monoclonal antibody (mAb [clone B29]) was developed, which was used as a model to examine the potential functionality of the immunological response to serpinB13. Studies with this antibody showed that neutralizing the serpinB13 molecule augmented catL activity, increased the number of pancreatic endocrine progenitor cells expressing neurogenin 3 (Ngn3), and ultimately helped to prevent severe diabetes. Together, the studies in humans and mice suggest that serpinB13 AA is a biomarker of improved islet biology. Since activation of the Notch pathway leads to inhibition of Ngn3 expression, it is hypothesized that catL, induced by antibody-mediated neuralization of serpinB13, helps to reverse this repression b impairing Notch function.

Approximately 60% of the patients with chronic pancreatitis who receive islet autotransplant remain insulin dependent after surgery, while 40% become insulin independent. While islet mass transplanted is an important predictor of insulin independence, other factors that influence this outcome remain elusive. The impact of baseline (pre-transplant) serpinB13 AA in these patients is tested. Specifically, serpinB13 AA expression is examined for its potential association with insulin dependence (on/off insulin), insulin dose, and fasting and stimulated C-peptide levels at 1 year after islet autotransplant. In addition, the association of serpinB13 AA detected in the sera of patients with pancreatitis is examined, with an in vitro function of the islets isolated from the same patients (e.g., the islets from strong and weak secretors of serpinB13 AA, for β-cell proliferation, apoptosis, insulin secretion, the presence of Ngn3+ endocrine progenitors, and expression of genes associated with islet cell regeneration are examined). SerpinB13 AA is examined using a Luminex methodology.

Recently, several fully human mAbs to serpinB13 were developed that maintain binding to the target at similar levels compared with the mouse mAb, clone B29 (discussed above). Gene expression and protein levels of Ngn3 following inhibition of serpinB13 with human anti-serpinB13 mAb is examined. The impact of Notch and catL on the response to human antiserpinB13 mAb is assessed using transgenic mice that either express the constitutively active Notch intracellular domain or are genetically deficient for catL. Finally, the degradomic profile of Notch following induction of catL with human anti-serpinB13 mAb is examined. The studies examine the biological impact of endogenous anti-serpinB13 activity on islet biology on case-by-case basis in humans and, leverage the development of passive immunization with anti-serpinB13 mAb as an approach to reduce the incidence of diabetes after TPIAT. In addition, these studies help to determine whether anti-serpin activity provides an important function by dismantling Notch signaling, thereby allowing a more efficient generation of the endocrine progenitor cells. Ultimately, the findings are applicable to the development of new therapeutic interventions in diabetes and other diseases with a deregulated Notch pathway.

Protease activity is critical for the survival of multicellular organisms. It is not surprising, therefore that proteases are modulated by a number of inhibitors, which themselves are regulated. The research focuses on a fundamental problem of regulation of the balance between proteases and their inhibitors, and its role in islet biology and diabetes). It has been discovered that proteases are key players in regulation of molecules that haven been linked to development and increased regenerative potential in insulin-producing cells, and that by doing so they contribute to better clinical outcomes in diabetes. Specifically, in both human and mouse a novel autoantibody (AA) to serpinB13 protease inhibitor of cathepsin L (catL) has been identified and it was found that this immunological response blocks inhibitory function of serpin, thereby allowing the protease activity of catL to increase. It is believed that low level extracellular catL, through the cleavage of several distinct molecules expressed on the cell-surface in the pancreas positively influences regenerative potential of islet cells thereby offering a lead for therapy development in patients with type 1 diabetes (T1D) and other settings that would benefit from improved biology of β-cells, e.g., in the setting of islet autotransplantation that is offered to patients with painful pancreatitis undergoing total pancreatectomy.

SerpinB13. SerpinB13 is a member of the clade B family of potent cysteine and serine protease inhibitors. It is expressed in the exocrine pancreatic ducts and several other tissues. Although clade B serpins are mainly intracellular, serpinB1 (a close relative of serpinB13) has been observed to be released from keratinocytes exposed to UVB light. In addition, serpinB13 functions in the extracellular matrix to suppress angiogenesis, indicating that these serpins can be released under certain conditions. It has been shown that serpinB13 can reach the extracellular milieu during culture of embryonic pancreas explants. Ultimately, release of clade B serpins from cells facilitate induction of an AA response against these molecules.

Anti-serpinB13 activity is a modifying protective factor that actively contributes to protecting pancreatic islets. This is in sharp contrast to many other AAs associated with T1D, which are assumed to be predominantly biomarkers of pathological changes in pancreatic islets during development of T1D. The idea that stimulating protease activity promotes β-cell regenerative changes through impeded Notch signaling is original. Autoantibody response to serpinB13 is a biomarker of improved clinical outcome in human T1D. To assess whether serpinB13 AA promotes β-cell health in humans, the association of this antibody response with residual β-cell function in children with a recent diagnosis of T1D was examined, and who were previously enrolled as placebo subjects in one of several Type 1 Diabetes TrialNet double-blind placebo-controlled intervention protocols.

Figure 7A:
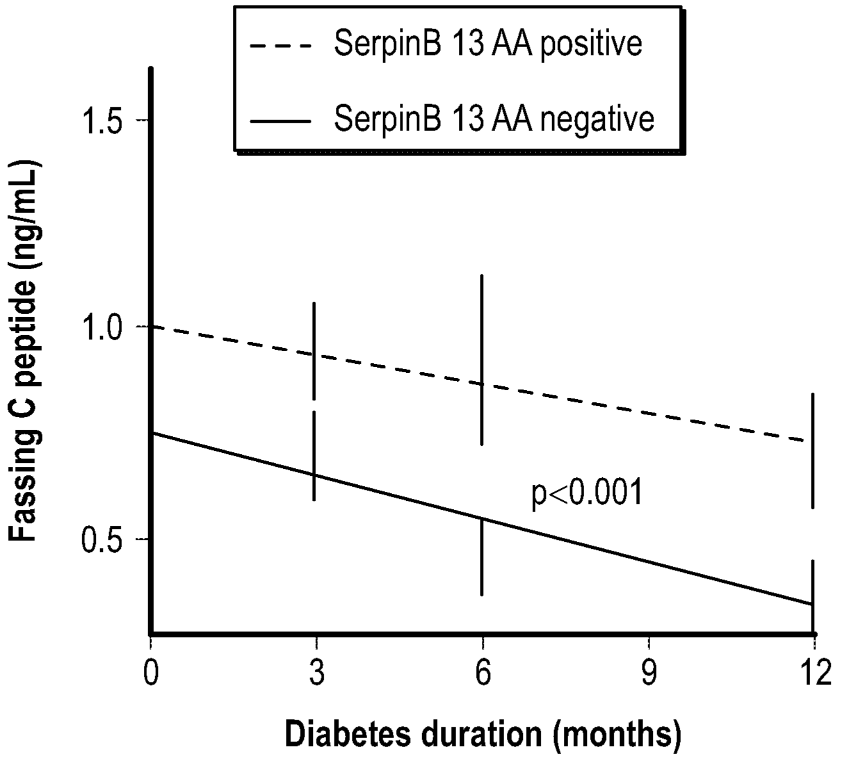
FIGS. 7A and 7B. Impact of baseline serpinB13 AAs on beta cell function in recent onset T1D patients. The placebo subjects previously recruited to Type 1 Diabetes TrialNet protocols TN02 MMF/DZB, TN08 GAD-Alum Vaccine, TN09 CTLA-4 or TN14 Anti-IL1b were examined. The impact of baseline serpin response was examined with regard to C-peptide, either fasting (A) or stimulated at 90 min. during mixed-meal tolerance test (MMTT) (B). Linear regression was used for the analysis.
Figure 7B:
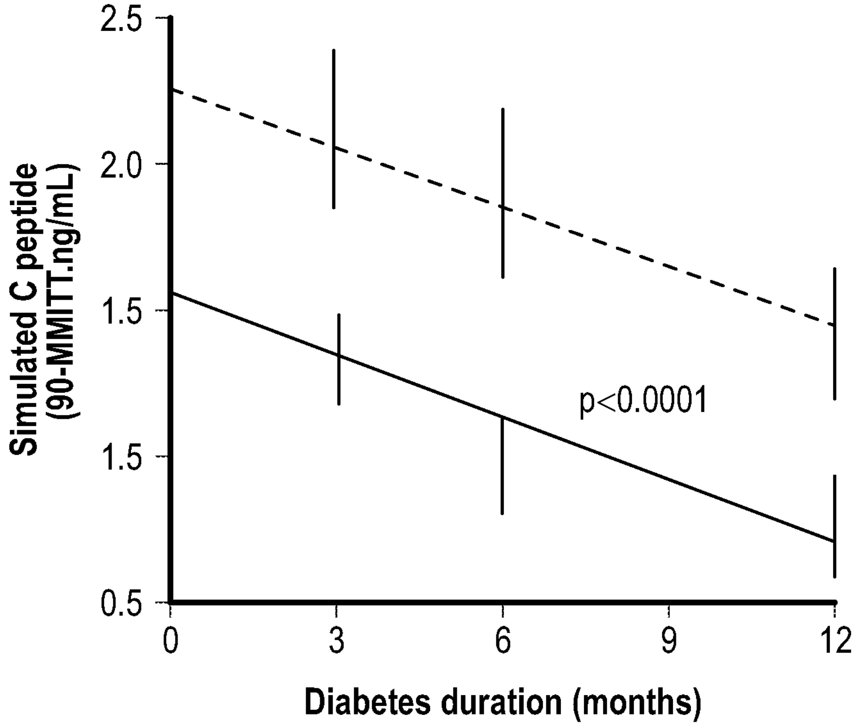

It was found that subjects with serpinB13 AAs had higher fasting and stimulated Cpeptide levels during the first-year post-diagnosis, compared with serpinB13 AA-negative subjects (FIGS. 7A and 7B). Remarkably, the results are very similar to those published by Herold et al. on CD3 mAb, the gold standard in research on novel immunointerventions in T1D (Herold et al., Teplizumab (anti-CD3 mAb) treatment preserves C-peptide responses in patients with new-onset type 1 diabetes in a randomized controlled trial. Diabetes 62: 3766-3774, 2013.). It was then investigated whether serpinB13 AA also influences the pre-diabetes period and progression to T1D. To address this question, serum from individuals who had been enrolled in the DPT-1 study was examined. In baseline samples, a strong significant correlation with diabetes-free status was found. SerpinB13 AA frequency inversely correlated with risk for T1D (FIG. 12A), fewer individuals positive for serpinB13 AA developed diabetes (FIG. 12B) and developed it later (FIG. 12C), compared to serpinB13 AA-negative subjects. Therefore, it is believed that serpinB13 AA offers a high level of islet protection.

Cathepsin L protease activity is upregulated following inhibition of serpinB13 with a mAb (clone B29). CatL has been implicated as a serpinB13 protease target. To examine the consequences of inhibiting serpinB13 using a mAb (clone B29), the catalytic activity of catL was measured. First, it was noted that serpinB13 mAb dose-dependently enhanced the protease activity of catL when added to a cell extract from pancreatic tissue in vitro. To measure catL activity in vivo, the activity-based probe, ProSense 680, was used. A significant increase in catL activity was observed in the intact pancreas following injection of anti-serpinB13 mAb into mice. This increase was limited to the pancreas in wild-type Balb/c mice and was not observed in the liver, where serpinB13 is not expressed, or in the pancreas of catL-deficient Balb/c mice. Together, these data show that mAb-mediated inhibition of serpinB13 influences the activity of catL in vivo and provides a reliable model that will allow us to examine the role of catL protease activity in islet biology in more detail.

Figure 8A:
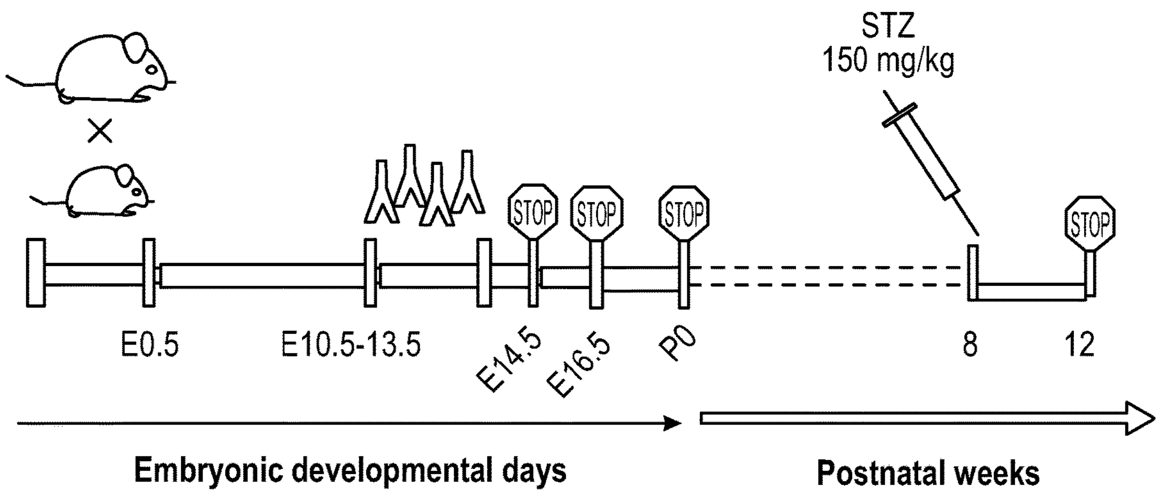
FIGS. 8A-8F. A mAb to serpinB13, clone B29, promotes development of pancreatic Ngn3+ endocrine progenitor cells and helps to prevent severe diabetes. (A) A schematic of the experiment. Healthy Balb/c females were i.p. injected four times with 50 μg of B29 (αB13), or control IgG, during mid pregnancy. The pancreatic tissue in the offspring was examined on embryonic day E14.5 and E16.5, at birth (PO) (B and C), or in adulthood at 12 weeks of age following induction of diabetes with STZ at 8 weeks of age (D-F). (B-C) Quantitative analysis of Ngn3+ cells by I.F microscopy (B; insert in B shows the impact of CatL deficiency), and flowcytometry analysis of active Notch intracellular domain (NICD) using Val1744 polyclonal antibody (C), in embryonic pancreases. The right panel in C shows the average mean fluorescence channel of antibody staining from three independent experiments. (D-F) A follow-up of diabetic mice with gestational exposure to anti-serpinB13 mAb. The quantitative analysis is shown for the residual β-ell mass at 4 weeks after STZ injection (D), random blood glucose at 1, 2, 3, and 4 weeks after STZ injection (E), and serum creatinine at 4 weeks after STZ injection (F). * $p<0.05$,  $p<0.01$, and * $p<0.001$.
Figure 8B:
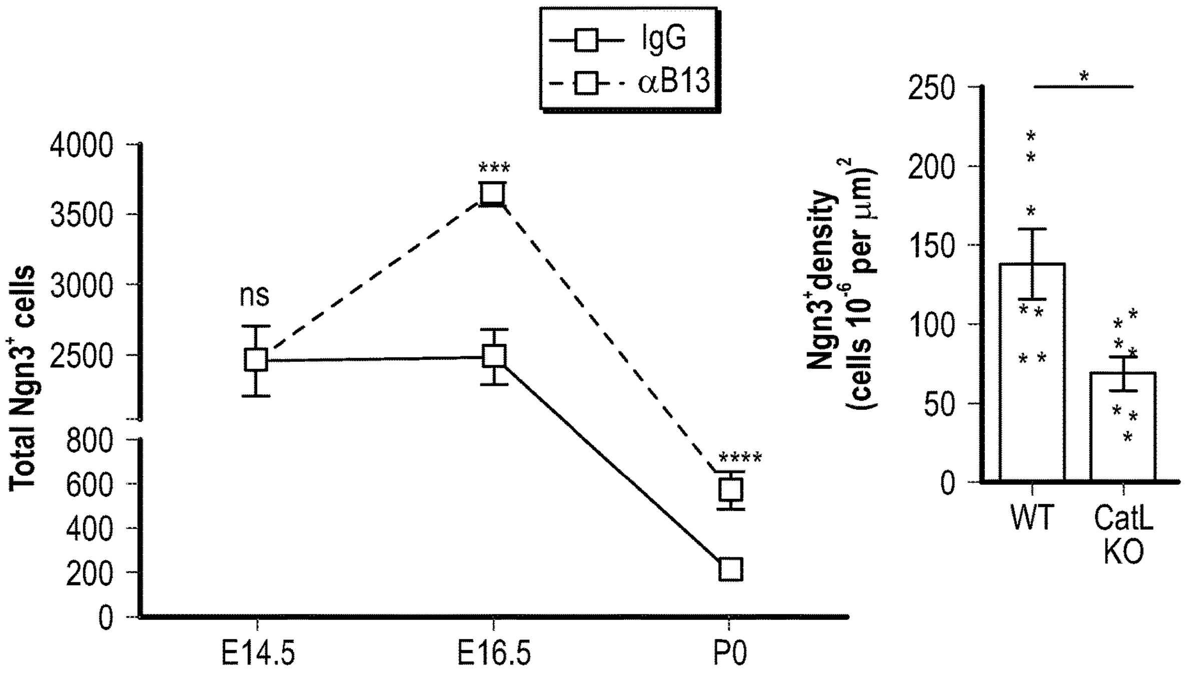
Figure 8C:
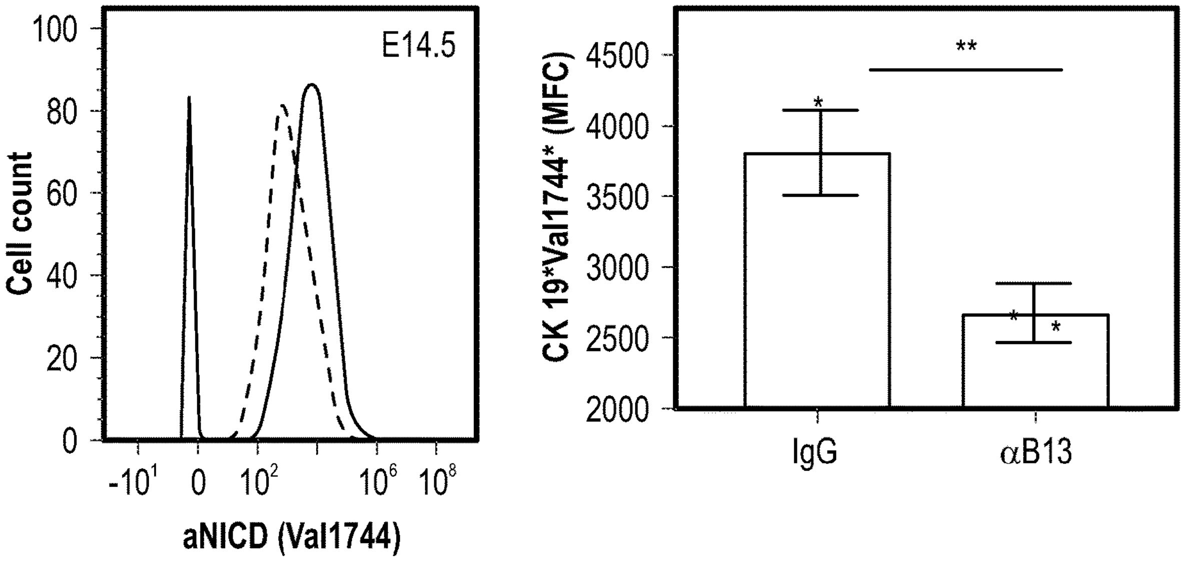

Exposure to anti-serpinB13mAb increases the number of Ngn3+ endocrine progenitor cells in the pancreas and improves outcomes in mouse models of diabetes. To better understand the role of interplay between serpinB13 and catL, and to identify potential novel targets of cleavage by catL that may be relevant to diabetes development, the effect of anti-serpinB13 mAb on the development, of the endocrine pancreas was studied using the protocol depicted in FIG. 8A. It was found that inhibiting serpinB13 with serpinB13 mAb (clone B29) caused a significant increase in the number of Ngn3+ cells in the embryonic pancreas (FIG. 8B), while a genetic deficiency of CatL decreased this cell population (FIG. 8B insert). This effect was observed over a wide range of mAb concentrations and was specific for Ngn3+ cells as the number of CK19+ epithelial cells remained unchanged. Moreover, the level of active Notch intracellular domain (NICD), a fragment of the Notch receptor that restricts endocrine cell development and β-cell function, was diminished in the antibody treated group, compared with the control group (FIG. 8C). These data suggest that CatL can antagonize Notch signaling so that serpinB13 AA may enhance endocrine cell development by enhancing catL activity in the pancreas.

Figure 8D:
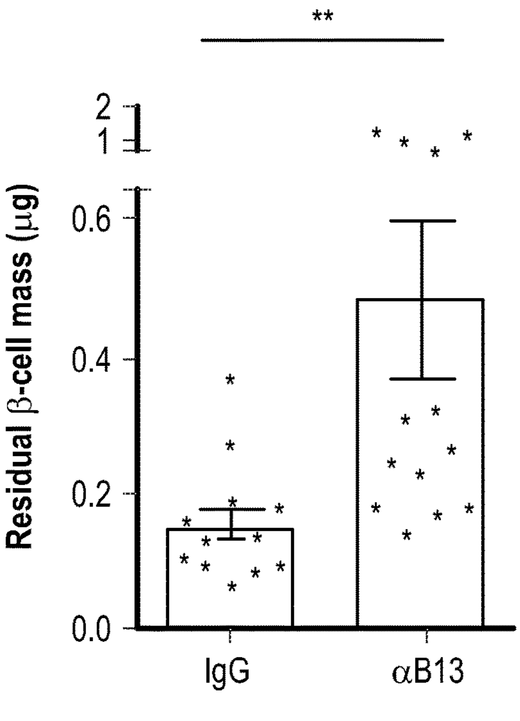
Figure 8E:
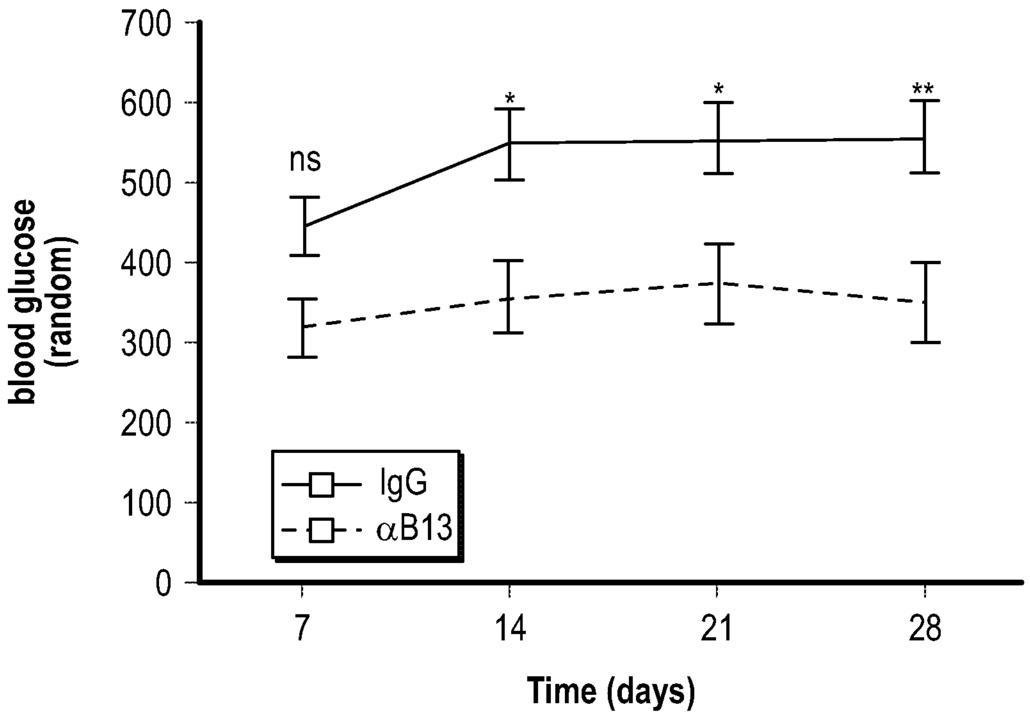
Figure 8F:
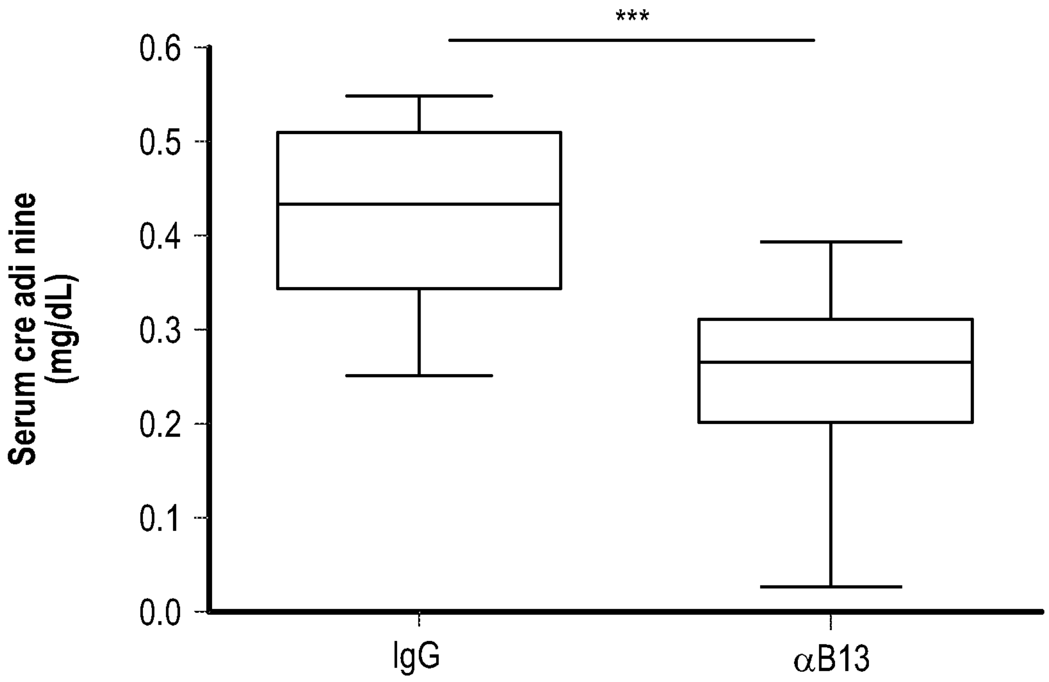

To assess the long-term impact of developmental changes induced by inhibiting serpinB13, newborn mice from Balb/c mothers were followed that received anti-serpinB13 mAb during pregnancy. Prenatal exposure to this mAb led to a significant increase in the number of pancreatic islets and total β-cell number, although the total pancreas and body weight at birth and in adulthood remained the same in the two groups. Of note, prenatal exposure to serpinB13 mAb led to a striking increase in postnatal β-cell mass in the setting of STZ-induced diabetes in adulthood, with a higher preserved residual β-cell mass (FIG. 8D) and reduced severity of disease (FIGS. 8E-8F). Therefore, the studies show that an increase in the number of Ngn3+ endocrine progenitors following inhibition of serpinB13 offers a clinically significant long-term benefit against abrupt loss of insulin-producing cells later in life.

Human anti-serpinB13 mAbs bind specifically to serpinB13, but not to other members of the clade B protein family. To produce human antibody to serpinB13, three rounds of biopanning were performed, using Fab library ($1\times10^{11}$ antibody specificities), against recombinant human serpinB13 produced in baculovirus and immobilized on solid matrix. Screening of individual clones by ELISA led to DNA fingerprinting and sequencing of three unique clones. Positive antibodies were tested by ELISA for binding to the target antigen and cross-reactivity with other proteins. The Fab fragments were then reformatted into fully human full-length IgG1. This approach resulted in generation of three novel fully human mAbs (mAbs1, mAb2 and mAb3), which specifically recognize human serpinB13 but no other serpins of clade B family. It was also noticed that these mAbs recognize both mouse and human serpinB13. The affinity validation by surface plasmon resonance indicated that the novel human antibodies had comparable affinity to the mouse mAb, clone B29.

Materials and Methods

Cell proliferation: Cy5-azide is used to measure thymidine analogue (e.g., 5-Edu) incorporation during DNA synthesis by the islets. Alternatively, the cells are stained with anti-Ki67 antibody. The islets are cultured in vitro for 24 to 72 hours. These analyses are performed in both insulin-positive and insulin-negative islet cells.

Apoptosis: Cell death in the islets is assessed using the transferase-mediated dUTP nick end-labeling (TUNEL) on rehydrated and trypsin-predigested islet sections, or alternatively by flow cytometry using staining of islet cell suspensions with Violet Annexin C/Dead Cell Apoptosis kit. Islet sections or cell suspensions are co-stained with anti-insulin or anti-glucagon antibodies to examine individual endocrine subtypes.

Insulin content and secretion: After overnight incubation, groups of islets (5 per sample) are preincubated in Krebs-Ringer bicarbonate buffer supplemented with 0.5% BSA, then stimulated with 5 or 25 mM glucose in the same buffer for 60 min. at 37° C. Following glucose stimulation, the media is collected, and secreted insulin is evaluated using the ELISA kit (Mercodia). To determine insulin content inside the islets, the islets are treated with 0.1 mL acidified ethanol and kept frozen until ELISA for insulin.

Gene expression: Quantitative RT-PCR analysis is performed to monitor expression of genes that (1) drive cells toward the endocrine lineage (e.g., Ngn3, insulinoma1, and NeuroD1/β1), (2) act as beta-cell differentiation factors (Pdx1, Pax4, NeuroD1/β2, MafA, Nkx6.1, and Nkx2.2), (3) help regulate expression of insulin (Pdx1, MafA, β2, and Nkx2.2), and (4) participate in R-cell proliferation (Pax4). In addition, Reg genes that are expressed in the regenerating islet tissue following subtotal pancreatectomy are examined. The RT-PCR data is confirmed by Western blot analysis for genes that show the most reproducible and prominent changes.

Example 6

SerpinB13 Antibodies Promote 3-Cell Development and Resistance to Type 1 Diabetes Endocrine cell development is dependent on the rescue of neurogenin3 (Ngn3) transcription factor from repression by Notch. The signals that prevent Notch signaling, allowing the formation of pancreatic endocrine cells, remain unclear. We show that inhibiting serpinB13, a cathepsin L (CatL) protease inhibitor expressed in the pancreatic epithelium, causes cleavage of the extracellular domain of Notch 1. This is followed by a two-fold increase in $Ngn3^+$ progenitor cell population and enhanced conversion of these cells to express insulin. Conversely, both recombinant serpinB13 protein and CatL-deficiency downregulate $Ngn3^+$ cell output. The embryonic exposure to inhibitory anti-serpinB13 antibody results in increased islet cell mass and improved outcomes in streptozotocin-induced diabetes after birth. Moreover, anti-serpinB13 autoantibodies (AAs) impede progression to type 1 diabetes (T1D) in children and stimulate $Ngn3^+$ endocrine progenitor formation in the pancreas. These data demonstrate long-term impact of serpinB13 activity on islet biology and suggest that promoting protease activity by blocking this serpin has therapeutic potential in T1D.

SerpinB13 is an inhibitor of cathepsin L (CatL) and a member of the clade B serpins, a protein family that plays a critical role in limiting tissue injury by inhibiting proteinases, either expressed in the host or derived from microbes and parasites. Based on the critical role that proteases play in inducing tissue patterning signals during embryogenesis, additional important roles could be hypothesized for the clade B serpins. For example, inhibition of a protease that shares a similarity with CatL results in inhibition of dorsoventral polarity in *Xenopus* embryos. However, whether the interplay between CatL and serpinB13 modulate tissue patterning in the pancreas, and to what extent this potential role may be exploited for the benefit of humans with decreased insulin-producing cells (e.g., in type 1 diabetes [T1D] patients, or those who are clinically healthy but at risk for this disease), remains unknown.

The Notch signaling pathway is a highly conserved developmental pathway that is important in pancreatic development and growth, and in mature β-cell function. Activation of transmembrane Notch receptors via their interaction with membrane-bound ligands, e.g. the Delta-like 4 leads to proteolytic steps that release the Notch intracellular domain (NICD) from the plasma membrane to the nucleus. The nuclear NICD enters into a transcriptional complex enabling activation of Notch target genes, which in turn negatively regulate expression of neurogenin-3 (Ngn3) transcription factor—a master regulator of pancreatic endocrine cell formation. In support of this model are studies demonstrating that disruption of Notch/ligand communication, or overexpression of Ngn3 in combination with other transcription factors, increases the output of hormone-producing cells in the pancreas and other organs.

Figure 9A:
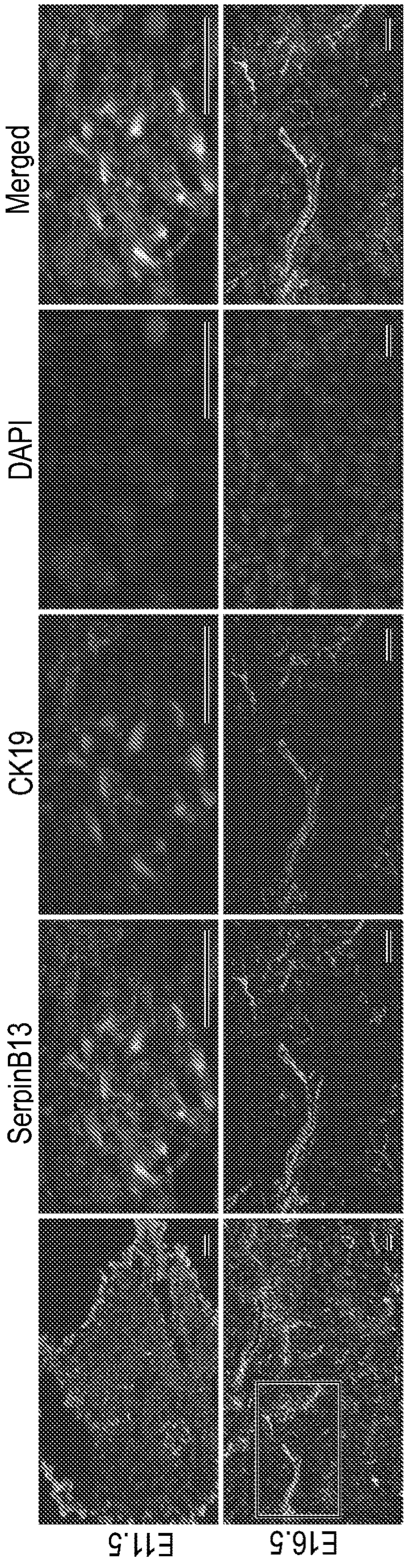
FIGS. 9A-9M. SerpinB13 impedes development of endocrine progenitor cells in the pancreas. (A) Microscopic images of serpinB13 expression in the embryonic pancreas. (B) Quantitative analysis by ELISA of serpinB13 release into the extracellular environment in vitro. The supernatants were collected and examined after 48 hours of culturing E12.5 explants of the pancreas (3 combined embryonic rudiments per well, n=6), heart (n=7) or media alone (n=7), two independent experiments. (C to E) Impact of serpinB13 on $Ngn3^+$ cells in vitro. (C) A schematic of the experiment. (D) Number of $Ngn3^+$ cells after 72 hours of incubation with recombinant serpinB13 of mouse (rmB13, n=8) or human (rhB13, n=10), chicken ovalbumin (OVA, n=6) (10 μg/mL each), buffer control (buffer, n=8), or control Ab (n=6) and anti-serpinB13 mAb (αB13, n=5) (both antibodies at 1 μg/mL), two independent experiments. (E) Representative microscopic images of data shown in (D). (F to H) Impact of inhibition of serpinB13 on $Ngn3^+$ cells in vivo. (F) A schematic of the experiment. (G) The quantitative analysis by IF microscopy of $Ngn3^+$ cells (following injection of anti-serpinB13 mAb into pregnant mothers) in embryonic pancreases isolated at day E14.5 (control Ab/αB13, n=5), E16.5 (control Ab/αB13, n=5) and birth (OP) (control Ab, n=9; αB13, n=10), two independent experiments. (H) Representative microscopic images of data shown in (G). (I to K) The genetic lineage tracing of $Ngn3^+$ cells in the pancreas following in vivo injections of anti-serpinB13 mAb. (I) A schematic of the experiment. (J) The quantitative analysis of $insulin^+YFP^+$ cells (control Ab/αB13, n=4). (K) Representative microscopic IF images of data depicted in (J), two independent experiments. (L and M) Impact of inhibition of serpinB13 on insulin-positive area in E16.5 pancreas in vivo. (L) A quantitative analysis by IF microscopy of the area occupied by insulin-positive cells (control Ab, n=9; αB13, n=8), two independent experiments. (M) The representative microscopic IF images of data shown in (L). In (F) and (I), each pregnant mouse received one daily i.p injection of 50 g of anti-serpinB13 mAb (or control antibody) on gestational day E10.5 through E13.5 (total dose 200 μg). Data are presented as the mean±SEM. One-way ANOVA with Dunnet's test (D), unpaired two-sided Student t test (G, J and L). Scale bars, 20 μm (A), 50 μm (E, H, K and M). NS, not significant. αB13, anti-serpinB13 mouse mAb.
Figure 9B:
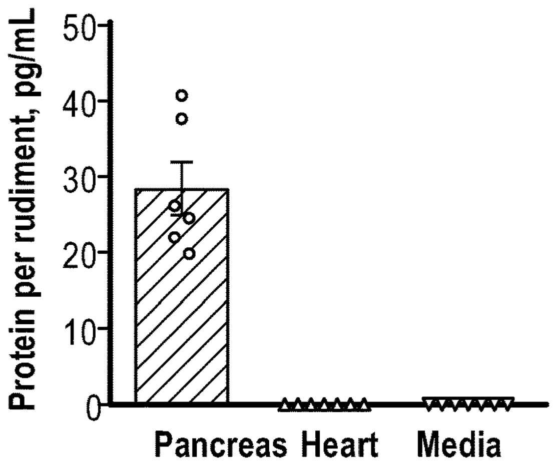
Figure 9C:
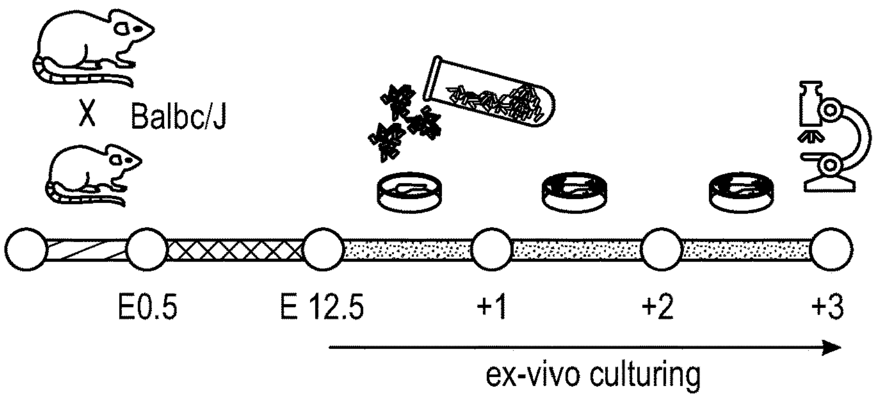
Figure 9D:
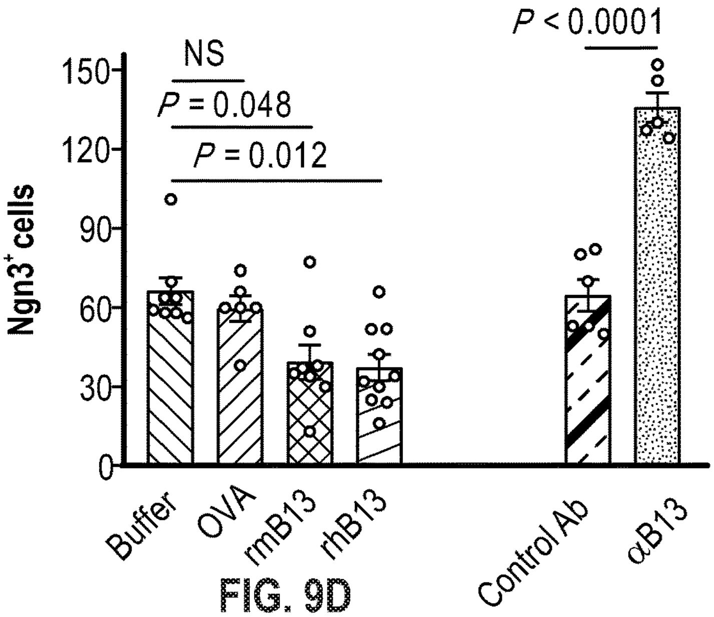
Figure 9E:
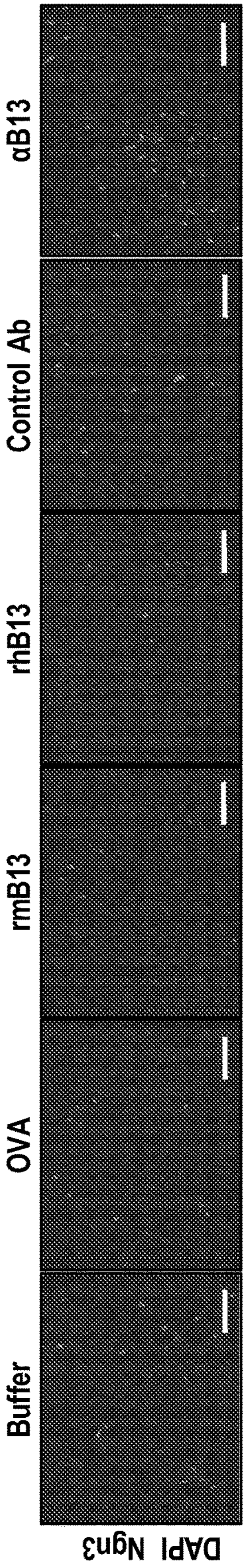
Figure 13:
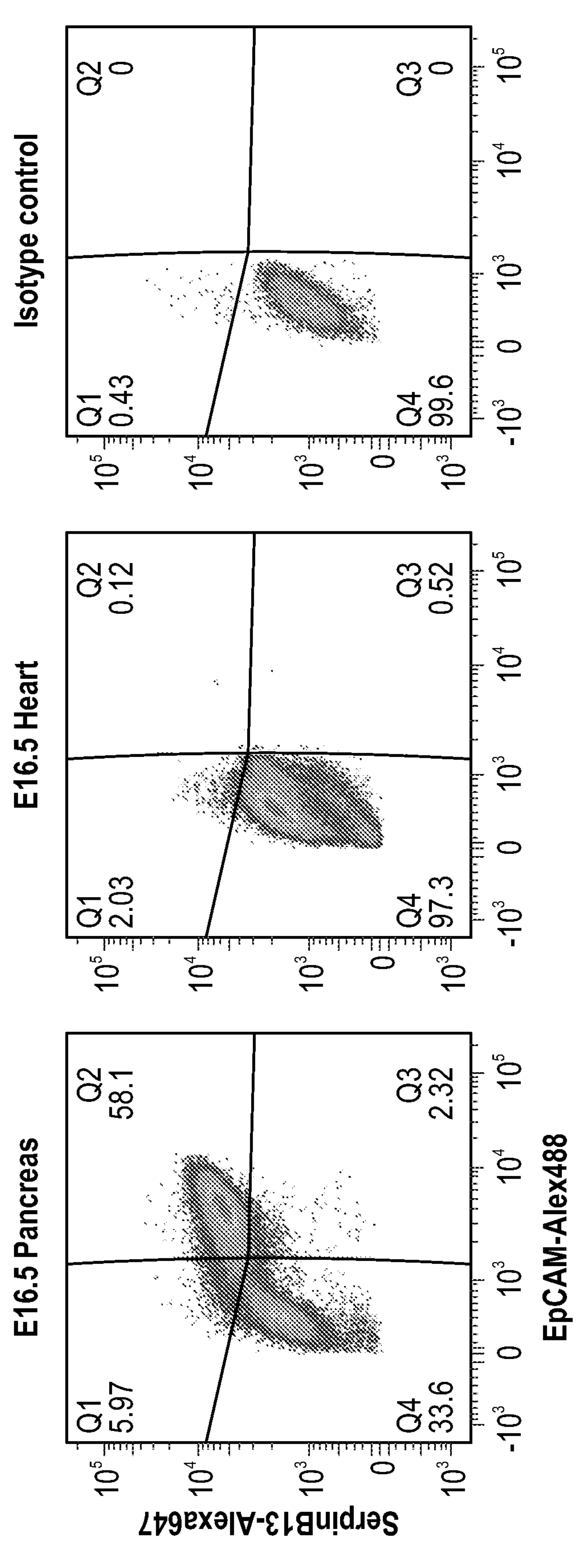
FIG. 13. Flow cytometry analysis of serpinB13 expression in the pancreatic epithelium during embryonic development. Representative flow cytometry scatter plots are shown for the pancreas and heart isolated from embryos at gestational day E16.5. $CD31^-CD45^-$ cell suspensions were stained with antibodies against epithelial marker (anti-EpCAM) and serpinB13 (clone B29).
Figure 14A:
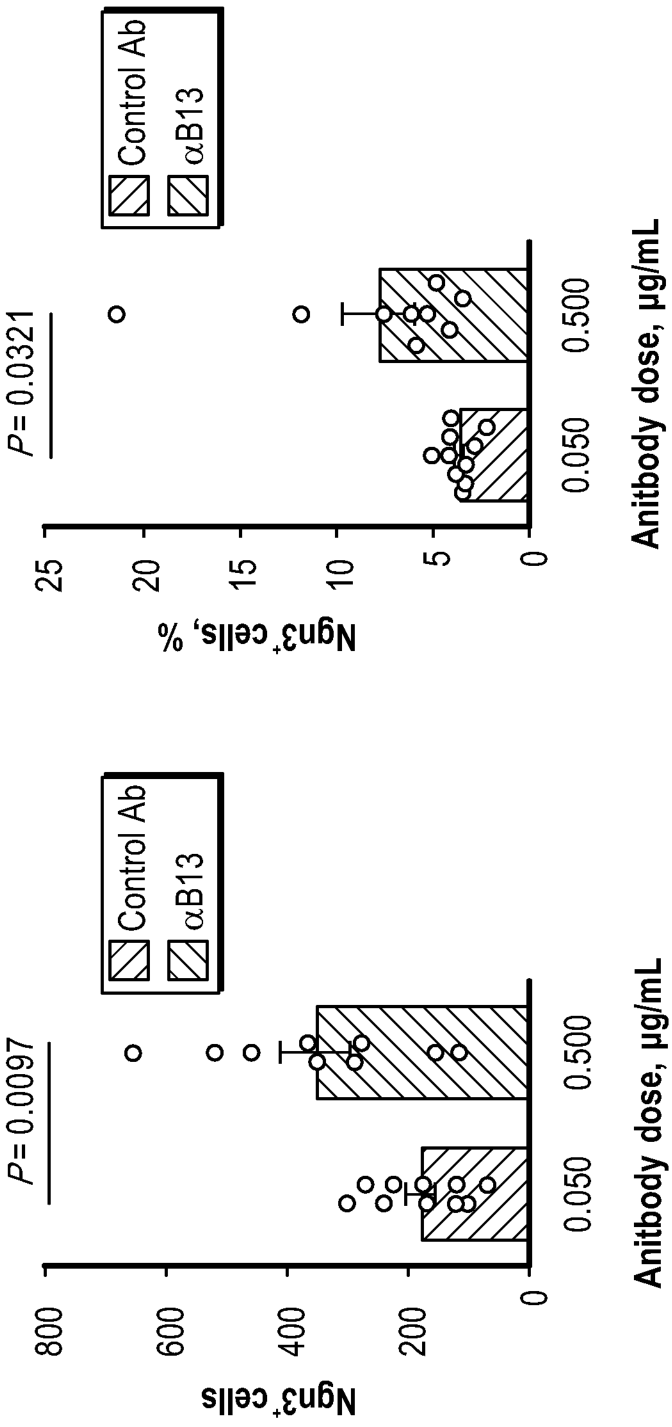
FIGS. 14A-14C. Quantitative analysis of $Ngn3^+$ cells (in vitro). (A) Flow cytometry analysis of $Ngn3^+$ cells. The Balb/c pancreatic explants at embryonic day E12.5 were cultured in vitro with anti-serpinB13 mAb (or control Ab) at 1.0 μg/mL for 48 hours, and then examined for the number of $Ngn3^+$ and $CK19^+$ cells. Data are displayed both in absolute numbers (left) and as the percentages of $CK19^+$ cells that express Ngn3 (right). (B) Representative flow cytometry scatter plots of data shown in (A). (C) Quantitative analysis by flow cytometry of $CK19^+$ cells. For (A) and (C), n=10 (control Ab); n=9 (αB13), three independent experiments. Data are presented as the mean±SEM. Unpaired two-sided Student t test. NS, not significant. αB13, anti-serpinB13 mouse mAb.
Figure 14B:
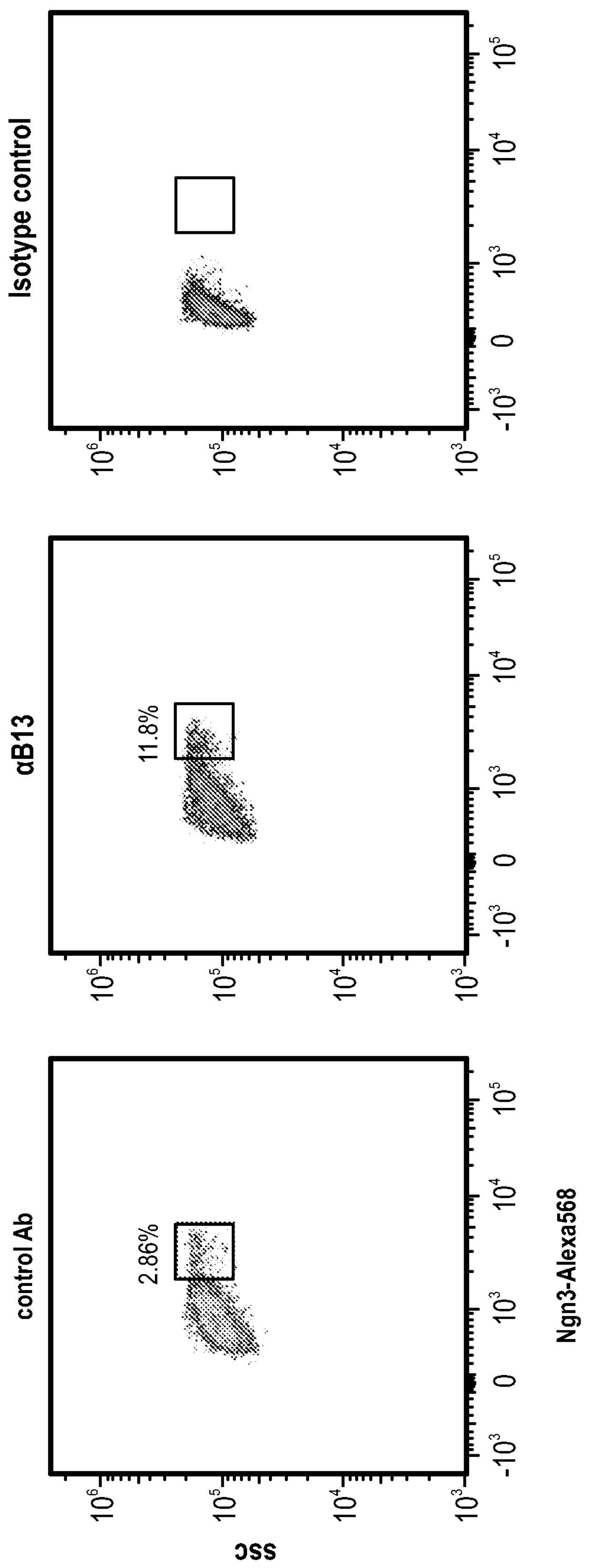
Figure 14C:
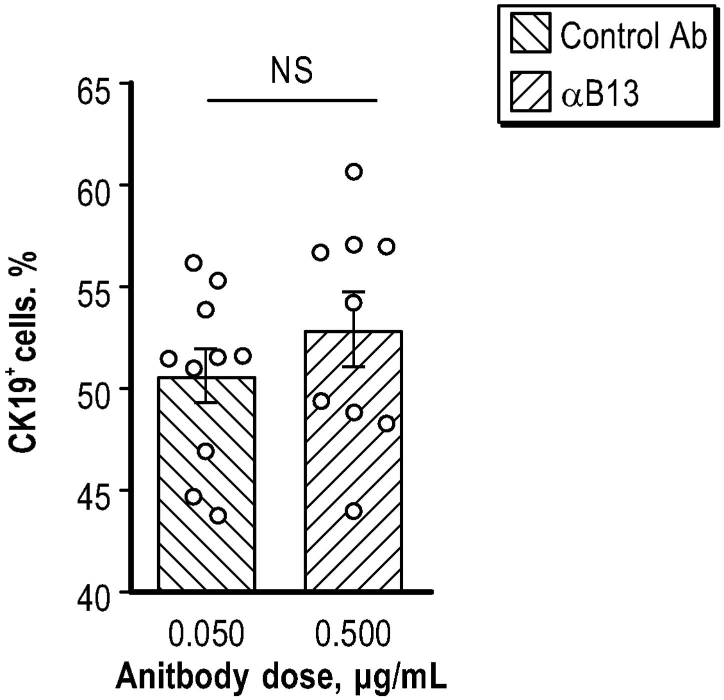
Figure 15A:
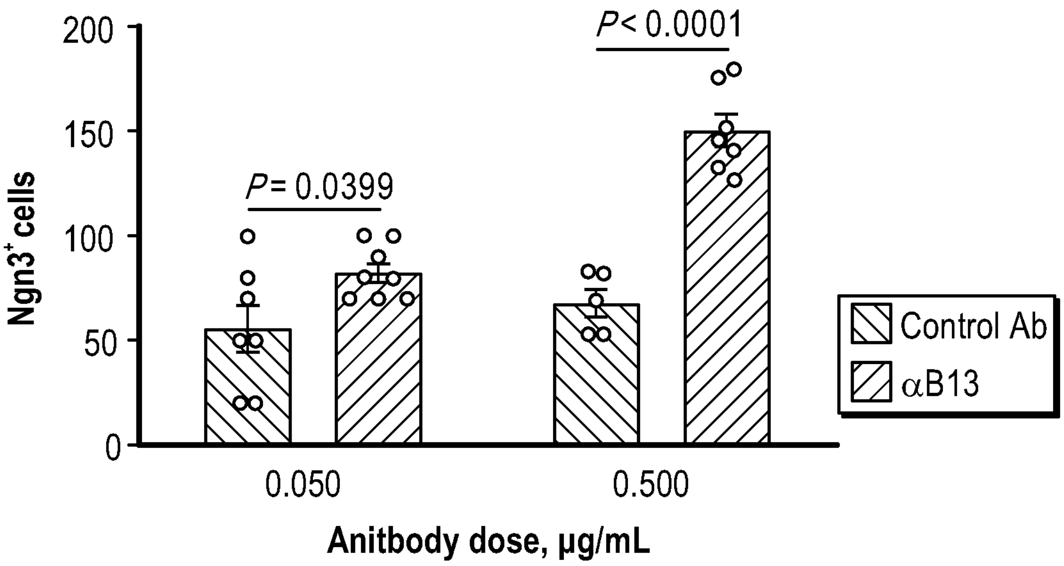
FIGS. 15A-15C. Changes in $Ngn3^+$ cell number following inhibition of serpinB13 in embryonic pancreas explants cultured in vitro. (A and B) Quantitative analysis by IF microscopy. The pancreas explants at embryonic day E12.5 were cultured in vitro with varying concentrations of anti-serpinB13 mAb (or control Ab) for 48 hours, as indicated. The pancreatic sections were then analyzed for the number of $Ngn3^+$ cells (A) and the percentage of the total area occupied by $CK19^+$ cells per explant (B). n=7 (control Ab/0.050); n=8 (αB13/0.050); n=5 (control Ab/0.500); n=7 (αB13/0.500); two independent experiments. (C) Representative microscopic IF images of data shown in (A) (upper panel) and (B) (lower panel). Data are presented as the mean±SEM. Two-way ANOVA with Sidak test. Scale bars, 50 μm. NS, not significant. αB13, anti-serpinB13 mouse mAb.
Figure 15B:
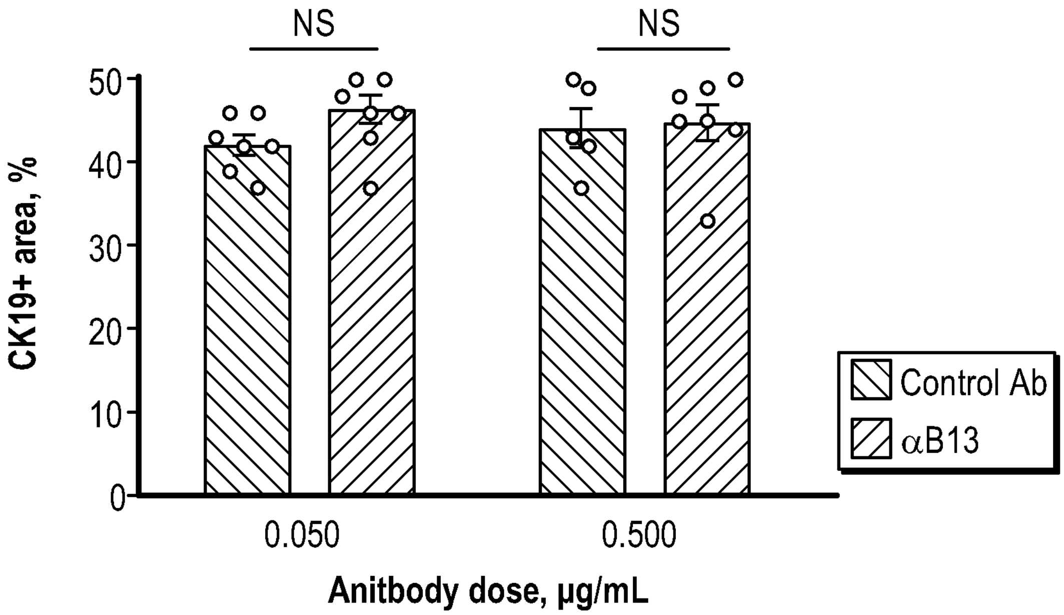
Figure 15C:
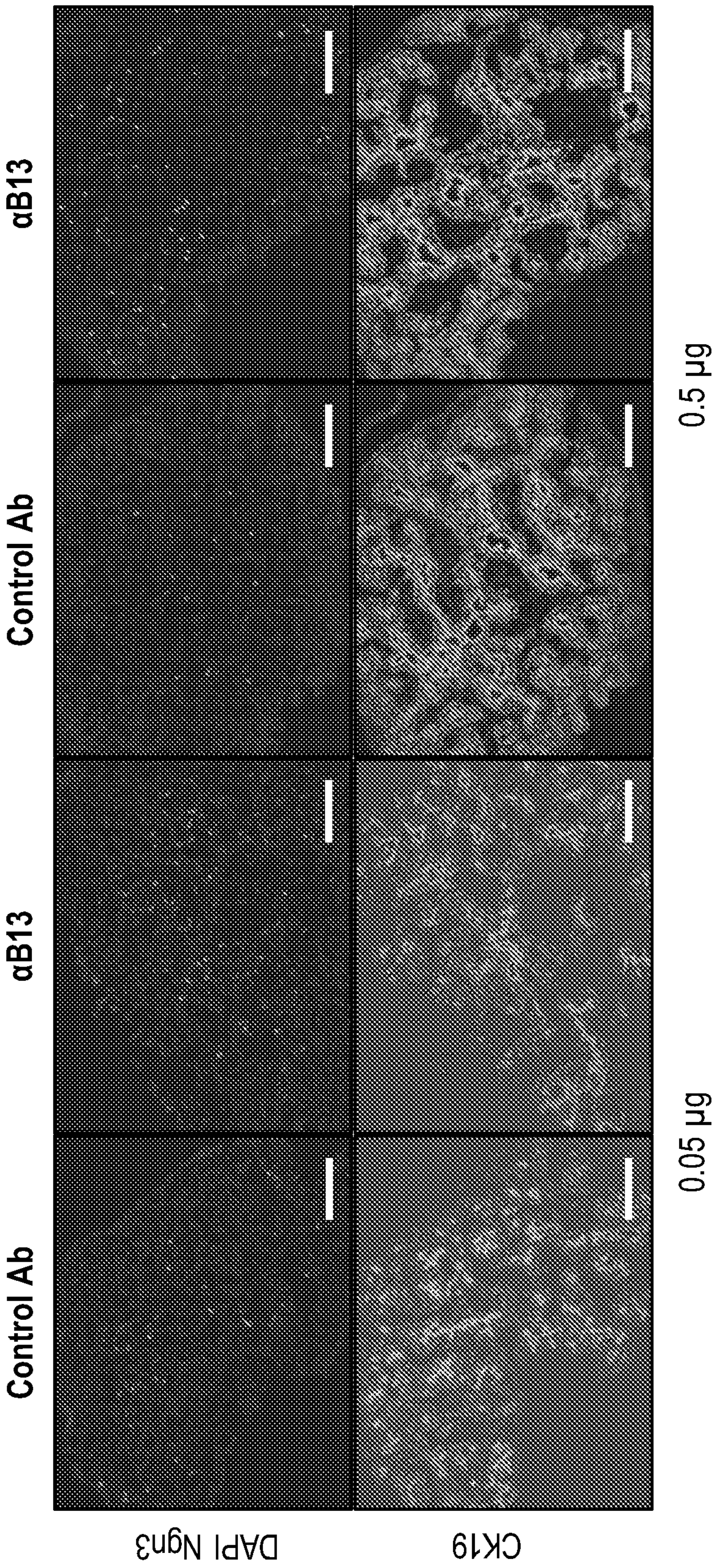
Figure 16A:
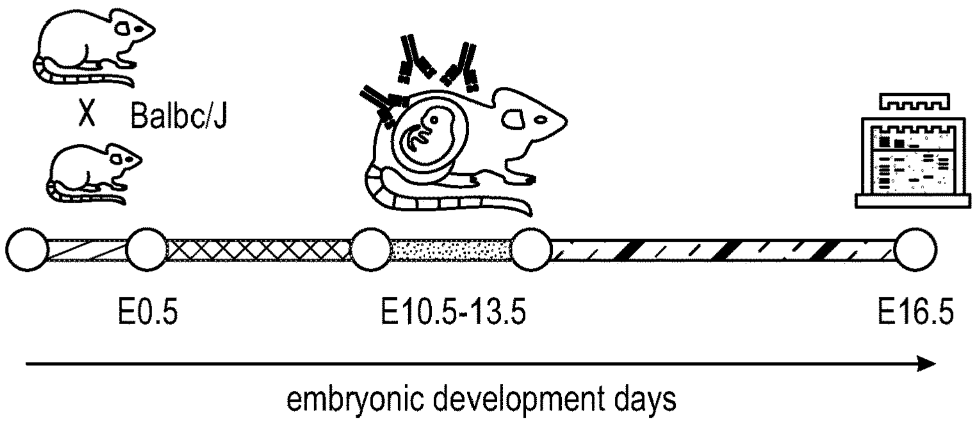
FIGS. 16A-16C. Western blot analysis of Ngn3 expression in vivo. (A) A schematic of the experiment. Pregnant Balb/c females received one daily i.p injection of 50 g of anti-serpinB13 mAb (or control Ab) on gestational day E10.5 through E13.5 (total dose 200 μg). On day E16.5, embryonic pancreases were isolated and directly used for analysis. (B) Representative Western blot. (C) Densitometry analysis of Western blots. n=11 (control Ab/αB13), five independent experiments. Data are presented as the mean±SEM. Unpaired two-sided Student t test. αB13, anti-serpinB13 mouse mAb.
Figure 16B:
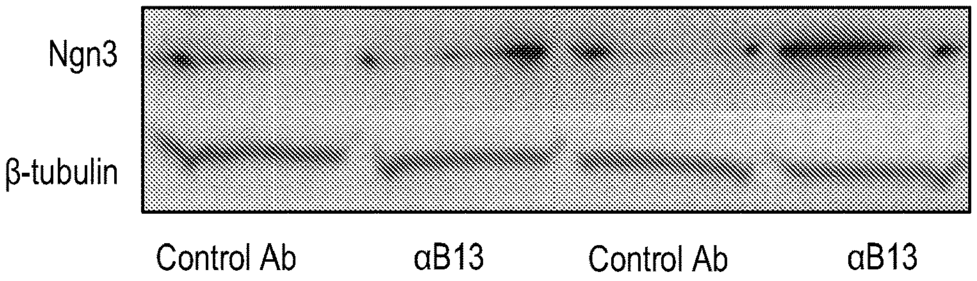
Figure 16C:
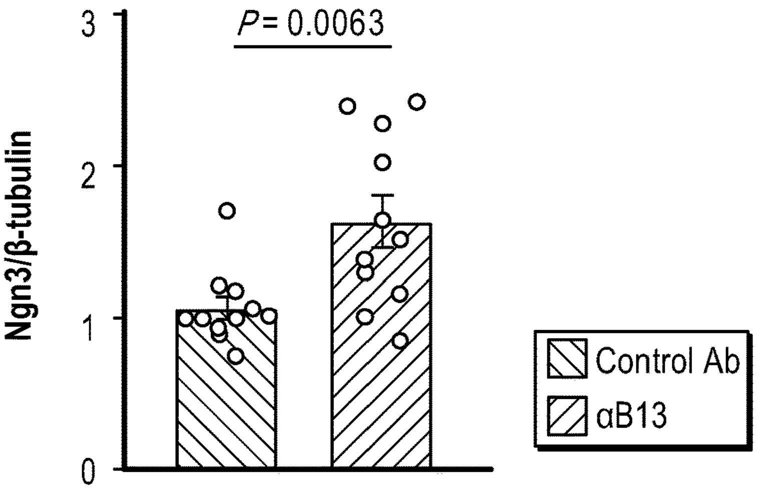

In the first attempt to gain insight into the potential role of serpinB13 in the development of the endocrine pancreas we examined its expression. We found this serpin to be confined to the cytokeratin-$19^+$ ($CK19^+$) epithelium as early as day E11.5 of gestation (FIG. 9A, FIG. 13). Furthermore, culturing embryonic pancreas explants at E12.5 for two days resulted in detectable serpinB13 level in the supernatant (FIG. 9B), suggesting that this molecule can be released to the extracellular milieu. When added to these in vitro cultures (FIG. 9C), both mouse and human recombinant serpinB13, but not chicken ovalbumin (a non-inhibitory structural homolog and founding member of the clade B serpin family), caused a significant drop in the number of Ngn3+ endocrine progenitor cells (FIGS. 9D and 9E). Conversely, inhibiting serpinB13 with a monoclonal antibody (mAb) originally developed in our laboratory, resulted in a significant increase in the number of $Ngn3^+$ cells, compared with cultures treated with control Ab (FIGS. 9D and 9E, FIGS. 14A and 14B). This effect was observed over a wide mAb concentration range (FIGS. 15A and 15C) and was specific for $Ngn3^+$ cells as the number of $CK19^+$ epithelial cells did not change (FIG. 14C, FIGS. 15B and 15C).

Figure 9F:
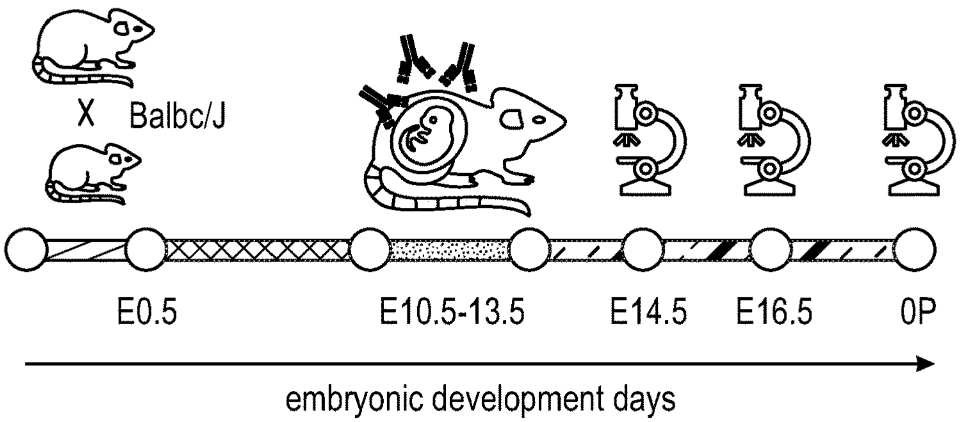

In addition to the above-mentioned increase in the number of pancreatic $Ngn3^+$ cells in vitro, we also observed a significant expansion of the pancreatic $Ngn3^+$ lineage in vivo. Mouse embryos isolated from pregnant mothers that had been injected for several days (E10.5 through E13.5) with anti-serpinB13 mAb (clone B29) (FIG. 9F) showed a robust increase in the number of $Ngn3^+$ cells and protein levels at both embryonic day E16.5 and birth (OP) (FIGS. 9G and 9H, FIG. 16A-16C). Of note, clone B34 of anti-serpinB13 mAb, which fails to stain pancreatic epithelium (despite its ability to stain the epidermis, FIG. 17C), completely failed to have any effect on $Ngn3^+$ cells (FIGS. 17A and 17B), thereby confirming the specificity of the changes we observed. Therefore, both in vitro and in vivo approaches to modify the extracellular level of serpinB13 impacted the development of pancreatic $Ngn3^+$ cells.

Figure 9G:
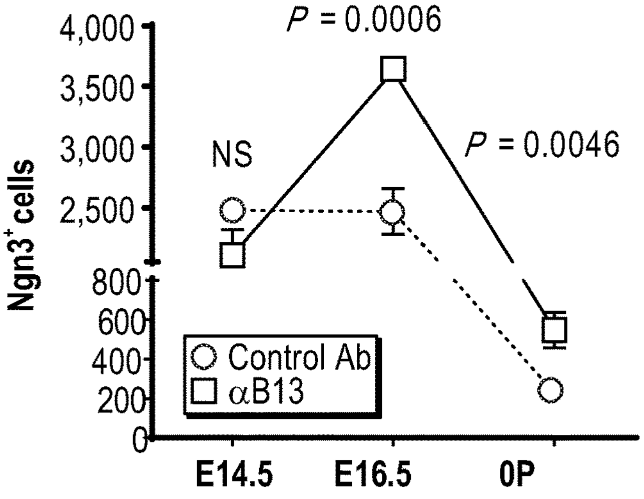
Figure 9H:
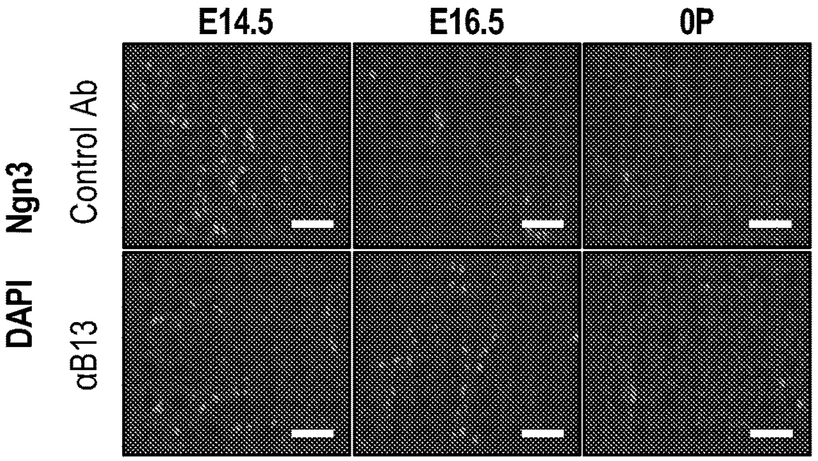
Figure 9I:
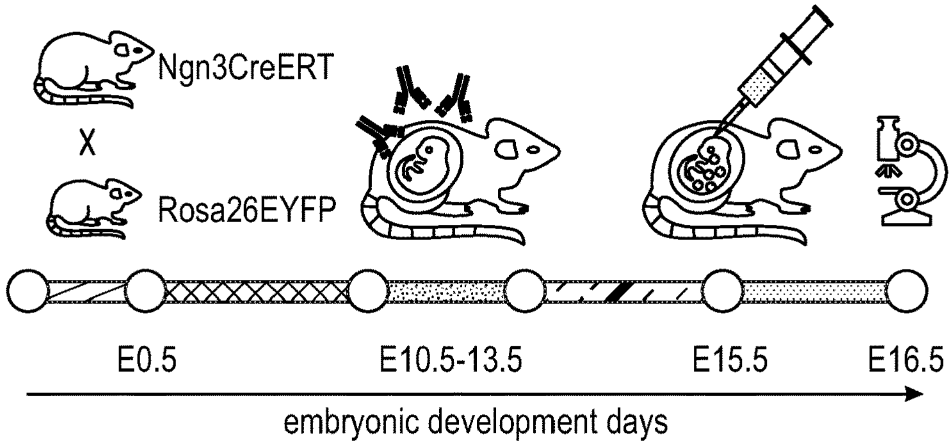
Figure 9J:
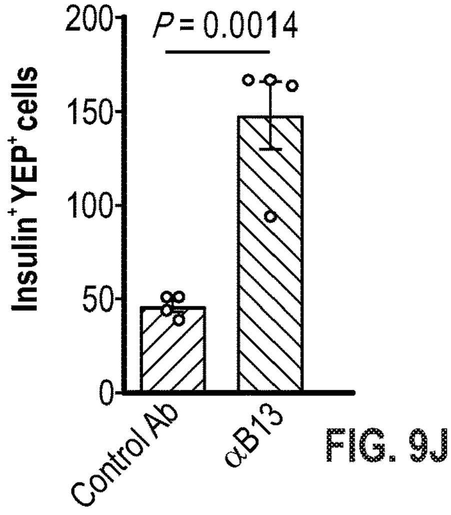
Figure 9K:
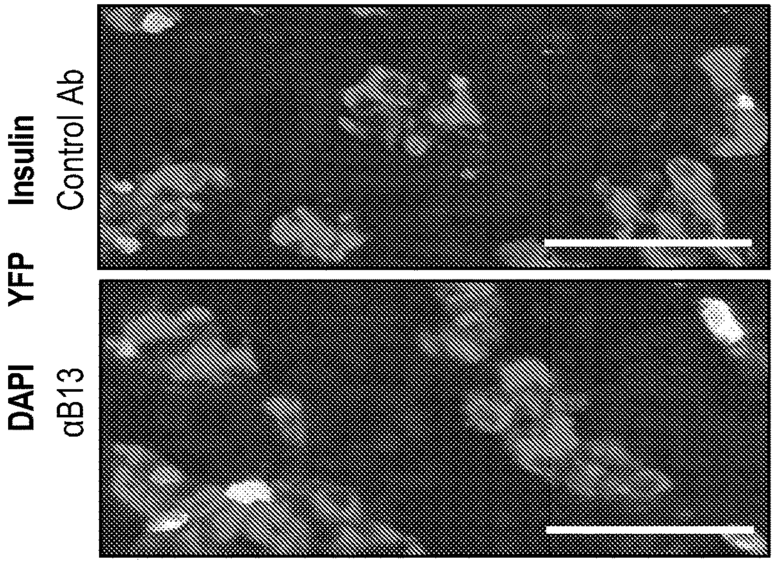
Figure 9L:
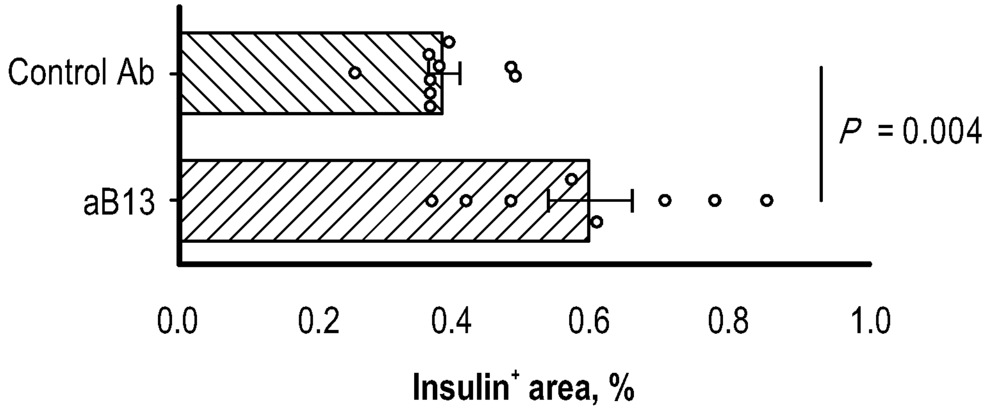
Figure 9M:
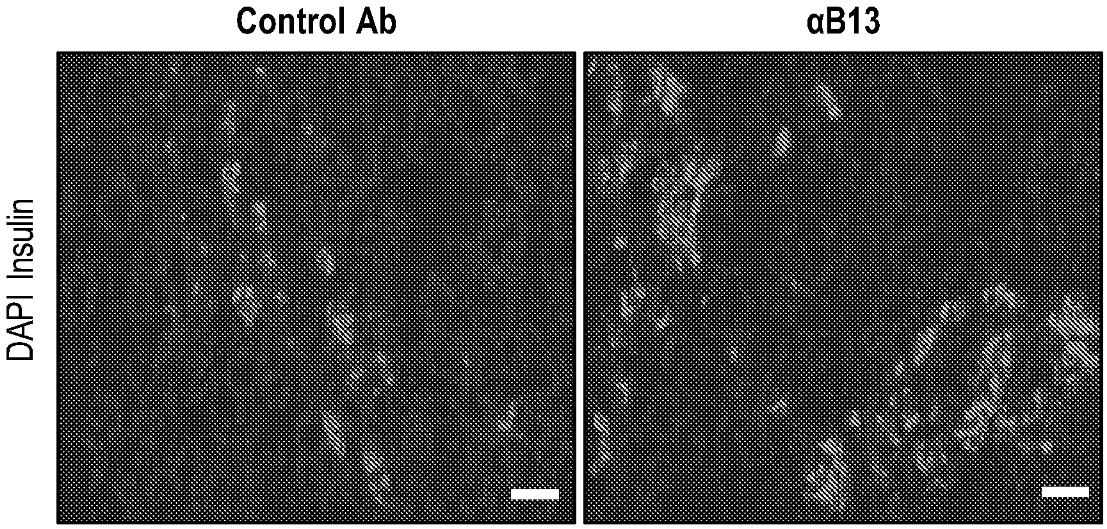
Figure 18A:
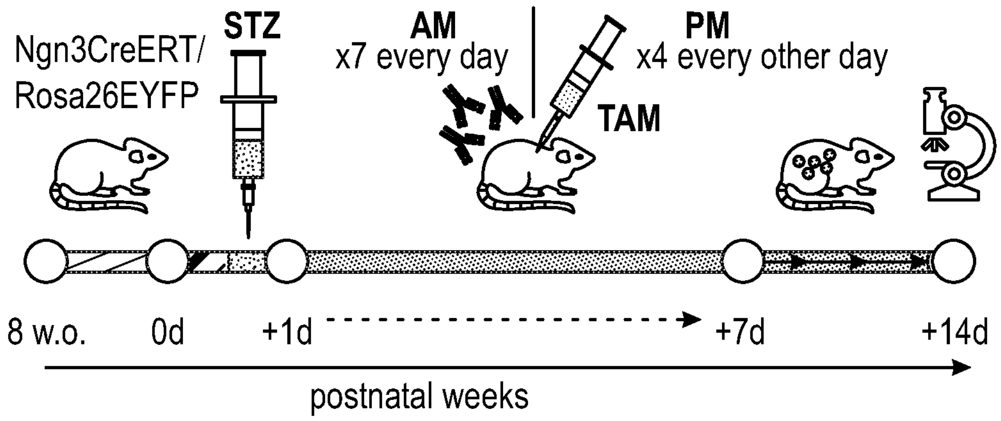
FIGS. 18A-18C. Genetic tracing of $Ngn3^+$ cells in the pancreas of healthy and diabetic adult mice treated with anti-serpinB13 mAb. (A) The protocol of mice treatment with streptozotocin (STZ), tamoxifen (TAM), and anti-serpinB13 mAb (or control Ab). Eight-week old $Ngn3Cre^{ERT}R26^{YFP}$ mice were induced into diabetes with STZ (150 mg/kg) and genetically labelled with YFP to mark $Ngn3^+$ cells, using TAM one day after injection of STZ, and an additional three times every other day thereafter. The antibodies were injected every day for 7 days at 100 μg/injection during the first week after STZ treatment. (B) Quantitative analysis by IF microscopy of $YFP^+$ cells expressing insulin at two weeks following induction of diabetes with STZ. Note that a diabetic state was necessary to demonstrate an increase in the number of double-positive cells following inhibition of serpinB13 with mAb. n=5 (groups treated with STZ), n=4 (groups without STZ), the average of two independent experiments. (C) Representative microscopic IF images of $YFP^+insulin^+$ cells depicted in (B). Data are presented as the mean±SEM. Ordinary one-way ANOVA with Sidak test. Scale bars, 10 μm. NS, not significant. αB13, anti-serpinB13 mouse mAb.
Figure 18B:
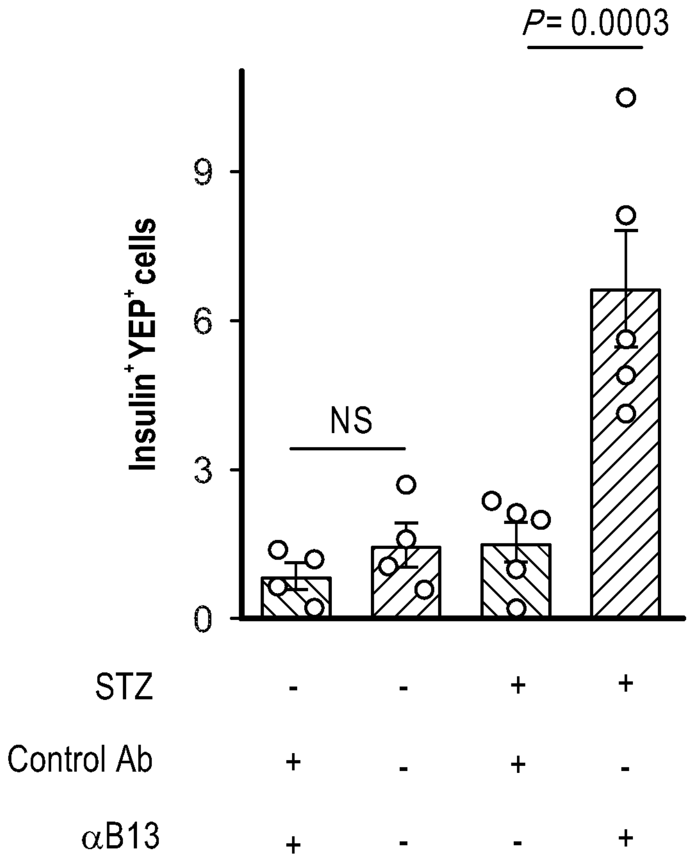
Figure 18C:
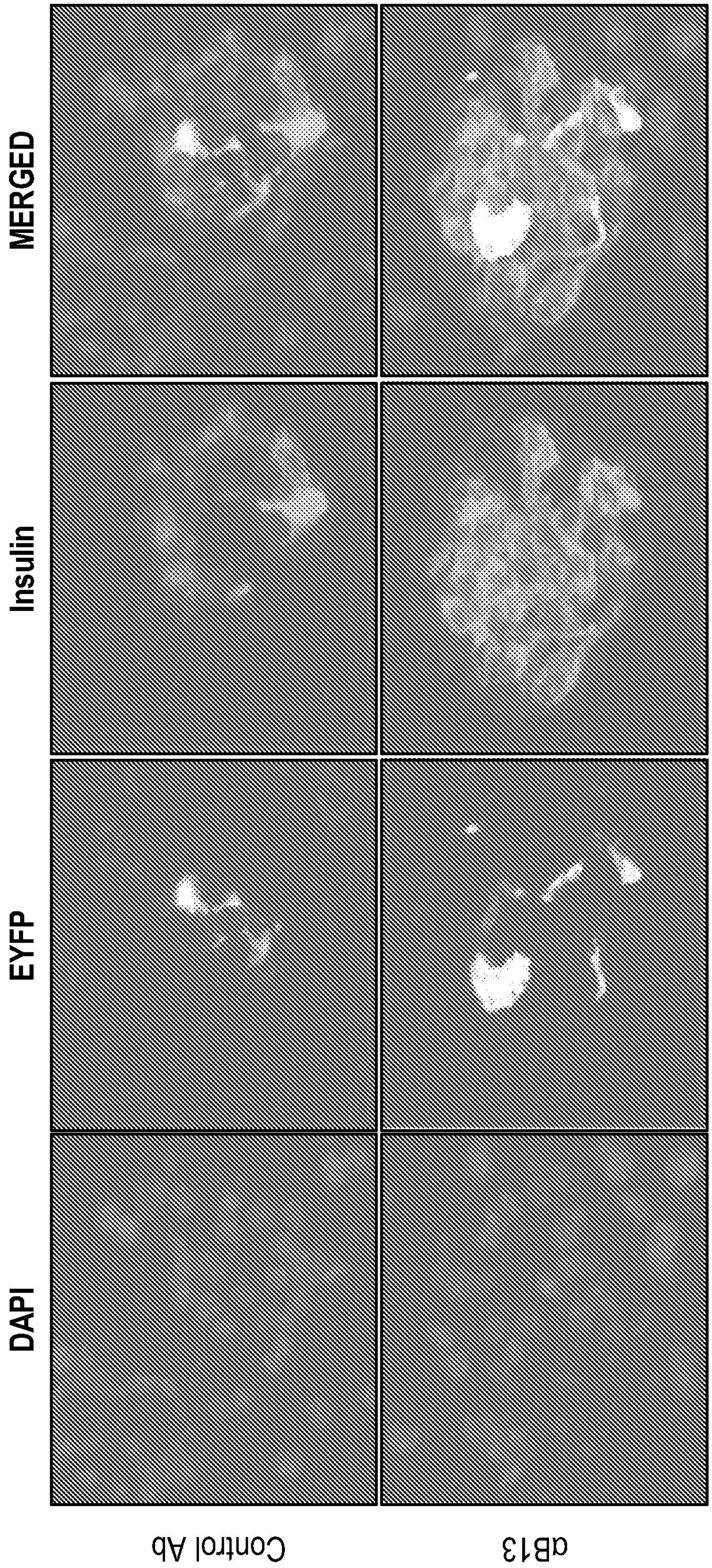
Figure 19A:
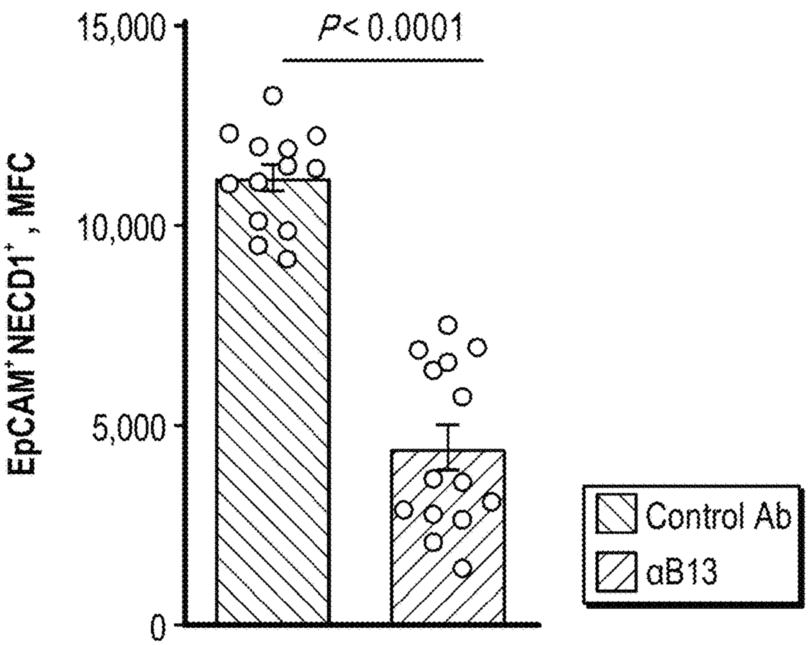
FIGS. 19A-19B. Examination of the extracellular domain of Notch1 receptor. (A) Flow cytometry analysis. Anti-serpinB13 mAb (or control Ab) was injected daily into pregnant Balb/c females for four days during gestation (day E10.5 through E13.5, 50 g/injection), and on day E15.5 the embryonic pancreases were isolated and examined. Single cell suspensions were stained with a mAb that recognizes the extracellular portion of Notch1 (clone 22E5) and analyzed by FACS. The bars represent the average MFC of antibody staining. n=13 (control Ab); n=14 (αB13); three independent experiments. (B) A representative flow cytometry histogram of data shown in (A). Data are presented as the mean±SEM. Unpaired two-sided Student t test. αB13, anti-serpinB13 mouse mAb. MFC, mean fluorescent channel.
Figure 19B:
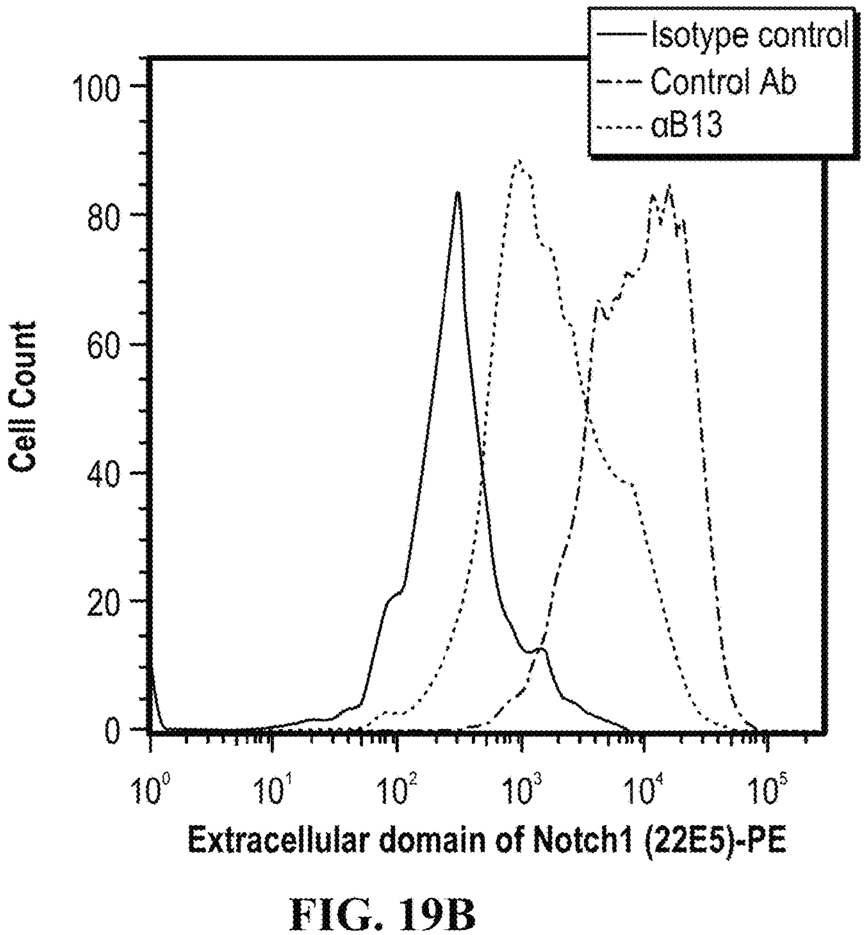

Importantly, genetic labelling of $Ngn3^+$ cells following injection of anti-serpinB13 mAb during gestation (FIG. 91) demonstrated an enhanced conversion of these cells to acquire insulin-positive status (FIGS. 9J and 9K). Consistent with this observation, the embryos that had been exposed in vivo to inhibition of serpinB13 with a mAb showed significantly higher fractions of pancreatic microscopic sections positively stained with anti-insulin antibody, compared with the embryos exposed to control Ab (FIGS. 9L and 9M). This enhanced transition from Ngn3 to insulin expression was not limited to the gestational period but was also observed during de novo formation of β-cells in the adult mice with streptozotocin (STZ)-induced pancreatic damage and inhibited serpinB13 (FIG. 18A-18C). Taken together, our observations thus far demonstrate that serpinB13 represses the generation of $Ngn3^+$ cells, while its inhibition with a neutralizing antibody increases the $Ngn3^+$ cell population and β-cell presence in the pancreas.

Figure 10A:
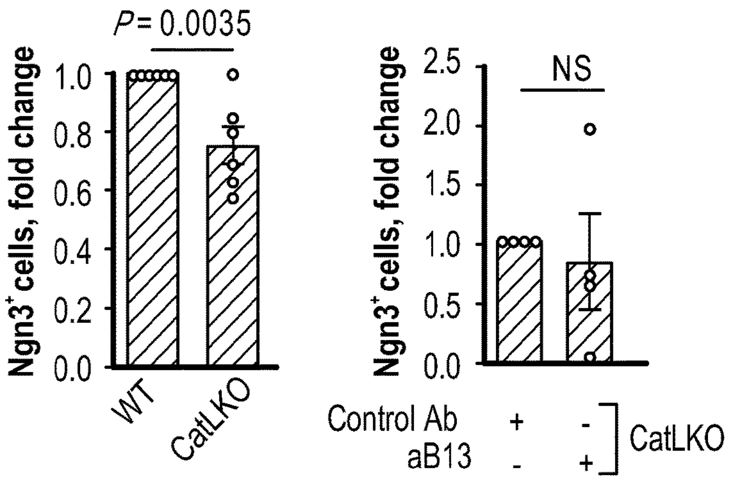
FIGS. 10A-10J. Notch receptor-mediated repression of $Ngn3^+$ cell development is controlled by the inhibitory function of serpinB13 on its protease target. (A to D) The quantitative analysis of $Ngn3^+$ cells by IF microscopy. In (A), the wild-type (WT) and CatL-deficient (CatLKO) embryonic pancreases were isolated from pregnant mice at day E12.5, and after 48-hour culture of the explants, either alone or in the presence of anti-serpinB13 mAb or control Ab as indicated, they were harvested and processed for staining with anti-Ngn3 antibody. For (A left), n=6 (WT/CatLKO), six independent experiments. For (A right), n=4 (control Ab/αB13), four independent experiments. In (C), E12.5 WT pancreas explants were cultured for 48 hours with E64 protease inhibitor (10 μM) or DMSO solvent, as indicated (n=9 per group, three independent experiments). (B) and (D) show representative microscopic IF images of data depicted in (A) and (C), respectively. (E to J) Western blot analysis of the Notch1 receptor ectodomain. The experimental approach to examine extra- and intracellular domains of intact (left) and cleaved by CatL (right) Notch1 is depicted in (E). The embryonic pancreas explants isolated at E12.5, were cultured with anti-serpinB13 mAb or control Ab at 1 μg/mL for 24 hours (F) (control Ab/αB13, n=6; six independent experiments) or 48 hours (G) (control Ab/αB13, n=4; four independent experiments), and examined for Notch 1. The representative Western blot images and the average of independent experiments are shown. Alternatively, E12.5 embryonic pancreas explants were treated for 48 hours (H, data from one of seven independent experiments are shown) or incubated with recombinant mouse CatL (rmCatL) at 2.5 μg/mL for the last 4 hours of the 48-hour incubation period (I, data from one of three independent experiments is shown), and assessed for the degradation fragments of the Notch1 receptor. In (J), in addition to treatment with antibodies for 48 hours, the embryonic pancreas explants were treated with E64 (1 μM) or DMSO, as indicated (n=3 per group, three independent experiments). The representative Western blot image and the average of independent experiments are shown. For all Western blot analyses, the cells from three cultured embryonic pancreases were combined for each lane and examined using antibody raised against the N-terminal portion (Ala9-Gln526) of Notch1. Data are presented as the mean±SEM. Unpaired two-sided Student t test (A, C, F and G), one-way ANOVA with Sidak test (J). Scale bars, 20 μm. *(H, I, J) indicates cleavage fragments of Notch1. NS, not significant. αB13, anti-serpinB13 mouse mAb.
Figure 10B:
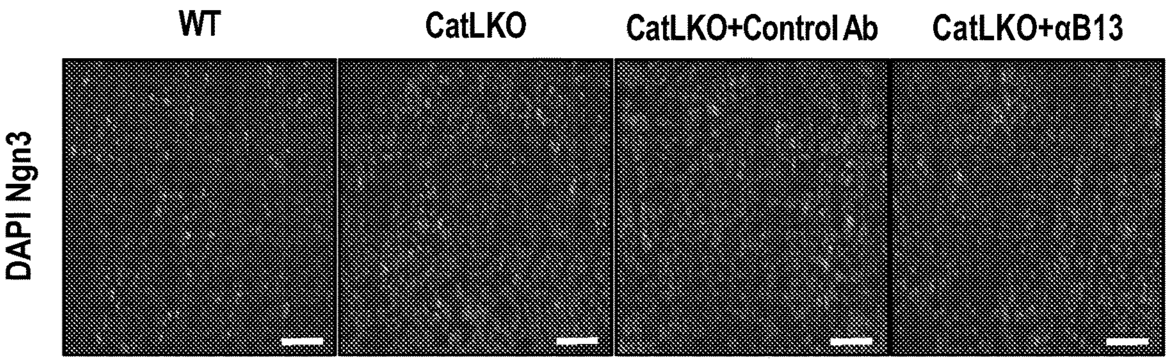
Figure 10C:
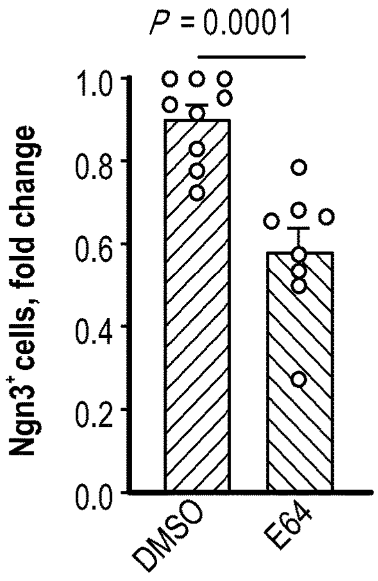
Figure 10D:
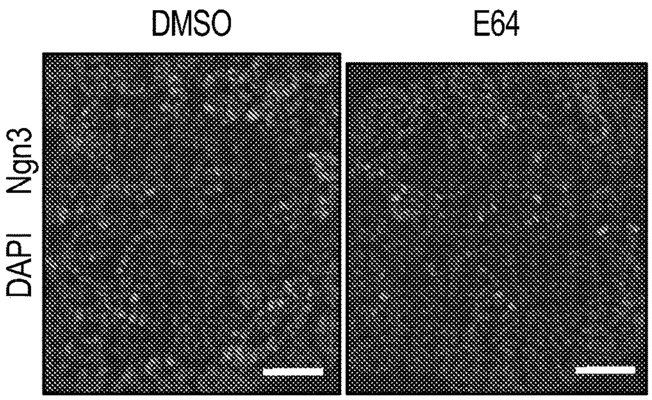

To better understand the role of the interplay between serpinB13 and CatL in the development of the endocrine pancreas we examined embryonic in vitro cultures for changes in $Ngn3^+$ cells in CatL-deficient mice as well as after exposure to E64, which inhibits several proteases including CatL. In these settings, the size of the $Ngn3^+$ cell population in the pancreas was significantly reduced (FIGS. 10A—left and 10B, FIGS. 10C and 10D) and completely refractory to upregulation by anti-serpinB13 mAb (FIGS. 10A—right and 10B). We continued to use anti-serpinB13 mAb (clone B29) as we previously showed that it blocked inhibitory properties of serpinB13 and allowed for the activity of its protease target, CatL to increase.

Figure 10E:
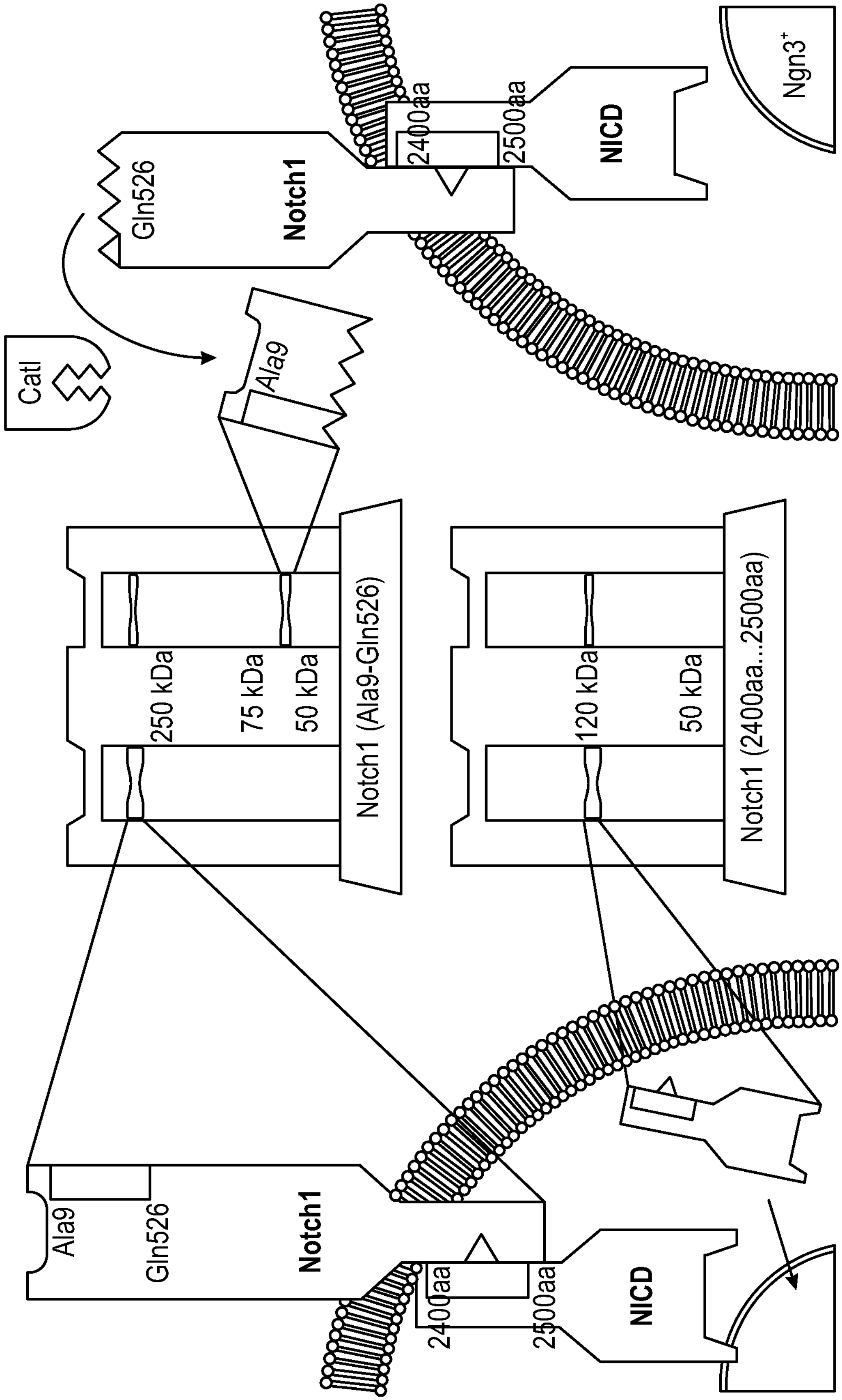
Figure 10F:
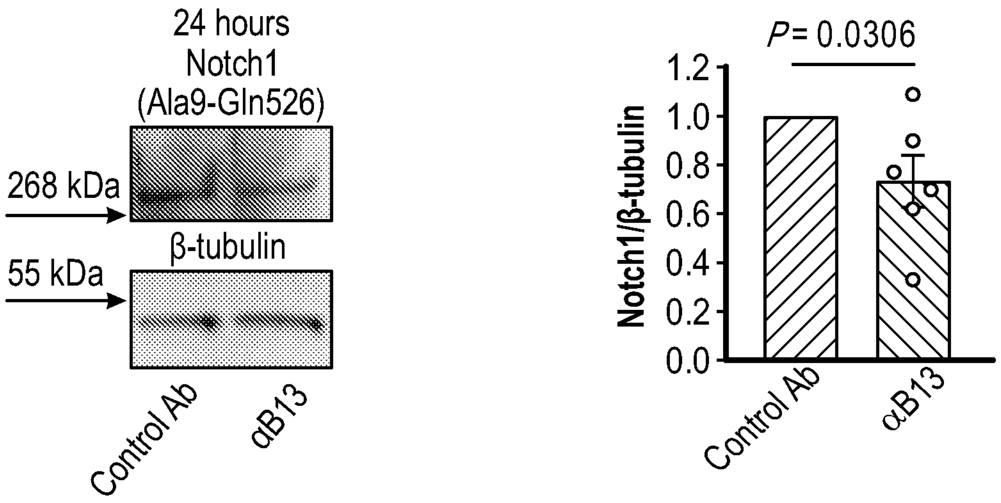
Figure 10G:
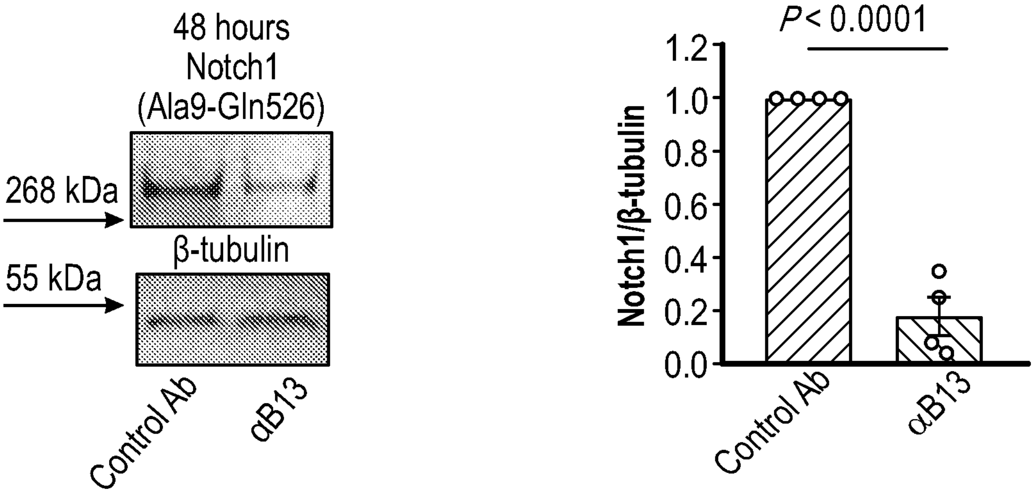
Figure 10J:
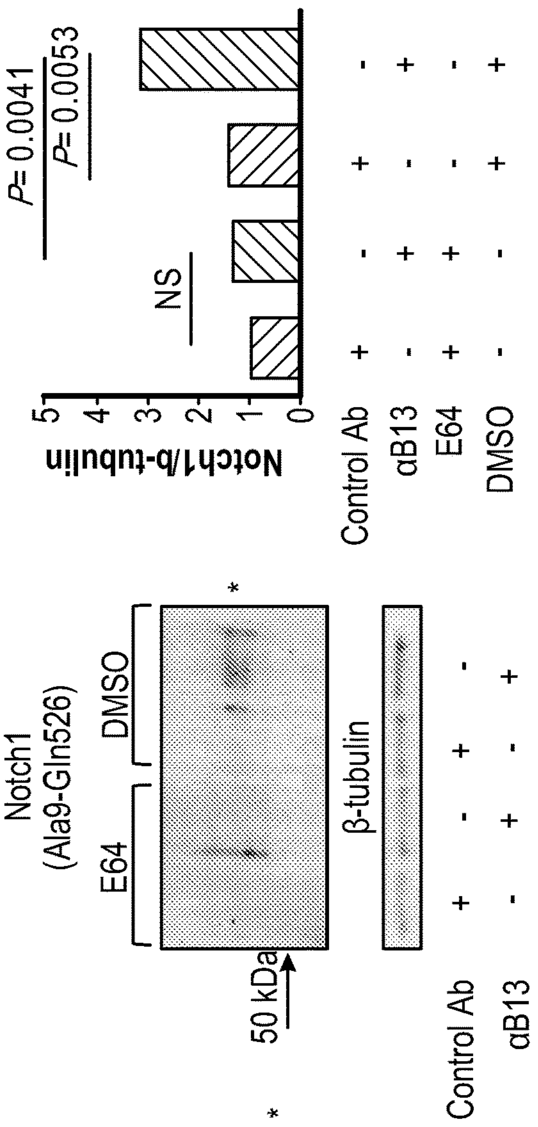
Figure 10I:
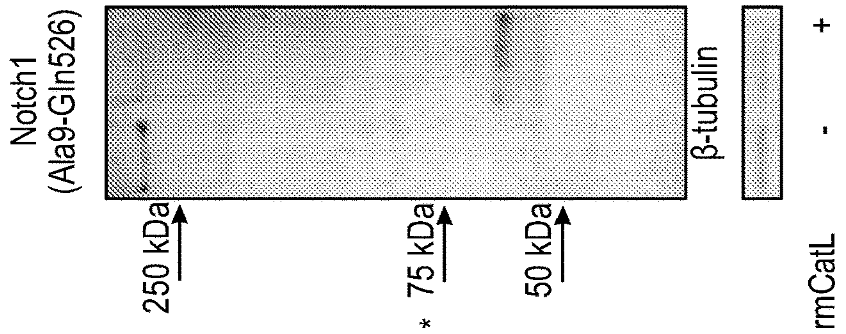
Figure 10H:
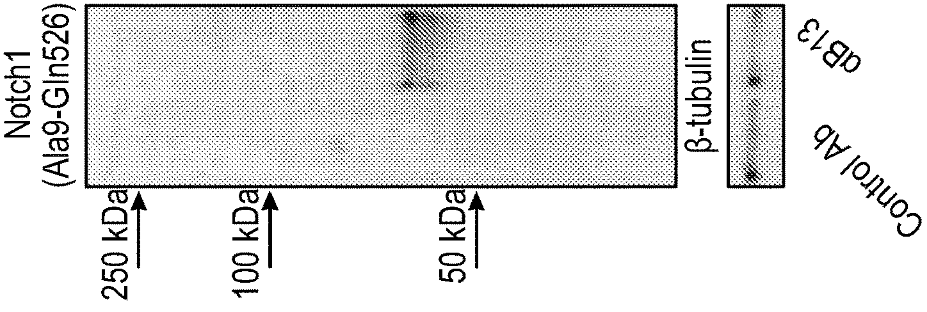
Figure 20A:
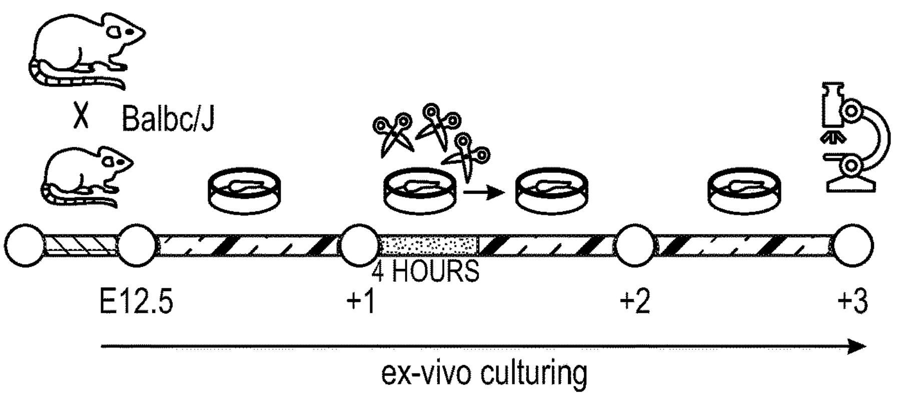
FIGS. 20A-20C. Impact of cathepsin L on the number of $Ngn3^+$ cells. (A) A schematic of the experiment. The embryonic pancreas explants isolated at day E12.5 of gestation, were cultured in media for the first 24 hours, followed by recombinant mouse cathepsin L at 2.5 μg/mL (rmCatL, n=7) or pH-buffer control (pH 6.0) (buffer, n=8) for 4 hours. The pancreas explants were then washed, incubated for an additional 48 hours, and harvested for analysis. (B) Quantitative analysis by IF microscopy of $Ngn3^+$ cells. The average of three independent experiments is shown. (C) A representative microscopic IF images of data depicted in (B). Data are presented as the mean±SEM. Unpaired, two-sided Student t test. Scale bars, 100 μm.
Figure 20B:
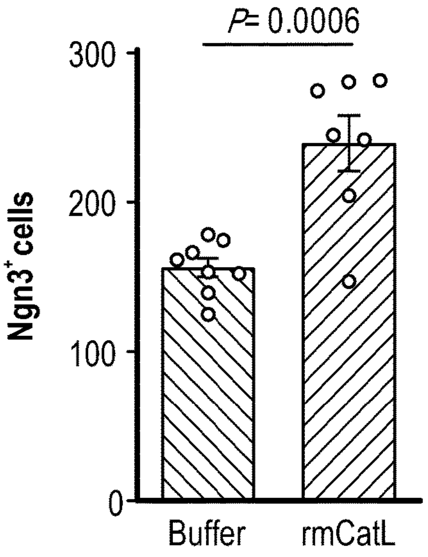
Figure 20C:
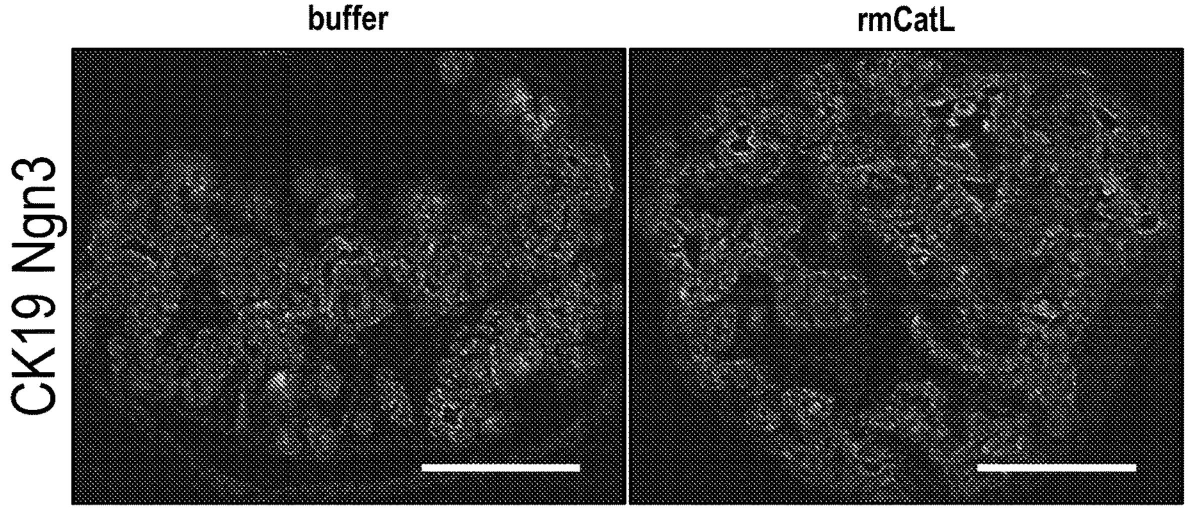
Figure 21A:
FIGS. 21A-21C. Examination of the intracellular domain of the Notch1 receptor. (A) Western blot analysis. The embryonic pancreases isolated at day E12.5 of gestation from Balb/c females were cultured with anti-serpinB13 mAb (n=7) or control Ab (n=7) at 1 μg/mL for 48 hours and harvested. Three culture harvests were combined for Western blotting with mAb recognizing the intracellular portion of Notch1 (clone D1E11). The bars represent the average of seven independent experiments by densitometry analysis. (B and C) Flow cytometry analysis. Anti-serpinB13 mAb (or control Ab) was injected daily into pregnant Balb/c female mice, from day E10.5 through to E13.5 (50 μg/injection). On day E15.5 of gestation the embryonic pancreases were isolated and examined. n=11 (control Ab), n=9 (αB13), two independent experiments (B). Alternatively, the antibodies were directly added to E12.5 embryonic pancreas explants and cultured for 48 hours in vitro. n=3 (control Ab), n=4 (αB13), two independent experiments (C). The single cell suspensions (B and C) were stained with the polyclonal antibody, Val1744, which recognizes the active Notch intracellular domain (aNICD) that is cleaved by the γ-secretase complex. Representative flow cytometry histograms (B left, C left), and the average MFC of antibody staining (B right, C right), are shown. Data are presented as the mean±SEM.
Figure 21B:
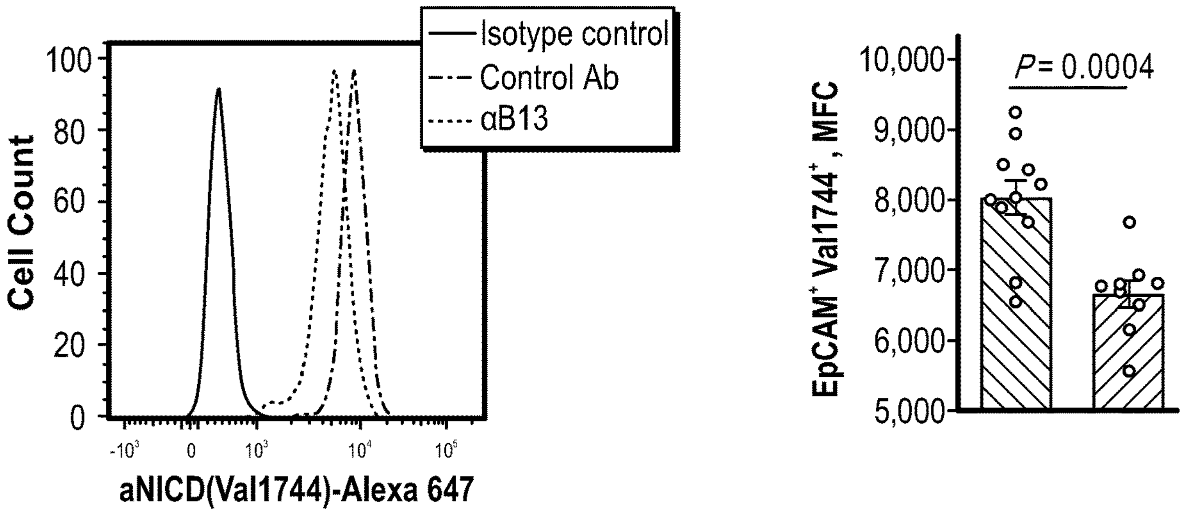
Figure 21C:
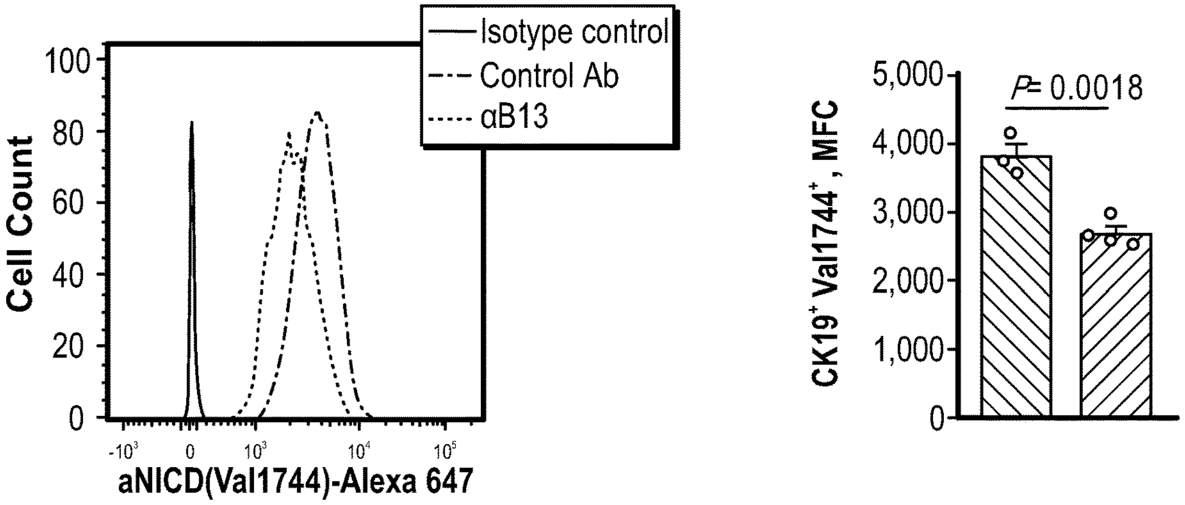

Since Ngn3 expression is negatively regulated by the Notch communication system, we wondered whether upregulation of the pool of $Ngn3^+$ cells following inhibition of serpinB13 with mAb could stem from disruption of the Notch receptor expressed on the cell surface. Following experimental scheme for examination of the extracellular and intracellular domains of Notch1, depicted in FIG. 10E, we found that both in vivo and in vitro exposure to neutralizing mAb against serpinB13 resulted in a time-dependent reduced expression of the ectodomain of the Notch1 receptor in embryonic pancreatic tissue (FIGS. 10F and 10G, FIG. 19A-19B) with concomitant induction of several ~60 kD degradation fragments (FIG. 10H); which were almost completely prevented by the protease inhibitor, E64 (FIG. 10J). Similar results were obtained with recombinant CatL, which both cleaved the extracellular domain of Notch1 (FIG. 10I) and induced additional Ngn3 cells (FIG. 20A-20C). The partial loss of extracellular Notch was followed by markedly reduced levels of active Notch intracellular domain (aNICD) (FIG. 21A-21C), indicating that Notch signaling was inhibited. Of note, the transcriptional level of Notch1 was relatively intact (FIG. 22A-22B). These results suggest that serpinB13 helps to maintain the Notch receptor-mediated repression of pancreatic endocrine progenitors, and that perturbation of this serpinB13 functionality enables proteinase activity to dismantle Notch signaling, thereby allowing for more efficient development of $Ngn3^+$ progenitors cells.

Figure 11A:
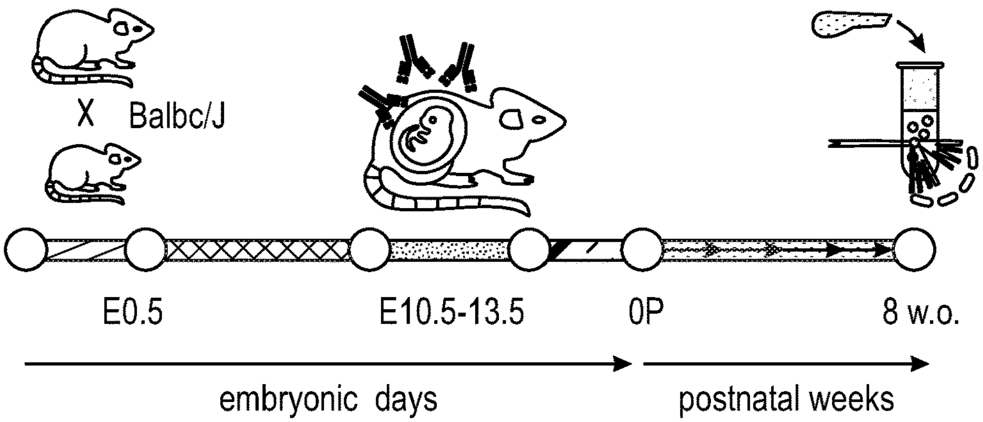
FIGS. 11A-11N. Inhibition of serpinB13 during embryogenesis results in a greater expansion of β-cell mass and prevents severe diabetes in adulthood. (A to F) A follow up of healthy mice with gestational exposure to anti-serpinB13 mAb. (A) A schematic of the experiment. The quantitative analysis of the islet number (B), endocrine cell number (C), and representative flow cytometry scatter plots (D) (control Ab, n=11; αB13, n=10; three independent experiments). (E) Quantification of β-cell mass. (F) Representative microscopic IF images of data depicted in (E) (control Ab, n=4; αB13, n=4; two independent experiments). (G to N) A follow up of diabetic mice with gestational exposure to anti-serpinB13 mAb. (G) A schematic of the experiment. (H) Quantification of the residual β-cell mass at 4 weeks after STZ injection (150 mg/kg). (I) Representative microscopic IF images of data depicted in (H). (J) Glucose tolerance test (ipGTT) and (K) AUC at 2 weeks after streptozotocin (STZ) injection. (L) Random blood glucose levels at 1, 2, 3, and 4 weeks after STZ injection. (M) Serum creatinine 4 weeks after STZ injection. (N) Body weight at 1, 2, 3 and 4 weeks after STZ injection (for G to N, control Ab, n=11; αB13, n=10; two independent experiments). Data are presented as mean±SEM. Unpaired two-sided Student t test (B, C, E, H, K, M) and two-way ANOVA with Sidak test (J, L, N). Scale bars, 1 mm. NS, not significant. αB13, anti-serpinB13 mouse mAb; AUC, area under curve.
Figure 11B:
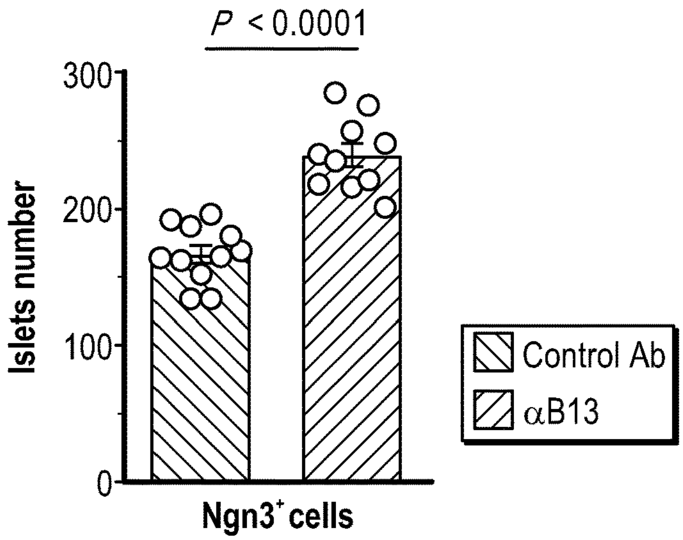
Figure 11C:
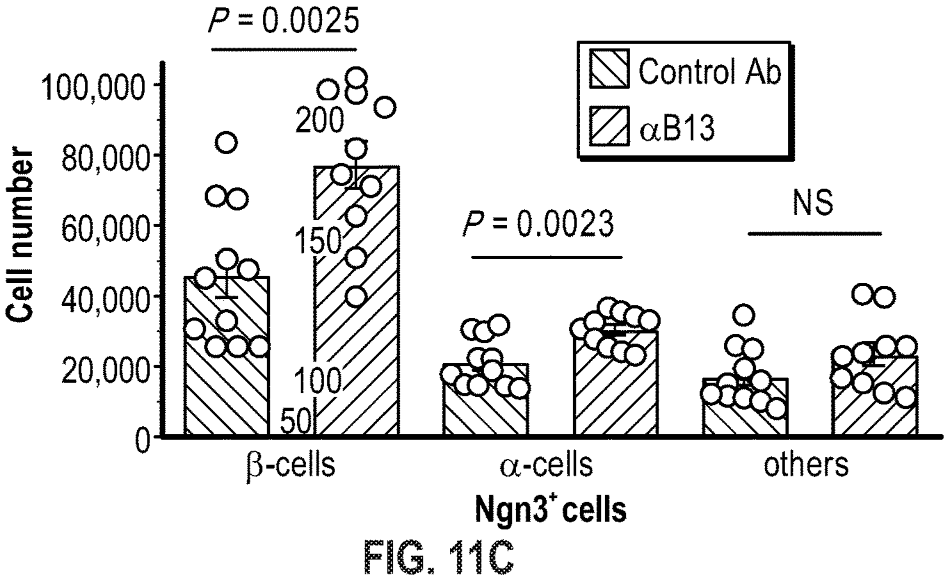
Figure 11D:
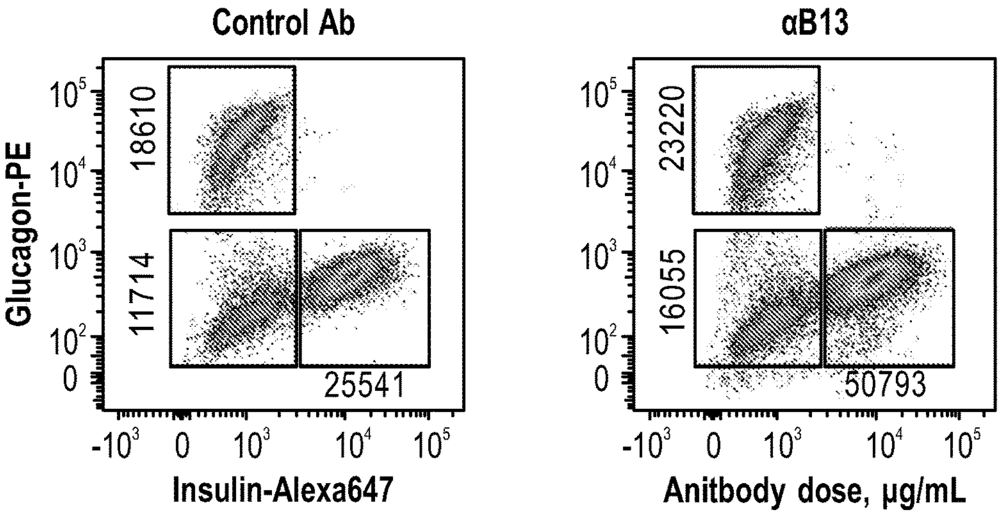
Figure 11E:
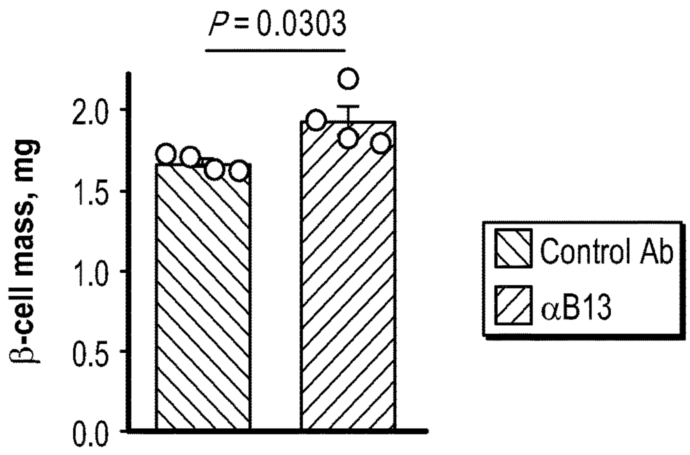
Figure 11F:
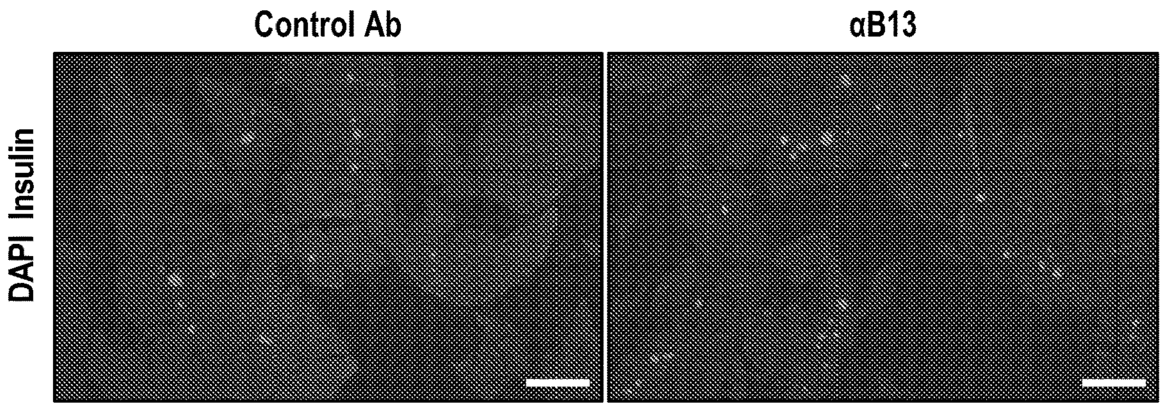
Figure 11G:
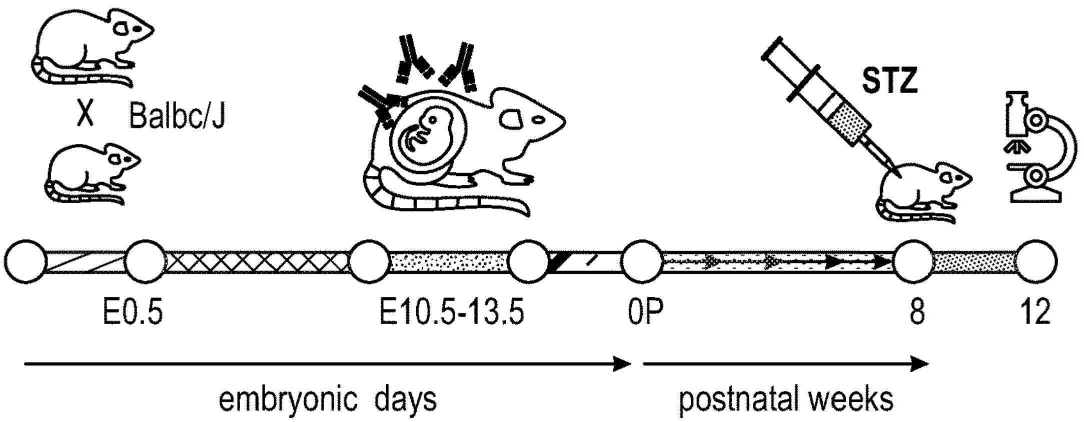
Figure 11H:
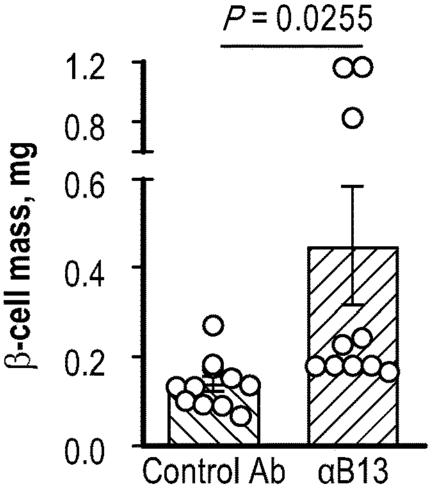
Figure 11I:
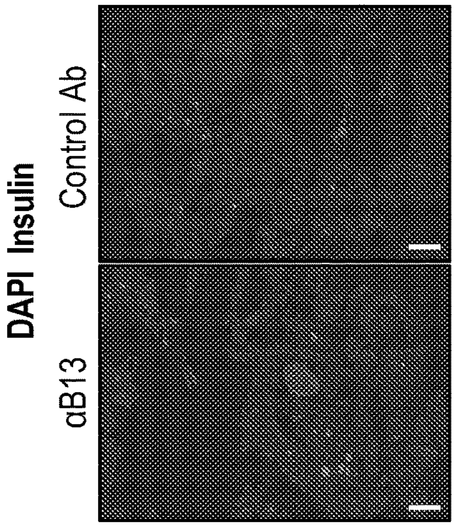
Figure 11J:
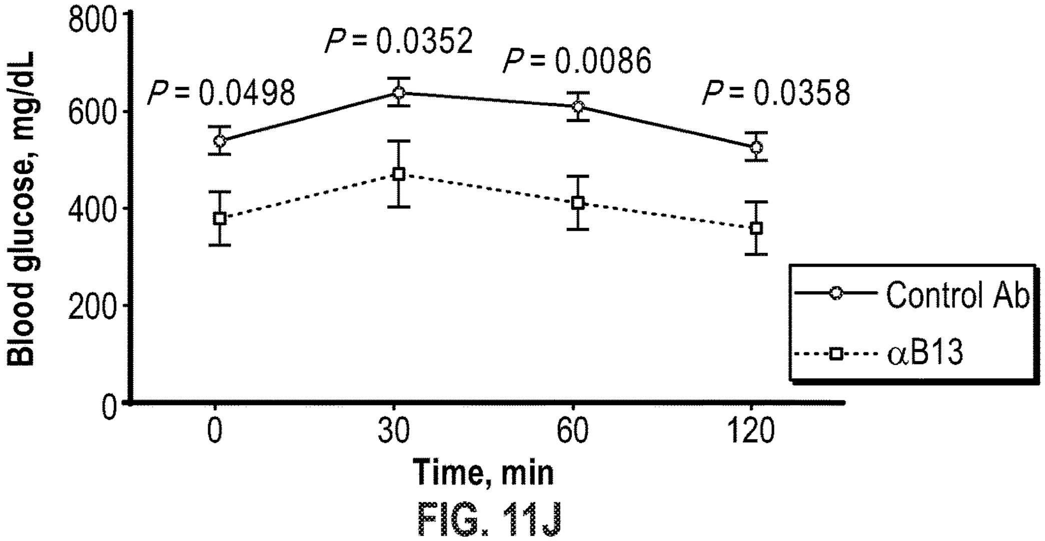
Figure 11K:
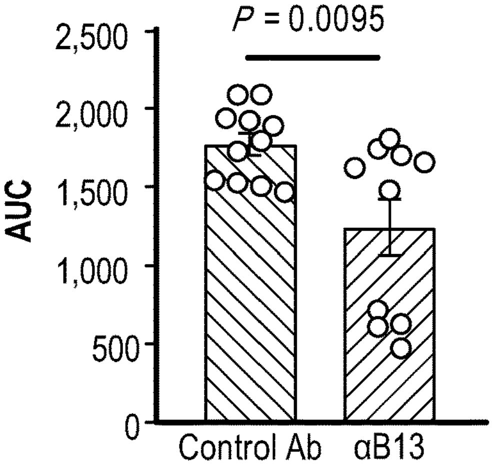
Figure 11L:
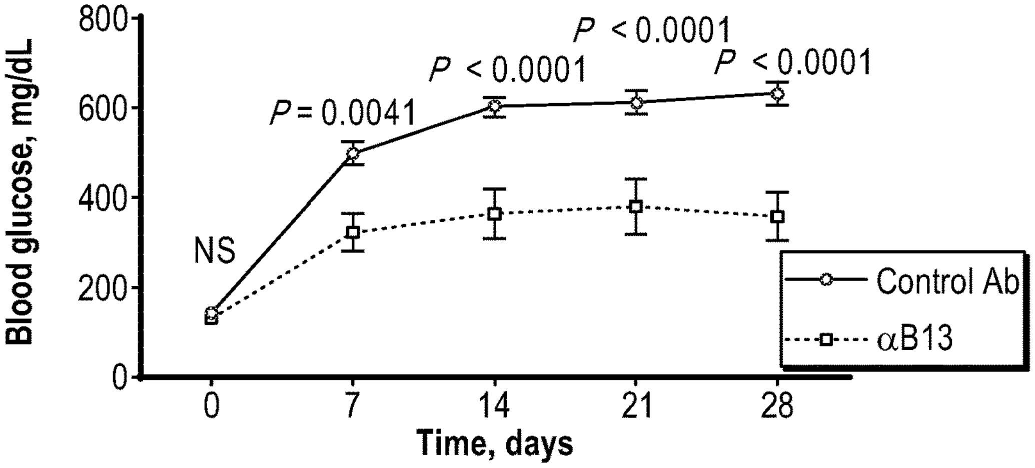
Figure 11M:
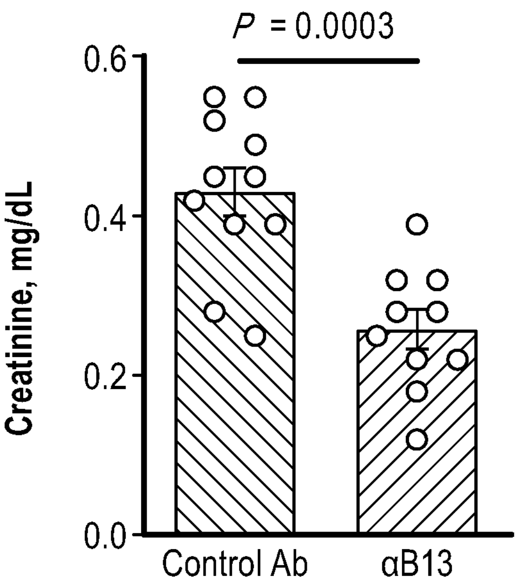
Figure 11N:
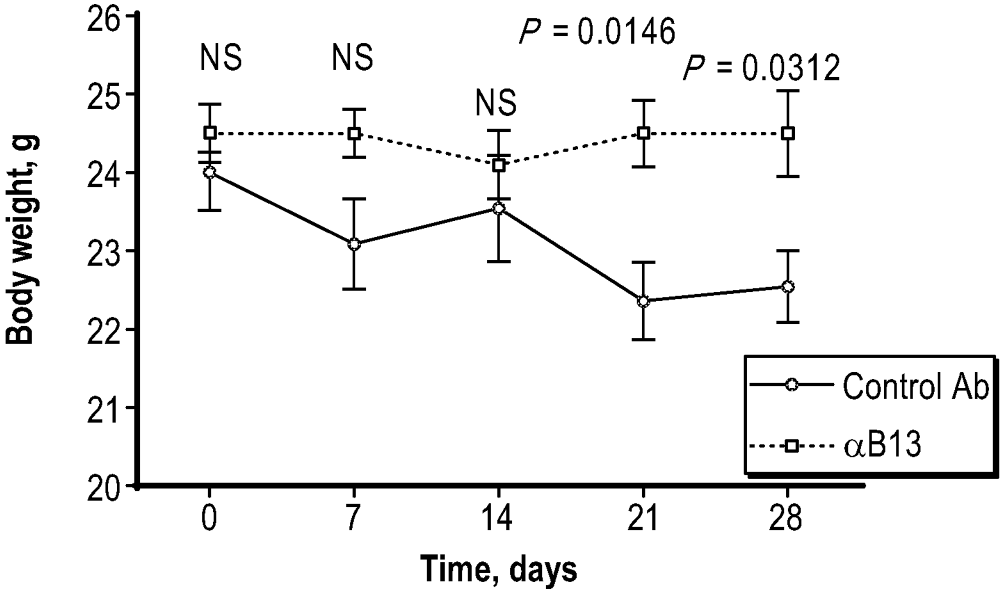

To assess the long-term impact of developmental changes induced by serpinB13 and its inhibition in the pancreas, we followed newborn mice for several months born from Balb/c mothers receiving anti-serpinB13 mAb during pregnancy (FIG. 11A). The prenatal inhibition of serpinB13 led to a significant increase in the number of pancreatic islets (FIG. 11B), total β-cell number (FIGS. 11C and 11D) and β-cell mass per animal (FIGS. 11E and 11F) in the 8-week old offspring (although the total pancreas and body weight at birth and in adulthood remained the same between the two groups, FIG. S123A-23B1). The α-cell population was also significantly increased, albeit to a lesser degree compared with the β-cells (FIG. 11C). Moreover, the postnatal increase in β-cell mass due to inhibition of serpinB13 during embryogenesis, was advantageous in the setting of diabetes induced with STZ injected in adulthood (FIG. 11G). It resulted in an over two-fold greater preserved residual β-cell mass (FIGS. 11H and 11I) and either completely protected against diabetes (FIG. 24A-24B), or ameliorated the severity of the disease (e.g., blood glucose control [FIGS. 11J, 11K and 11L] and serum creatinine as a measure of renal function [FIG. 11M] were improved while loss of body weight was prevented [FIG. 11N]) compared with the STZ-injected offspring of mothers that had received control antibody. Therefore, embryonal increase in the number of Ngn3+ endocrine progenitors by inhibition of serpinB13 offered a long-term benefit against abrupt loss of insulin-producing cells.

Figure 12A:
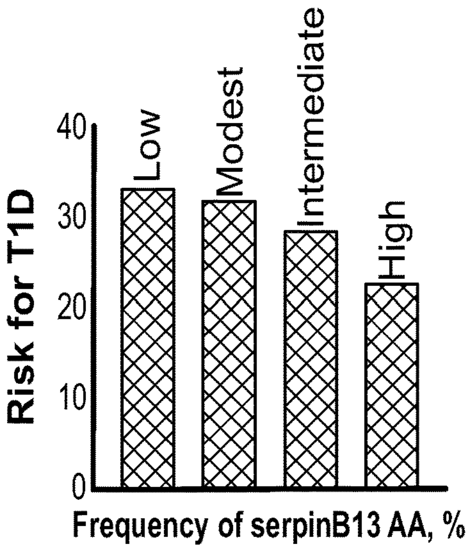
FIGS. 12A-12L. Impact of autoantibodies to serpinB13 on progression to type 1 diabetes in humans and pancreatic $Ngn3^+$ cell output during embryogenesis. (A) The frequency of serpinB13 AAs in human subjects with low (n=69), modest (n=69), intermediate (n=70) and high (n=70) risk levels for T1D. (B) Incidence of diabetes and (C) time to diabetes onset in high and intermediate risk groups combined (n=140), either negative (n=102) or positive (n=38) for serpinB13 AA. (D) Quantitative analysis by IF microscopy of $Ngn3^+$ cells in mouse embryonic pancreas explants (E12.5) incubated in vitro for 48 hours with individual human serum samples from Diabetes Prevention Trial for Type 1 Diabetes (DPT-1) enrolled subjects, either negative (serpinB13 $AA^-$, n=9) or positive (serpinB13 $AA^+$, n=8) for serpinB13 AA; three independent experiments. (E) Representative microscopic IF images of data shown in (D). (F) Cleavage of the substrate by CatL in the presence of serpinB13 and human mAb to serpinB13 (hαB13) or control human antibody (h.Control Ab) over time. The average of three independent experiments (left) and quantification of their AUC (right) is shown. (G) Quantitative analysis by IF microscopy of $Ngn3^+$ cells in mouse embryonic pancreas explants (E12.5) incubated in vitro for 48 hours with serpinB13 AA-negative human serum samples from DPT-1 subjects, which were reconstituted with hαB13 at 10 μg/mL (n=9) or h.Control Ab (n=9); three independent experiments. (H). Representative microscopic IF images of data shown in (G). (I) Experimental approach to deplete DPT-1 sera of serpinB13 AA. (J) Quantitative analysis by IF microscopy of $Ngn3^+$ cells in mouse embryonic pancreas explants (E12.5) incubated in vitro for 48 hours with human serum samples from DPT-1 subjects, which were depleted for serpinB13 AA (n=6) or sham depleted (n=6); two independent experiments. Both positive (left) and negative (right) serum samples examined. (K) Representative microscopic IF images of data shown in (K). (L) A model of spatial relationship between serpinB13, cathepsin L and antibody response, and its influence on progression to T1D. Data are presented as the mean±SEM. Log-rank (Mantel-Cox) test, hazard ratio 1.898 (C); unpaired two-sided Student t test (D); unpaired one-sided Student t test (G); one-way Anova with Sidak test (F-right, J) (F). Scale bars, 100 μm. NS, not significant. αB13, anti-serpinB13 mouse mAb; hαB13, anti-serpinB13 human recombinant antibody; rhB13, recombinant human serpinB13; h.Control Ab, recombinant human IgG1 isotype control; #, fluorescent signal reading limit; AUC, area under curve.
Figure 12B:
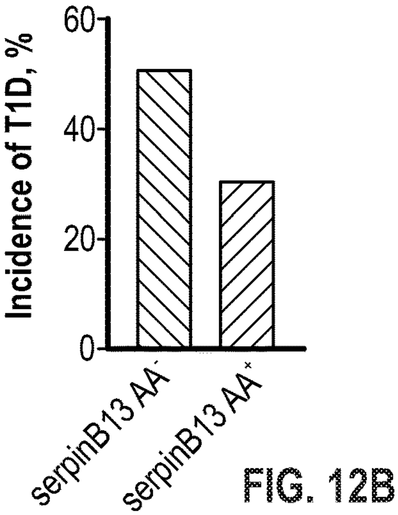
Figure 12C:
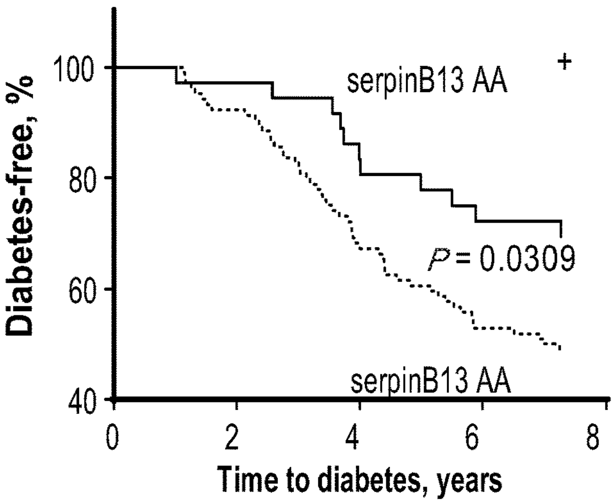
Figure 12D:
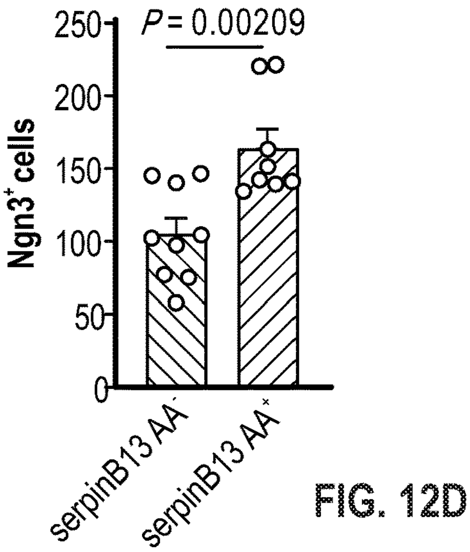
Figure 12E:
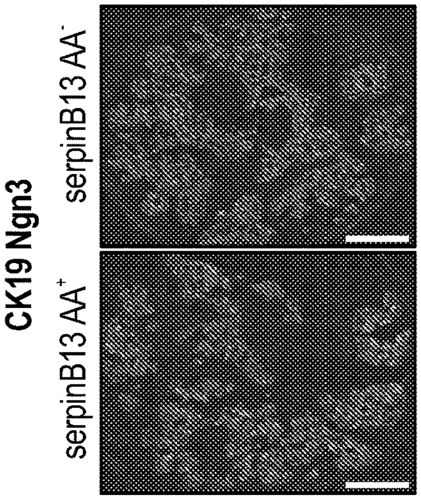
Figure 12F:
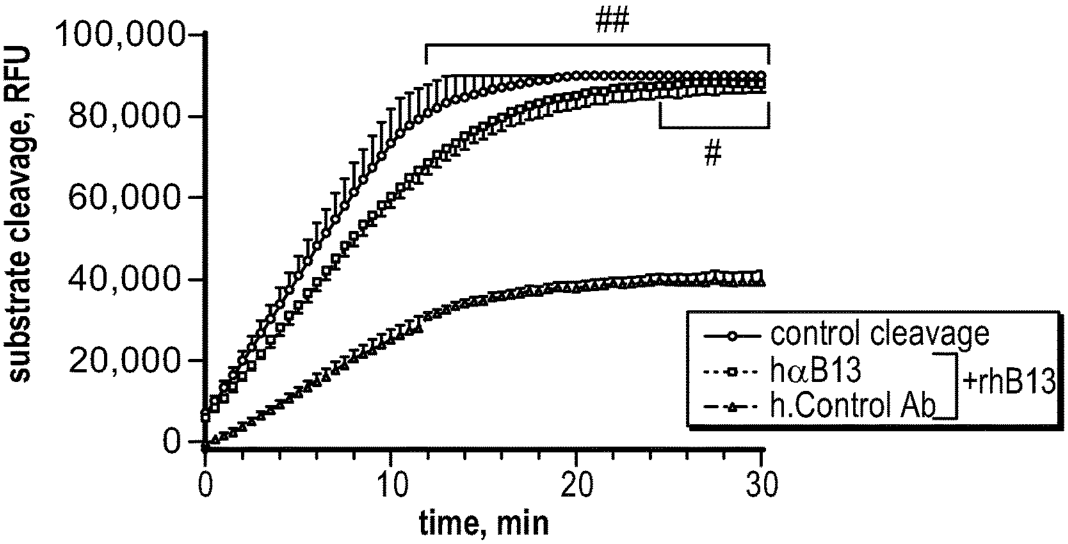
Figure 12G:
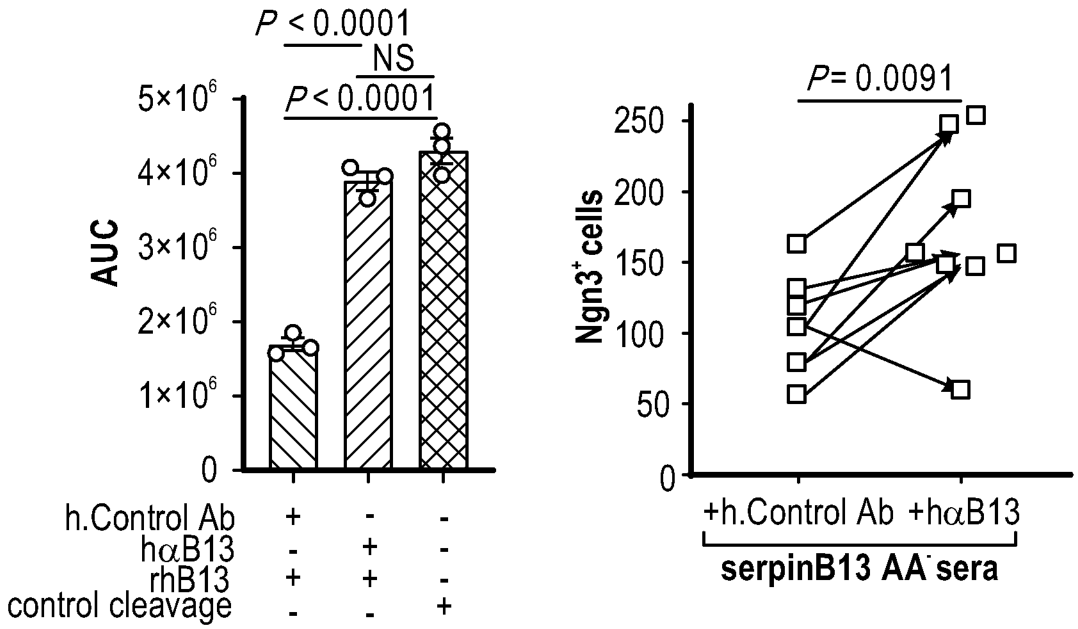
Figure 12H:
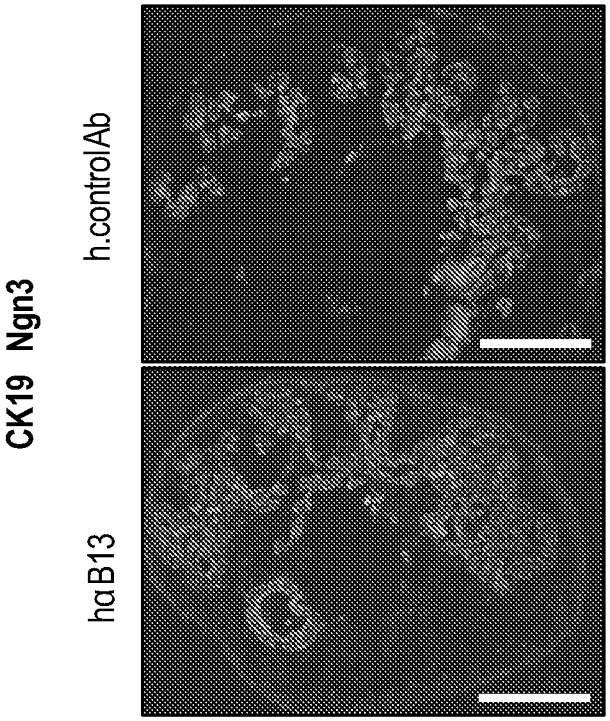
Figure 12I:
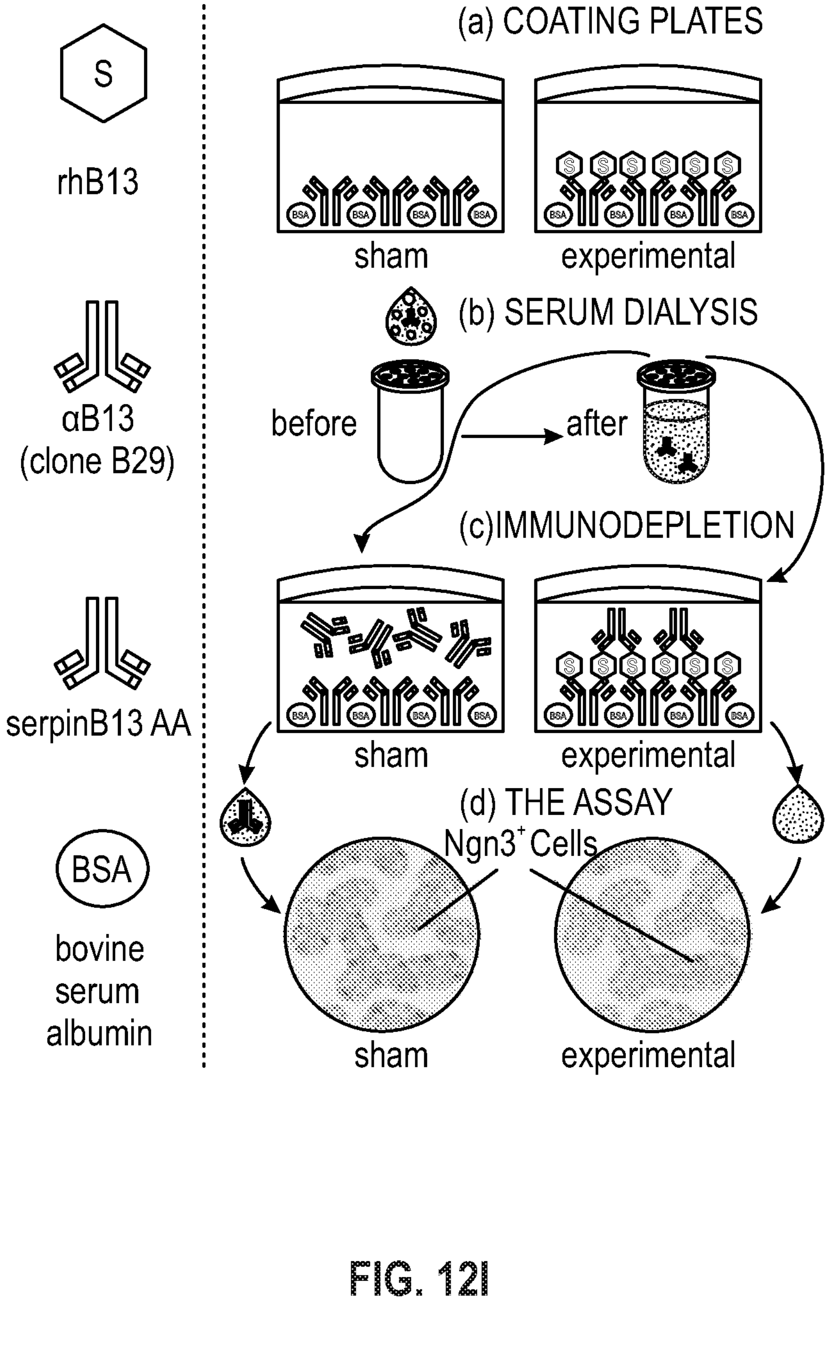
Figure 12J:
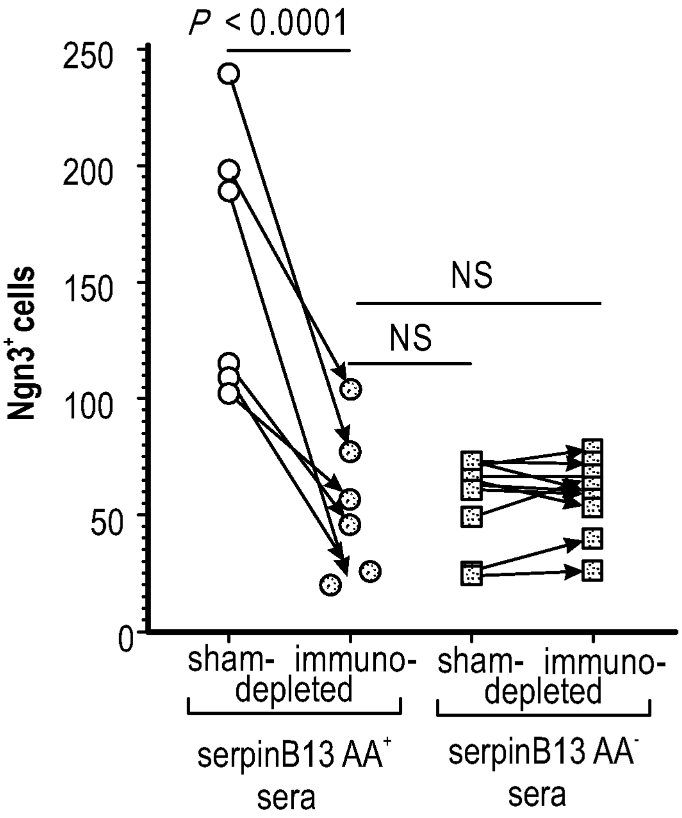
Figure 12K:
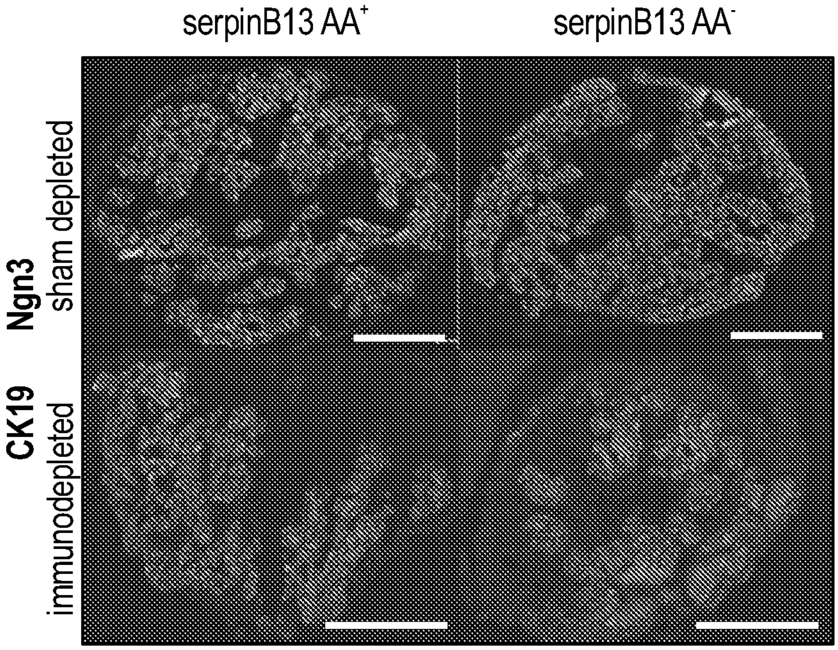

Previous studies in our laboratory revealed a novel autoantibody (AA) to serpinB13 and its association at baseline with higher residual fasting and stimulated C-peptide levels in humans with a recent-onset diagnosis of T1D. Encouraged by this finding as well as our observations on serpinB13-mediated developmental changes in the pancreas and their impact on diabetes in mice we wondered whether serpinB13 AA influences the pre-diabetes period and progression to T1D. To address this question, we measured baseline serpinB13 AA in subjects that were meticulously staged for risk of T1D during enrollment in the Diabetes Prevention Trial for Type 1 Diabetes (DPT-1). The serological serpinB13 binding activity inversely correlated with the risk level for T1D (FIG. 12A). Moreover, we found that the baseline serpinB13 AA was associated with a reduction in the overall incidence of diabetes (FIG. 12B) as well as longer diabetes-free survival in those who progressed to clinical disease (FIG. 12C). The phenotype in humans with serpinB13 AA could be explained by the potential functionality of this AA, which may mimic the function of the mouse mAb to serpinB13. Indeed, the dialyzed DPT-1 serum samples positive for serpinB13 AA significantly stimulated the development of $Ngn3^+$ cells in in vitro cultures (FIGS. 12D and 12E). Similar results were obtained with a human recombinant antibody to serpinB13 (FIG. 25), which in a similar fashion to previously described by us mouse mAb to serpinB13 rescues CatL protease activity from inhibition by this serpin (FIG. 12F, FIG. 26A-26B). Specifically, when added to the dialyzed DPT-1 serum samples that originally were negative for serpinB13 AA, human antibody to serpinB13 induced additional $Ngn3^+$ cells (FIGS. 12G and 12H). On the other hand, following experimental scheme do delete serpinB13AA from serum, depicted in FIG. 121, serpinB13 positive serum samples failed to induce additional $Ngn3^+$ cells after immunodepletion of this AA (FIGS. 12J and 12K). Taken together, serpinB13 AA may be actively involved in regulating the Notch pathway and diabetes prevention in a way that is similar to that described by us in our model using mouse anti-serpinB13 mAb.

Figure 12L:
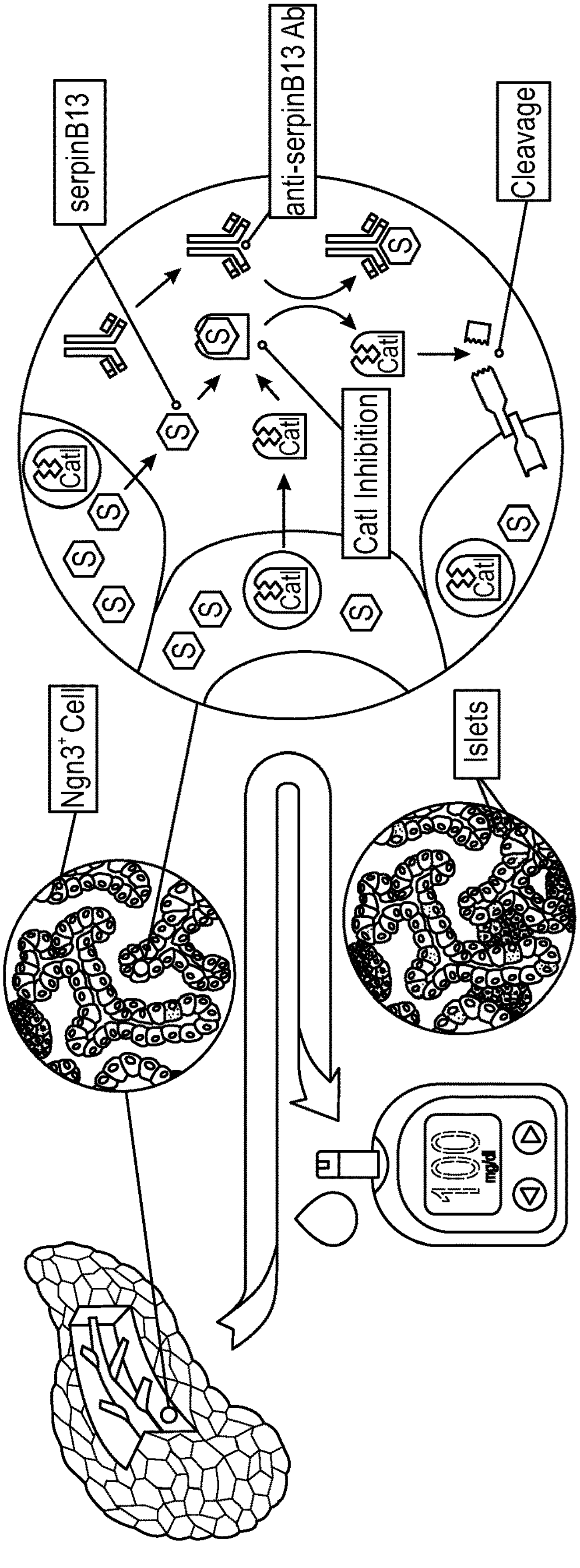

This Example describes a novel function of a clade B serpin in the developing pancreas. We propose that the interplay between serpinB13 and its CatL proteinase target influences cell fate decision in differentiating pancreatic epithelium by limiting Notch signaling. Specifically, we argue that repressing the inhibitory function of serpinB13 allows for CatL-mediated partial impairment of Notch1 on the cell surface (FIG. 12L), the event that is known to promote the endocrine fate. The incomplete inhibition of Notch could be explained by a relatively limited presence of CatL and serpinB13 outside the cell. Although serpinB13 is primarily an intracellular molecule, we found that it can be detected in the extracellular space. This feature is not unique to serpinB13, as other members of the clade B serpin family have also been found extracellularly or expressed on the cell surface.

Influencing Notch signaling as part of a programming paradigm has a strong potential for therapy. We used diabetes as a model to demonstrate that our approach to inactivate serpinB13 with mAb modifies the Notch pathway in a way that offers a better clinical outcome. However, it is possible that therapeutic inhibition of serpinB13, or other clade B serpin members, could go beyond the prevention of diabetes and be applicable for therapeutic approaches to other pathological processes involving deregulated Notch signaling.

Finally, our examination of young humans at risk for T1D revealed that natural autoantibodies to serpinB13 offer a higher level of protection against the clinical onset of diabetes. This positive outcome may be attributed to the enhanced yield of Ngn3+ endocrine progenitors, which according to some authors can arise after birth under conditions of cellular injury or inflammatory cytokine stress in the pancreatic exocrine ductal cells or their vicinity. However, based on our previous studies we cannot exclude that serpinB13 AA in T1D subjects also stimulate CatL-mediated cleavage of key cell-surface receptors, including those expressed in lymphocytes, e.g., CD4 in T cells and CD19 in B cells. Hence, both islet adaptive changes by newly generated Ngn3+ endocrine progenitor cells and the impediment of autoimmune inflammation in this tissue compartment may account for the protective impact of anti-serpinB13 activity in humans with T1D.

Materials and Methods:

Experimental animals. Balb/cJ mice (stock No: 000651), C57BL/6J (stock No: 000664), Ngn3Cre:Tg(Neurog3-cre/Esr1*)1Dam/J (stock No: 008119) and Rosa26EYFP: B6.129X1-Gt(ROSA)26Sortm1(EYFP)Cos/J (stock No: 006148) were from the Jackson Laboratory (Bar Harbor, ME, USA). The CatL-deficient NOD mice (stock No. 008352) were back-crossed to the Balb/c background for at least 20 generations. The Institutional Animal Care and Use Committee approved all mice experiments.

SerpinB13 mAbs and other antibodies used in functional studies. The mouse mAb to serpinB13, clone B29, has been described previously (J. Czyzyk, O. Henegariu, P. Preston-Hurlburt, R. Baldzizhar, C. Fedorchuk, E. Esplugues, K. Bottomly, F. K. Gorus, K. Herold, R. A. Flavell, Enhanced anti-serpin antibody activity inhibits autoimmune inflammation in type 1 diabetes. *J. Immunol.* 188, 6319-6327 (2012)). The mouse mAb to serpin B13, clone B34, has also been previously developed in our laboratory but not published before. The epitope specificity of B34 is distinct from that of B29 and corresponds to the following amino acid sequence of mouse serpinB13—SEEEEIEKREEIHHQLQMLL.

The recombinant human antibodies to serpinB13 were developed from a human Fab library, constituting sequences derived from the antibody repertoire of approximately 120 individuals, with a diversity/complexity of approximately $1\times10^{11}$ clones (ProMab Biotechnologies, Richmond, CA, USA). Briefly, a scFv surface-display library was subjected to multiple rounds of screening by panning and flow cytometry against human serpinB13, following which the positive clones were isolated, re-tested for their binding to serpinB13, and selected for detailed testing. The clones were then selected for sequencing of the CDR region of heavy and light immunoglobulin chains. The heavy and light chain regions were amplified from cDNA by a two-step, nested PCR reaction using advantage 3 cDNA polymerase and primer mixes specific for germline families (VBASE database). Expression plasmids encoding sequences of full-length heavy and light-chain were used to produce recombinant antibodies in HTEK203 cell expression system. The sequences for the heavy and light chains for the antibodies are provided in Table 2 below.

TABLE 2

Table of Sequences

| SEQ ID NO | Description | Sequence |
|---|---|---|
| 30 | Clone1-H(m1)-DNA | CAGGTGCAGCTGCAGGAGTCCGGGGGAGGCGTGGTCCAGCCTGGGA GGTCCCTGAGACTCTCCTGTGCAGCCTCTGGATTCACCTTCAGTAG CTATGGCATGCACTGGGTCCGCCAGGCTCCAGGCAAGGGGCTGGAG TGGGTGGCAGTTATATCATATGATGGAAGTAATAAATACTATGCAG ACTCCGTGAAGGGCCGATTCACCATCTCCAGAGACAATTCCAAGAA CACGCTGTATCTGCAAATGAACAGCCTGAGAGCCGAGGACACGGCT GTGTATTACTGTGCGAGAGATCTCGGCGCCGTTATAGCAGTGGCTG GTACTTCCACCCCGTACAACTGGTTCGACCCCTGGGGCCAGGGAAC CCTGGTCACCGTCTCAAGCGCCTCCACCAAGGGCCCATCGGTCTTC CCCCTGGCACCCTCCTCCAAGAGCACCTCTGGGGGCACAGCGGCCC TGGGCTGCCTGGTCAAGGACTACTTCCCCGAACCGGTGACGGTGTC GTGGAACTCAGGCGCCCTGACCAGCGGCGTCCACACCTTCCCGGCT GTCCTACAGTCCTCAGGACTCTACTCCCTCAGCAGCGTAGTGACCG TGCCCTCCAGCAGCTTGGGCACCCAGACCTACATCTGCAACGTGAA TCACAAGCCCAGCAACACCAAGGTGGACAAGAAAGTTGAGCCCAAA TCTTGTGACAAAACTCACACATGCCCACCGTGCCCAGCACCTGAAC TCCTGGGGGGACCGTCAGTCTTCCTCTTCCCCCCAAAACCCAAGGA CACCCTCATGATCTCCCGGACCCCTGAGGTCACATGCGTGGTGGTG GACGTGAGCCACGAAGACCCTGAGGTCAAGTTCAACTGGTACGTGG ACGGCGTGGAGGTGCATAATGCCAAGACAAAGCCGCGGGAGGAGCA GTACAACAGCACGTACCGTGTGGTCAGCGTCCTCACCGTCCTGCAC CAGGACTGGCTGAATGGCAAGGAGTACAAGTGCAAGGTCTCCAACA AAGCCCTCCCAGCCCCCATCGAGAAAACCATCTCCAAAGCCAAAGG GCAGCCCCGAGAACCACAGGTGTACACCCTGCCCCCATCCCGGGAT GAGCTGACCAAGAACCAGGTCAGCCTGACCTGCCTGGTCAAAGGCT TCTATCCCAGCGACATCGCCGTGGAGTGGGAGAGCAATGGGCAGCC GGAGAACAACTACAAGACCACGCCTCCCGTGCTGGACTCCGACGGC TCCTTCTTCCTCTACAGCAAGCTCACCGTGGACAAGAGCAGGTGGC AGCAGGGGAACGTCTTCTCATGCTCCGTGATGCATGAGGCTCTGCA CAACCACTACACGCAGAAGAGCCTCTCCCTGTCTCCGGGTAAATGA |
| 31 | Clone1-H(m1)-protein | QVQLQESGGGVVQPGRSLRLSCAASGFTFSSYGMHWVRQAPGKGLE WVAVISYDGSNKYYADSVKGRFTISRDNSKNTLYLQMNSLRAEDTA VYYCARDLGAVIAVAGTSTPYNWFDPWGQGTLVTVSSASTKGPSVF PLAPSSKSTSGGTAALGCLVKDYFPEPVTVSWNSGALTSGVHTFPA VLQSSGLYSLSSVVTVPSSSLGTQTYICNVNHKPSNTKVDKKVEPK SCDKTHTCPPCPAPELLGGPSVFLFPPKPKDTLMISRTPEVTCVVV DVSHEDPEVKFNWYVDGVEVHNAKTKPREEQYNSTYRVVSVLTVLH QDWLNGKEYKCKVSNKALPAPIEKTISKAKGQPREPQVYTLPPSRD ELTKNQVSLTCLVKGFYPSDIAVEWESNGQPENNYKTTPPVLDSDG SFFLYSKLTVDKSRWQQGNVFSCSVMHEALHNHYTQKSLSLSPGK |
| 32 | vector DNA | *ATGGAGACAGACACACTCCTGCTATGGGTACTGCTGCTCTGGGTTC CAGGTTCCACTggcgccggatca* |

TABLE 2-continued

Table of Sequences

| SEQ ID NO | Description | Sequence |
|---|---|---|
| 33 | Clone1-H(m1)-Recombinant DNA Sequence (vector: pYD5-hFC(Amp)) | *ATGGAGACAGACACACTCCTGCTATGGGTACTGCTGCTCTGGGTTC* *CAGGTTCCACTggcgccggatca* CAGGTGCAGCTGCAGGAGTCCGGGGGAGGCGTGGTCCAGCCTGGGA GGTCCCTGAGACTCTCCTGTGCAGCCTCTGGATTCACCTTCAGTAG CTATGGCATGCACTGGGTCCGCCAGGCTCCAGGCAAGGGGCTGGAG TGGGTGGCAGTTATATCATATGATGGAAGTAATAAATACTATGCAG ACTCCGTGAAGGGCCGATTCACCATCTCCAGAGACAATTCCAAGAA CACGCTGTATCTGCAAATGAACAGCCTGAGAGCCGAGGACACGGCT GTGTATTACTGTGCGAGAGATCTCGGCGCCGTTATAGCAGTGGCTG GTACTTCCACCCCGTACAACTGGTTCGACCCCTGGGGCCAGGGAAC CCTGGTCACCGTCTCAAGCGCCTCCACCAAGGGCCCATCGGTCTTC CCCCTGGCACCCTCCTCCAAGAGCACCTCTGGGGGCACAGCGGCCC TGGGCTGCCTGGTCAAGGACTACTTCCCCGAACCGGTGACGGTGTC GTGGAACTCAGGCGCCCTGACCAGCGGCGTCCACACCTTCCCGGCT GTCCTACAGTCCTCAGGACTCTACTCCCTCAGCAGCGTAGTGACCG TGCCCTCCAGCAGCTTGGGCACCCAGACCTACATCTGCAACGTGAA TCACAAGCCCAGCAACACCAAGGTGGACAAGAAAGTTGAGCCCAAA TCTTGTGACAAAACTCACACATGCCCACCGTGCCCAGCACCTGAAC TCCTGGGGGGACCGTCAGTCTTCCTCTTCCCCCCAAAACCCAAGGA CACCCTCATGATCTCCCGGACCCCTGAGGTCACATGCGTGGTGGTG GACGTGAGCCACGAAGACCCTGAGGTCAAGTTCAACTGGTACGTGG ACGGCGTGGAGGTGCATAATGCCAAGACAAAGCCGCGGGAGGAGCA GTACAACAGCACGTACCGTGTGGTCAGCGTCCTCACCGTCCTGCAC CAGGACTGGCTGAATGGCAAGGAGTACAAGTGCAAGGTCTCCAACA AAGCCCTCCCAGCCCCCATCGAGAAAACCATCTCCAAAGCCAAAGG GCAGCCCCGAGAACCACAGGTGTACACCCTGCCCCCATCCCGGGAT GAGCTGACCAAGAACCAGGICAGCCIGACCIGCCIGGTCAAAGGCT TCTATCCCAGCGACATCGCCGTGGAGTGGGAGAGCAATGGGCAGCC GGAGAACAACTACAAGACCACGCCTCCCGTGCTGGACTCCGACGGC TCCTTCTTCCTCTACAGCAAGCTCACCGTGGACAAGAGCAGGTGGC AGCAGGGGAACGTCTTCTCATGCTCCGTGATGCATGAGGCTCTGCA CAACCACTACACGCAGAAGAGCCICICCCTGTCTCCGGGTAAATGA |
| 34 | vector protein | METDTLLLWVLLLWVPGSTGAGS |
| 35 | Clone1-H(m1) - Recombinant protein Sequence (vector: pYD5-hFC(Amp)) | METDTLLLWVLLLWVPGSTGAGS QVQLQESGGGVVQPGRSLRLSCAASGFTFSSYGMHWVRQAPGKGLE WVAVISYDGSNKYYADSVKGRFTISRDNSKNTLYLQMNSLRAEDTA VYYCARDLGAVIAVAGTSTPYNWFDPWGQGTLVTVSSASTKGPSVF PLAPSSKSTSGGTAALGCLVKDYFPEPVTVSWNSGALTSGVHTFPA VLQSSGLYSLSSVVTVPSSSLGTQTYICNVNHKPSNTKVDKKVEPK SCDKTHTCPPCPAPELLGGPSVFLFPPKPKDTLMISRTPEVTCVVV DVSHEDPEVKFNWYVDGVEVHNAKTKPREEQYNSTYRVVSVLTVLH QDWLNGKEYKCKVSNKALPAPIEKTISKAKGQPREPQVYTLPPSRD ELTKNQVSLTCLVKGFYPSDIAVEWESNGQPENNYKTTPPVLDSDG SFFLYSKLTVDKSRWQQGNVFSCSVMHEALHNHYTQKSLSLSPGK |
| 36 | Clone1-L(m1) DNA | GATGTTGTGATGACTCAGTCTCCACTCTCCCTGCCCGTCACCCCTG GAGAGCCGGCCTCCATCTCCTGCAGGTCTCGTCAGAGCCTCCTGCA TAGCAATGGACACAACTATTTGGGTTGGTACCTGCAGAAGCCAGGG CAGTCTCCACAGCTCCTGATCTATCTGGCTTCTATTCGGGCCTCCG GGATCCCTGACAGGTTCAGTGGCAGTGGATCAGGCACAGATTTTAC ACTGAAAATCAGCAGAGTGGAGGCTGAGGATGTTGGCGTTTATTAC TGCATGCAAGCTCTACAAACACCCTACACTTTTGGCCAGGGGACCA AGCTGGAGATCAAGCGAACTGTGGCTGCACCATCTGTCTTCATCTT CCCGCCATCTGATGAGCAGTTGAAATCTGGAACTGCCTCTGTTGIG TGCCTGCTGAATAACTTCTATCCCAGAGAGGCCAAAGTACAGTGGA AGGTGGATAACGCCCTCCAATCGGGTAACTCCCAGGAGAGTGTCAC AGAGCAGGACAGCAAGGACAGCACCTACAGCCTCAGCAGCACCCTG ACGCTGAGCAAAGCAGACTACGAGAAACACAAAGTCTACGCCTGCG AAGTCACCCATCAGGGCCTGAGCTCGCCCGTCACAAAGAGCTTCAA CAGGGGAGAGTGTTAG |
| 37 | Clone1-L(m1) protein | DVVMTQSPLSLPVTPGEPASISCRSRQSLLHSNGHNYLGWYLQKPG QSPQLLIYLASIRASGIPDRFSGSGSGTDFTLKISRVEAEDVGVYY CMQALQTPYTFGQGTKLEIKRTVAAPSVFIFPPSDEQLKSGTASVV CLLNNFYPREAKVQWKVDNALQSGNSQESVTEQDSKDSTYSLSSTL TLSKADYEKHKVYACEVTHQGLSSPVTKSFNRGEC |

TABLE 2-continued

| Table of Sequences | | |
|---|---|---|
| SEQ ID NO | Description | Sequence |
| 38 | Clone1-L(m1) - Recombinant DNA Sequence (Vector: pYD5-hFC(Amp)) | *ATGGAGACAGACACACTCCTGCTATGGGTACTGCTGCTCTGGGTTC*<br>*CAGGTTCCACTggcgccggatca*<br>GATGTTGTGATGACTCAGTCTCCACTCTCCCTGCCCGTCACCCCTG<br>GAGAGCCGGCCTCCATCTCCTGCAGGTCTCGTCAGAGCCTCCTGCA<br>TAGCAATGGACACAACTATTTGGGTTGGTACCTGCAGAAGCCAGGG<br>CAGTCTCCACAGCTCCTGATCTATCTGGCTTCTATTCGGGCCTCCG<br>GGATCCCTGACAGGTTCAGTGGCAGTGGATCAGGCACAGATTTTAC<br>ACTGAAAATCAGCAGAGTGGAGGCTGAGGATGTTGGCGTTTATTAC<br>TGCATGCAAGCTCTACAAACACCCTACACTTTTGGCCAGGGGACCA<br>AGCTGGAGATCAAGCGAACTGTGGCTGCACCATCTGTCTTCATCTT<br>CCCGCCATCTGATGAGCAGTTGAAATCTGGAACTGCCTCTGTTGTG<br>TGCCTGCTGAATAACTTCTATCCCAGAGAGGCCAAAGTACAGTGGA<br>AGGTGGATAACGCCCTCCAATCGGGTAACTCCCAGGAGAGTGTCAC<br>AGAGCAGGACAGCAAGGACAGCACCTACAGCCTCAGCAGCACCCTG<br>ACGCTGAGCAAAGCAGACTACGAGAAACACAAAGTCTACGCCTGCG<br>AAGTCACCCATCAGGGCCTGAGCTCGCCCGTCACAAAGAGCTTCAA<br>CAGGGGAGAGTGTTAG |
| 39 | Clone1-L(m1) - Recombinant Protein Sequence (Vector: pYD5-hFC(Amp)) | *METDTLLLWVLLLWVPGSTGAGS*<br>DVVMTQSPLSLPVTPGEPASISCRSRQSLLHSNGHNYLGWYLQKPG<br>QSPQLLIYLASIRASGIPDRFSGSGSGTDFTLKISRVEAEDVGVYY<br>CMQALQTPYTFGQGTKLEIKRTVAAPSVFIFPPSDEQLKSGTASVV<br>CLLNNFYPREAKVQWKVDNALQSGNSQESVTEQDSKDSTYSLSSTL<br>TLSKADYEKHKVYACEVTHQGLSSPVTKSFNRGEC |
| 40 | CLONE2-H(m1) DNA Sequence | CAGATGCAGCTGGTGCAGTCGGGGGGAGGTGTGGTACGGCCTGGGG<br>GGTCCCTGAGACTCTCCTGTGCAGCCTCTGGATTCACCTTTGATGA<br>TTATGGCATGAGCTGGGTCCGCCAAGCTCCAGGGAAGGGGCTGGAG<br>GGGTCTCTGGTATTAATTGGAATGGTGGTAGCACAGGTTATGCAG<br>ACTCTGTGAAGGGCCGATTCACCATCTCCAGAGACAACGCCAAGAA<br>CTCCCTGTATCTGCAAATGAACAGTCTGAGAGCCGAGGACACGGCC<br>TTGTATTACTGTGCGAGAGAAAGCTCGATGACTACAGTAACTACGT<br>ATCTCCTACGGGAAGTAGGGGTAGGGTTGGACTTTGACTACTGGGG<br>CCAGGGCACCCTGGTCACCGTCTCAAGCGCCTCCACCAAGGGCCCA<br>TCGGTCTTCCCCCTGGCACCCTCCTCCAAGAGCACCTCTGGGGGCA<br>CAGCGGCCCTGGGCTGCCTGGTCAAGGACTACTTCCCCGAACCGGT<br>GACGGTGTCGTGGAACTCAGGCGCCCTGACCAGCGGCGTCCACACC<br>TTCCCGGCTGTCCTACAGTCCTCAGGACTCTACTCCCTCAGCAGCG<br>TAGTGACCGTGCCCTCCAGCAGCTTGGGCACCCAGACCTACATCTG<br>CAACGTGAATCACAAGCCCAGCAACACCAAGGTGGACAAGAAAGTT<br>GAGCCCAAATCTTGTGACAAAACTCACACATGCCCACCGTGCCCAG<br>CACCTGAACTCCTGGGGGGACCGTCAGTCTTCCICTTCCCCCCAAA<br>ACCCAAGGACACCCTCATGATCTCCCGGACCCCTGAGGTCACATGC<br>GTGGTGGTGGACGTGAGCCACGAAGACCCTGAGGTCAAGTTCAACT<br>GGTACGTGGACGGCGTGGAGGTGCATAATGCCAAGACAAAGCCGCG<br>GGAGGAGCAGTACAACAGCACGTACCGTGTGGTCAGCGTCCTCACC<br>GTCCTGCACCAGGACTGGCTGAATGGCAAGGAGTACAAGTGCAAGG<br>TCTCCAACAAAGCCCTCCCAGCCCCCATCGAGAAAACCATCTCCAA<br>AGCCAAAGGGCAGCCCCGAGAACCACAGGTGTACACCCTGCCCCCA<br>TCCCGGGATGAGCTGACCAAGAACCAGGTCAGCCTGACCTGCCTGG<br>TCAAAGGCTTCTATCCCAGCGACATCGCCGTGGAGTGGGAGAGCAA<br>TGGGCAGCCGGAGAACAACTACAAGACCACGCCTCCCGTGCTGGAC<br>TCCGACGGCTCCTTCTTCCTCTACAGCAAGCTCACCGTGGACAAGA<br>GCAGGTGGCAGCAGGGGAACGTCTTCTCATGCTCCGTGATGCATGA<br>GGCTCTGCACAACCACTACACGCAGAAGAGCCTCTCCCTGTCTCCG<br>GGTAAATGA |
| 41 | CLONE2-H(m1) Protein Sequence | QMQLVQSGGGVVRPGGSLRLSCAASGFTFDDYGMSWVRQAPGKGLE<br>WVSGINWNGGSTGYADSVKGRFTISRDNAKNSLYLQMNSLRAEDTA<br>LYYCARESSMTTVTTYLLREVGVGLDFDYWGQGTLVTVSSASTKGP<br>SVFPLAPSSKSTSGGTAALGCLVKDYFPEPVTVSWNSGALTSGVHT<br>FPAVLQSSGLYSLSSVVTVPSSSLGTQTYICNVNHKPSNTKVDKKV<br>EPKSCDKTHTCPPCPAPELLGGPSVFLFPPKPKDTLMISRTPEVTC<br>VVVDVSHEDPEVKFNWYVDGVEVHNAKTKPREEQYNSTYRVVSVLT<br>VLHQDWLNGKEYKCKVSNKALPAPIEKTISKAKGQPREPQVYTLPP<br>SRDELTKNQVSLTCLVKGFYPSDIAVEWESNGQPENNYKTTPPVLD<br>SDGSFFLYSKLTVDKSRWQQGNVFSCSVMHEALHNHYTQKSLSLSP<br>GK |

TABLE 2-continued

| Table of Sequences | | |
|---|---|---|
| SEQ ID NO | Description | Sequence |
| 42 | CLONE2-H(m1) Recombinant DNA Sequence (Vector: pYD5-hFC(Amp)) | *ATGGAGACAGACACACTCCTGCTATGGGTACTGCTGCTCTGGGTTC CAGGTTCCACTggcgccggatca* CAGATGCAGCTGGTGCAGTCGGGGGGAGGTGTGGTACGGCCTGGGG GGTCCCTGAGACTCTCCTGTGCAGCCTCTGGATTCACCTTTGATGA TTATGGCATGAGCTGGGTCCGCCAAGCTCCAGGGAAGGGGCTGGAG TGGGTCTCTGGTATTAATTGGAATGGTGGTAGCACAGGTTATGCAG ACTCTGTGAAGGGCCGATTCACCATCTCCAGAGACAACGCCAAGAA CTCCCTGTATCTGCAAATGAACAGTCTGAGAGCCGAGGACACGGCC TTGTATTACTGTGCGAGAGAAAGCTCGATGACTACAGTAACTACGT ATCTCCTACGGGAAGTAGGGGTAGGGTTGGACTTTGACTACTGGGG CCAGGGCACCCTGGTCACCGTCTCAAGCGCCTCCACCAAGGGCCCA TCGGTCTTCCCCCTGGCACCCTCCTCCAAGAGCACCTCTGGGGGCA CAGCGGCCCTGGGCTGCCTGGTCAAGGACTACTTCCCCGAACCGGT GACGGTGTCGTGGAACTCAGGCGCCCTGACCAGCGGCGTCCACACC TTCCCGGCTGTCCTACAGTCCTCAGGACTCTACTCCCTCAGCAGCG TAGTGACCGTGCCCTCCAGCAGCTTGGGCACCCAGACCTACATCTG CAACGTGAATCACAAGCCCAGCAACACCAAGGTGGACAAGAAAGTT GAGCCCAAATCTTGTGACAAAACTCACACATGCCCACCGTGCCCAG CACCTGAACTCCTGGGGGGACCGTCAGTCTTCCTCTTCCCCCCAAA ACCCAAGGACACCCTCATGATCTCCCGGACCCCTGAGGTCACATGC GTGGTGGTGGACGTGAGCCACGAAGACCCTGAGGTCAAGTTCAACT GGTACGTGGACGGCGTGGAGGTGCATAATGCCAAGACAAAGCCGCG GGAGGAGCAGTACAACAGCACGTACCGTGTGGTCAGCGTCCTCACC GTCCTGCACCAGGACTGGCTGAATGGCAAGGAGTACAAGTGCAAGG TCTCCAACAAAGCCCTCCCAGCCCCCATCGAGAAAACCATCTCCAA AGCCAAAGGGCAGCCCCGAGAACCACAGGTGTACACCCTGCCCCCA TCCCGGGATGAGCTGACCAAGAACCAGGTCAGCCTGACCTGCCTGG TCAAAGGCTTCTATCCCAGCGACATCGCCGTGGAGTGGGAGAGCAA TGGGCAGCCGGAGAACAACTACAAGACCACGCCTCCCGTGCTGGAC TCCGACGGCTCCTTCTTCCTCTACAGCAAGCTCACCGTGGACAAGA GCAGGTGGCAGCAGGGGAACGTCTTCTCATGCTCCGTGATGCATGA GGCTCTGCACAACCACTACACGCAGAAGAGCCTCTCCCTGTCTCCG GGTAAATGA |
| 43 | CLONE2-H(m1) Recombinant Protein Sequence (Vector: pYD5-hFC(Amp)) | *METDTLLLWVLLLWVPGSTGAGS* QMQLVQSGGGVVRPGGSLRLSCAASGFTFDDYGMSWVRQAPGKGLE WVSGINWNGGSTGYADSVKGRFTISRDNAKNSLYLQMNSLRAEDTA LYYCARESSMTTVTTYLLREVGVGLDFDYWGQGTLVTVSSASTKGP SVFPLAPSSKSTSGGTAALGCLVKDYFPEPVTVSWNSGALTSGVHT FPAVLQSSGLYSLSSVVTVPSSSLGTQTYICNVNHKPSNTKVDKKV EPKSCDKTHTCPPCPAPELLGGPSVFLFPPKPKDTLMISRTPEVTC VVVDVSHEDPEVKFNWYVDGVEVHNAKTKPREEQYNSTYRVVSVLT VLHQDWLNGKEYKCKVSNKALPAPIEKTISKAKGQPREPQVYTLPP SRDELTKNQVSLTCLVKGFYPSDIAVEWESNGQPENNYKTTPPVLD SDGSFFLYSKLTVDKSRWQQGNVFSCSVMHEALHNHYTQKSLSLSP GK |
| 44 | CLONE2-L(m1) DNA Sequence | GAAACGACACTCACGCAGTCTCCAGGCACCCTGTCCTTGTCTCCAG GGGAAAGAGCCACCCTCTCCTGCAGGGCCAGTCAGACTGTTAGCGG CAGCTACTTAGCCTGGTACCAGCAGAAACCTGGCCAGCCTCCCAGG CTCCTCATCTATGGTGCATCCAGCAGGGCCACTGGCATCCCAGACA GGTTCAGTGGCAGTGGGTCCGGGACAGACTTCACTCTCACCATCAG CAGACTGGAGCCTGAAGATTTTGCAGTGTATTACTGTCAGGACTAT GGTAGCTCACGGACGTTCGGCCAAGGGACCAAGGTGGAACTCAAAC GAACTGTGGCTGCACCATCTGTCTTCATCTTCCCGCCATCTGATGA GCAGTTGAAATCTGGAACTGCCTCTGTTGTGTGCCTGCTGAATAAC TTCTATCCCAGAGAGGCCAAAGTACAGTGGAAGGTGGATAACGCCC TCCAATCGGGTAACTCCCAGGAGAGTGTCACAGAGCAGGACAGCAA GGACAGCACCTACAGCCTCAGCAGCACCCTGACGCTGAGCAAAGCA GACTACGAGAAACACAAACTCTACGCCTGCGAAGICACCCATCAGG GCCTGAGCTCGCCCGTCACAAAGAGCTTCAACAGGGGAGAGTGTTA G |
| 45 | CLONE2-L(m1) Protein Sequence | ETTLTQSPGTLSLSPGERATLSCRASQTVSGSYLAWYQQKPGQPPR LLIYGASSRATGIPDRFSGSGSGTDFTLTISRLEPEDFAVYYCQDY GSSRTFGQGTKVELKRTVAAPSVFIFPPSDEQLKSGTASVVCLLNN FYPREAKVQWKVDNALQSGNSQESVTEQDSKDSTYSLSSTLTLSKA DYEKHKLYACEVTHQGLSSPVTKSFNRGEC |

TABLE 2-continued

| SEQ ID NO | Description | Sequence |
|---|---|---|
| 46 | CLONE2-L(m1) Recombinant DNA Sequence (Vector: pYD5-hFC(Amp)) | *ATGGAGACAGACACACTCCTGCTATGGGTACTGCTGCTCTGGGTTC CAGGTTCCACTggcgccggatca* GAAACGACACTCACGCAGTCTCCAGGCACCCTGTCCTTGTCTCCAG GGGAAAGAGCCACCCTCTCCTGCAGGGCCAGTCAGACTGTTAGCGG CAGCTACTTAGCCTGGTACCAGCAGAAACCTGGCCAGCCTCCCAGG CTCCTCATCTATGGTGCATCCAGCAGGGCCACTGGCATCCCAGACA GGTTCAGTGGCAGTGGGTCCGGGACAGACTTCACTCTCACCATCAG CAGACTGGAGCCTGAAGATTTTGCAGTGTATTACTGTCAGGACTAT GGTAGCTCACGGACGTTCGGCCAAGGGACCAAGGTGGAACTCAAAC GAACTGTGGCTGCACCATCTGTCTTCATCTTCCCGCCATCTGATGA GCAGTTGAAATCTGGAACTGCCTCTGTTGTGTGCCTGCTGAATAAC TTCTATCCCAGAGAGGCCAAAGTACAGTGGAAGGTGGATAACGCCC TCCAATCGGGTAACTCCCAGGAGAGTGTCACAGAGCAGGACAGCAA GGACAGCACCTACAGCCTCAGCAGCACCCTGACGCTGAGCAAAGCA GACTACGAGAAACACAAACTCTACGCCTGCGAAGTCACCCATCAGG GCCTGAGCTCGCCCGTCACAAAGAGCTTCAACAGGGGAGAGTGTTA G |
| 47 | CLONE2-L(m1) Recombinant Protein Sequence (Vector: pYD5-hFC(Amp)) | *METDTLLLWVLLLWVPGSTGAGS* ETTLTQSPGTLSLSPGERATLSCRASQTVSGSYLAWYQQKPGQPPR LLIYGASSRATGIPDRFSGSGSGTDFTLTISRLEPEDFAVYYCQDY GSSRTFGQGTKVELKRTVAAPSVFIFPPSDEQLKSGTASVVCLLNN FYPREAKVQWKVDNALQSGNSQESVTEQDSKDSTYSLSSTLTLSKA DYEKHKLYACEVTHQGLSSPVTKSFNRGEC |
| 48 | CLONE3-H(m1) DNA Sequence | CAGGTGCAGCTACAGCAGTGGGGCGCAGGACTGTTGAAGCCTTCGG AGACCCTGTCCCTCACCTGCGCTGTCTATGGTGGGTCCTTCAGTGG TTACTACTGGAGCTGGATCCGCCAGCCCCCAGGGAAGGGGCTGGAG TGGATTGGGGAAATCAATCATAGTGGAAGCACCAACTACAACCCGT CCCTCAAGAGTCGAGTCACCATATCAGTAGACACGTCCAAGAACCA GTTCTCCCTGAAGCTGAGCTCTGTGACCGCCGCGGACACGGCTGTG TATTACTGTGCGAGACGATATTGTAGTGGTGGTAGCTGCTACTTAG TTGGAACGGGGTCTGAATTGGACTACTGGGGCCAGGGAACCCTGGT CACCGTCTCAAGCGCCTCCACCAAGGGCCCATCGGTCTTCCCCCTG GCACCCTCCTCCAAGAGCACCTCTGGGGGCACAGCGGCCCTGGGCT GCCTGGTCAAGGACTACTTCCCCGAACCGGTGACGGTGTCGTGGAA CTCAGGCGCCCTGACCAGCGGCGTCCACACCTTCCCGGCTGTCCTA CAGTCCTCAGGACTCTACTCCCTCAGCAGCGTAGTGACCGTGCCCT CCAGCAGCTTGGGCACCCAGACCTACATCTGCAACGTGAATCACAA GCCCAGCAACACCAAGGTGGACAAGAAAGTTGAGCCCAAATCTTGT GACAAAACTCACACATGCCCACCGTGCCCAGCACCTGAACTCCTGG GGGGACCGTCAGTCTTCCTCTTCCCCCCAAAACCCAAGGACACCCT CATGATCTCCCGGACCCCTGAGGTCACATGCGTGGTGGTGGACGTG AGCCACGAAGACCCTGAGGTCAAGTTCAACTGGTACGTGGACGGCG TGGAGGTGCATAATGCCAAGACAAAGCCGCGGGAGGAGCAGTACAA CAGCACGTACCGTGTGGTCAGCGTCCTCACCGTCCTGCACCAGGAC TGGCTGAATGGCAAGGAGTACAAGTGCAAGGTCTCCAACAAAGCCC TCCCAGCCCCCATCGAGAAAACCATCTCCAAAGCCAAAGGGCAGCC CCGAGAACCACAGGTGTACACCCTGCCCCCATCCCGGGATGAGCTG ACCAAGAACCAGGTCAGCCTGACCTGCCTGGTCAAAGGCTTCTATC CCAGCGACATCGCCGTGGAGTGGGAGAGCAATGGGCAGCCGGAGAA CACTACAAGACCACGCCTCCCGTGCTGGACTCCGACGGCTCCTTC TTCCTCTACAGCAAGCTCACCGTGGACAAGAGCAGGTGGCAGCAGG GGAACGTCTTCTCATGCTCCGTGATGCATGAGGCTCTGCACAACCA CTACACGCAGAAGAGCCTCTCCCTGTCTCCGGGTAAATGA |
| 49 | CLONE3-H(m1) Protein Sequence | QVQLQQWGAGLLKPSETLSLTCAVYGGSFSGYYWSWIRQPPGKGLE WIGEINHSGSTNYNPSLKSRVTISVDTSKNQFSLKLSSVTAADTAV YYCARRYCSGGSCYLVGTGSELDYWGQGTLVTVSSASTKGPSVFPL APSSKSISGGTAALGCLVKDYFPEPVTVSWNSGALISGVHTFPAVL QSSGLYSLSSVVTVPSSSLGTQTYICNVNHKPSNTKVDKKVEPKSC DKTHTCPPCPAPELLGGPSVFLFPPKPKDTLMISRTPEVTCVVVDV SHEDPEVKFNWYVDGVEVHNAKTKPREEQYNSTYRVVSVLTVLHQD WLNGKEYKCKVSNKALPAPIEKTISKAKGQPREPQVYTLPPSRDEL TKNQVSLTCLVKGFYPSDIAVEWESNGQPENNYKTTPPVLDSDGSF FLYSKLTVDKSRWQQGNVFSCSVMHEALHNHYTQKSLSLSPGK |
| 50 | CLONE3-H(m1) Recombinant DNA Sequence (Vector: pYD5-hFC(Amp)) | *ATGGAGACAGACACACTCCTGCTATGGGTACTGCTGCTCTGGGTTC CAGGTTCCACTggcgccggatca* CAGGTGCAGCTACAGCAGTGGGGCGCAGGACTGTTGAAGCCTTCGG AGACCCTGTCCCTCACCTGCGCTGTCTATGGTGGGTCCTTCAGTGG TTACTACTGGAGCTGGATCCGCCAGCCCCCAGGGAAGGGGCTGGAG TGGATTGGGGAAATCAATCATAGTGGAAGCACCAACTACAACCCGT |

TABLE 2-continued

| SEQ ID NO | Description | Sequence |
|---|---|---|
| | | CCCTCAAGAGTCGAGTCACCATATCAGTAGACACGTCCAAGAACCA GTTCTCCCTGAAGCTGAGCTCTGTGACCGCCGCGGACACGGCTGTG TATTACTGTGCGAGACGATATTGTAGTGGTGGTAGCTGCTACTTAG TTGGAACGGGGTCTGAATTGGACTACTGGGGCCAGGGAACCCTGGT CACCGTCTCAAGCGCCTCCACCAAGGGCCCATCGGTCTTCCCCCTG GCACCCTCCTCCAAGAGCACCTCTGGGGGCACAGCGGCCCTGGGCT GCCTGGTCAAGGACTACTTCCCCGAACCGGTGACGGTGTCGTGGAA CTCAGGCGCCCTGACCAGCGGCGTCCACACCTTCCCGGCTGTCCTA CAGTCCTCAGGACTCTACTCCCTCAGCAGCGTAGTGACCGTGCCCT CCAGCAGCTTGGGCACCCAGACCTACATCTGCAACGTGAATCACAA GCCCAGCAACACCAAGGTGGACAAGAAAGTTGAGCCCAAATCTTGT GACAAAACTCACACATGCCCACCGTGCCCAGCACCTGAACTCCTGG GGGGACCGTCAGTCTTCCTCTTCCCCCCAAAACCCAAGGACACCCT CATGATCTCCCGGACCCCTGAGGTCACATGCGTGGTGGTGGACGTG AGCCACGAAGACCCTGAGGTCAAGTTCAACTGGTACGTGGACGGCG TGGAGGTGCATAATGCCAAGACAAAGCCGCGGGAGGAGCAGTACAA CAGCACGTACCGTGTGGTCAGCGTCCTCACCGTCCTGCACCAGGAC TGGCTGAATGGCAAGGAGTACAAGTGCAAGGTCTCCAACAAAGCCC TCCCAGCCCCCATCGAGAAAACCATCTCCAAAGCCAAAGGGCAGCC CCGAGAACCACAGGTGTACACCCTGCCCCCATCCCGGGATGAGCTG ACCAAGAACCAGGTCAGCCTGACCTGCCTGGTCAAAGGCTTCTATC CCAGCGACATCGCCGTGGAGTGGGAGAGCAATGGGCAGCCGGAGAA CAACTACAAGACCACGCCTCCCGTGCTGGACTCCGACGGCTCCTTC TTCCTCTACAGCAAGCTCACCGTGGACAAGAGCAGGTGGCAGCAGG GGAACGTCTTCTCATGCTCCGTGATGCATGAGGCTCTGCACAACCA CTACACGCAGAAGAGCCTCTCCCTGTCTCCGGGTAAATGA |
| 51 | CLONE3-H(m1) Recombinant Protein Sequence (Vector: pYD5-hFC(Amp)) | *METDTLLLWVLLLWVPGSTGAGS* QVQLQQWGAGLLKPSETLSLTCAVYGGSFSGYYWSWIRQPPGKGLE WIGEINHSGSTNYNPSLKSRVTISVDTSKNQFSLKLSSVTAADTAV YYCARRYCSGGSCYLVGTGSELDYWGQGTLVTVSSASTKGPSVFPL APSSKSTSGGTAALGCLVKDYFPEPVTVSWNSGALTSGVHTFPAVL QSSGLYSLSSVVTVPSSSLGTQTYICNVNHKPSNTKVDKKVEPKSC DKTHTCPPCPAPELLGGPSVFLFPPKPKDTLMISRTPEVTCVVVDV SHEDPEVKFNWYVDGVEVHNAKTKPREEQYNSTYRVVSVLTVLHQD WLNGKEYKCKVSNKALPAPIEKTISKAKGQPREPQVYTLPPSRDEL TKNQVSLTCLVKGFYPSDIAVEWESNGQPENNYKTTPPVLDSDGSF FLYSKLTVDKSRWQQGNVFSCSVMHEALHNHYTQKSLSLSPGK |
| 52 | CLONE3-L(m1) DNA Sequence | GACATCCAGATGACCCAGTCTCCTTCCACCCTGTCTGCATCTGTAG GAGACAGAGTCACCATAACTTGCCGGGCCAGTCAGAGCATTAGTAG CTGGTTGGCCTGGTATCAGCAGAAACCAGGGAAAGCCCCTAAACTC CTAATCTATAAGGCGTCTAGTTTAGAAATTGGGGTCCCATCAAGGT TCAGCGGCAGTGGATATGGGACAGAATTCACTCTCACCATCAGCAG CCTGCAGCCTGATGATTTCGCAACTTATTATTGCCTACAGTATAGT ACTCATTCGACGTTCGGCCAAGGGACCAGGGTGGAAATCAAACGAA CTGTGGCTGCACCATCTGTCTTCATCTTCCCGCCATCTGATGAGCA GTTGAAATCTGGAACTGCCTCTGTTGTGTGCCTGCTGAATAACTTC TATCCCAGAGAGGCCAAAGTACAGTGGAAGGTGGATAACGCCCTCC AATCGGGTAACTCCCAGGAGAGTGTCACAGAGCAGGACAGCAAGGA CAGCACCTACAGCCTCAGCAGCACCCTGACGCTGAGCAAAGCAGAC TACGAGAAACACAAACTCTACGCCTGCGAAGTCACCCATCAGGGCC TGAGCTCGCCCGTCACAAAGAGCTTCAACAGGGGAGAGTGTTAG |
| 53 | CLONE3-L(m1) Protein Sequence | DIQMTQSPSTLSASVGDRVTITCRASQSISSWLAWYQQKPGKAPKL LIYKASSLEIGVPSRFSGSGYGTEFTLTISSLQPDDFATYYCLQYS THSTFGQGTRVEIKRTVAAPSVFIFPPSDEQLKSGTASVVCLLNNF YPREAKVQWKVDNALQSGNSQESVTEQDSKDSTYSLSSTLTLSKAD YEKHKLYACEVTHQGLSSPVTKSFNRGEC |
| 54 | CLONE3-L(m1) Recombinant DNA Sequence (Vector: pYD5-hFC(Amp)) | *ATGGAGACAGACACACTCCTGCTATGGGTACTGCTGCTCTGGGTTC CAGGTTCCACTggcgccggatca* GACATCCAGATGACCCAGTCTCCTTCCACCCTGTCTGCATCTGTAG GAGACAGAGTCACCATAACTTGCCGGGCCAGTCAGAGCATTAGTAG CTGGTTGGCCTGGTATCAGCAGAAACCAGGGAAAGCCCCTAAACTC CTAATCTATAAGGCGTCTAGTTTAGAAATTGGGGTCCCATCAAGGT TCAGCGGCAGTGGATATGGGACAGAATTCACTCTCACCATCAGCAG CCTGCAGCCTGATGATTTCGCAACTTATTATTGCCTACAGTATAGT ACTCATTCGACGTTCGGCCAAGGGACCAGGGTGGAAATCAAACGAA CTGTGGCTGCACCATCTGTCTTCATCTTCCCGCCATCTGATGAGCA GTTGAAATCTGGAACTGCCTCTGTTGTGTGCCTGCTGAATAACTTC TATCCCAGAGAGGCCAAAGTACAGTGGAAGGTGGATAACGCCCTCC AATCGGGTAACTCCCAGGAGAGTGTCACAGAGCAGGACAGCAAGGA CAGCACCTACAGCCTCAGCAGCACCCTGACGCTGAGCAAAGCAGAC |

TABLE 2-continued

Table of Sequences

| SEQ ID NO | Description | Sequence |
|---|---|---|
| | | TACGAGAAACACAAACTCTACGCCTGCGAAGTCACCCATCAGGGCC TGAGCTCGCCCGTCACAAAGAGCTTCAACAGGGGAGAGTGTTAG |
| 55 | CLONE3-L(m1) Recombinant Protein Sequence (Vector: pYD5-hFC(Amp)) | *METDTLLLWVLLLWVPGSTGAGS* DIQMTQSPSTLSASVGDRVTITCRASQSISSWLAWYQQKPGKAPKL LIYKASSLEIGVPSRFSGSGYGTEFTLTISSLQPDDFATYYCLQYS THSTFGQGTRVEIKRTVAAPSVFIFPPSDEQLKSGTASVVCLLNNF YPREAKVQWKVDNALQSGNSQESVTEQDSKDSTYSLSSTLTLSKAD YEKHKLYACEVTHQGLSSPVTKSFNRGEC |

The control mouse mAb (clone TIB92) was from ATCC (Manassas, VA, USA). The recombinant human control Ab (cat. No 403502) was from BioLegend (San Diego, CA). In most of the experiments, anti-serpinB13 mAb (clone B29) or control mouse mAb was injected i.p. into pregnant female mice at 50 μg for four consecutive days, starting at gestational day E10.5 (total dose of 200 μg). In the lineage tracing experiments in adult mice, B29 was injected i.p. for 7 days at 100 μg/injection during the first week after STZ treatment (total dose of 700 μg).

Recombinant proteins and their expression. The purified recombinant serpinB13 expressed in baculovirus was obtained from GenScript (Nanjing, China) and used as a competitive inhibitor in the Luminex assay, as well as directly in in vitro cultures of embryonic pancreas explants. To express individual molecules as antigens in the Luminex assay, cDNAs samples encoding human serpinB1 through serpinB13 (serpinB2 and serpinB4 failed to express and were no included in the analysis), green fluorescent protein (Gfp) and secretagogin (Scgn) were subcloned into a pcDNA3.1 Directional V5-His-TOPO vector (cat. no. K490001; Invitrogen, Carlsbad, CA, USA and expressed for 48 hours in 293 cells using lipofectamine 2000 transfection reagent (cat. no. 11668-019; Invitrogen).

Other reagents. Fibronectin (cat. no. F1141-2 mg; Sigma-Aldrich, St. Louis, MO, USA) was used at 50 μg/mL to precoat tissue culture plates to grow ex vivo embryonic pancreas explants. Chicken ovalbumin (cat. no. LS003056; Worthlington, Lakewood, NJ, USA) was used as a control in culture studies with recombinant serpinB13. Cathepsin L was used to stimulate the generation of Ngn3$^+$ cells in vitro (cat. no. 1515-CY-010; Biotechne, Minneapolis, MN). The Quant-iT PicoGreen Assay Kit (cat. no. P11496, Thermo Fisher Scientific, Waltham, MA, USA) was used to adjust the amount of released serpinB13 measured by ELISA. DNase I (cat. no. 10104159001; Roche, Basel, Switzerland) and collagenase P (cat. no. 11249002001; Roche) were used to isolate pancreatic islets. The Foxp3/Transcription Factor Staining Buffer Set (cat. no. 00-5523-00; Thermo Fisher Scientific), eBiosciencemFlow Cytometry Staining Buffer (cat no. 00-4222-26; Invitrogen), and IC Fixation Buffer (00-8222-49; Invitrogen) were used to perform staining for FACS analysis. 7-Amino-Actinomycin D (7-AAD) was used to exclude nonviable cells in FACS analysis (cat. no. 51-68981E; BD Biosciences, San Jose, CA). DAPI (4',6-Diamidino-2-Phenylindole, Dihydrochloride, cat. no. D1306, Thermofisher, 1 μg/mL in mounting media) was used to stain nuclei for immunofluorescence microscopy. Tamoxifen (cat. no. T5648-5G; Sigma-Aldrich) was used to induce Cre recombinase expression in Ngn3Cre mice. Streptozotocin (cat. no. S0130-500 mg; Sigma-Aldrich) was used to induce diabetes in C57BL/6J male mice. RIPA buffer (cat. no. 89900; Thermo Fisher Scientific) was used to obtain cell lysates for Western blotting. The BCA protein assay kit (cat. no. 23225; Thermo Fisher Scientific) was used to measure protein concentration in cell lysates. The Mouse Creatinine Assay Kit (cat. no. 80350; CrystalChem, Elk Grove Village, IL, USA) was used to measure creatinine levels in the sera of diabetic mice. E64 protease inhibitor was from Millipore (cat. no. 324890; Billerica, MA, USA). Streptavidin R-PE (cat. no. SA10044, Invitrogen, 1:200) was used to develop the Luminex assay.

Isolation and culture of embryonic pancreas explants. The isolation and culture of embryonic pancreas explants was performed as described elsewhere, with minor modifications.

Preparation of cell suspensions from embryonic pancreas explants. The embryonic pancreases were dissected from the embryos and subjected to treatment with 0.25% Trypsin-EDTA (cat. no. 25200-056; Life Technologies, Carlsbad, CA, USA) followed by gentle pipetting to obtain a single cell suspension. The cells were then fixed and permeabilized, using the Foxp3/Transcription Factor Staining Buffer Set, to permit intracellular staining. Alternatively, to preserve extracellular cell-surface molecules, the embryonic pancreas explants were treated with TrypLE (cat. no. 12605-10; Life Technologies) followed by gentle pipetting. The embryonic pancreatic cells were then fixed for 10 minutes in a mix of equal proportions of 2×IC Fixation Buffer and eBioscience Flow Cytometry Staining Buffer, and finally stained with antibodies for extracellular markers.

Preparation of the islets and single islet-cell suspensions. The adult pancreases were subjected to digestion with collagenase P and passed through the 100-μm strainers to separate the islets from debris. The blindly digested pancreatic samples were manually counted for the number of pancreatic islets under a dissecting microscope with a warm halogen light from below. The islets were defined as any visible, distinct cluster of cells with smooth edges and light- to dark-brown glowing color and diameter greater than 100 μm. The hand-picked islets were then dispersed with Cell-Stripper (cat. no. 25-056-CI; Corning, Corning, NY). The cells were fixed and permeabilized, using the Foxp3/Transcription Factor Staining Buffer Set to permit intracellular staining.

Staining for flow cytometry. BD LSRFortessa X-20, LSR-II and FACSCanto-II were used for FACS analysis. Positive populations of cells were gated and counted using FlowJo ver.10 software. For the islet cells isolated from adult mice, intracellular staining to detect glucagon and insulin was used to count single-positive as well as double-negative cells. In the cells isolated from embryonic pancreas explants, intracellular staining was performed to detect Ngn3, CK19, and active Notch, and extracellular staining was used to detect the extracellular Notch domain, EpCAM, CD31 and CD45.

Processing of pancreatic tissue for immunofluorescence microscopy. The pancreatic tissues were isolated and fixed either overnight (adult pancreases), or for one hour (embryonic pancreas explants), in 2% PFA (pH 7.4), followed by a two-step saturation process: first in a 30% sucrose solution in PBS and then in optimal cutting temperature (OCT) compound. After complete saturation, the tissues were imbedded in OCT using Cryomold and then snap frozen in an ethanol/dry ice bath. The OCT blocks were serially cut through the entire organ to obtain representative sections every 600 μm (6 to 8 sections per adult pancreas), 50 μm (12 to 14 sections per E16.5 embryonic pancreas), 35 μm (10 to 12 sections per E14.5 embryonic pancreas), or 15 μm (10 to 12 sections per E12.5 embryonic pancreas cultured for 1 to 3 days). For the embryonic linage tracing experiments, three largest sections were taken for the analysis. For all other experiments involving immunofluorescence microscopy, all obtained sections were analyzed.

Staining for immunofluorescence microscopy. In adult mice, pancreatic sections were stained with anti-insulin antibody to measure islet mass. In addition, the skin and pancreas sections from adult mice were used to compare staining patterns with mAbs to serpinB13: clone B29 versus clone B34.

Figure 17A:
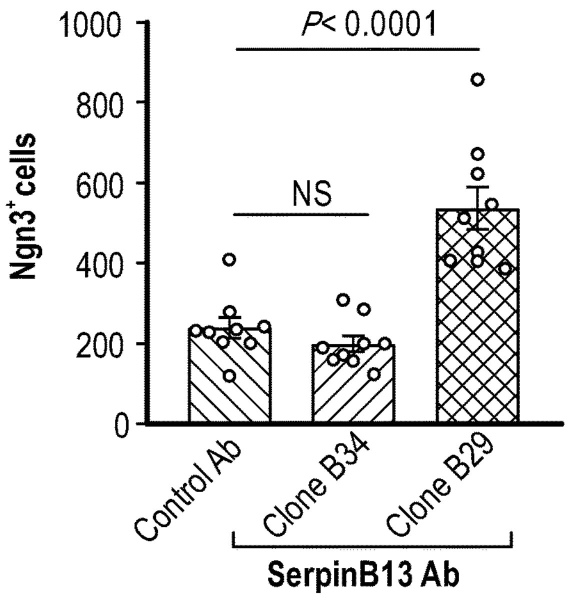
FIGS. 17A-17C. Expression of serpinB13 and the impact of binding to distinct monoclonal antibodies on the number of $Ngn3^+$ pancreatic endocrine progenitor cells at birth. (A) Quantitative analysis by IF microscopy of $Ngn3^+$ cells. Pregnant Balb/c female mice were injected i.p. with anti-serpinB13 mAbs (either clone B29 or B34), or control Ab, exactly as described in FIG. 1F. The number of $Ngn3^+$ cells in the pancreas of the newborn pups (OP) was assessed. n=9 for each group, two independent experiments. (B) The representative microscopic IF images of data shown in (A). (C) Microscopic images of IF staining of the skin and the pancreas isolated from adult mice with antiserpinB13 mAbs or control Ab, as indicated. Data are presented as the mean±SEM. Ordinary one-way ANOVA with Dunnett test. Scale bars, 50 μm (b), 20 am (c). NS, not significant. αB13, anti-serpinB13 mouse mAb.
Figure 17B:
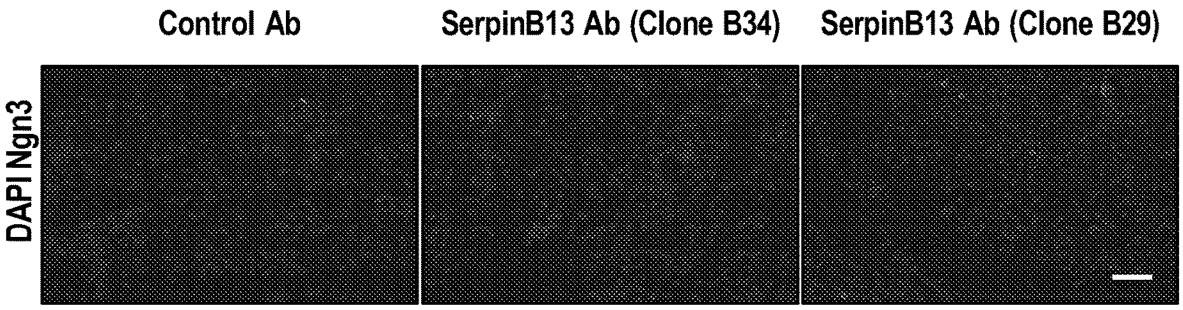
Figure 17C:
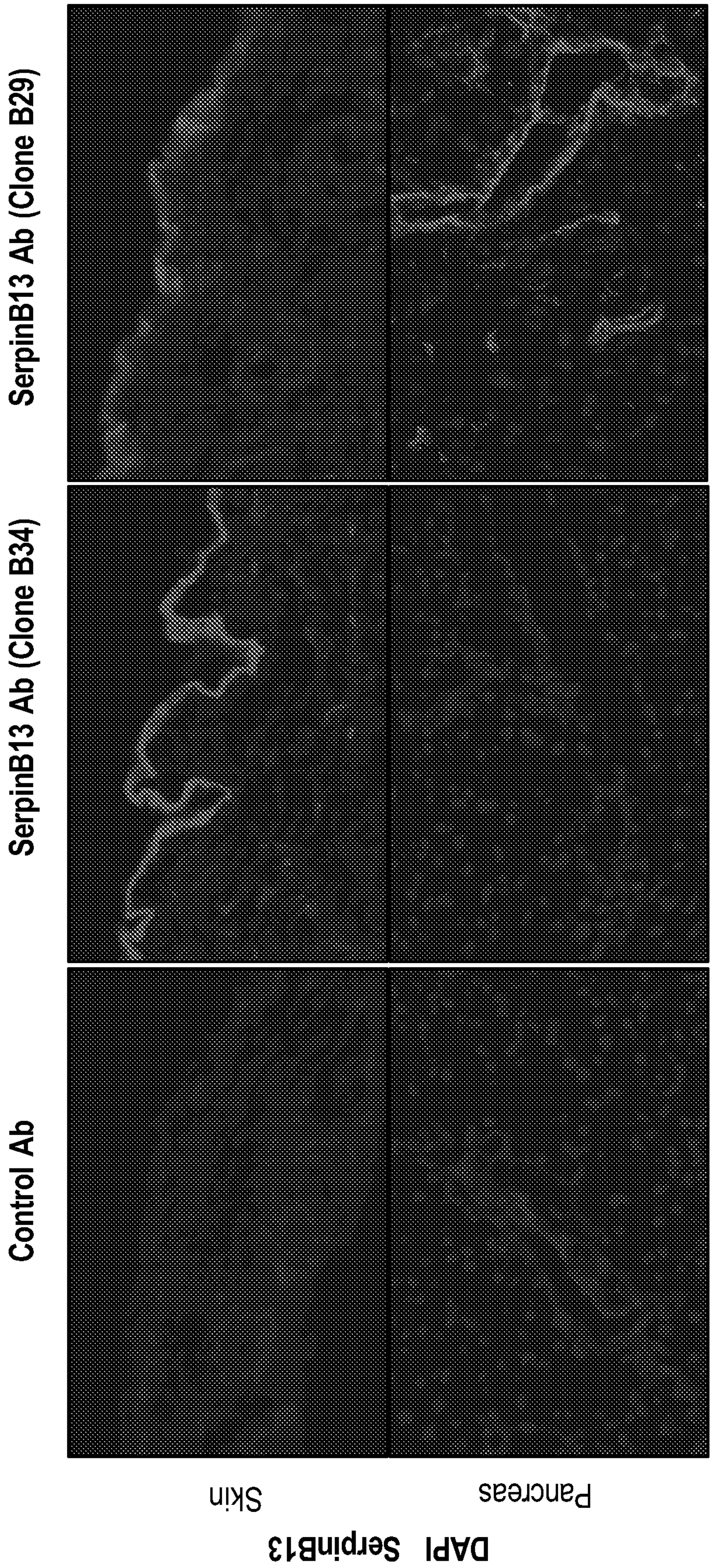

The sections from the pancreases of embryos at age E14.5 and E16.5, and newborn pups (OP), were stained with anti-Ngn3 antibody to determine the total number of endocrine progenitors cells for all sections per explant combined (FIG. 9G, FIG. 17A). Alternatively, the sections representing the pancreases of embryos at age E12.5 (which are considerably smaller) were stained with both anti-Ngn3 and anti-CK19 antibodies to determine the fraction of CK19-positive area that was occupied by Ngn3– positive staining (FIGS. 9D, 10A, 10C, 12D, 12G, 12J and FIGS. 15A, 20B). The following formula was used to adjust for any differences in the pancreas size: ($Ngn3^+$ cell number/$\mu m^2$ of $CK19^+$ cells)$\times 10^5$.

The sections from the pancreases of embryos at age E11.5 and E16.5 were stained with anti-serpinB13 and anti-CK19 antibodies to determine the level of epithelial expression of serpinB13 during development. In lineage tracing studies determining the number of double positive cells, the pancreatic sections from adult mice and embryos were stained with anti-insulin antibody and anti-GFp antibody, which was used to enhance YFP signal. After staining, images were generated using the Olympus VS120-Fluorescence Virtual Slide Microscope Scanner (Olympus, Tokyo, Japan) and Leica DM5500 B fluorescent microscope.

Image analysis. Embryonic images were processed with a plugin-Trainable Weka Segmentation v3.2.28 (Hamilton, New Zealand) for ImageJ v.1.52jv software. To classify and quantify the images in unbiased fashion, we defined the following four classes for the analysis: $Ngn3^+$ cells, the clusters of cytokeratin $19^+$ cells, the negatively stained areas, and background (e.g., the area outside of tissue sample). Alternatively, the Visiopharm version 6.0 software (Visiopharm, Hoerholm, Denmark) with Author module was used to create applications to outline $Ngn3^+$ cells or double positive cells expressing YFP and insulin using preprocessing and postprocessing steps, when necessary. In addition, the Engine module of the Visiophram module was used to execute created applications and unbiasedly analyze the images. For the unbiased quantitative analysis of β-cells and islets in the whole pancreatic sections, Visiopharm Author module was trained to recognize insulin-positive β-cell clusters with diameter greater than 50 μm as well as negatively stained section area. In all studies involving microscopy the treatment assignments were blinded to investigators who performed data analysis.

Calculation of the islet mass. In embryos, the β-cell mass was expressed as the percentage of the area of all pancreatic sections combined, that positively stained with anti-insulin antibody. To calculate β-cell mass in adult mice, the percentage insulin-positive area was multiplied by the pancreas weight expressed in milligrams.

Estimating the number of islets and islet cells. The islets were manually counted under a dissecting microscope. To estimate the number of α and β cells, the islet cells were dispersed, intracellularly stained with antibodies to insulin and glucagon, respectively, and their counts measured by FACS.

Diabetes induction and monitoring. C57BL/6 male mice, which are susceptible to STZ-induced diabetes, were subjected to a 6-hour period of bedding removal and fasting with unlimited access to drinking water. At the end of fasting, STZ was dissolved in a freshly prepared buffer (50 mM Sodium Citrate, pH 4.5) and immediately injected i.p. at 150 mg/kg. The glucose levels in tail blood were measured at random every 7 days for 4 weeks. Alternatively, to perform the glucose tolerance test, STZ-treated C57BL/6J male mice were first fasted for 6 hours with unlimited access to drinking water, and then injected i.p. with a 10% D-(+)-glucose solution (10 μL/g body weight). A glucometer (One-Touch Ultra) was used to monitor glucose levels using tail blood collected before glucose injection, and after injection at 30-min intervals for 2 hours. For glucometer glucose readings "above 600 mg/dL", the data were extrapolated to the value of 700 mg/dL for algebraic statistical purposes only.

Linage tracing. In the developmental studies, the $Rosa26^{EYFP}$ females were initially set up for overnight breeding with $NgnCre^{ERT}$ males and the following morning examined for the presence of a vaginal plug to indicate embryonic day E0.5. On embryonic day E10.5, E11.5, E12.5 and 13.5, anti-serpinB13 mAb (or control Ab) was injected i.p. at a dose of 50 μg per animal per day (total dose of 200 μg). Two days after the last antibody treatment (E15.5), tamoxifen (20 mg/mL) was injected in a single dose of 3 mg per animal to label the cells. Finally, at 24 hours after tamoxifen injection, the animals were sacrificed, and embryonic pancreas explants were fixed, frozen in OCT blocks, and subjected to IF staining for examination of double-positive ($YFP^+insulin^+$) cells. In the diabetes studies, 8-week old $Rosa26^{EYFP}NgnCre^{ERT}$ males were injected with STZ and treated as described in the legend to FIG. 18A.

Western blotting. Pancreatic tissues were processed from E16.5 embryos as single samples and directly used for lysis. Embryonic pancreas explants from E12.5 embryos were cultured in vitro with anti-serpinB13 mAb (or control Ab) for 24 or 48 hours, then, three explant cultures were combined and lysed. The samples were washed two times in ice-cold PBS and lysed with gentle pipetting for 10 minutes with additional tap-vortexing for 15 minutes in RIPA buffer containing Halt protease inhibitors (cat. no. 1862209, Thermo Fisher Scientific). Equal amounts of protein in each sample were run under reducing conditions on Bis-Tris BOLT gradient gel (4-12%) or NUPAGE Tris-acetate gradient gels (4-12%) (both from Thermo Fisher Scientific), and transferred onto 45 μm nitrocellulose or activated PVDF membranes. The membranes were blocked with 5% skim milk and stained with primary and secondary antibodies, as indicated. The Western blots were developed with SuperSignal West Pico Chemiluminescent Substrate or West Femto Maximum Sensitivity Substrate (cat. nos. 34096 and 34096, respectively; both from Thermo Scientific), and scanned using the ChemiDoc™ MP Imaging System (Bio-Rad, Hercules, VA, USA).

Examination of extracellular serpinB13 by ELISA. The pools of three embryonic pancreas explants or single embryonic heart explants isolated from the wild-type Balb/cJ embryos at E12.5, were cultured in a volume of 110 μL of BME media in a 96-well plate precoated with fibronectin, for 48 hours. After incubation, the culture media was collected and serpinB13 concentration measured using a mouse ELISA assay (cat no. MBS912659; MyBioSource, San Diego, CA, USA). The tissues were harvested to normalize the ELISA results to dsDNA content using the PicoGreen dsDNA Assay Kit (cat. no. P11496; Thermo Fisher Scientific).

Quantitative real-time PCR. Total RNA from embryonic pancreases was extracted using the RNeasy UCP Micro kit (cat. no. 73934; Qiagen, Hilden, Germany) to measure expression of the Notch1 gene. One hundred to 200 μg of the total RNA per group was reverse transcribed to cDNA using the iScript cDNA Synthesis Kit (cat. no. 1708891; Bio-Rad). Quantitative PCR assays were performed on an Applied Biosystems QuantStudio 3 real-time PCR system using cDNA and the Kapa Sybr Fast reagent (cat. no. 0795959100; Roche). Actin-R was used as a reference gene. The primer sequence for Notch1 was as follows: forward—5'CTACAGGGGACACCACCCAC3' and reverse—5' TACAGTACTGACCCGTCCACTC3'.

The primer sequence for Actin-0 was as follows:

```
forward -
5'CTCTGGCTCCTAGCACCATGAAGA3'
and

reverse -
5'GTAAAACGCAGCTCAGTAACAGTCCG3'
```

Examination of cathepsin L protease activity. Cathepsin L Inhibitor Screening Kit from BioVision (cat. no. K161-100; Milpitas, CA, USA) was used according to the manufacturer's recommendations with modifications. To measure impact of binding of antibodies on the inhibitor activity of serpinB13, the two reagents were mixed (e.g., 1 μL of antibody at 1 mg/mL was added to 1 μL of serpinB13 at 100 μg/mL), incubated for one hour at room temperature, and then added to PBS containing BSA at 1 mg/mL and CatL for 15 minutes. The substrate was added as the final step to perform the assay, which was run for 30 min. at 37° C. in kinetic mode using SynergyMx fluorescence microplate reader (BioTek Instruments, Winooski, VT, USA).

Human subjects. SerpinB13 AA were measured in 278 first-degree relatives of T1D probands, who were staged for risk for T1D (high, intermediate, modest, and low risk) during enrollment in the Diabetes Prevention Trial for Type 1 Diabetes (DPT-1). The criteria defining these risk categories have been described in the DPT-1 protocol. Briefly, the high-risk subjects (n=70, male to female ratio 1.08, mean age 8.6±3.4 years) were defined as having islet cell cytoplasm autoantibodies (ICA), and abnormal first phase insulin response and/or impaired glucose tolerance. The intermediate-risk subjects (n=70, male to female ratio 1.08, mean age 8.4±3.6 years) were defined as having more than one islet autoantibody but no metabolic abnormalities. The modest-risk subjects (n=69, male to female ratio 1.22, mean age 8.7±3.4 years) were defined as being positive for ICA but negative for autoantibodies to native insulin. The low-risk individuals (n=69, male to female ratio 1.09, mean age 8.698±3.4 years) were defined as ICA-negative. Treated subjects from intermediate- and high-risk groups that were enrolled in the DPT-1, were not included in our study. There is no association between serpinB13 AA and protective HLA II haplotype, e.g., HLA-DQB1*0602 or secretion of islet AAs. The Institutional Review Board at the University of Rochester and the University of Minnesota approved all studies with human samples.

Luminex assay. Luminex-based technology was used to measure serpinB13 AA in human samples. Initially, the Luminex beads were precoated with serpinB13, Gfp and Scgn, using precleared lysates of 293 cells that had been transfected with individual cDNAs. Biotinylated mouse anti-human κ and λ chain mAbs (BD Biosciences) (dilution 1:300) and streptavidin (Invitrogen) (dilution 1:200) were used as secondary reagents to measure human serum binding activity to individual antigens. The data were expressed as fluorescence intensity (F.I.) due to serum binding activity in the presence of beads precoated with serpinB13 and after subtracting the average F.I. due to serum binding activity in the presence of beads precoated with control proteins, Gfp and Scgn (e.g. $F.I.^{B13}-[F.I.^{GFP}+F.I.^{Scgn}]/2$). The samples were evaluated based on the level of F.I. and the degree of inhibition of binding to serpin-B13 coated beads with soluble serpinB13 (2.5 μg/mL), compared with the bovine serum albumin (BSA). Specifically, a result was considered positive if binding activity to Luminex bead-bound serpinB13 was 500 to 900 FI units, and the degree of inhibition of this binding with soluble serpinB13 was >25%, or in which binding activity to Luminex bead-bound serpinB13 was >900 FI units, regardless of the degree of inhibition of this binding with soluble serpinB13. All samples were run blind on three independent occasions. Subjects with serum samples that produced a positive results three times were considered positive. Subjects with serum samples that produced a negative result on at least one occasion were considered negative.

To determine whether anti-serpin activity is specific, binding of three human recombinant antibodies to serpinB13 was examined for potential cross-reactivity with other clade B serpins. Binding to the beads conjugated with Gfp and Scgn was used to subtract the background and the assay was developed using the same reagents as those described above for measuring serpinB13 AA in serum samples.

Culturing Human Sera with Mouse Embryonic Pancreatic Explants and Immunodepletion Studies.

Serum samples were dialyzed with the Tube-O-DIALYZER Micro, 50 kDa MWCO. (cat. no. 786-614; G-Biosciences, St. Louis, MO, USA) overnight at 4° C., according to the manufacturer's recommendations. In experiments without immunodepletion, the aliquots of 40 L of dialyzed sera, either positive or negative for serpinB13 AA, were mixed with 70 μL of BME culture media (cat. no. B1522, Sigma) containing 10% FBS, 1% Penicillin-Streptomycin-Glutamine (cat. no. 10378-016, Life Technologies), 50 μg/mL Gentamycin (cat. no. 15750-060, Gibco) and directly added for 48 hours to the in vitro cultured E12.5 pancreatic explants (FIGS. 12D and 12E). Alternatively, the aliquots of 80 μL of dialyzed sera negative for endogenous serpinB13 AA were divided in two parts, reconstituted with 10 μg/mL of either recombinant human IgG1 isotype control antibody or recombinant human anti-serpinB13 antibody, and added to the in vitro cultured E12.5 pancreatic explants as described above (FIGS. 12G and 12H). In immunodepletion experiments (FIG. 12I-12K), the samples were divided in two parts and incubated in 96 well EIA/RIA assay microplates plates (cat. no. CLS3369, Corning), precoated with anti-serpinB13 mAb (clone B29, 10 μg/mL) and either serpinB13 (5 μg/mL), or 2% BSA (sham depletion). After two hours of incubation on a shaker at 4° C., the samples were transferred to the new, same-way treated wells, and incubated for the additional two hours, following which they were premixed with 70 μL of BME culture media and added for 48 hours to the embryonic pancreas explants cultured in vitro, exactly as described above.

Statistics. The data were analyzed using the Prism 8.0 software. Statistical analyses were performed using unpaired two-sided Student's t test, one-way and two-way ANOVA, and the Mantel-Cox test. A P value<0.05 was used to indicate significance. The data are presented as the mean±SEM.

Antibodies Used in Nonfunctional Studies

Western blotting: Anti-Notch1 (Ala19-Gln526, polyclonal sheep IgG, cat. no. AF5267, Bio-Techne, 1 μg/mL), anti-Notch1 (clone D1E11, rabbit mAb, cat. no. 3608S, Cell Signaling, 1:1000), anti-Ngn3 (clone C-7, mouse mAb, cat. no. sc-374442, Santa Cruz, 0.7 μg/mL), anti-β-tubulin (clone 9F3, rabbit mAb, cat. no. 2128L, Cell Signaling, 1:1000). Secondary antibodies: HRP-conjugated anti-sheep IgG (polyclonal donkey IgG, cat. no. HAF016, Bio-Techne, 1:1000), HRP-conjugated anti-rabbit IgG (polygoclonal goat IgG, cat. no. A27036, Invitrogen, 0.1 μg/mL) and HRP-conjugated anti-mouse IgG (rabbit polygoclonal, cat. no. A27025, Invitrogen, 0.1 g/mL).

Flow Cytometry:

Anti-serpinB13 (clone B29, mouse mAb, 2.3 μg/mL), anti-cytokeratin19 (clone B-1, mouse mAb, cat. no. sc-374192, Santa Cruz, 1 μg/mL), anti-Ngn3 (M-80, rabbit polyclonal, cat. no. Sc25655, Santa Cruz, 1 μg/mL), anti-Notch1-PE (clone 22E5, rat mAb, cat. no. 12-5765-82, eBioscience, 1 μg/mL), anti-activated Notch1 (Val1744, rabbit polyclonal whole antiserum, cat. no. ab8925, Abcam, 1:800), anti-EpCAM-Alexa488 (clone G8.8, rat IgG, cat. no. 118210, BioLegend, 0.625 μg/mL), anti-insulin-Alexa647 (clone T56-706, mouse mAb, cat. no. 565689, BD Biosciences, 1 μg/mL), anti-glucagon-PE (clone U16-850, mouse mAb cat. no. 565860, BD Biosciences, 1:400).

Secondary antibodies: Alexa Fluor 488 goat anti-mouse IgG (H+L) (cat. no. A11001, Invitrogen, 2 μg/mL) and Alexa Fluor 568 goat anti-rabbit IgG (H+L) (cat. no. A11036, Invitrogen, 2 μg/mL). Isotype controls: TIB92 (10-3.6.2, mouse mAb, ATCC, 2.3 μg/mL), rabbit polyclonal IgG (cat. no. 02-6102, Invitrogen), PE rat IgG2a kappa (eBR2a) (cat. no. 12-4321-80, eBiosciense), Alexa Fluor 488 Rat IgG2a, kappa (cat. no. 400525, Biolegend) were diluted to the same concentrations.

IF Microscopy: Anti-serpinB13 (clone B29, mouse mAb, 10 μg/mL), anti-serpinB13 (clone B34, mouse mAb, 10 μg/mL), TIB92 (10-3.6.2, mouse Isotype control, ATCC, 10 μg/mL), anti-cytokeratin 19 (clone B-1, mouse mAb, cat. no. Sc-374192, Santa Cruz, 1 μg/mL), anti-cytokeratin 17/19 (clone D4G2, rabbit mAb, cat. no. 12434S, Cell Signaling, 1:50), anti-cytokeratin 19-Alexa488 (clone EP1580Y, rabbit mAb, cat. no. ab192643, Abcam, 1:100), anti-Ngn3 (M-80, rabbit polyclonal antibody, cat. no. sc-25655, Santa Cruz, 2 μg/mL), anti-insulin (polyclonal guinea pig antibody, cat. no. A0564, DAKO, 2 μg/mL), anti-GFP (rabbit polyclonal antibody, cat. no. A21311, Life Technologies, 2 μg/mL).

Secondary antibodies: Alexa Fluor 488 goat anti-mouse IgG (H+L) (cat. no. A11001, Invitrogen, 2 μg/mL), Alexa Fluor 488 goat anti-rabbit IgG (H+L), (cat no. A11034, Invitrogen, 2 g/mL), Alexa Fluor 568 goat anti-mouse IgG (H+L) (cat. no. A11031, Invitrogen, 5 μg/mL), Alexa Fluor 594 goat anti-guinea pig IgG (H+L) (cat. no. A11076, Invitrogen, 1 μg/mL), Alexa Fluor 568 goat anti-rabbit IgG (H+L), (cat. no. A11036, Invitrogen, 5 μg/mL), Alexa Fluor 647 goat anti-mouse IgG (H+L) (cat. no. A21235, Invitrogen, 5 μg/mL), and Alexa Fluor 647 goat anti-guinea pig IgG (H+L), (cat. no. A21450, Invitrogen, 5 μg/mL).

Luminex assay: Anti-V5 epitope tag (rabbit polyclonal, cat. no. 903801, BioLegend), biotin anti-human kappa light immunoglobulin chain (clone JDC-12, mouse mAb, cat. no. 555794, BD Biosciences, 1:300), and biotin anti-human lambda light immunoglobulin chain (clone G20-193, mouse mAb, cat. no. 555790, BD Biosciences, 1:300).

Example 7

Recombinant fully human antibody sequences were developed and are provided below. The CDRs are indicated in bold. The Sequence Identifiers for the CDRs are provided in Table 3 below.

Clone1-H(m1)
DNA: 1380 nt
CAGGTGCAGCTGCAGGAGTCCGGGGGAGGCGTGGTCCAGCCTGGGAGGTCCCTGAGACTCTCCT

GTGCAGCCTCTGGATTCACCTTCAGTAGCTATGGCATGCACTGGGTCCGCCAGGCTCCAGGCAA

GGGGCTGGAGTGGGTGGCAGTTATATCATATGATGGAAGTAATAAATACTATGCAGACTCCGTG

AAGGGCCGATTCACCATCTCCAGAGACAATTCCAAGAACACGCTGTATCTGCAAATGAACAGCC

TGAGAGCCGAGGACACGGCTGTGTATTACTGTGCGAGAGATCTCGGCGCCGTTATAGCAGTGGC

TGGTACTTCCACCCCGTACAACTGGTTCGACCCCTGGGGCCAGGGAACCCTGGTCACCGTCTCA

AGCGCCTCCACCAAGGGCCCATCGGTCTTCCCCCTGGCACCCTCCTCCAAGAGCACCTCTGGGG

GCACAGCGGCCCTGGGCTGCCTGGTCAAGGACTACTTCCCCGAACCGGTGACGGTGTCGTGGAA

CTCAGGCGCCCTGACCAGCGGCGTCCACACCTTCCCGGCTGTCCTACAGTCCTCAGGACTCTAC

TCCCTCAGCAGCGTAGTGACCGTGCCCTCCAGCAGCTTGGGCACCCAGACCTACATCTGCAACG

TGAATCACAAGCCCAGCAACACCAAGGTGGACAAGAAAGTTGAGCCCAAATCTTGTGACAAAAC

-continued

TCACACATGCCCACCGTGCCCAGCACCTGAACTCCTGGGGGGACCGTCAGTCTTCCTCTTCCCC

CCAAAACCCAAGGACACCCTCATGATCTCCCGGACCCCTGAGGTCACATGCGTGGTGGTGGACG

TGAGCCACGAAGACCCTGAGGTCAAGTTCAACTGGTACGTGGACGGCGTGGAGGTGCATAATGC

CAAGACAAAGCCGCGGGAGGAGCAGTACAACAGCACGTACCGTGTGGTCAGCGTCCTCACCGTC

CTGCACCAGGACTGGCTGAATGGCAAGGAGTACAAGTGCAAGGTCTCCAACAAAGCCCTCCCAG

CCCCCATCGAGAAAACCATCTCCAAAGCCAAAGGGCAGCCCCGAGAACCACAGGTGTACACCCT

GCCCCCATCCCGGGATGAGCTGACCAAGAACCAGGTCAGCCTGACCTGCCTGGTCAAAGGCTTC

TATCCCAGCGACATCGCCGTGGAGTGGGAGAGCAATGGGCAGCCGGAGAACAACTACAAGACCA

CGCCTCCCGTGCTGGACTCCGACGGCTCCTTCTTCCTCTACAGCAAGCTCACCGTGGACAAGAG

CAGGTGGCAGCAGGGGAACGTCTTCTCATGCTCCGTGATGCATGAGGCTCTGCACAACCACTAC

ACGCAGAAGAGCCTCTCCCTGTCTCCGGGTAAATGA (SEQ ID NO: 30)

Protein: 460aa/50 kD
QVQLQESGGGVVQPGRSLRLSCAASGFTFSSYGMHWVRQAPGKGLEWVAVISYDGSNKYYADSV

KGRFTISRDNSKNTLYLQMNSLRAEDTAVYYCARDLGAVIAVAGTSTPYNWFDPWGQGTLVIVS

SASTKGPSVFPLAPSSKSTSGGTAALGCLVKDYFPEPVTVSWNSGALTSGVHTFPAVLQSSGLY

SLSSVVTVPSSSLGTQTYICNVNHKPSNTKVDKKVEPKSCDKTHTCPPCPAPELLGGPSVFLFP

PKPKDTLMISRTPEVTCVVVDVSHEDPEVKFNWYVDGVEVHNAKTKPREEQYNSTYRVVSVLTV

LHQDWLNGKEYKCKVSNKALPAPIEKTISKAKGQPREPQVYTLPPSRDELTKNQVSLTCLVKGF

YPSDIAVEWESNGQPENNYKTTPPVLDSDGSFFLYSKLTVDKSRWQQGNVFSCSVMHEALHNHY

TQKSLSLSPGK (SEQ ID NO: 31)

Recombinant Sequence (vector: pYD5-hFC(Amp))
DNA: 1449 nt
*ATGGAGACAGACACACTCCTGCTATGGGTACTGCTGCTCTGGGTTCCAGGTTCCACTggcgccg*

*gatca*

CAGGTGCAGCTGCAGGAGTCCGGGGGAGGCGTGGTCCAGCCTGGGAGGTCCCTGAGACTCTCCT

GTGCAGCCTCTGGATTCACCTTCAGTAGCTATGGCATGCACTGGGTCCGCCAGGCTCCAGGCAA

GGGGCTGGAGTGGGTGGCAGTTATATCATATGATGGAAGTAATAAATACTATGCAGACTCCGTG

AAGGGCCGATTCACCATCTCCAGAGACAATTCCAAGAACACGCTGTATCTGCAAATGAACAGCC

TGAGAGCCGAGGACACGGCTGTGTATTACTGTGCGAGAGATCTCGGCGCCGTTATAGCAGTGGC

TGGTACTTCCACCCCGTAGAACTGGTTCGACCCCTGGGGCCAGGGAACCCTGGTCACCGTCTCA

AGCGCCTCCACCAAGGGCCCATCGGTCTTCCCCCTGGCACCCTCCTCCAAGAGCACCTCTGGGG

GCACAGCGGCCCTGGGCTGCCTGGTCAAGGACTACTTCCCCGAACCGGTGACGGTGTCGTGGAA

CTCAGGCGCCCTGACCAGCGGCGTCCACACCTTCCCGGCTGTCCTACAGTCCTCAGGACTCTAC

TCCCTCAGCAGCGTAGTGACCGTGCCCTCCAGCAGCTTGGGCACCCAGACCTACATCTGCAACG

TGAATCACAAGCCCAGCAACACCAAGGTGGACAAGAAAGTTGAGCCCAAATCTTGTGACAAAAC

TCACACATGCCCACCGTGCCCAGCACCTGAACTCCTGGGGGGACCGTCAGTCTTCCTCTTCCCC

CCAAAACCCAAGGACACCCTCATGATCTCCCGGACCCCTGAGGTCACATGCGTGGTGGTGGACG

TGAGCCACGAAGACCCTGAGGTCAAGTTCAACTGGTACGTGGACGGCGTGGAGGTGCATAATGC

CAAGACAAAGCCGCGGGAGGAGCAGTACAACAGCACGTACCGTGTGGTCAGCGTCCTCACCGTC

CTGCACCAGGACTGGCTGAATGGCAAGGAGTACAAGTGCAAGGTCTCCAACAAAGCCCTCCCAG

CCCCCATCGAGAAAACCATCTCCAAAGCCAAAGGGCAGCCCCGAGAACCACAGGTGTACACCCT

GCCCCCATCCCGGGATGAGCTGACCAAGAACCAGGTCAGCCTGACCTGCCTGGTCAAAGGCTTC

-continued

TATCCCAGCGACATCGCCGTGGAGTGGGAGAGCAATGGGCAGCCGGAGAACAACTACAAGACCA

CGCCTCCCGTGCTGGACTCCGACGGCTCCTTCTTCCTCTACAGCAAGCTCACCGTGGACAAGAG

CAGGTGGCAGCAGGGGAACGTCTTCTCATGCTCCGTGATGCATGAGGCTCTGCACAACCACTAC

ACGCAGAAGAGCCTCTCCCTGTCTCCGGGTAAATGA (vector (italicized) = SEQ ID NO: 32) (full-length = SEQ ID NO: 33)

Protein: 483aa/52.6 kD
*METDTLLLWVLLLWVPGSTGAGS*

QVQLQESGGGVVQPGRSLRLSCAASGFTFSSYGMHWVRQAPGKGLEWVAVISYDGSNKYYADSV

KGRFTISRDNSKNTLYLQMNSLRAEDTAVYYCARDLGAVIAVAGTSTPYNWFDPWGQGTLVTVS

SASTKGPSVFPLAPSSKSTSGGTAALGCLVKDYFPEPVTVSWNSGALTSGVHTFPAVLQSSGLY

SLSSVVTVPSSSLGTQTYICNVNHKPSNTKVDKKVEPKSCDKTHTCPPCPAPELLGGPSVFLFP

PKPKDTLMISRTPEVTCVVVDVSHEDPEVKFNWYVDGVEVHNAKTKPREEQYNSTYRVVSVLTV

LHQDWLNGKEYKCKVSNKALPAPIEKTISKAKGQPREPQVYTLPPSRDELTKNQVSLTCLVKGF

YPSDIAVEWESNGQPENNYKTTPPVLDSDGSFFLYSKLTVDKSRWQQGNVFSCSVMHEALHNHY

TQKSLSLSPGK (vector (italicized) = SEQ ID NO: 34), (full-length = SEQ ID NO: 35)

Clone1-L(m1)
DNA: 660 nt
GATGTTGTGATGACTCAGTCTCCACTCTCCCTGCCCGTCACCCCTGGAGAGCCGGCCTCCATCT

CCTGCAGGTCTCGTCAGAGCCTCCTGCATAGCAATGGACACAACTATTTGGGTTGGTACCTGCA

GAAGCCAGGGCAGTCTCCACAGCTCCTGATCTATCTGGCTTCTATTCGGGCCTCCGGGATCCCT

GACAGGTTCAGTGGCAGTGGATCAGGCACAGATTTTACACTGAAAATCAGCAGAGTGGAGGCTG

AGGATGTTGGCGTTTATTACTGCATGCAAGCTCTACAAACACCCTACACTTTTGGCCAGGGGAC

CAAGCTGGAGATCAAGCGAACTGTGGCTGCACCATCTGTCTTCATCTTCCCGCCATCTGATGAG

CAGTTGAAATCTGGAACTGCCTCTGTTGTGTGCCTGCTGAATAACTTCTATCCCAGAGAGGCCA

AAGTACAGTGGAAGGTGGATAACGCCCTCCAATCGGGTAACTCCCAGGAGAGTGTCACAGAGCA

GGACAGCAAGGACAGCACCTACAGCCTCAGCAGCACCCTGACGCTGAGCAAAGCAGACTACGAG

AAACACAAAGTCTACGCCTGCGAAGTCACCCATCAGGGCCTGAGCTCGCCCGTCACAAAGAGCT

TCAACAGGGGAGAGTGTTAG (SEQ ID NO: 36)

Protein: 220aa/24 kD
DVVMTQSPLSLPVTPGEPASISCRSRQSLLHSNGHNYLGWYLQKPGQSPQLLIYLASIRASGIP

DRFSGSGSGTDFTLKISRVEAEDVGVYYCMQALQTPYTFGQGTKLEIKRTVAAPSVFIFPPSDE

QLKSGTASVVCLLNNFYPREAKVQWKVDNALQSGNSQESVTEQDSKDSTYSLSSTLTLSKADYE

KHKVYACEVTHQGLSSPVTKSFNRGEC (SEQ ID NO: 37)

Recombinant Sequence (Vector: pYD5-hFC(Amp))
DNA: 729 nt
*ATGGAGACAGACACACTCCTGCTATGGGTACTGCTGCTCTGGGTTCCAGGTTCCACTggcgccg*

*gatca*

GATGTTGTGATGACTCAGTCTCCACTCTCCCTGCCCGTCACCCCTGGAGAGCCGGCCTCCATCT

CCTGCAGGTCTCGTCAGAGCCTCCTGCATAGCAATGGACACAACTATTTGGGTTGGTACCTGCA

GAAGCCAGGGCAGTCTCCACAGCTCCTGATCTATCTGGCTTCTATTCGGGCCTCCGGGATCCCT

GACAGGTTCAGTGGCAGTGGATCAGGCACAGATTTTACACTGAAAATCAGCAGAGTGGAGGCTG

AGGATGTTGGCGTTTATTACTGCATGCAAGCTCTACAAACACCCTACACTTTTGGCCAGGGGAC

CAAGCTGGAGATCAAGCGAACTGTGGCTGCACCATCTGTCTTCATCTTCCCGCCATCTGATGAG

CAGTTGAAATCTGGAACTGCCTCTGTTGTGTGCCTGCTGAATAACTTCTATCCCAGAGAGGCCA

-continued

AAGTACAGTGGAAGGTGGATAACGCCCTCCAATCGGGTAACTCCCAGGAGAGTGTCACAGAGCA

GGACAGCAAGGACAGCACCTACAGCCTCAGCAGCACCCTGACGCTGAGCAAAGCAGACTACGAG

AAACACAAAGTCTACGCCTGCGAAGTCACCCATCAGGGCCTGAGCTCGCCCGTCACAAAGAGCT

TCAACAGGGGAGAGTGTTAG (vector (italicized) = SEQ ID NO: 32), (full-length = SEQ ID NO: 38)

Protein: 243aa/ 26.5 kD
*METDTLLLWVLLLWVPGSTGAGS*

DVVMTQSPLSLPVTPGEPASISCRSRQSLLHSNGHNYLGWYLQKPGQSPQLLIYLASIRASGIP

DRFSGSGSGTDFTLKISRVEAEDVGVYYCMQALQTPYTFGQGTKLEIKRTVAAPSVFIFPPSDE

QLKSGTASVVCLLNNFYPREAKVQWKVDNALQSGNSQESVTEQDSKDSTYSLSSTLTLSKADYE

KHKVYACEVTHQGLSSPVTKSFNRGEC (vector (italicized) = SEQ ID NO: 34), (full-length = SEQ ID NO: 39)

CLONE2-H(m1)
DNA: 1389 nt
CAGATGCAGCTGGTGCAGTCGGGGGGAGGTGTGGTACGGCCTGGGGGGTCCCTGAGACTCTCCT

GTGCAGCCTCTGGATTCACCTTTGATGATTATGGCATGAGCTGGGTCCGCCAAGCTCCAGGGAA

GGGGCTGGAGTGGGTCTCTGGTATTAATTGGAATGGTGGTAGCACAGGTTATGCAGACTCTGTG

AAGGGCCGATTCACCATCTCCAGAGACAACGCCAAGAACTCCCTGTATCTGCAAATGAACAGTC

TGAGAGCCGAGGACACGGCCTTGTATTACTGTGCGAGAGAAAGCTCGATGACTACAGTAACTAC

GTATCTCCTACGGGAAGTAGGGGTAGGGTTGGACTTTGACTACTGGGGCCAGGGCACCCTGGTC

ACCGTCTCAAGCGCCTCCACCAAGGGCCCATCGGTCTTCCCCCTGGCACCCTCCTCCAAGAGCA

CCTCTGGGGGCACAGCGGCCCTGGGCTGCCTGGTCAAGGACTACTTCCCCGAACCGGTGACGGT

GTCGTGGAACTCAGGCGCCCTGACCAGCGGCGTCCACACCTTCCCGGCTGTCCTACAGTCCTCA

GGACTCTACTCCCTCAGCAGCGTAGTGACCGTGCCCTCCAGCAGCTTGGGCACCCAGACCTACA

TCTGCAACGTGAATCACAAGCCCAGCAACACCAAGGTGGACAAGAAAGTTGAGCCCAAATCTTG

TGACAAAACTCACACATGCCCACCGTGCCCAGCACCTGACTCCTGGGGGGACCGTCAGTCTTC

CTCTTCCCCCCAAAACCCAAGGACACCCTCATGATCTCCCGGACCCCTGAGGTCACATGCGTGG

TGGTGGACGTGAGCCACGAAGACCCTGAGGTCAAGTTCAACTGGTACGTGGACGGCGTGGAGGT

GCATAATGCCAAGACAAAGCCGCGGGAGGAGCAGTACAACAGCACGTACCGTGTGGTCAGCGTC

CTCACCGTCCTGCACCAGGACTGGCTGAATGGCAAGGAGTACAAGTGCAAGGTCTCCAACAAAG

CCCTCCCAGCCCCCATCGAGAAAACCATCTCCAAAGCCAAAGGGCAGCCCCGAGAACCACAGGT

GTACACCCTGCCCCCATCCCGGGATGAGCTGACCAAGAACCAGGTCAGCCTGACCTGCCTGGTC

AAAGGCTTCTATCCCAGCGACATCGCCGTGGAGTGGGAGAGCAATGGGCAGCCGGAGAACAACT

ACAAGACCACGCCTCCCGTGCTGGACTCCGACGGCTCCTTCTTCCTCTACAGCAAGCTCACCGT

GGACAAGAGCAGGTGGCAGCAGGGGAACGTCTTCTCATGCTCCGTGATGCATGAGGCTCTGCAC

AACCACTACACGCAGAAGAGCCTCTCCCTGTCTCCGGGTAAATGA (SEQ ID NO: 40)

Protein: 463aa/50.4 kD
QMQLVQSGGGVVRPGGSLRLSCAASGFTFDDYGMSWVRQAPGKGLEWVSGINWNGGSTGYADSV

KGRFTISRDNAKNSLYLQMNSLRAEDTALYYCARESSMTTVTTYLLREVGVGLDFDYWGQGTLV

TVSSASTKGPSVFPLAPSSKSTSGGTAALGCLVKDYFPEPVTVSWNSGALTSGVHTFPAVLQSS

GLYSLSSVVTVPSSSLGTQTYICNVNHKPSNTKVDKKVEPKSCDKTHTCPPCPAPELLGGPSVF

LFPPKPKDTLMISRTPEVTCVVVDVSHEDPEVKFNWYVDGVEVHNAKTKPREEQYNSTYRVVSV

LTVLHQDWLNGKEYKCKVSNKALPAPIEKTISKAKGQPREPQVYTLPPSRDELTKNQVSLTCLV

-continued

KGFYPSDIAVEWESNGQPENNYKTTPPVLDSDGSFFLYSKLTVDKSRWQQGNVFSCSVMHEALH

NHYTQKSLSLSPGK (SEQ ID NO: 41)

Recombinant Sequence (Vector: pYD5-hFC(Amp))
DNA: 1458 nt
*ATGGAGACAGACACACTCCTGCTATGGGTACTGCTGCTCTGGGTTCCAGGTTCCACTggcgccg*

*gatca*

CAGATGCAGCTGGTGCAGTCGGGGGGAGGTGTGGTACGGCCTGGGGGGTCCCTGAGACTCTCCT

GTGCAGCCTCTGGATTCACCTTTGATGATTATGGCATGAGCTGGGTCCGCCAAGCTCCAGGGAA

GGGGCTGGAGTGGGTCTCTGGTATTAATTGGAATGGTGGTAGCACAGGTTATGCAGACTCTGTG

AAGGGCCGATTCACCATCTCCAGAGACAACGCCAAGAACTCCCTGTATCTGCAAATGAACAGTC

TGAGAGCCGAGGACACGGCCTTGTATTACTGTGCGAGAGAAAGCTCGATGACTAGAGTAACTAC

GTATCTCCTACGGGAAGTAGGGGTAGGGTTGGACTTTGACTACTGGGGCCAGGGCACCCTGGTC

ACCGTCTCAAGCGCCTCCACCAAGGGCCCATCGGTCTTCCCCCTGGCACCCTCCTCCAAGAGCA

CCTCTGGGGGCACAGCGGCCCTGGGCTGCCTGGTCAAGGACTACTTCCCCGAACCGGTGACGGT

GTCGTGGAACTCAGGCGCCCTGACCAGCGGCGTCCACACCTTCCCGGCTGTCCTACAGTCCTCA

GGACTCTACTCCCTCAGCAGCGTAGTGACCGTGCCCTCCAGCAGCTTGGGCACCCAGACCTACA

TCTGCAACGTGAATCACAAGCCCAGCAACACCAAGGTGGACAAGAAAGTTGAGCCCAAATCTTG

TGACAAAACTCACACATGCCCACCGTGCCCAGCACCTGACTCCTGGGGGGACCGTCAGTCTTC

CTCTTCCCCCCAAAACCCAAGGACACCCTCATGATCTCCCGGACCCCTGAGGTCACATGCGTGG

TGGTGGACGTGAGCCACGAAGACCCTGAGGTCAAGTTCAACTGGTACGTGGACGGCGTGGAGGT

GCATAATGCCAAGACAAAGCCGCGGGAGGAGCAGTACAACAGCACGTACCGTGTGGTCAGCGTC

CTCACCGTCCTGCACCAGGACTGGCTGAATGGCAAGGAGTACAAGTGCAAGGTCTCCAACAAAG

CCCTCCCAGCCCCCATCGAGAAAACCATCTCCAAAGCCAAAGGGCAGCCCCGAGAACCACAGGT

GTACACCCTGCCCCCATCCCGGGATGAGCTGACCAAGAACCAGGTCAGCCTGACCTGCCTGGTC

AAAGGCTTCTATCCCAGCGACATCGCCGTGGAGTGGGAGAGCAATGGGCAGCCGGAGAACAACT

ACAAGACCACGCCTCCCGTGCTGGACTCCGACGGCTCCTTCTTCCTCTACAGCAAGCTCACCGT

GGACAAGAGCAGGTGGCAGCAGGGGAACGTCTTCTCATGCTCCGTGATGCATGAGGCTCTGCAC

AACCACTACACGCAGAAGAGCCTCTCCCTGTCTCCGGGTAAATGA (vector
(italicized) = SEQ ID NO: 32), (full-length = SEQ ID NO: 42)

Protein: 486aa/52.9 kD
*METDTLLLWVLLLWVPGSTGAGS*

QMQLVQSGGGVVRPGGSLRLSCAASGFTFDDYGMSWVRQAPGKGLEWVSGINWNGGSTGYADSV

KGRFTISRDNAKNSLYLQMNSLRAEDTALYYCARESSMTTVTTYLLREVGVGLDFDYWGQGTLV

TVSSASTKGPSVFPLAPSSKSTSGGTAALGCLVKDYFPEPVTVSWNSGALTSGVHTFPAVLQSS

GLYSLSSVVTVPSSSLGTQTYICNVNHKPSNTKVDKKVEPKSCDKTHTCPPCPAPELLGGPSVF

LFPPKPKDTLMISRTPEVTCVVVDVSHEDPEVKFNWYVDGVEVHNAKTKPREEQYNSTYRVVSV

LTVLHQDWLNGKEYKCKVSNKALPAPIEKTISKAKGQPREPQVYTLPPSRDELTKNQVSLTCLV

KGFYPSDIAVEWESNGQPENNYKTTPPVLDSDGSFFLYSKLTVDKSRWQQGNVFSCSVMHEALH

NHYTQKSLSLSPGK (vector (italicized) = SEQ ID NO: 34), (full-
length = SEQ ID NO: 43)

CLONE2-L(m1)
DNA: 645 nt
GAAACGACACTCACGCAGTCTCCAGGCACCCTGTCCTTGTCTCCAGGGGAAAGAGCCACCCTCT

CCTGCAGGGCCAGTCAGACTGTTAGCGGCAGCTACTTAGCCTGGTACCAGCAGAAACCTGGCCA

-continued

GCCTCCCAGGCTCCTCATCTATGGTGCATCCAGCAGGGCCACTGGCATCCCAGACAGGTTCAGT

GGCAGTGGGTCCGGGACAGACTTCACTCTCACCATCAGCAGACTGGAGCCTGAAGATTTTGCAG

TGTATTACTGTCAGGACTATGGTAGCTCACGGACGTTCGGCCAAGGGACCAAGGTGGAACTCAA

ACGAACTGTGGCTGCACCATCTGTCTTCATCTTCCCGCCATCTGATGAGCAGTTGAAATCTGGA

ACTGCCTCTGTTGTGTGCCTGCTGAATAACTTCTATCCCAGAGAGGCCAAAGTACAGTGGAAGG

TGGATAACGCCCTCCAATCGGGTAACTCCCAGGAGAGTGTCACAGAGCAGGACAGCAAGGACAG

CACCTACAGCCTCAGCAGCACCCTGACGCTGAGCAAAGCAGACTACGAGAAACACAAACTCTAC

GCCTGCGAAGTCACCCATCAGGGCCTGAGCTCGCCCGTCACAAAGAGCTTCAACAGGGGAGAGT

GTTAG (SEQ ID NO: 44)

Protein: 215aa/23.3 kD

ETTLTQSPGILSLSPGERATLSCRASQTVSGSYLAWYQQKPGQPPRLLIYGASSRATGIPDRFS

GSGSGTDFTLTISRLEPEDFAVYYCQDYGSSRTFGQGTKVELKRTVAAPSVFIFPPSDEQLKSG

TASVVCLLNNFYPREAKVQWKVDNALQSGNSQESVTEQDSKDSTYSLSSTLTLSKADYEKHKLY

ACEVTHQGLSSPVTKSFNRGEC (SEQ ID NO: 45)

Recombinant Sequence (Vector: pYD5-hFC(Amp)
DNA: 714 nt
*ATGGAGACAGACACACTCCTGCTATGGGTACTGCTGCTCTGGGTTCCAGGTTCCACTggcgccg*

*gatca*

GAAACGACACTCACGCAGTCTCCAGGCACCCTGTCCTTGTCTCCAGGGGAAAGAGCCACCCTCT

CCTGCAGGGCCAGTCAGACTGTTAGCGGCAGCTACTTAGCCTGGTACCAGCAGAAACCTGGCCA

GCCTCCCAGGCTCCTCATCTATGGTGCATCCAGCAGGGCCACTGGCATCCCAGACAGGTTCAGT

GGCAGTGGGTCCGGGACAGACTTCACTCTCACCATCAGCAGACTGGAGCCTGAAGATTTTGCAG

TGTATTACTGTCAGGACTATGGTAGCTCACGGACGTTCGGCCAAGGGACCAAGGTGGAACTCAA

ACGAACTGTGGCTGCACCATCTGTCTTCATCTTCCCGCCATCTGATGAGCAGTTGAAATCTGGA

ACTGCCTCTGTTGTGTGCCTGCTGAATAACTTCTATCCCAGAGAGGCCAAAGTACAGTGGAAGG

TGGATAACGCCCTCCAATCGGGTAACTCCCAGGAGAGTGTCACAGAGCAGGACAGCAAGGACAG

CACCTACAGCCTCAGCAGCACCCTGACGCTGAGCAAAGCAGACTACGAGAAACACAAACTCTAC

GCCTGCGAAGTCACCCATCAGGGCCTGAGCTCGCCCGTCACAAAGAGCTTCAACAGGGGAGAGT

GTTAG (vector (italicized) = SEQ ID NO: 32), (full-length = SEQ ID NO: 46)

Protein: 238aa/25.8 kD
*METDTLLLWVLLLWVPGSTGAGS*

ETTLTQSPGILSLSPGERATLSCRASQTVSGSYLAWYQQKPGQPPRLLIYGASSRATGIPDRFS

GSGSGTDFTLTISRLEPEDFAVYYCQDYGSSRTFGQGTKVELKRTVAAPSVFIFPPSDEQLKSG

TASVVCLLNNFYPREAKVQWKVDNALQSGNSQESVTEQDSKDSTYSLSSTLTLSKADYEKHKLY

ACEVTHQGLSSPVTKSFNRGEC (vector (italicized) = SEQ ID NO: 34), (full-length = SEQ ID NO: 47)

CLONE3-H(m1)
DNA: 1374 nt
CAGGTGCAGCTACAGCAGTGGGGCGCAGGACTGTTGAAGCCTTCGGAGACCCTGTCCCTCACCT

GCGCTGTCTATGGTGGGTCCTTCAGTGGTTACTACTGGAGCTGGATCCGCCAGCCCCCAGGGAA

GGGGCTGGAGTGGATTGGGGAAATCAATCATAGTGGAAGCACCAACTACAACCCGTCCCTCAAG

AGTCGAGTCACCATATCAGTAGACACGTCCAAGAACCAGTTCTCCCTGAAGCTGAGCTCTGTGA

CCGCCGCGGACACGGCTGTGTATTACTGTGCGAGACGATATTGTAGTGGTGGTAGCTGCTACTT

-continued

AGTTGGAACGGGGTCTGAATTGGACTACTGGGGCCAGGGAACCCTGGTCACCGTCTCAAGCGCC

TCCACCAAGGGCCCATCGGTCTTCCCCCTGGCACCCTCCTCCAAGAGCACCTCTGGGGGCACAG

CGGCCCTGGGCTGCCTGGTCAAGGACTACTTCCCCGAACCGGTGACGGTGTCGTGGAACTCAGG

CGCCCTGACCAGCGGCGTCCACACCTTCCCGGCTGTCCTACAGTCCTCAGGACTCTACTCCCTC

AGCAGCGTAGTGACCGTGCCCTCCAGCAGCTTGGGCACCCAGACCTACATCTGCAACGTGAATC

ACAAGCCCAGCAACACCAAGGTGGACAAGAAAGTTGAGCCCAAATCTTGTGACAAAACTCACAC

ATGCCCACCGTGCCCAGCACCTGAACTCCTGGGGGGACCGTCAGTCTTCCTCTTCCCCCCAAAA

CCCAAGGACACCCTCATGATCTCCCGGACCCCTGAGGTCACATGCGTGGTGGTGGACGTGAGCC

ACGAAGACCCTGAGGTCAAGTTCAACTGGTACGTGGACGGCGTGGAGGTGCATAATGCCAAGAC

AAAGCCGCGGGAGGAGCAGTACAACAGCACGTACCGTGTGGTCAGCGTCCTCACCGTCCTGCAC

CAGGACTGGCTGAATGGCAAGGAGTACAAGTGCAAGGTCTCCAACAAAGCCCTCCCAGCCCCCA

TCGAGAAAACCATCTCCAAAGCCAAAGGGCAGCCCCGAGAACCACAGGTGTACACCCTGCCCCC

ATCCCGGGATGAGCTGACCAAGAACCAGGTCAGCCTGACCTGCCTGGTCAAAGGCTTCTATCCC

AGCGACATCGCCGTGGAGTGGGAGAGCAATGGGCAGCCGGAGAACAACTACAAGACCACGCCTC

CCGTGCTGGACTCCGACGGCTCCTTCTTCCTCTACAGCAAGCTCACCGTGGACAAGAGCAGGTG

GCAGCAGGGGAACGTCTTCTCATGCTCCGTGATGCATGAGGCTCTGCACAACCACTACACGCAG

AAGAGCCTCTCCCTGTCTCCGGGTAAATGA (SEQ ID NO: 48)

Protein: 458aa/50 kD
QVQLQQWGAGLLKPSETLSLTCAVYGGSFSGYYWSWIRQPPGKGLEWIGEINHSGSTNYNPSLK

SRVTISVDTSKNQFSLKLSSVTAADTAVYYCARRYCSGGSCYLVGTGSELDYWGQGTLVTVSSA

STKGPSVFPLAPSSKSTSGGTAALGCLVKDYFPEPVTVSWNSGALTSGVHTFPAVLQSSGLYSL

SSVVTVPSSSLGTQTYICNVNHKPSNTKVDKKVEPKSCDKTHTCPPCPAPELLGGPSVFLFPPK

PKDTLMISRTPEVTCVVVDVSHEDPEVKFNWYVDGVEVHNAKTKPREEQYNSTYRVVSVLTVLH

QDWLNGKEYKCKVSNKALPAPIEKTISKAKGQPREPQVYTLPPSRDELTKNQVSLTCLVKGFYP

SDIAVEWESNGQPENNYKTTPPVLDSDGSFFLYSKLTVDKSRWQQGNVFSCSVMHEALHNHYTQ

KSLSLSPGK (SEQ ID NO: 49)

Recombinant Sequence (Vector: pYD5-hFC(Amp))
DNA: 1443 nt
*ATGGAGACAGACACACTCCTGCTATGGGTACTGCTGCTCTGGGTTCCAGGTTCCACTggcgccg*

*gatca*

CAGGTGCAGCTACAGCAGTGGGGCGCAGGACTGTTGAAGCCTTCGGAGACCCTGTCCCTCACCT

GCGCTGTCTATGGTGGGTCCTTCAGTGGTTACTACTGGAGCTGGATCCGCCAGCCCCCAGGGAA

GGGGCTGGAGTGGATTGGGGAAATCAATCATAGTGGAAGCACCAACTACAACCCGTCCCTCAAG

AGTCGAGTCACCATATCAGTAGACACGTCCAAGAACCAGTTCTCCCTGAAGCTGAGCTCTGTGA

CCGCCGCGGACACGGCTGTGTATTACTGTGCGAGACGATATTGTAGTGGTGGTAGCTGCTACTT

AGTTGGAACGGGGTCTGAATTGGACTACTGGGGCCAGGGAACCCTGGTCACCGTCTCAAGCGCC

TCCACCAAGGGCCCATCGGTCTTCCCCCTGGCACCCTCCTCCAAGAGCACCTCTGGGGGCACAG

CGGCCCTGGGCTGCCTGGTCAAGGACTACTTCCCCGAACCGGTGACGGTGTCGTGGAACTCAGG

CGCCCTGACCAGCGGCGTCCACACCTTCCCGGCTGTCCTACAGTCCTCAGGACTCTACTCCCTC

AGCAGCGTAGTGACCGTGCCCTCCAGCAGCTTGGGCACCCAGACCTACATCTGCAACGTGAATC

ACAAGCCCAGCAACACCAAGGTGGACAAGAAAGTTGAGCCCAAATCTTGTGACAAAACTCACAC

ATGCCCACCGTGCCCAGCACCTGAACTCCTGGGGGGACCGTCAGTCTTCCTCTTCCCCCCAAAA

-continued

CCCAAGGACACCCTCATGATCTCCCGGACCCCTGAGGTCACATGCGTGGTGGTGGACGTGAGCC

ACGAAGACCCTGAGGTCAAGTTCAACTGGTACGTGGACGGCGTGGAGGTGCATAATGCCAAGAC

AAAGCCGCGGGAGGAGCAGTACAACAGCACGTACCGTGTGGTCAGCGTCCTCACCGTCCTGCAC

CAGGACTGGCTGAATGGCAAGGAGTACAAGTGCAAGGTCTCCAACAAAGCCCTCCCAGCCCCCA

TCGAGAAAACCATCTCCAAAGCCAAAGGGCAGCCCCGAGAACCACAGGTGTACACCCTGCCCCC

ATCCCGGGATGAGCTGACCAAGAACCAGGTCAGCCTGACCTGCCTGGTCAAAGGCTTCTATCCC

AGCGACATCGCCGTGGAGTGGGAGAGCAATGGGCAGCCGGAGAACAACTACAAGACCACGCCTC

CCGTGCTGGACTCCGACGGCTCCTTCTTCCTCTACAGCAAGCTCACCGTGGACAAGAGCAGGTG

GCAGCAGGGGAACGTCTTCTCATGCTCCGTGATGCATGAGGCTCTGCACAACCACTACACGCAG

AAGAGCCTCTCCCTGTCTCCGGGTAAATGA (vector (italicized) = SEQ ID NO: 32), (full-length = SEQ ID NO: 50)

Protein: 481aa/ 52.4 kD
*METDTLLLWVLLLWVPGSTGAGS*

QVQLQQWGAGLLKPSETLSLTCAVYGGSFSGYYWSWIRQPPGKGLEWIGEINHSGSTNYNPSLK

SRVTISVDTSKNQFSLKLSSVTAADTAVYYCARRYCSGGSCYLVGTGSELDYWGQGTLVTVSSA

STKGPSVFPLAPSSKSTSGGTAALGCLVKDYFPEPVTVSWNSGALTSGVHTFPAVLQSSGLYSL

SSVVTVPSSSLGTQTYICNVNHKPSNTKVDKKVEPKSCDKTHTCPPCPAPELLGGPSVFLFPPK

PKDTLMISRTPEVTCVVVDVSHEDPEVKFNWYVDGVEVHNAKTKPREEQYNSTYRVVSVLTVLH

QDWLNGKEYKCKVSNKALPAPIEKTISKAKGQPREPQVYTLPPSRDELTKNQVSLTCLVKGFYP

SDIAVEWESNGQPENNYKTTPPVLDSDGSFFLYSKLTVDKSRWQQGNVFSCSVMHEALHNHYTQ

KSLSLSPGK (vector (italicized) = SEQ ID NO: 34), (full-length = SEQ ID NO: 51)

CLONE3-L(m1)
DNA: 642 nt
GACATCCAGATGACCCAGTCTCCTTCCACCCTGTCTGCATCTGTAGGAGACAGAGTCACCATAA

CTTGCCGGGCCAGTCAGAGCATTAGTAGCTGGTTGGCCTGGTATCAGCAGAAACCAGGGAAAGC

CCCTAAACTCCTAATCTATAAGGCGTCTAGTTTAGAAATTGGGGTCCCATCAAGGTTCAGCGGC

AGTGGATATGGGACAGAATTCACTCTCACCATCAGCAGCCTGCAGCCTGATGATTTCGCAACTT

ATTATTGCCTACAGTATAGTACTCATTCGACGTTCGGCCAAGGGACCAGGGTGGAAATCAAACG

AACTGTGGCTGCACCATCTGTCTTCATCTTCCCGCCATCTGATGAGCAGTTGAAATCTGGAACT

GCCTCTGTTGTGTGCCTGCTGAATAACTTCTATCCCAGAGAGGCCAAAGTACAGTGGAAGGTGG

ATAACGCCCTCCAATCGGGTAACTCCCAGGAGAGTGTCACAGAGCAGGACAGCAAGGACAGCAC

CTACAGCCTCAGCAGCACCCTGACGCTGAGCAAAGCAGACTACGAGAAACACAAACTCTACGCC

TGCGAAGTCACCCATCAGGGCCTGAGCTCGCCCGTCACAAAGAGCTTCAACAGGGGAGAGTGTT

AG (SEQ ID NO: 52)

Protein: 214aa/23.4 kD
DIQMTQSPSTLSASVGDRVTITCRASQSISSWLAWYQQKPGKAPKLLIYKASSLEIGVPSRFSG

SGYGTEFTLTISSLQPDDFATYYCLQYSTHSTFGQGTRVEIKRTVAAPSVFIFPPSDEQLKSGT

ASVVCLLNNFYPREAKVQWKVDNALQSGNSQESVTEQDSKDSTYSLSSTLTLSKADYEKHKLYA

CEVTHQGLSSPVTKSFNRGEC (SEQ ID NO: 53)

-continued

Recombinant Sequence (Vector: pYD5-hFC(Amp))
DNA: 711 nt
*ATGGAGACAGACACACTCCTGCTATGGGTACTGCTGCTCTGGGTTCCAGGTTCCACTggcgccg*

*gatca*

GACATCCAGATGACCCAGTCTCCTTCCACCCTGTCTGCATCTGTAGGAGACAGAGTCACCATAA

CTTGCCGGGCCAGTCAGAGCATTAGTAGCTGGTTGGCCTGGTATCAGCAGAAACCAGGGAAAGC

CCCTAAACTCCTAATCTATAAGGCGTCTAGTTTAGAAATTGGGGTCCCATCAAGGTTCAGCGGC

AGTGGATATGGGACAGAATTCACTCTCACCATCAGCAGCCTGCAGCCTGATGATTTCGCAACTT

ATTATTGCCTACAGTATAGTACTCATTCGACGTTCGGCCAAGGGACCAGGGTGGAAATCAAACG

AACTGTGGCTGCACCATCTGTCTTCATCTTCCCGCCATCTGATGAGCAGTTGAAATCTGGAACT

GCCTCTGTTGTGTGCCTGCTGAATAACTTCTATCCCAGAGAGGCCAAAGTACAGTGGAAGGTGG

ATAACGCCCTCCAATCGGGTAACTCCCAGGAGAGTGTCACAGAGCAGGACAGCAAGGACAGCAC

CTACAGCCTCAGCAGCACCCTGACGCTGAGCAAAGCAGACTACGAGAAACACAAACTCTACGCC

TGCGAAGTCACCCATCAGGGCCTGAGCTCGCCCGTCACAAAGAGCTTCAACAGGGGAGAGTGTT

AG (vector (italicized) = SEQ ID NO: 32), (full-length = SEQ ID NO: 54)

Protein: 237aa/26 kD
*METDTLLLWVLLLWVPGSTGAGS*

DIQMTQSPSTLSASVGDRVTITCRASQSISSWLAWYQQKPGKAPKLLIYKASSLEIGVPSRFSG

SGYGTEFTLTISSLQPDDFATYYCLQYSTHSTFGQGTRVEIKRTVAAPSVFIFPPSDEQLKSGT

ASVVCLLNNFYPREAKVQWKVDNALQSGNSQESVTEQDSKDSTYSLSSTLTLSKADYEKHKLYA

CEVTHQGLSSPVTKSFNRGEC (vector (italicized) = SEQ ID NO: 32), (full-length = SEQ ID NO: 55)

Clone 1
Heavy chain variable region sequence
CAGGTGCAGCTGCAGGAGTCCGGGGGAGGCGTGGTCCAGCCTGGGAGGTCCCTGAGACTCTCCT

GTGCAGCCTCTGGATTCACCTTCAGTAGCTATGGCATGCACTGGGTCCGCCAGGCTCCAGGCAA

GGGGCTGGAGTGGGTGGCAGTTATATCATATGATGGAAGTAATAAATACTATGCAGACTCCGTG

AAGGGCCGATTCACCATCTCCAGAGACAATTCCAAGAACACGCTGTATCTGCAAATGAACAGCC

TGAGAGCCGAGGACACGGCTGTGTATTACTGTGCGAGAGATCTCGGCGCCGTTATAGCAGTGGC

TGGTACTTCCACCCCGTACAACTGGTTCGACCCCTGGGGCCAGGGAACCCTGGTCACCGTCTC (SEQ ID NO: 56)

Translated protein:
QVQLQESGGGVVQPGRSLRLSCAASGFTFSSYGMHWVRQAPGKGLEWVAVISYDGSNKYYADSV

KGRFTISRDNSKNTLYLQMNSLRAEDTAVYYCARDLGAVIAVAGTSTPYNWFDPWGQGTLVTVS (SEQ ID NO: 57)

Light chain variable region sequence
GATGTTGTGATGACTCAGTCTCCACTCTCCCTGCCCGTCACCCCTGGAGAGCCGGCCTCCATCT

CCTGCAGGTCTCGTCAGAGCCTCCTGCATAGCAATGGACACAACTATTTGGGTTGGTACCTGCA

GAAGCCAGGGCAGTCTCCACAGCTCCTGATCTATCTGGCTTCTATTCGGGCCTCCGGGATCCCT

GACAGGTTCAGTGGCAGTGGATCAGGCACAGATTTTACACTGAAAATCAGCAGAGTGGAGGCTG

AGGATGTTGGCGTTTATTACTGCATGCAAGCTCTACAAACACCCTACACTTTTGGCCAGGGGAC

CAAGCTGGAGATCAA (SEQ ID NO: 58)

-continued

Translated protein:
DVVMTQSPLSLPVTPGEPASISCRSRQSLLHSNGHNYLGWYLQKPGQSPQLLIYLASIRASGIP

DRFSGSGSGTDFTLKISRVEAEDVGVYYCMQALQTPYTFGQGTKLEIK (SEQ ID NO: 59)

The CDR Analysis for clone 1 is provided in FIG. 27A.

Clone 2
Heavy chain variable region sequence
(SEQ ID NO: 66)
CAGATGCAGCTGGTGCAGTCGGGGGGAGGTGTGGTACGGCCTGGGGGGTC

CCTGAGACTCTCCTGTGCAGCCTCTGGATTCACCTTTGATGATTATGGCA

TGAGCTGGGTCCGCCAAGCTCCAGGGAAGGGGCTGGAGTGGGTCTCTGGT

ATTAATTGGAATGGTGGTAGCACAGGTTATGCAGACTCTGTGAAGGGCCG

ATTCACCATCTCCAGAGACAACGCCAAGAACTCCCTGTATCTGCAAATGA

ACAGTCTGAGAGCCGAGGACACGGCCTTGTATTACTGTGCGAGAGAAAGC

TCGATGACTACAGTAACTACGTATCTCCTACGGGAAGTAGGGGTAGGGTT

GGACTTTGACTACTGGGGCCAGGGCACCCTGGTCACCGTCTC

Translated protein:
(SEQ ID NO: 67)
QMQLVQSGGGVVRPGGSLRLSCAASGFTFDDYGMSWVRQAPGKGLEWVSG

INWNGGSTGYADSVKGRFTISRDNAKNSLYLQMNSLRAEDTALYYCARES

SMTTVTTYLLREVGVGLDFDYWGQGTLVTVS

Light chain variable region sequence
(SEQ ID NO: 68)
GAAACGACACTCACGCAGTCTCCAGGCACCCTGTCCTTGTCTCCAGGGGA

AAGAGCCACCCTCTCCTGCAGGGCCAGTCAGACTGTTAGCGGCAGCTACT

TAGCCTGGTACCAGCAGAAACCTGGCCAGCCTCCCAGGCTCCTCATCTAT

GGTGCATCCAGCAGGGCCACTGGCATCCCAGACAGGTTCAGTGGCAGTGG

GTCCGGGACAGACTTCACTCTCACCATCAGCAGACTGGAGCCTGAAGATT

TTGCAGTGTATTACTGTCAGGACTATGGTAGCTCACGGACGTTCGGCCAA

GGGACCAAGGTGGAACTCAAAC

Translated protein:
(SEQ ID NO: 69)
ETTLTQSPGILSLSPGERATLSCRASQTVSGSYLAWYQQKPGQPPRLLIY

GASSRATGIPDRFSGSGSGTDFTLTISRLEPEDFAVYYCQDYGSSRTFGQ

GTKVELK

The CDR Analysis for clone 2 is provided in FIG. 27B.

Clone 3
Heavy chain variable region sequence
(SEQ ID NO: 76)
CAGGTGCAGCTACAGCAGTGGGGCGCAGGACTGTTGAAGCCTTCGGAGAC

CCTGTCCCTCACCTGCGCTGTCTATGGTGGGTCCTTCAGTGGTTACTACT

GGAGCTGGATCCGCCAGCCCCCAGGGAAGGGGCTGGAGTGGATTGGGGAA

ATCAATGATAGTGGAAGCACCAACTACAACCCGTCCCTCAAGAGTCGAGT

CACCATATCAGTAGACACGTCCAAGAACCAGTTCTCCCTGAAGCTGAGCT

CTGTGACCGCCGCGGACACGGCTGTGTATTACTGTGCGAGACGATATTGT

AGTGGTGGTAGCTGCTACTTAGTTGGAACGGGGTCTGAATTGGACTACTG

GGGCCAGGGAACCCTGGTCACCGTCTC

Translated protein:
(SEQ ID NO: 77)
QVQLQQWGAGLLKPSETLSLTCAVYGGSFSGYYWSWIRQPPGKGLEWIGE

INHSGSTNYNPSLKSRVTISVDTSKNQFSLKLSSVTAADTAVYYCARRYC

SGGSCYLVGTGSELDYWGQGTLVTVS

Light chain variable region sequence
(SEQ ID NO: 78)
GACATCCAGATGACCCAGTCTCCTTCCACCCTGTCTGCATCTGTAGGAGA

CAGAGTCACCATAACTTGCCGGGCCAGTCAGAGCATTAGTAGCTGGTTGG

CCTGGTATCAGCAGAAACCAGGGAAAGCCCCTAAACTCCTAATCTATAAG

GCGTCTAGTTTAGAAATTGGGGTCCCATCAAGGTTCAGCGGCAGTGGATA

TGGGACAGAATTCACTCTCACCATCAGCAGCCTGCAGCCTGATGATTTCG

CAACTTATTATTGCCTACAGTATAGTACTCATTCGACGTTCGGCCAAGGG

ACCAGGGTGGAAATCAAAC

Translated protein:
(SEQ ID NO: 79)
DIQMIQSPSTLSASVGDRVTITCRASQSISSWLAWYQQKPGKAPKLLIY

KASSLEIGVPSRFSGSGYGTEFTLTISSLQPDDFATYYCLQYSTHSTFG

QGTRVEIK

The CDR Analysis for clone 3 is provided in FIG. 27C.

TABLE 3

Table of Sequences

| SEQ ID NO | Description | Sequence |
|---|---|---|
| 56 | Clone 1 heavy chain variable sequence (DNA) | CAGGTGCAGCTGCAGGAGTCCGGGGGAGGCGTGGTCCAGCCTGGGA GGTCCCTGAGACTCTCCTGTGCAGCCTCTGGATTCACCTTCAGTAG CTATGGCATGCACTGGGTCCGCCAGGCTCCAGGCAAGGGGCTGGAG TGGGTGGCAGTTATATCATATGATGGAAGTAATAAATACTATGCAG ACTCCGTGAAGGGCCGATTCACCATCTCCAGAGACAATTCCAAGAA CACGCTGTATCTGCAAATGAACAGCCTGAGAGCCGAGGACACGGCT GTGTATTACTGTGCGAGAGATCTCGGCGCCGTTATAGCAGTGGCTG GTACTTCCACCCCGTACAACTGGTTCGACCCCTGGGGCCAGGGAAC CCTGGTCACCGTCTC |

TABLE 3-continued

| Table of Sequences | | |
|---|---|---|
| SEQ ID NO | Description | Sequence |
| 57 | Clone 1 heavy chain variable sequence Translated protein: | QVQLQESGGGVVQPGRSLRLSCAASGFTFSSYGMHWVRQAPGKGLEWVAVISYDGSNKYYADSVKGRFTISRDNSKNTLYLQMNSLRAEDTAVYYCARDLGAVIAVAGTSTPYNWFDPWGQGTLVTVS |
| 58 | Clone 1 Light chain variable region sequence | GATGTTGTGATGACTCAGTCTCCACTCTCCCTGCCCGTCACCCCTGGAGAGCCGGCCTCCATCTCCTGCAGGTCTCGTCAGAGCCTCCTGCATAGCAATGGACACAACTATTTGGGTTGGTACCTGCAGAAGCCAGGGCAGTCTCCACAGCTCCTGATCTATCTGGCTTCTATTCGGGCCTCCGGGATCCCTGACAGGTTCAGTGGCAGTGGATCAGGCACAGATTTTACACTGAAAATCAGCAGAGTGGAGGCTGAGGATGTTGGCGTTTATTACTGCATGCAAGCTCTACAAACACCCTACACTTTTGGCCAGGGGACCAAGCTGGAGATCAA |
| 59 | Translated protein: | DVVMTQSPLSLPVTPGEPASISCRSRQSLLHSNGHNYLGWYLQKPGQSPQLLIYLASIRASGIPDRFSGSGSGTDFTLKISRVEAEDVGVYYCMQALQTPYTFGQGTKLEIK |
| 60 | Clone 1 Heavy chain (IgG3) CDR1 | GFTFSSYG |
| 61 | Clone 1 Heavy chain (IgG3) CDR2 | ISYDGSNK |
| 62 | Clone 1 Heavy chain (IgG3) CDR3 | ARDLGAVIAVAGTSTPYNWFDP |
| 63 | Clone 1 Light chain (K) CDR1 | QSLLHSNGHNY |
| 64 | Clone 1 Light chain (K) CDR2 | LAS |
| 65 | Clone 1 Light chain (K) CDR3 | MQALQTPYT |
| 66 | Clone 2 Heavy chain variable region sequence | CAGATGCAGCTGGTGCAGTCGGGGGGAGGTGTGGTACGGCCTGGGGGGTCCCTGAGACTCTCCTGTGCAGCCTCTGGATTCACCTTTGATGATTATGGCATGAGCTGGGTCCGCCAAGCTCCAGGGAAGGGGCTGGAGTGGGTCTCTGGTATTAATTGGAATGGTGGTAGCACAGGTTATGCAGACTCTGTGAAGGGCCGATTCACCATCTCCAGAGACAACGCCAAGAACTCCCTGTATCTGCAAATGAACAGTCTGAGAGCCGAGGACACGGCCTTGTATTACTGTGCGAGAGAAAGCTCGATGACTACAGTAACTACGTATCTCCTACGGGAAGTAGGGGTAGGGTTGGACTTTGACTACTGGGGCCAGGGCACCCTGGTCACCGTCTC |
| 67 | Translated protein: | QMQLVQSGGGVVRPGGSLRLSCAASGFTFDDYGMSWVRQAPGKGLEWVSGINWNGGSTGYADSVKGRFTISRDNAKNSLYLQMNSLRAEDTALYYCARESSMTTVTTYLLREVGVGLDFDYWGQGTLVTVS |
| 68 | Light chain variable region sequence | GAAACGACACTCACGCAGTCTCCAGGCACCCTGTCCTTGTCTCCAGGGGAAAGAGCCACCCTCTCCTGCAGGGCCAGTCAGACTGTTAGCGGCAGCTACTTAGCCTGGTACCAGCAGAAACCTGGCCAGCCTCCCAGGCTCCTCATCTATGGTGCATCCAGCAGGGCCACTGGCATCCCAGACAGGTTCAGTGGCAGTGGGTCCGGGACAGACTTCACTCTCACCATCAGCAGACTGGAGCCTGAAGATTTTGCAGTGTATTACTGTCAGGACTATGGTAGCTCACGGACGTTCGGCCAAGGGACCAAGGTGGAACTCAAAC |
| 69 | Translated protein: | ETTLTQSPGTLSLSPGERATLSCRASQTVSGSYLAWYQQKPGQPPRLLIYGASSRATGIPDRFSGSGSGTDFTLTISRLEPEDFAVYYCQDYGSSRTFGQGTKVELK |
| 70 | Clone 2 Heavy chain (IgG3) CDR1 | GFTFDDYG |

TABLE 3-continued

Table of Sequences

| SEQ ID NO | Description | Sequence |
|---|---|---|
| 71 | Clone 2 Heavy chain (IgG3) CDR2 | INWNGGST |
| 72 | Clone 2 Heavy chain (IgG3) CDR3 | ARESSMTTVTTYLLREVGVGLDFDY |
| 73 | Clone 2 Light chain (K) CDR1 | QTVSGSY |
| 74 | Clone 2 Light chain (K) CDR2 | GAS |
| 75 | Clone 2 Light chain (K) CDR3 | QDYGSSRT |
| 76 | Clone 3 Heavy chain variable region sequence | CAGGTGCAGCTACAGCAGTGGGGCGCAGGACTGTTGAAGCCTTCGG AGACCCTGTCCCTCACCTGCGCTGTCTATGGTGGGTCCTTCAGTGG TTACTACTGGAGCTGGATCCGCCAGCCCCCAGGGAAGGGGCTGGAG TGGATTGGGGAAATCAATCATAGTGGAAGCACCAACTACAACCCGT CCCTCAAGAGTCGAGTCACCATATCAGTAGACACGTCCAAGAACCA GTTCTCCCTGAAGCTGAGCTCTGTGACCGCCGCGGACACGGCTGTG TATTACTGTGCGAGACGATATTGTAGTGGTGGTAGCTGCTACTTAG TTGGAACGGGGTCTGAATTGGACTACTGGGGCCAGGGAACCCTGGT CACCGTCTC |
| 77 | Translated protein: | QVQLQQWGAGLLKPSETLSLTCAVYGGSFSGYYWSWIRQPPGKGLE WIGEINHSGSTNYNPSLKSRVTISVDTSKNQFSLKLSSVTAADTAV YYCARRYCSGGSCYLVGTGSELDYWGQGTLVTVS |
| 78 | Light chain variable region sequence | GACATCCAGATGACCCAGTCTCCTTCCACCCTGTCTGCATCTGTAG GAGACAGAGTCACCATAACTTGCCGGGCCAGTCAGAGCATTAGTAG CTGGTTGGCCTGGTATCAGCAGAAACCAGGGAAAGCCCCTAAACTC CTAATCTATAAGGCGTCTAGTTTAGAAATTGGGGTCCCATCAAGGT TCAGCGGCAGTGGATATGGGACAGAATTCACTCTCACCATCAGCAG CCTGCAGCCTGATGATTTCGCAACTTATTATTGCCTACAGTATAGT ACTCATTCGACGTTCGGCCAAGGGACCAGGGTGGAAATCAAAC |
| 79 | Translated protein: | DIQMTQSPSTLSASVGDRVTITCRASQSISSWLAWYQQKPGKAPKL LIYKASSLEIGVPSRFSGSGYGTEFTLTISSLQPDDFATYYCLQYS THSTFGQGTRVEIK |
| 80 | Clone 3 Heavy chain (IgG4) CDR1 | GGSFSGYY |
| 81 | Clone 3 Heavy chain (IgG4) CDR2 | INHSGST |
| 82 | Clone 3 Heavy chain (IgG4) CDR3 | ARRYCSGGSCYLVGTGSELDY |
| 83 | Clone 3 Light chain (KV pseudogene) CDR1 | QSISSW |
| 84 | Clone 3 Light chain (KV pseudogene) CDR2 | KAS |

TABLE 3-continued

Table of Sequences

| SEQ ID NO | Description | Sequence |
|---|---|---|
| 85 | Clone 3 Light chain (KV pseudogene) CDR3 | LQYSTHST |

All publications, patents and patent applications cited herein are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

As used herein, the term "about" means approximately +10%.

Embodiments of this invention are described herein. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An isolated antibody or antigen-binding fragment thereof that binds to OVA-serine proteinase inhibitor (serpin) B 13 and comprises a heavy chain, wherein the heavy chain comprises a heavy chain CDR1, a heavy chain CDR2, a heavy chain CDR3, and a light chain, wherein the light chain comprises a light chain CDR1, a light chain CDR2, and a light chain CDR3, wherein:

(i) the heavy chain CDR1 comprises the amino acid sequence of SEQ ID NO:1, SEQ ID NO:2, SEQ ID NO:26, SEQ ID NO:60, SEQ ID NO:70 or SEQ ID NO:80, (ii) the heavy chain CDR2 comprises the amino acid sequence of SEQ ID NO:4, SEQ ID NO:27, SEQ ID NO:61, SEQ ID NO:71 or SEQ ID NO:81, (iii) the heavy chain CDR3 comprises the amino acid sequence of SEQ ID NO:6, SEQ ID NO:28, SEQ ID NO:62, SEQ ID NO:72 or SEQ ID NO:82, (iv) the light chain CDR1 comprises the amino acid sequence of SEQ ID NO:8, SEQ ID NO:29, SEQ ID NO:63, SEQ ID NO:73 or SEQ ID NO:83, (v) the light chain CDR2 comprises the amino acid sequence of SEQ ID NO:10, SEQ ID NO:64, SEQ ID NO:74 or SEQ ID NO:84, and (vi) the light chain CDR3 comprises the amino acid sequence of SEQ ID NO:12, SEQ ID NO:65, SEQ ID NO:75 or SEQ ID NO:85.

2. The isolated antibody or antigen-binding fragment thereof of claim 1, wherein the isolated antibody or antigen-binding fragment thereof is a humanized antibody.

3. The isolated antibody or antigen-binding fragment thereof of claim 1, wherein the isolated antibody or antigen-binding fragment thereof is a chimeric antibody.

4. The antigen-binding fragment of claim 1, wherein the antigen-binding fragment is selected from the group consisting of a Fab fragment, a F(ab')2 fragment, a scFv fragment, and a sc(Fv)2 diabody.

5. The isolated antibody or antigen-binding fragment of claim 2, wherein the heavy chain comprises the amino acid sequence of SEQ ID NO:18.

6. The isolated antibody or antigen-binding fragment of claim 2, wherein the light chain comprises the amino acid sequence of SEQ ID NO:20.

7. The isolated antibody or antigen-binding fragment of claim 3, wherein the heavy chain comprises the amino acid sequence of SEQ ID NO:22.

8. The isolated antibody or antigen-binding fragment of claim 3, wherein the light chain comprises the amino acid sequence of SEQ ID NO:24.

9. A composition comprising at least one isolated antibody or antigen-binding fragment of claim 1.

10. A method of inhibiting an OVA-serine proteinase inhibitor (serpin) B13-related disorder in a subject, the method comprising administering to the subject the isolated antibody or antigen-binding fragment thereof of claim 1.

11. The method of claim 10, wherein the serpin B13-related disorder is diabetes.

12. The method of claim 11, wherein the diabetes is type I diabetes, type 2 diabetes, or diabetes in patients with chronic pancreatitis who undergo total pancreatectomy with autologous islet transplantation and still remain insulin dependent.

13. The method of claim 11, wherein the diabetes is type I diabetes.

14. The method of claim 10, wherein the serpin B13-related disorder is inflammatory or central nervous system disease.

15. The method of claim 10, wherein the serpin B13-related disorder is a bone fracture, wound healing, hair loss, multiple sclerosis, or lupus.

* * * * *